US010941126B2

(12) United States Patent
Childers et al.

(10) Patent No.: US 10,941,126 B2
(45) Date of Patent: Mar. 9, 2021

(54) BRIDGED BICYCLOALKYL-SUBSTITUTED AMINOTHIAZOLES AND THEIR METHODS OF USE

(71) Applicant: Temple University—Of The Commonwealth System of Higher Education, Philadelphia, PA (US)

(72) Inventors: Wayne C. Childers, New Hope, PA (US); Magid A. Abou-Gharbia, Exton, PA (US); George C. Morton, Collegeville, PA (US); Jean-Pierre J. Issa, Philadelphia, PA (US); Hanghang Zhang, Philadelphia, PA (US)

(73) Assignee: TEMPLE UNIVERSITY-OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 16/479,317

(22) PCT Filed: Jan. 19, 2018

(86) PCT No.: PCT/US2018/014465
§ 371 (c)(1),
(2) Date: Jul. 19, 2019

(87) PCT Pub. No.: WO2018/136766
PCT Pub. Date: Jul. 26, 2018

(65) Prior Publication Data
US 2019/0352272 A1 Nov. 21, 2019

Related U.S. Application Data

(60) Provisional application No. 62/448,051, filed on Jan. 19, 2017.

(51) Int. Cl.
| A61K 31/426 | (2006.01) |
| A61K 31/427 | (2006.01) |
| C07D 277/42 | (2006.01) |
| A61P 35/00 | (2006.01) |
| C07D 417/06 | (2006.01) |
| A61K 31/05 | (2006.01) |
| A61K 31/11 | (2006.01) |
| A61K 31/166 | (2006.01) |
| A61K 31/167 | (2006.01) |
| A61K 31/352 | (2006.01) |
| A61K 31/365 | (2006.01) |
| A61K 31/404 | (2006.01) |
| A61K 31/496 | (2006.01) |
| A61K 31/4985 | (2006.01) |
| A61K 31/5377 | (2006.01) |
| C07K 16/28 | (2006.01) |

(52) U.S. Cl.
CPC .......... *C07D 277/42* (2013.01); *A61P 35/00* (2018.01); *C07D 417/06* (2013.01); *A61K 31/05* (2013.01); *A61K 31/11* (2013.01); *A61K 31/166* (2013.01); *A61K 31/167* (2013.01); *A61K 31/352* (2013.01); *A61K 31/365* (2013.01); *A61K 31/404* (2013.01); *A61K 31/496* (2013.01); *A61K 31/4985* (2013.01); *A61K 31/5377* (2013.01); *C07K 16/2818* (2013.01); *C07K 16/2827* (2013.01)

(58) Field of Classification Search
None
See application file for complete search history.

(56) References Cited

U.S. PATENT DOCUMENTS

| 6,613,753 B2 | 9/2003 | Rubinfeld |
| 2007/0167329 A1 | 7/2007 | Bastiaans |
| 2008/0145336 A1 | 6/2008 | Muller |
| 2009/0286793 A1 | 11/2009 | Ibrahim |
| 2010/0129363 A1 | 5/2010 | Zeldis |
| 2011/0269753 A1 | 11/2011 | Balasubramanian |

FOREIGN PATENT DOCUMENTS

| KR | 20160035878 | 4/2016 |
| WO | 9921845 | 5/1999 |
| WO | 2005063022 | 7/2005 |
| WO | 2005103034 A1 | 11/2005 |
| WO | 2008083098 | 7/2008 |
| WO | 2017015484 | 1/2017 |

OTHER PUBLICATIONS

Adelman et al., "Promoter-proximal pausing of RNA polymerase II: emerging roles in metazoans", 2012, Nature Review Genetics, 13:720-732.
Arrowsmith et al., "Epigenetic protein families: a new frontier for drug discovery", 2012, Nat. Rev. Drug Discov., 11:384-400.
Asghar et al., "The history and future of targeting cyclin-dependent kinases in cancer therapy", 2015, Nature Reviews Drug Discovery, 14:130-146.

(Continued)

*Primary Examiner* — Samantha L Shterengarts
(74) *Attorney, Agent, or Firm* — Riverside Law LLP

(57) ABSTRACT

The present invention includes novel bridged bicycloalkyl-substituted aminothiazole compounds useful in preventing or treating cancer in a subject in need thereof. The present invention also includes methods of preventing or treating cancer in a subject in need thereof by administering to the subject a therapeutically effective amount of a compound of the invention.

20 Claims, 76 Drawing Sheets

Specification includes a Sequence Listing.

(56) References Cited

OTHER PUBLICATIONS

Barboric et al., "NF-κB Binds P-TEFb to Stimulate Transcriptional Elongation by RNA Polymerase II", 2001, Molecular Cell, 8:327-337.
Baumli et al., "The structure of P☐TEFb (CDK9/cyclin T1), its complex with flavopiridol and regulation by phosphorylation", 2008, EMBO J., 27:1907-1918.
Baylin et al, "A decade of exploring the cancer epigenomebiological and translational implications", 2011, Nat. Rev. Cancer, 11:726-734.
Brocks et al., "DNMT and HDAC inhibitors induce cryptic transcription start sites encoded in long terminal repeats", 2017, Nat. Genet., 49:1052-1060.
Busk et al., "Involvement of cyclin D activity in left ventricle hypertrophy in vivo and in vitro", 2002, Cardiovasc. Res., 56:64-75.
Canavese et al., "Cyclin dependent kinases in cancer", 2012, Cancer Biol. Ther., 13:451-457.
Cerami et al., "The cBio cancer genomics portal: an open platform for exploring multidimensional cancer genomics data", 2012, Cancer Discov., 2:401-404.
Chiappinelli et al., "Inhibiting DNA methylation causes an interferon response in cancer via dsRNA including endogenous retroviruses", 2015, Cell, 162:974-986.
Elizabeth R. Sharlow et al: "Development and Implementation of a Miniaturized High-Throughput Time-Resolved Fluorescence Energy Transfer Assay to Identify Small Molecule Inhibitors of Polo-Like Kinase 1", Assay and Drug Development Technologies, vol. 5, No. 6, Dec. 1, 2007 (Dec. 1, 2007), pp. 723-736.
Gao et al., "Integrative analysis of complex cancer genomics and clinical profiles using the cBioPortal", 2013, Sci. Signal, 6:pl1, 20 pages.
Garriga et al., "CDK9 inhibition strategy defines distinct sets of target genes", 2014, BMC Res. Notes, 7:301, 10 pages.
Garriga et al., "Cellular control of gene expression by T-type cyclin/CDK9 complexes", 2004, Gene, 337:15-23.
Ghia et al., "Efficacy and safety of dinaciclib vs ofatumumab in patients with relapsed/refractory chronic lymphocytic leukemia", 2017, Blood, 129:1876-1878.
Goel et al., "CDK4/6 inhibition triggers anti-tumour immunity", 2017, Nature, 548:471-475.
Gregory et al., "CDK9 inhibition by dinaciclib potently suppresses Mcl-1 to induce durable apoptotic responses in aggressive MYC-driven B-cell lymphoma in vivo", 2015, Leukemia, 29:1437-1441.
Harjai, "Potential New Cardiovascular Risk Factors: Left Ventricular Hypertrophy, Homocysteine, Lipoprotein(a), Triglycerides, Oxidative Stress, and Fibrinogen", 1999, Ann. Intern. Med., 131:376-386.
Holcakova et al., "The Inhibitor of Cyclin-Dependent Kinases, Olomoucine II, Exhibits Potent Antiviral Properties", 2010, Antiviral Chem. Chemother., 20:133-142.
Hole et al., "Comparative structural and functional studies of 4-(thiazol-5-yl)-2-(phenylamino) pyrimidine-5-carbonitrile CDK9 inhibitors suggest the basis for isotype selectivity", 2013, J. Med. Chem., 56:660-670.
Jones et al., "Targeting the cancer epigenome for therapy", 2016, Nat. Rev. Genet., 17:630-641.
Juergens et al., Combination Epigenetic Therapy Has Efficacy in Patients with Refractory Advanced Non-Small Cell Lung Cancer, 2011, Cancer Discov., 1:589-607.
Kadoch et al., "Mammalian SWI/SNF chromatin remodeling complexes and cancer: Mechanistic insights gained from human genomics", 2015, Sci. Adv., 1:e1500447, 18 pages.
Kadoch et al., "Proteomic and bioinformatic analysis of mammalian SWI/SNF complexes identifies extensive roles in human malignancy", 2013, Nat. Genet., 45:592-601.
Kelly et al., "Epigenetic Modifications as Therapeutic Targets", Nat. Biotechnol., 2010, 28:1069-1078.
Keskin et al., "Complex effects of flavopiridol on the expression of primary response genes", 2012, Cell Div., 7:11, 13 pages.
Krystof et al., "Pharmacological targeting of CDK9 in cardiac hypertrophy", 2010, Med. Res. Rev., 30:646-666.
Lavigne et al., "Interaction of HP1 and Brg1/Brm with the globular domain of histone H3 is required for HP1-mediated repression", 2009, PLoS Genet., 5:e1000769, 11 pages.
Leitch et al., "Cyclin☐dependent kinase inhibitor drugs as potential novel anti☐inflammatory and pro☐resolution agents", 2009, Brit. J. Pharmacol., 158:1004-1016.
Li et al., "Immune regulation by low doses of the DNA methyltransferase inhibitor 5-azacitidine in common human epithelial cancers", 2014, Oncotarget, 5:587-598.
Licht, "DNA methylation inhibitors in cancer therapy: the immunity dimension", 2015, Cell, 162:938-939.
Lu et al., "Toward understanding the structural basis of cyclin-dependent kinase 6 specific inhibition", 2006, J. Med. Chem. 49:3826-3831.
Lu, et al., "Compensatory induction of MYC expression by sustained CDK9 inhibition via a BRD4-dependent mechanism", 2015, Elife 4:e06535, 26 pages.
MacCallum et al., "Seliciclib (CYC202, R-Roscovitine) Induces Cell Death in Multiple Myeloma Cells by Inhibition of RNA Polymerase II—Dependent Transcription and Down-regulation of Mcl-1", 2005, Cancer Research, 65:5399-5407.
Müller et al., "The ins and outs of selective kinase inhibitor development", 2015, Nat. Chem. Biol., 11:818-821.
Nozato et al., "Overexpression of cdk Inhibitor p16INK4a by Adenovirus Vector Inhibits Cardiac Hypertrophy in vitro and in vivo: a Novel Strategy for the Gene Therapy of Cardiac Hypertrophy", 2001, J. Mol. Cell Cardiol., 33:1493-1504.
Ortega et al., "Cyclin D-dependent kinases, INK4 inhibitors and cancer", 2002, Biochim. Biophys. Acta 1602:73-87.
Pal et al., "Epigenetics and aging", 2016, Sci. Adv., 2: e1600584, 20 pages.
PubChem CID-53297996, Create Date: Aug. 2, 2011, p. 3, Figure, 10 pages.
Qin et al., "Epigenetic synergy between decitabine and platinum derivatives", 2015, Clin. Epigenetics, 7:97, 14 pages.
Rahl et al., "c-Myc Regulates Transcriptional Pause Release", 2010, Cell, 141:432-445.
Raynal et al., "DNA methylation does not stably lock gene expression but instead serves as a molecular mark for gene Silencing memory", 2012, Cancer Res., 72:1170-1181.
Roskoski, R. "Classification of small molecule protein kinase inhibitors based upon the structures of their drug-enzyme complexes", 2016, Pharmacol. Res., 103:26-48.
Rouillard et al., "The harmonizome: a collection of processed datasets gathered to serve and mine knowledge about genes and proteins", 2016, Database (Oxford), 2016:1-16.
Roulois et al., "DNA-demethylating agents target colorectal cancer cells by inducing viral mimicry by endogenous transcripts", 2015, Cell, 162:961-973.
Schang, "Cyclin-dependent kinases as cellular targets for antiviral drugs", 2002, J. Antimicrob. Chemother., 50:779-792.
Schmitz et al., "Cyclin-Dependent Kinases as Coregulators of Inflammatory Gene Expression", 2016, Trends Pharmacol. Sci., 37:101-113.
Selvetella et al., "Mechanisms of Cardiac Hypertrophy", 2005, Heart Failure Clin., 1:263-273.
Sherr et al., "Targeting CDK4 and CDK6: From Discovery to Therapy", 2016, Cancer Disco., 6:353-367.
Si et al., "Chromatin remodeling is required for gene reactivation after decitabine-mediated DNA hypomethylation", 2010, Cancer Res., 70:6968-6977.
Snyder et al., "Genetic basis for clinical response to CTLA-4 blockade in melanoma", 2014, N. Engl. J. Med., 371:2189-2199.
St Pierre et al.,"Mammalian SWI/SNF complexes in cancer: emerging therapeutic opportunities", 2017, Curr. Opin. Genet. Dev., 42:56-67.
Taby et al., "Cancer Epigenetics", 2010, CA Cancer J. Clin., 60:376-392.
Taylor et al., "Multiple new phenotypes induced in 10T12 and 3T3 cells treated with 5-azacytidine", 1979, Cell, 17:771-779.

(56) References Cited

OTHER PUBLICATIONS

The Cancer Genome Atlas Network, "Comprehensive molecular characterization of human colon and rectal cancer", 2012, Nature, 487:330-337.

The Cancer Genome Atlas Network, "Genomic Classification of Cutaneous Melanoma", 2015, Cell, 161:1681-1696.

Uhlen et al., "A pathology atlas of the human cancer transcriptome", 2017, Science, 357, 13 pages.

Van Duyne et al., "Varying modulation of HIV-1 LTR activity by Baf complexes", 2011, J. Mol. Biol., 411:581-596.

Vangamudi et al., "The SMARCA2/4 ATPase domain surpasses the bromodomain as a drug target in SWI/SNF-mutant cancers: insights from cDNA rescue and PFI-3 inhibitor studies", 2015, Cancer Res., 75:3865-3878.

Wang et al., "A structural atlas of kinases inhibited by clinically approved drugs", 2014, Methods Enzymol., 548:23-67.

Wang et al., "CDK7-Dependent Transcriptional Addiction in Triple-Negative Breast Cancer", 2015, Cell, 163:174-186.

Wilson et al., "SWI/SNF nucleosome remodellers and cancer", 2011, Nat. Rev. Cancer, 11:481-492.

Wu et al., "Histone deacetylase inhibitor depsipeptide activates silenced genes through decreasing both CpG and H3K9 methylation on the promoter", 2008, Mol. Cell Biol., 28:3219-3235.

Zhao et al., "TSGene 2.0: an updated literature-based knowledgebase for tumor suppressor genes", 2016, Nucleic Acids Res., 44:D1023-1031.

Schonbrunn et al., "Development of Highly Potent and Selective Diaminothiazole Inhibitors of Cyclin-Dependent Kinases", 2013, J. Medicin. Chem., 56:3768-3782.

Figure 4A-C

| Target IC50s (nM) | iCDK9 | SNS-032 | Dinaciclib |
|---|---|---|---|
| CDK1 | 1700 | 480 | 3 |
| CDK2 | 240 | 38 | 1 |
| CDK4 | 1800 | 925 | 100 |
| CDK6 | ND | little effect | ND |
| CDK9 | 0.4 | 4 | 4 |

Figure 13

Reaction Scheme for MC180295
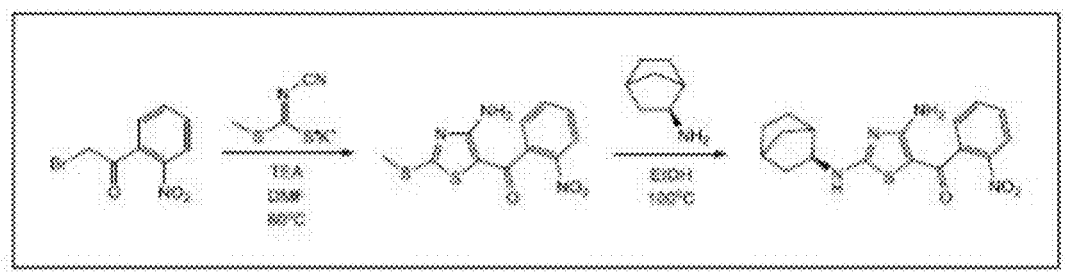
Reaction Scheme for MC180349
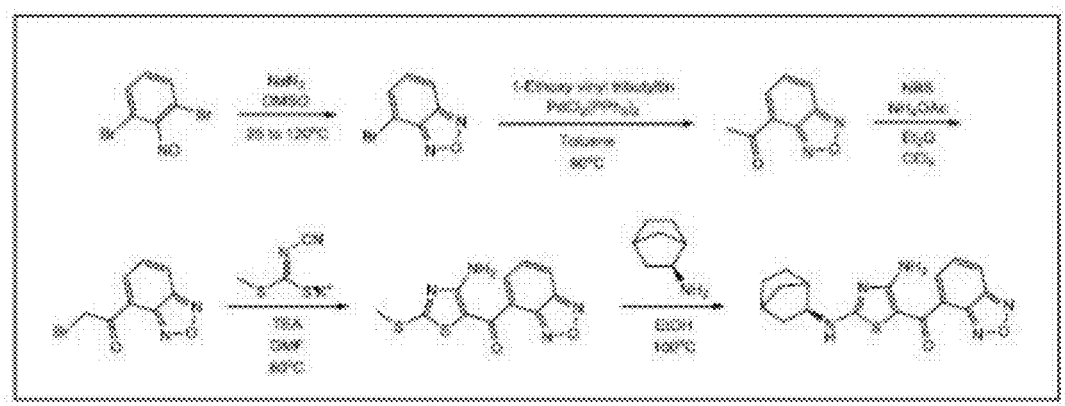
Reaction Scheme for MC180343
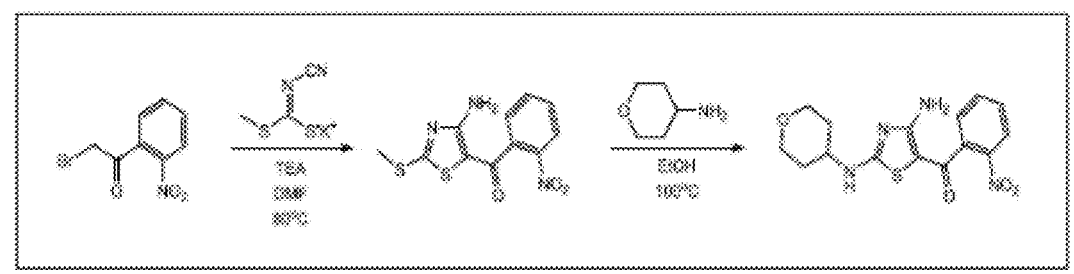
Reaction Scheme for MC180342
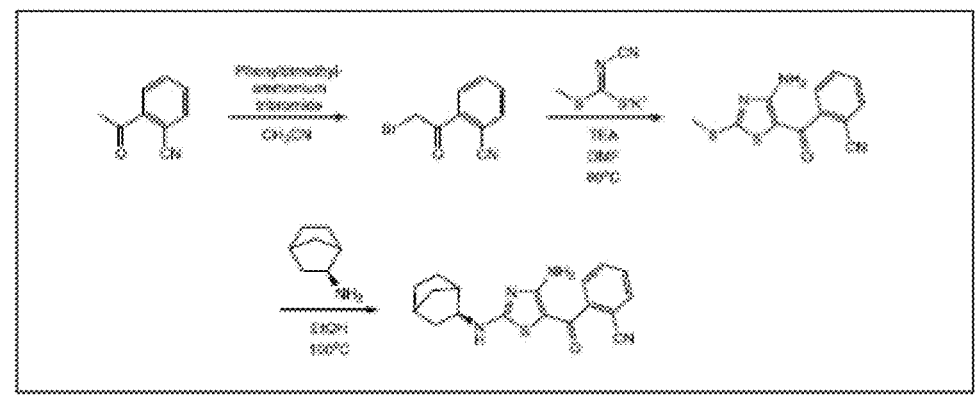
Figure 19

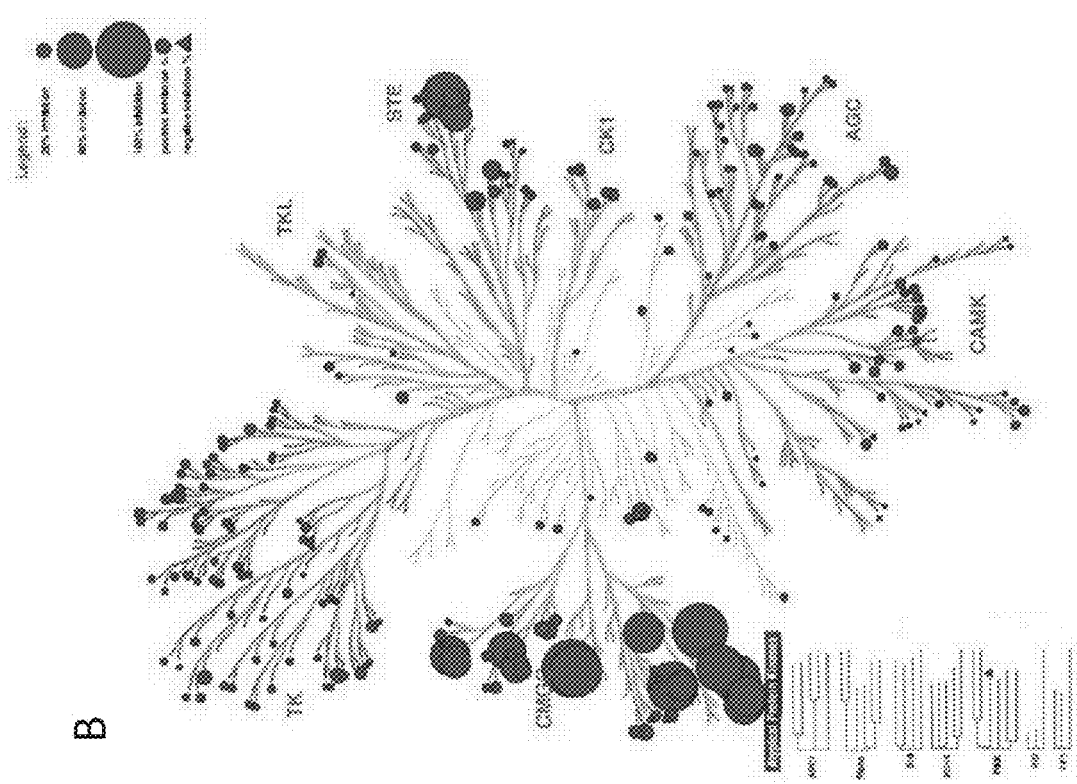
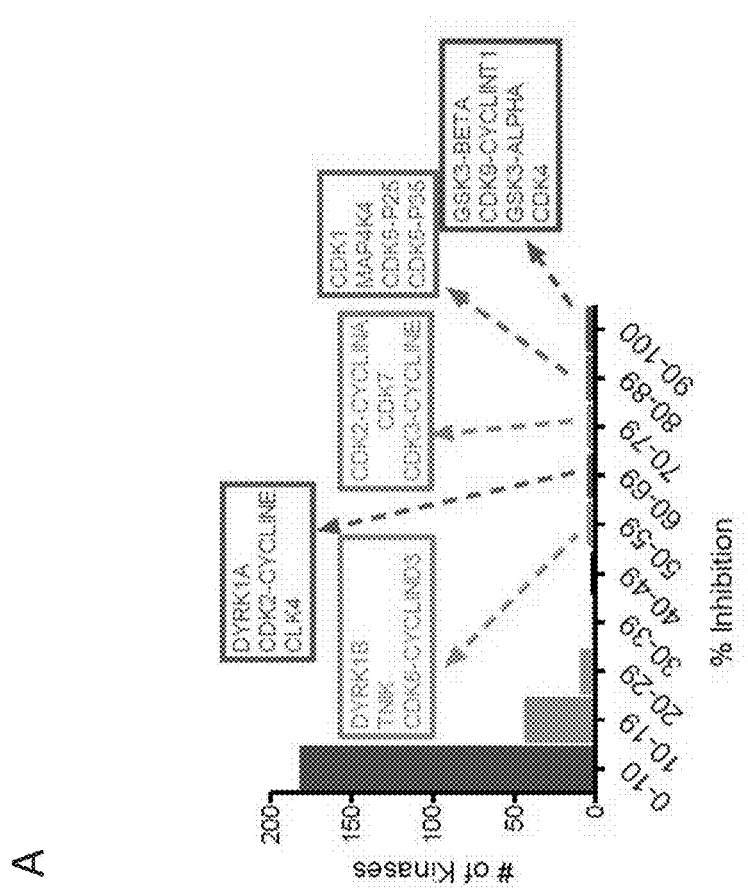
Figure 20A-B

A

| MC180295 | IC50 (nM) |
|---|---|
| CDK1-Cyclin B | 138 |
| CDK2-Cyclin A | 233 |
| CDK2-Cyclin E | 367 |
| CDK3-Cyclin E | 399 |
| CDK4-Cyclin D | 112 |
| CDK5-P35 | 159 |
| CDK5-P25 | 186 |
| CDK6-Cyclin D3 | 712 |
| CDK7-CycH/MAT1 | 555 |
| CDK9-Cyclin T1 | 5 |

A
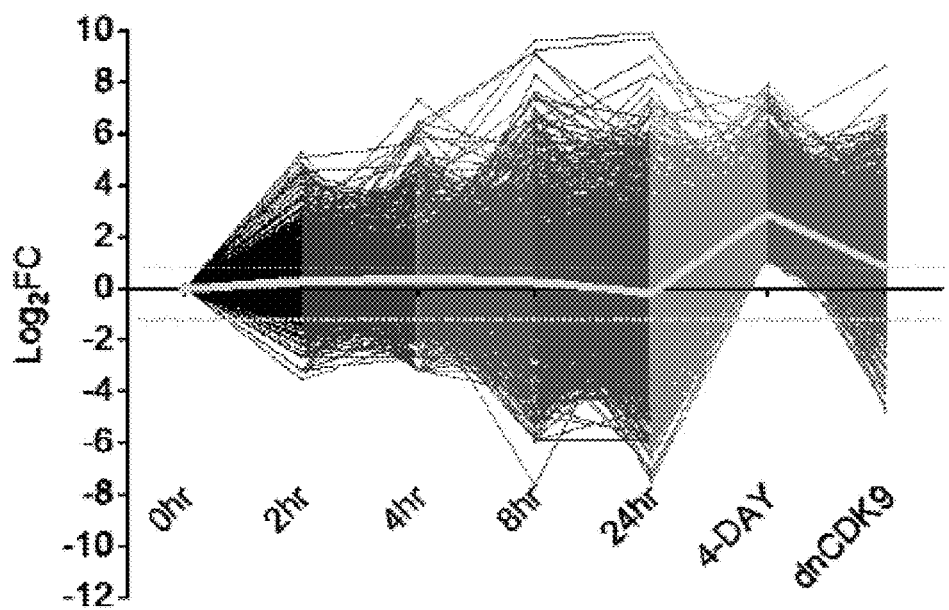
B
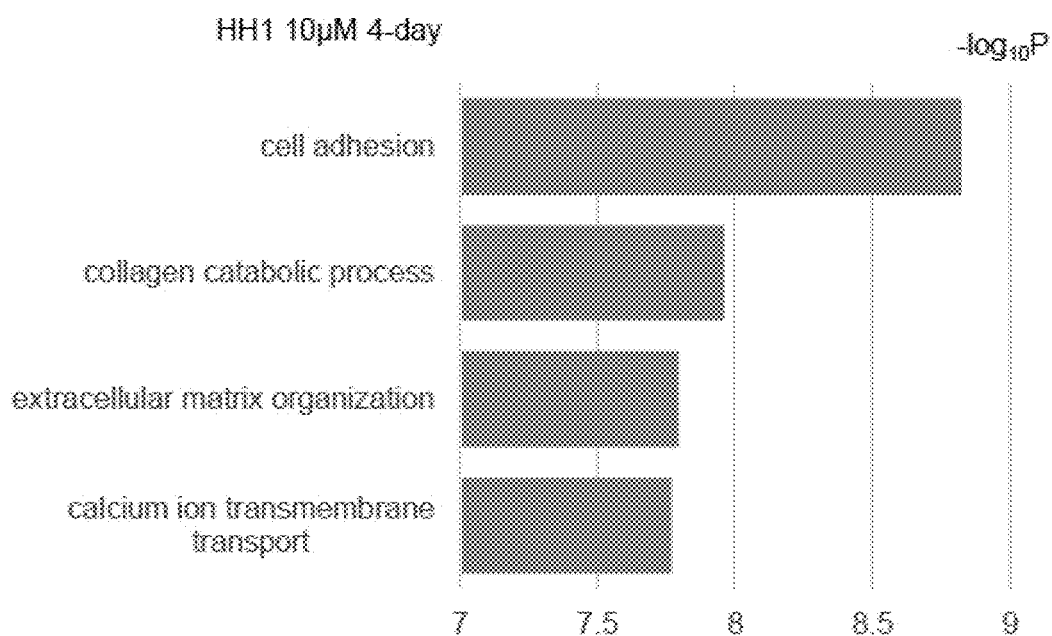
Figure 35A-B

HH1 10µM 4-day

| Upstream Regulator | Predicted Activation State | Activation z-score | p-value of overlap |
|---|---|---|---|
| tretinoin | Activated | 6.42 | 4.82E-04 |
| decitabine | Activated | 6.37 | 3.44E-04 |
| SMARCA4 | Activated | 6.15 | 1.14E-03 |
| IFNG | Activated | 4.93 | 7.31E-03 |
| CBX5 | Inhibited | -3.86 | 1.67E-02 |

Figure 39

| Upstream Regulator | Predicted Activation State | Activation z-score | p-value of overlap |
|---|---|---|---|
| tretinoin | Activated | 6.53 | 5.31E-04 |
| SMARCA4 | Activated | 5.72 | 2.60E-03 |
| IL4 | Activated | 4.04 | 1.09E-02 |
| decitabine | Activated | 3.64 | 8.01E-03 |
| IRF7 | Activated | 3.52 | 1.92E-02 |
| TLR7 | Activated | 3.38 | 1.76E-02 |
| IFNG | Activated | 3.35 | 3.58E-02 |
| CBX5 | Inhibited | -3.32 | 9.34E-03 |

Figure 41

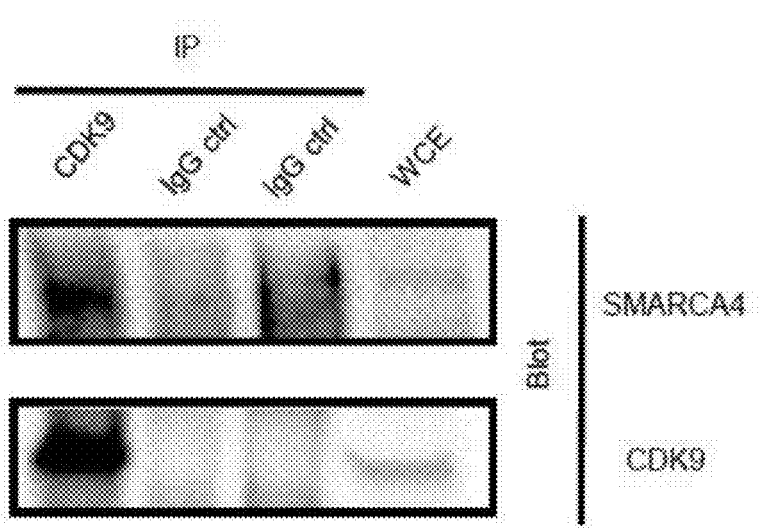
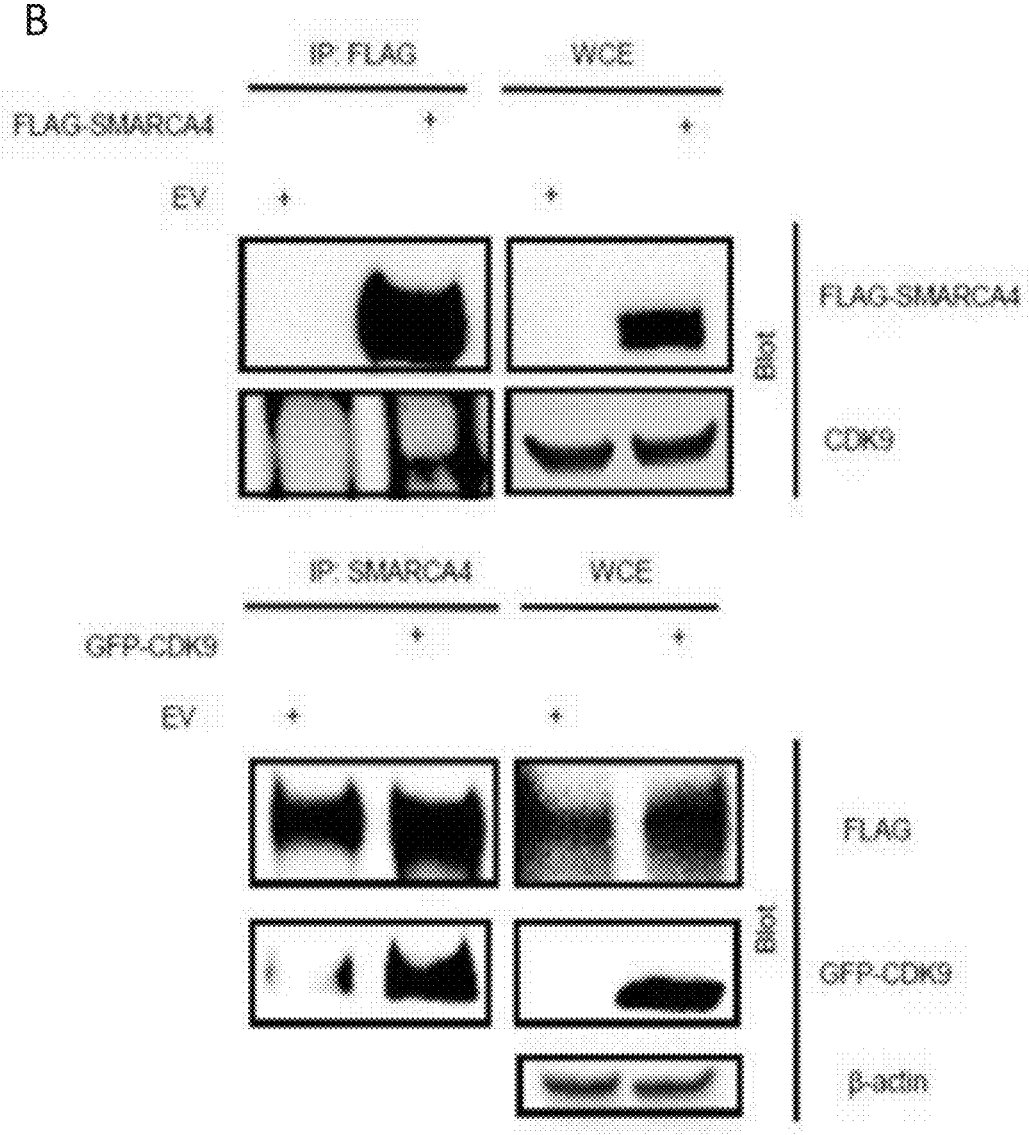
Figure 43A-B

A
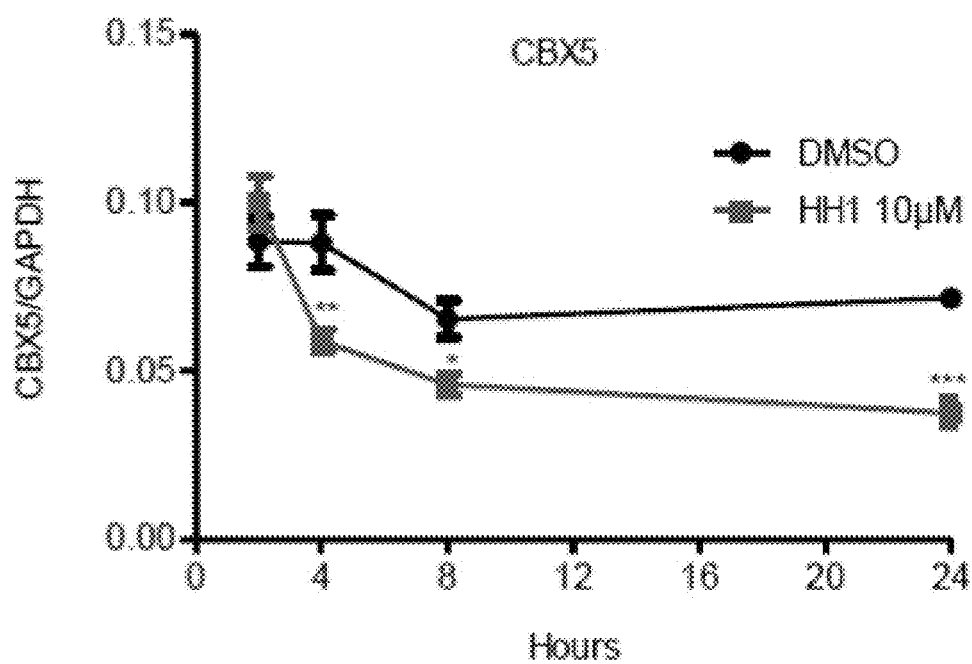
B
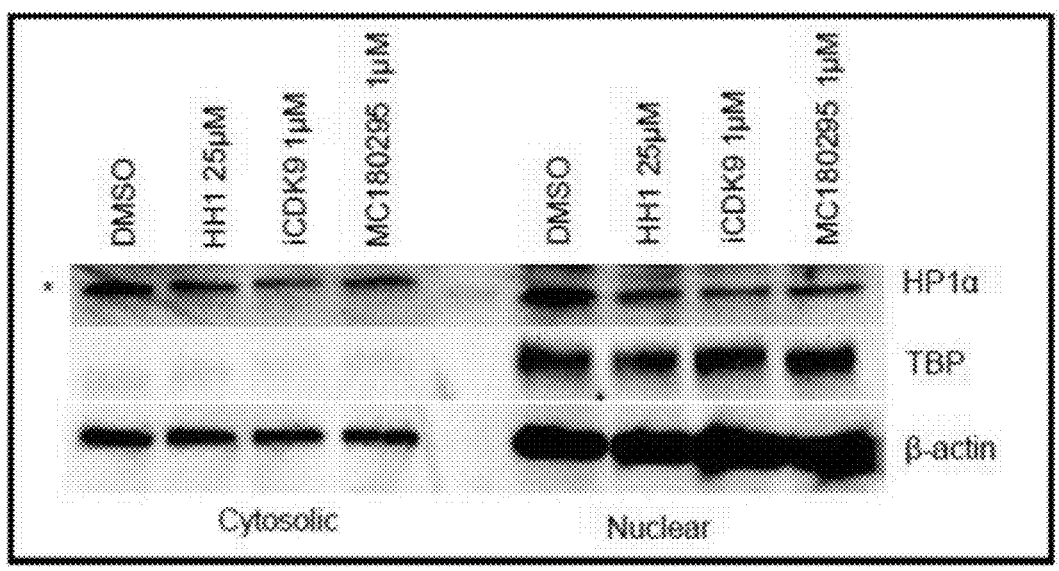
Figure 46A-B

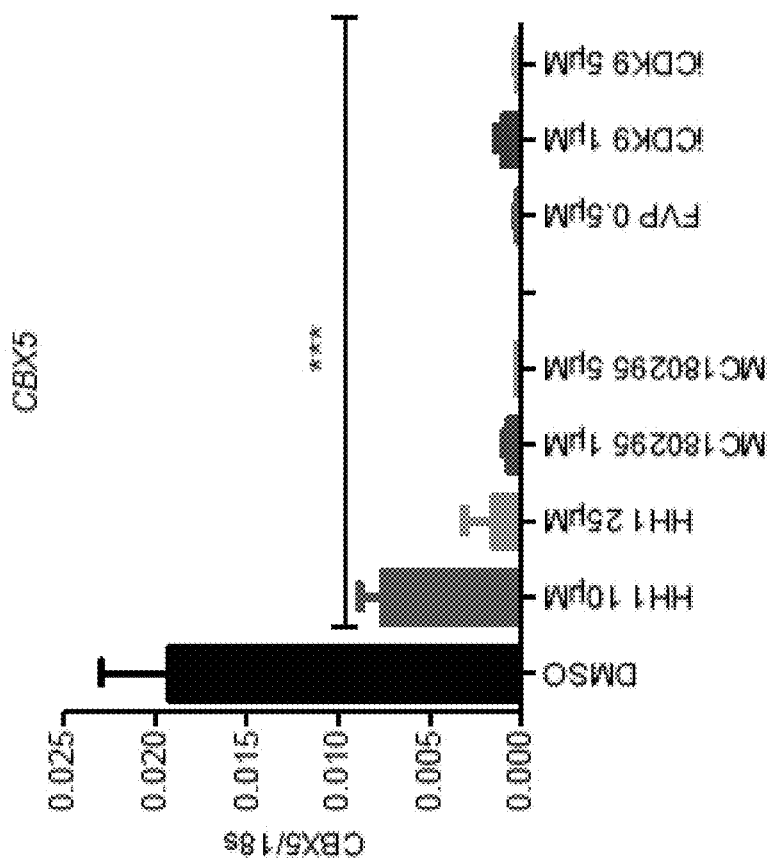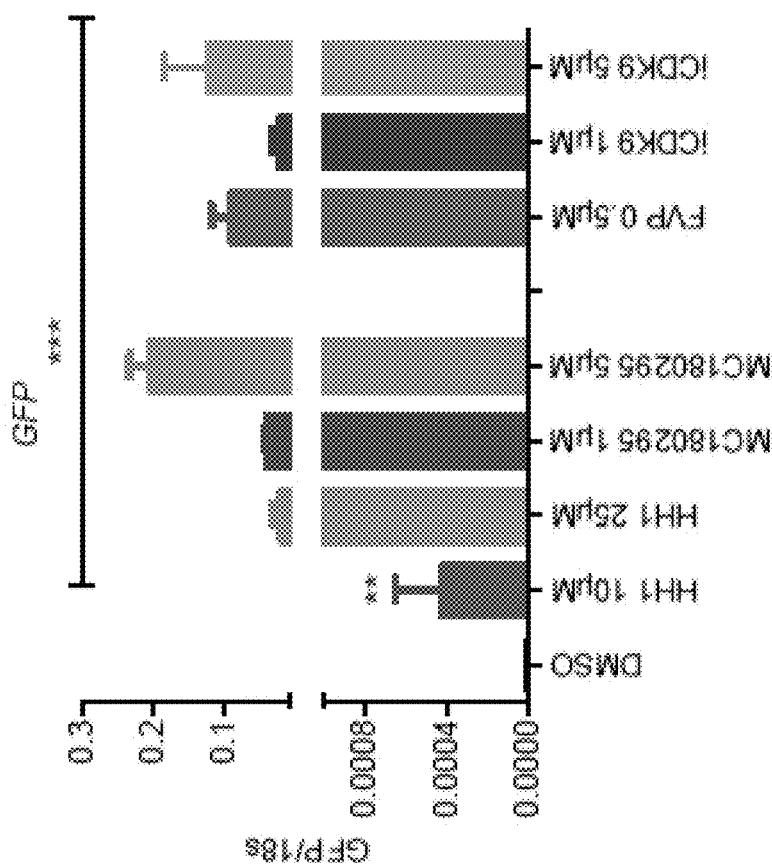
Figure 47

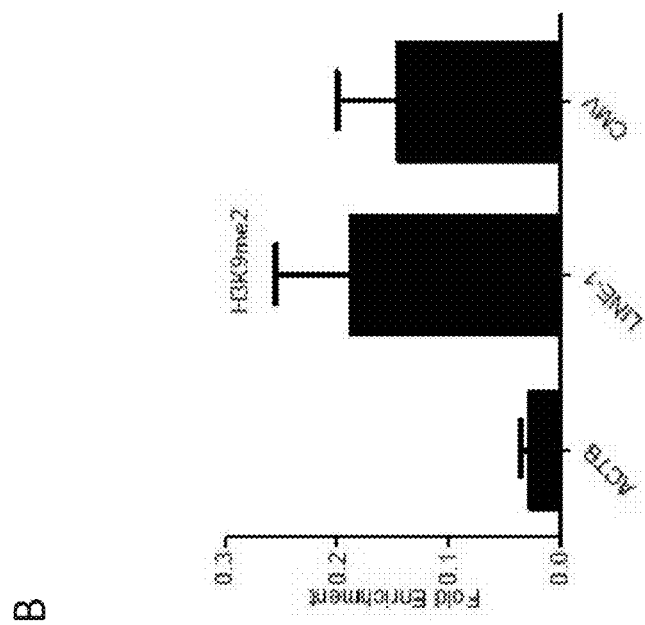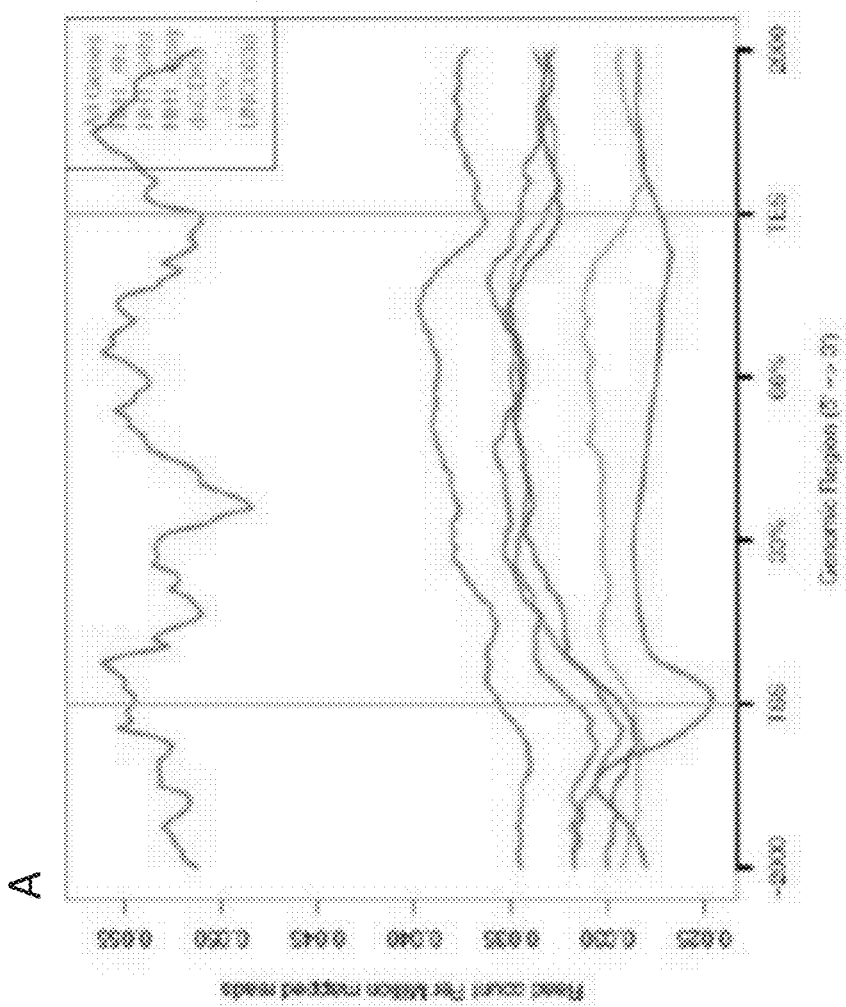
Figure 51A-B

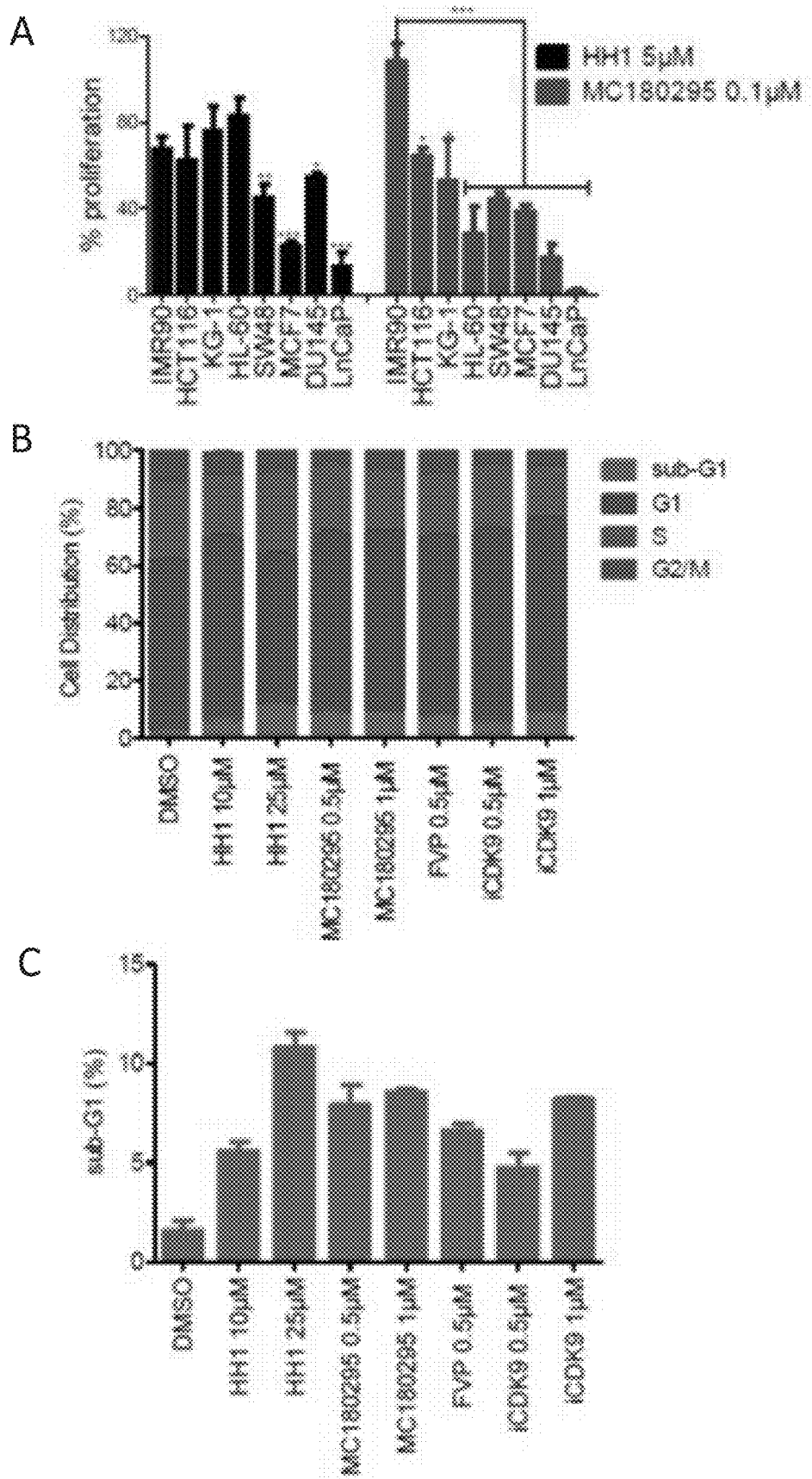
Figure 52A-C

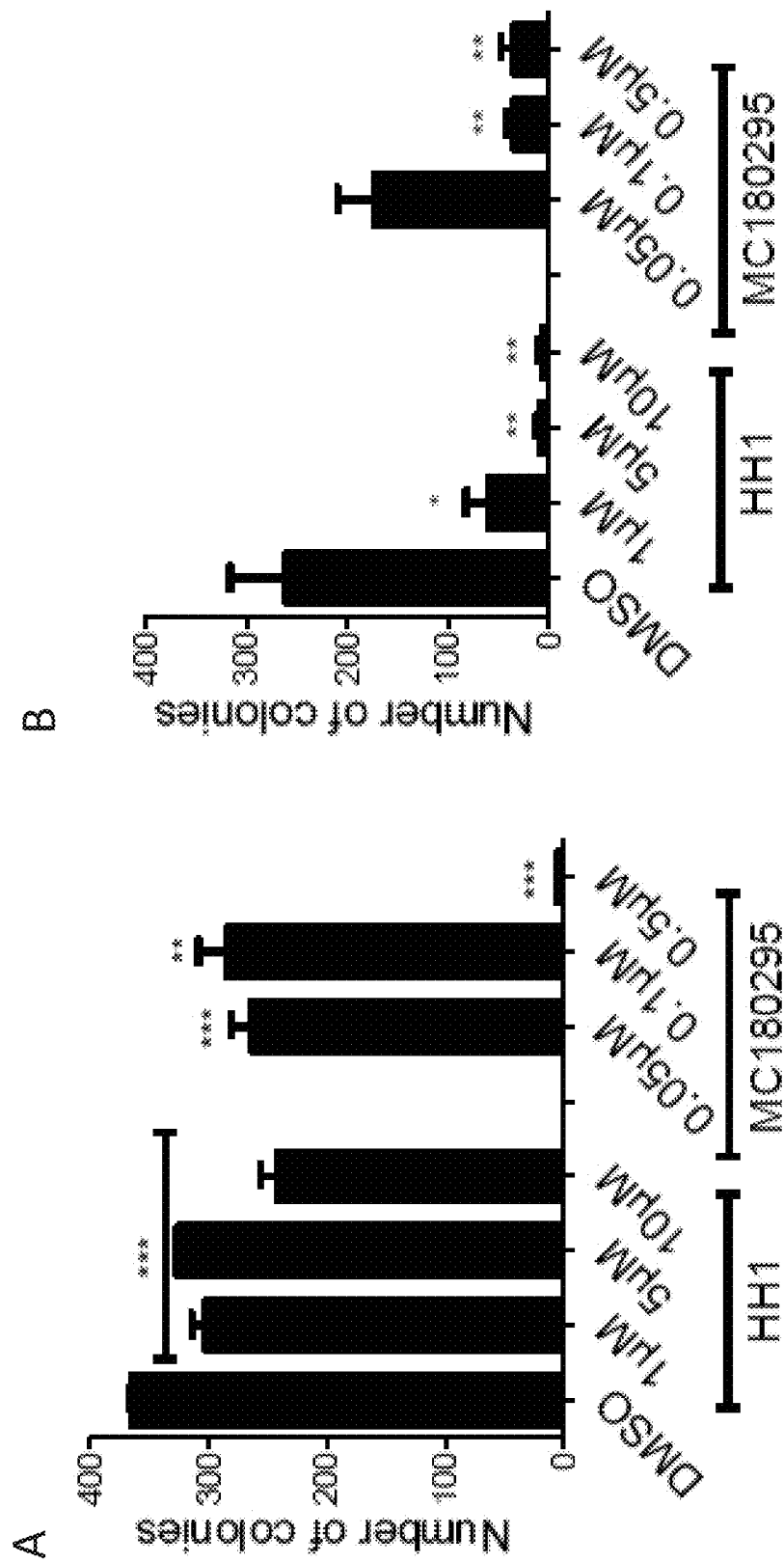
Figure 53A-B

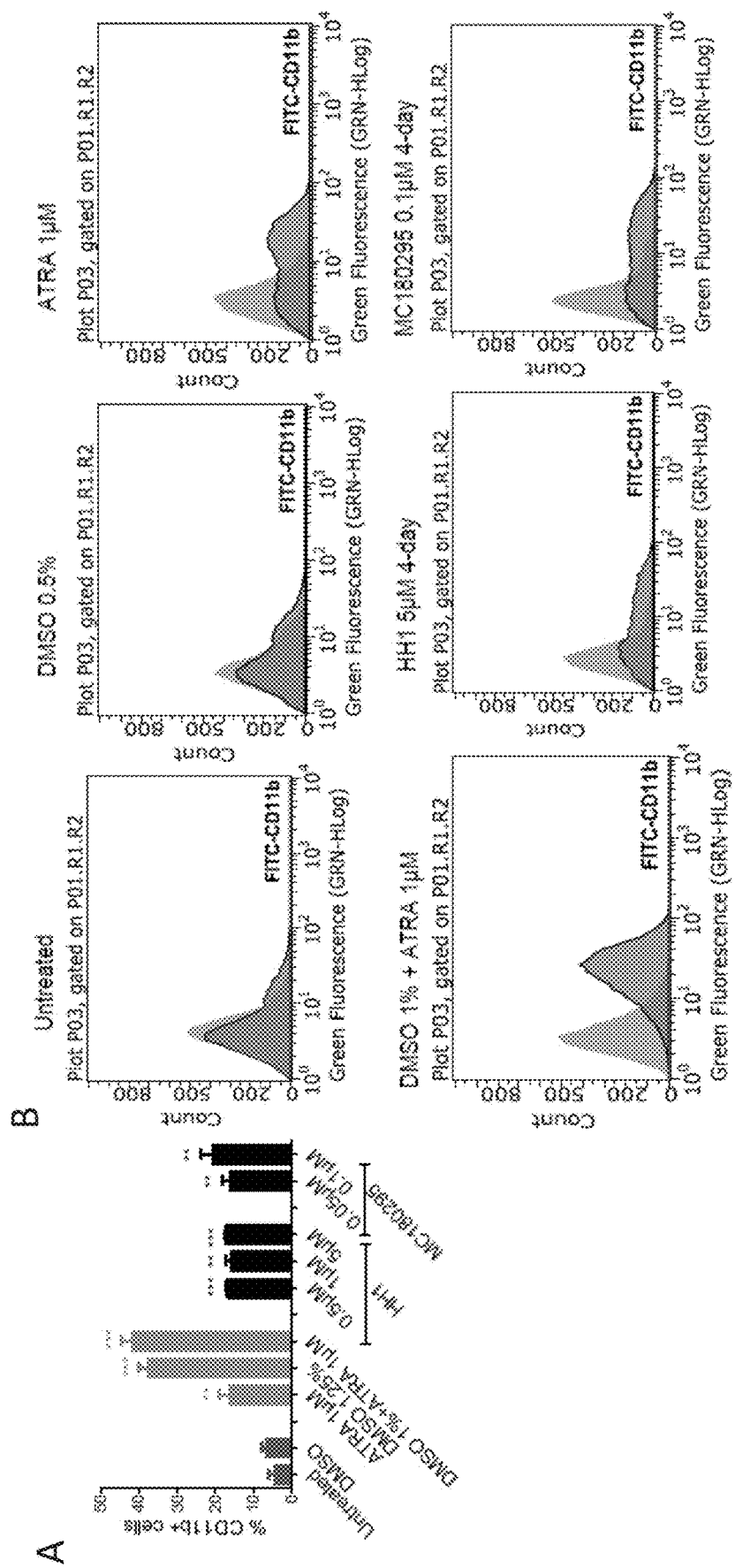
Figure 54A-B

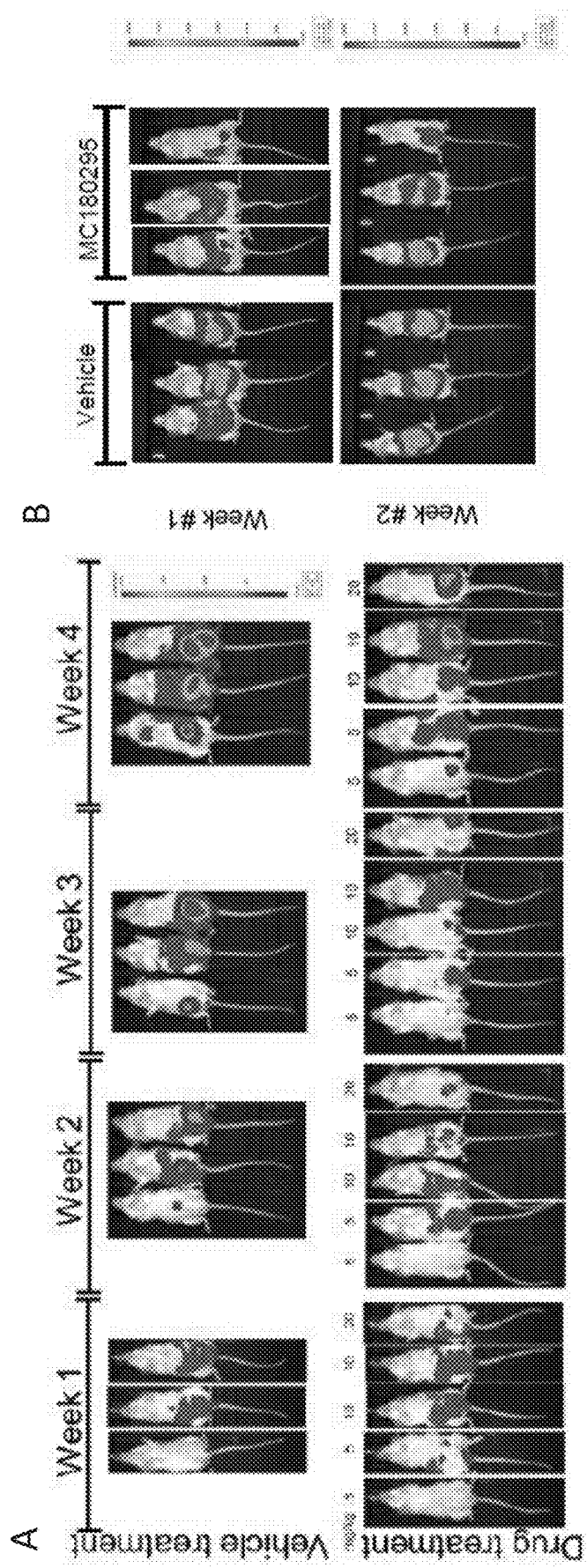
Figure 55A-B

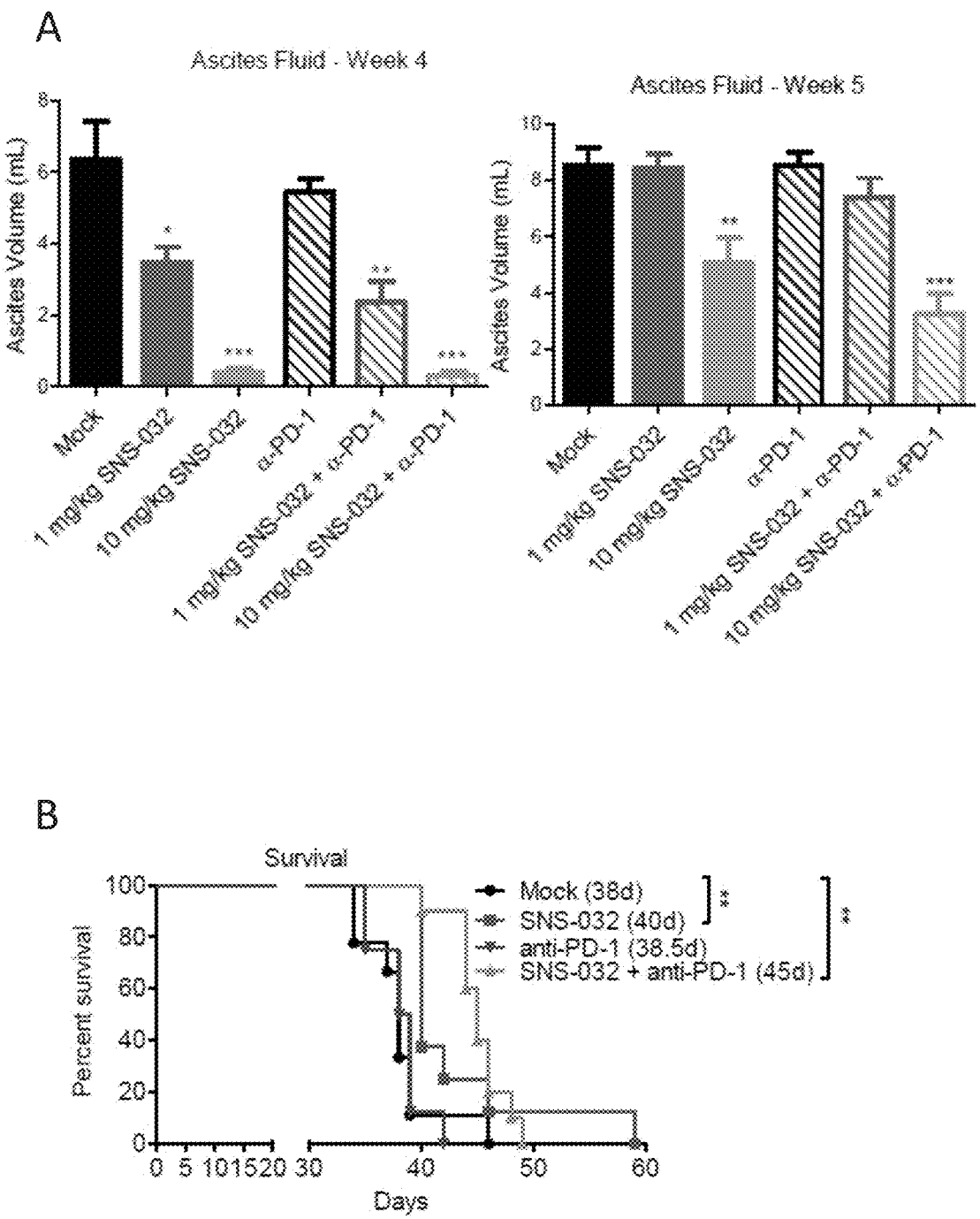
Figure 56A-B

| Drug | CDK9 | CDK1 | CDK2 | CDK4 | CDK6 | Clinical data |
|---|---|---|---|---|---|---|
| MC180295 | 5 | 138 | 367 | 112 | 712 | ND |
| Dinaciclib | 4 | 3 | 1 | 100 | ND | Toxic |
| Abemaciclib | 57 | >1000 | >500 | 2 | 5 | FDA approved breast cancer |
| Palbociclib | ND | >1000 | >1000 | 9-11 | 15 | |
| Ribociclib | ND | >1000 | >1000 | 10 | 39 | |
| SNS-032 | 4 | 480 | 38 | 925 | >1000 | Safe; minimally tested. One response in CLL |
| Flavopiridol | 7 | 50 | 70 | 100 | 80 | Active in AML and CLL but toxic |

Figure 66

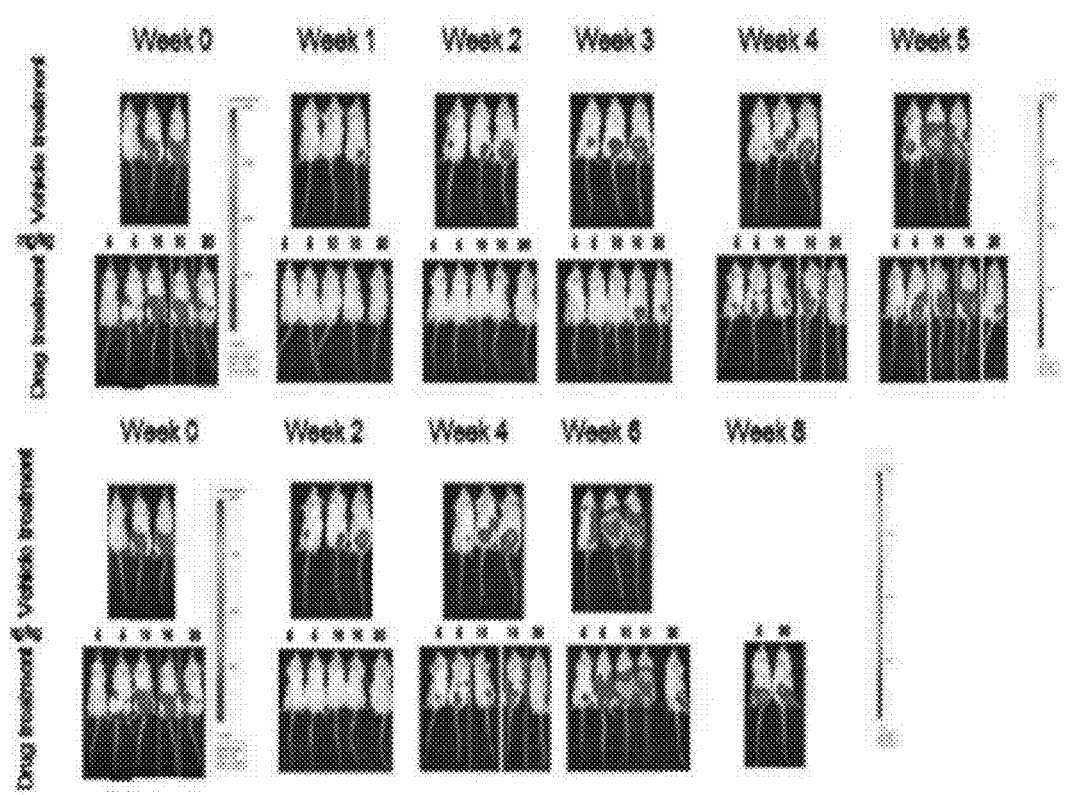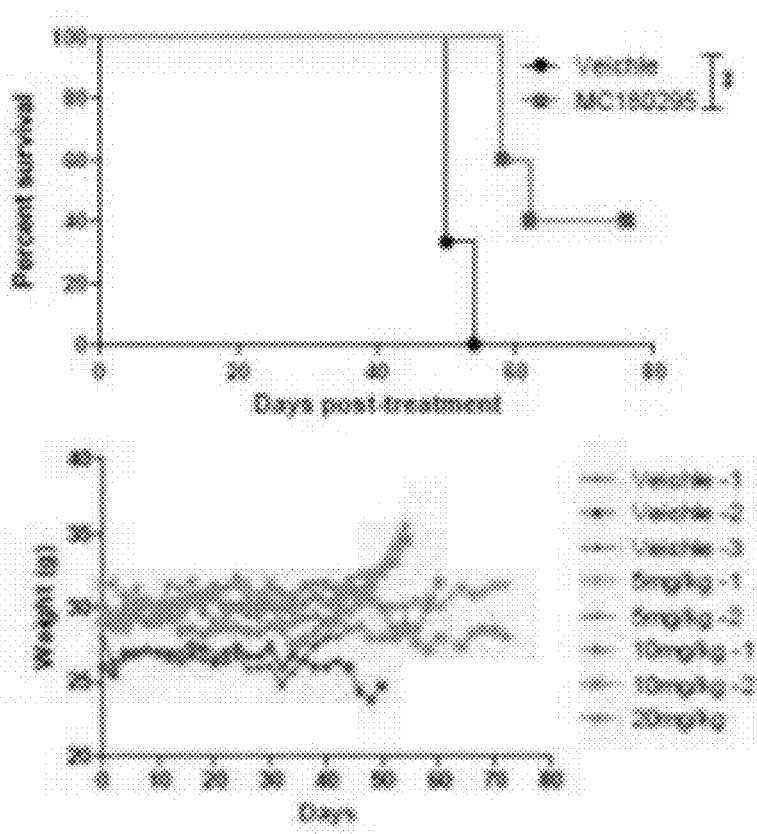
Figure 67

| | MC-180295 | MC-180349 | MC-180343 |
|---|---|---|---|
| logP, TPSA | 4.15, 111 | 2.95, 107 | 4.0, 92 |
| Solubility, PBS (pH 7.4) | 50 uM | 76 uM | ND |
| Microsomal Stability, t1/2 (min) | | | |
| Mouse | 5 | TBD | ND |
| Human | 20 | TBD | ND |
| hERG Inhibition (10 uM) | 0% | 0% | ND |
| PDSP | submitted | submitted | ND |
| MDCK-MR1 | In progress | In progress | ND |
| Plasma Protein Binding, Microsomal Partitioning | In progress | In progress | ND |

Figure 71

| | 415.11 |
|---|---|
| logP, TPSA | |
| Solubility PBS (pH 7.4) | 2 uM |
| Microsomal Stability, t1/2 (min) | |
| Mouse | >60 |
| Human | >60 |
| hERG Inhibition (10 uM) | ND |
| PDSP | ND |
| MDCK-MR1 | ND |
| Plasma Protein Binding, Microsomal Partitioning | In progress |

```
                       SEQUENCE LISTING

<160> NUMBER OF SEQ ID NOS: 16

<210> SEQ ID NO 1
<211> LENGTH: 21
<212> TYPE: RNA
<213> ORGANISM: Artificial sequence
<220> FEATURE:
<223> OTHER INFORMATION: chemically synthesized

<400> SEQUENCE: 1
ggauugcccu gagcuaauuu u                                         21

<210> SEQ ID NO 2
<211> LENGTH: 6
<212> TYPE: DNA
<213> ORGANISM: Artificial sequence
<220> FEATURE:
<223> OTHER INFORMATION: chemically synthesized

<400> SEQUENCE: 2 cccggg                                                           6

<210> SEQ ID NO 3
<211> LENGTH: 23
<212> TYPE: PRT
<213> ORGANISM: Artificial sequence
<220> FEATURE:
<223> OTHER INFORMATION: chemically synthesized

<400> SEQUENCE: 3

Lys Ile Pro Asp Pro Asp Ser Asp Asp Val Ser Glu Val Asp Ala Arg
1               5                   10                  15

His Ile Ile Glu Asn Ala Lys
            20

<210> SEQ ID NO 4
<211> LENGTH: 20
<212> TYPE: PRT
<213> ORGANISM: Artificial sequence
<220> FEATURE:
<223> OTHER INFORMATION: chemically synthesized

<400> SEQUENCE: 4

Tyr Lys Asp Ser Ser Ser Gly Arg Gln Leu Ser Glu Val Phe Ile Gln
```

Leu Pro Ser Arg
        20

<210> SEQ ID NO 5
<211> LENGTH: 23
<212> TYPE: DNA
<213> ORGANISM: Artificial sequence
<220> FEATURE:
<223> OTHER INFORMATION: chemically synthesized

<400> SEQUENCE: 5
gaattcagtg ccactaagca gac                                          23

<210> SEQ ID NO 6
<211> LENGTH: 23
<212> TYPE: DNA
<213> ORGANISM: Artificial sequence
<220> FEATURE:
<223> OTHER INFORMATION: chemically synthesized

<400> SEQUENCE: 6
tcggtatatc caagacatga tcc                                          23

<210> SEQ ID NO 7
<211> LENGTH: 24
<212> TYPE: DNA
<213> ORGANISM: Artificial sequence
<220> FEATURE:
<223> OTHER INFORMATION: chemically synthesized

<400> SEQUENCE: 7
atatccctca ccacgatcct aata                                         24

<210> SEQ ID NO 8
<211> LENGTH: 24
<212> TYPE: DNA
<213> ORGANISM: Artificial sequence
<220> FEATURE:
<223> OTHER INFORMATION: chemically synthesized

<400> SEQUENCE: 8
ccctctgtag tgcaaagact gata                                         24

<210> SEQ ID NO 9
<211> LENGTH: 23
<212> TYPE: DNA
<213> ORGANISM: Artificial sequence
<220> FEATURE:
<223> OTHER INFORMATION: chemically synthesized

<400> SEQUENCE: 9
tcttggagtc ctcactcaaa ctc                                          23

<210> SEQ ID NO 10
<211> LENGTH: 23
<212> TYPE: DNA
<213> ORGANISM: Artificial sequence
<220> FEATURE:
<223> OTHER INFORMATION: chemically synthesized

<400> SEQUENCE: 10
actgctgcaa ctacccttaa aca                                          23

<210> SEQ ID NO 11

<211> LENGTH: 23
<212> TYPE: DNA
<213> ORGANISM: Artificial sequence
<220> FEATURE:
<223> OTHER INFORMATION: chemically synthesized

<400> SEQUENCE: 11
caggaaacta actttcagcc aga                                              23

<210> SEQ ID NO 12
<211> LENGTH: 23
<212> TYPE: DNA
<213> ORGANISM: Artificial sequence
<220> FEATURE:
<223> OTHER INFORMATION: chemically synthesized

<400> SEQUENCE: 12
taaagagggc atggagtaat tga                                              23

<210> SEQ ID NO 13
<211> LENGTH: 20
<212> TYPE: DNA
<213> ORGANISM: Artificial sequence
<220> FEATURE:
<223> OTHER INFORMATION: chemically synthesized

<400> SEQUENCE: 13
tctcacaatc ctggaggctg                                                  20

<210> SEQ ID NO 14
<211> LENGTH: 20
<212> TYPE: DNA
<213> ORGANISM: Artificial sequence
<220> FEATURE:
<223> OTHER INFORMATION: chemically synthesized

<400> SEQUENCE: 14
gaccaagaag caagccctca                                                  20

<210> SEQ ID NO 15
<211> LENGTH: 19
<212> TYPE: DNA
<213> ORGANISM: Artificial sequence
<220> FEATURE:
<223> OTHER INFORMATION: chemically synthesized

<400> SEQUENCE: 15
cagacagaca ctggcaaca                                                   19

<210> SEQ ID NO 16
<211> LENGTH: 19
<212> TYPE: DNA
<213> ORGANISM: Artificial sequence
<220> FEATURE:
<223> OTHER INFORMATION: chemically synthesized

<400> SEQUENCE: 16
acatctcccc cttctcctt                                                   19

BRIDGED BICYCLOALKYL-SUBSTITUTED AMINOTHIAZOLES AND THEIR METHODS OF USE

CROSS-REFERENCE TO RELATED APPLICATIONS

This application is the U.S. national stage application filed under 35 § U.S.C. 371 claiming benefit to International Patent Application No. PCT/US2018/014465, filed Jan. 19, 2018, which is entitled to priority under 35 U.S.C. § 119(e) to U.S. Provisional Patent Application No. 62/448,051, filed Jan. 19, 2017, each of which applications are incorporated by reference herein in their entireties.

STATEMENT REGARDING FEDERALLY SPONSORED RESEARCH OR DEVELOPMENT

This invention was made with U.S. government support under Grant Nos. CA100632, CA158112, and GM110174, awarded by the National Institutes of Health, and Grant Nos. MCB130049 and ACI-154856, awarded by the National Science Foundation. The U.S. government has certain rights in the invention.

BACKGROUND OF THE INVENTION

In cancer, the epigenome is aberrantly reprogrammed leading to a wide range of heritable changes in gene expression such as silencing of tumor suppressor genes (TSG) (Kelly et al., 2010, Nat. Biotechnol. 28:1069-1078). The most studied epigenetic aberrations in cancer involve DNA methylation and histone post-translational modifications. Acquisition of de novo methylation in cytosine of CpG dinucleotide at the promoter region of TSG results in stable gene silencing through direct inhibition of transcription factor binding or by recruitment of methyl-binding domain (MBD) proteins such as MeCP2 (Kelly et al., 2010, Nat. Biotechnol. 28:1069-1078; Taby and Issa, 2010, CA Cancer J. Clin. 60:376-392). These MBDs are associated with other repressor complexes including histone deacetylases (HDAC) that are responsible for global loss of histone acetylation resulting in gene silencing and heterochromatin formation (Taby and Issa, 2010, CA Cancer J. Clin. 60:376-392).

Since these epigenetic modifications are reversible, one goal of epigenetic therapy of cancer is to reverse these alterations and induce TSG reactivation leading to cancer cell differentiation and cancer cell death (Baylin and Jones, 2011, Nat. Rev. Cancer 11:726-734). Clinical trials with epigenetic cancer drugs have led to the approval of two DNA methylation inhibitors (decitabine and azacitidine) and several histone deacetylase inhibitors (vorinostat, panobinostat, belinostat, chidamide and romidepsin (also known as depsipeptide). These drugs are primarily approved for treatment of hematological malignancies and occasional proof-of-principal responses can be seen in solid tumors (Taby and Issa, 2010, CA Cancer J. Clin. 60:376-392; Juergens et al., 2011, Cancer Discov. 1:598-607). However, there is a significant need to discover new epigenetic cancer drugs that act through different mechanisms.

Cyclin-dependent kinases (CDKs) play a major role in cancer (Canavese et al., 2010, Cancer Biol. Ther. 13:451-457). Cyclin-dependent kinases are specific serine-threonine kinases that play an essential role in cell cycle regulation, allowing transition between phases. Many of the genes involved in cell cycle progression are frequently mutated in human cancers leading to uncontrolled cell division and tumor growth. Furthermore, several components of the CDK system are deregulated in different malignancies (Ortega et al., 2002, Biochim. Biophys. Acta 1602:73-87). Thus, CDK inhibitors represent a target for cancer drug discovery.

Cyclin-dependent kinases (CDKs) come in two broad classes—regulators of the cell cycle (e.g. CDK1, 2, 4, 6, 7) and regulators of transcription (e.g. CDK7, 8, 9, 10-13). It is well established that CDK9, the catalytic subunit of P-TEFb, is a transcriptional activator. CDK9 in complex with its regulatory subunit, Cyclin T1 or T2, is recruited by multiple mechanisms to promote RNAPII promoter-proximal pause release by phosphorylating negative elongation factors (DSIF and NELF) (Adelman and Lis, 2012; Garriga and Graña, 2004). In addition, phosphorylation of the C-terminal domain (CTD) of RNAPII on Serine-2 allows recruitment of RNA processing factors, which work on the nascent RNA as it emerges from RNAPII. P-TEFb promotes transcriptional elongation of several signal-responsive genes that regulate proliferation, development, stress and/or damage responses (Adelman and Lis, 2012; Garriga and Graña, 2004), such as MYC (Rahl et al., 2010), NFkB (Barboric et al., 2001) and Mcl-1 (MacCallum et al., 2005). Several CDK9 inhibitors have been developed and tested in MYC-driven pre-clinical models (Gregory et al., 2015; Huang et al., 2014) and clinical trials (Asghar et al., 2015) with promising activity in hematologic malignancies but also substantial chemotherapy-like toxicity. However, most of these actually inhibit multiple CDKs and it is possible that the toxicity is due to targeting CDKs other than CDK9 (Asghar et al., 2015).

The mammalian genome has 12 loci encoding CDKs. Cyclins, so named because their activity cycles up and down during the cell cycle, restrict the action of their bound kinases to particular substrates. There are multiple families of cyclins which are active during particular phases of the cell cycle. These families bind to CDKs during particular cell cycle phases, controlling their actions. There are 6 known CDKs (CDK1-CDK6) that participate in the progression from one phase of the cell cycle to another. CDK-1, CDK-2 and three additional CDKs (CDK7-CDK9) play a role in transcription in mitosis through their phosphorylation of RNA polymerase II and the general transcription factors TFIID and TFIIH. A significant body of evidence implicates abnormalities in the CDK-cyclin D/INK4/pRb/E2F system and its impact on G1/S phase transition in various cancers, but growing evidence suggests that aberrations in the transcriptional CDKs (7-9) may also contribute to uncontrolled cell growth.

A number of CDK inhibitors have entered into clinical trials for cancer. Most of these inhibit CDKs by binding to the ATP binding site of the enzymes. Consequently, these compounds inhibit multiple CDKs. The first prototype CDK inhibitor was flavopyridol, a potent inhibitor of CDKs 2, 7 and 9. Since the discovery of flavopyridol a number of CDK inhibitors comprising multiple chemical scaffolds have been disclosed, including the aminothiazole analog SNS-032 (which is also a potent inhibitor of CDKs 2, 7 and 9). Currently there are several CDK inhibitors in Phase III clinical trials for various cancers. These include the CDK4/6 inhibitor abamaciclib and the CDK 1/4/6 inhibitor ribociclib. Palbociclib, a CDK4/6 inhibitor, also recently received FDA approval for the treatment of estrogen receptor positive and HER2 negative breast cancer.

Typically, viruses hijack the host's genome for their transcriptional activity. As a modulator of transcription, CDKs play a role in viral infections. In particular, there is evidence that CDK2-, CDK7- and CDK9-associated phosphorylations are a critical component of viral invasion and reproduction in a number of viruses, including human immunodeficiency virus-1 (HIV-1), human simplex virus (HSV), Epstein-Barr virus (EBV) and human cytomegalovirus (HCV) (Schang, 2002, J. Antimicrob. Chemother. 50:779-792). Studies with a number of CDK inhibitors have revealed that these compounds exert antiviral activity (Schang, 2002, J. Antimicrob. Chemother. 50:779-792; Holcakova et al., 2010, Adv. Chem. Chemother. 20:133-142).

Cardiac hypertrophy (a thickening of the walls of the heart, especially the ventricles) is a serious independent risk factor for cardiovascular disease (Harjai, 1999, Ann. Intern. Med. 131:376-386). Common causes of cardiac hypertrophy include hypertension, and heart valve stenosis (Selvetella and Lembo, 2005, Heart Failure Clin. 1:263-273). Only partial reversal of hypertension-associated hypertrophy can be achieved through treatment of antihypertensive drugs. Kinase pathways control normal and aberrant heart growth, including CDKs. In particular, CDK4, CDK6 and CDK9 seem to be involved in cardiac hypertrophy (Nozato et al., 2010, M. Mol. Cell Cardiol. 33:1493-1504; Busk et al., 2002, Cardiovasc. Res. 56:64-75; Krystof et al., 2010, Med. Res. Rev. 30:646-666). Therefore, inhibition of these CDKs represents a drug discovery target for preventing or treating cardiac hypertrophy.

Recent studies show that CDKs support the expression if inflammatory mediators (Schmits and Kracht, 2016, Trends Pharmacol. Sci. 37:101-113). Induced transcription of many pro-inflammatory genes is increased during the G1 phase in a CDK-dependent manner. In addition, CDKs are involved in neutrophil regulation. CDK inhibitors can reduce inflammation by inducing caspase-associated neutrophil apoptosis (Leitch et al., 2009, Brit. J. Pharmacol. 158:1004-1016). Evidence implicates CDKs 1, 2, 4, 6, 7 and 9 and their regulators in inflammatory processes. Thus, inhibitors of these CDKs would be expected to exert anti-inflammatory effects.

Epigenetic mediators of gene silencing are validated cancer targets (Jones, P. A., Issa, J. P., and Baylin, S. (2016), Nat Rev Genet 17, 630-641) and there is growing interest in their use for non-cancer conditions. The clinical efficacy of DNA methylation and histone deacetylase inhibitors led to their US FDA approval against hematological malignancies (Taby, R., and Issa, J. P. (2010), CA Cancer J Clin 60, 376-392). Resistance to these drugs commonly develops and their clinical activity in solid tumors is limited despite occasional proof-of-principle responses.

There is a need in the art to identify novel compounds which are useful for the treatment of cancer, in addition to other diseases and disorder, and do not cause deleterious side effects in the subject. The present invention fulfills this need.

BRIEF SUMMARY OF THE INVENTION

The present invention includes a compound of Formula (I):

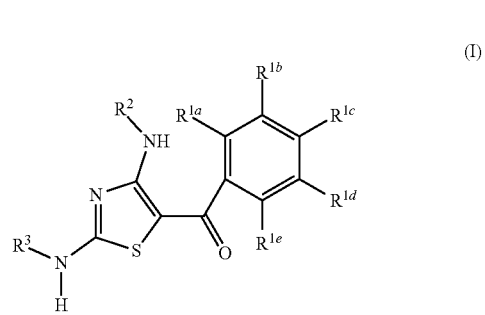

including enantiomers, diastereomers, hydrates, solvates, pharmaceutically acceptable salts, prodrugs and complexes thereof;

wherein in Formula (I):

$R^{1a}$, $R^{1b}$, $R^{1c}$, $R^{1d}$ and $R^{1e}$ are each independently selected from the group consisting of hydrogen, halogen, hydroxyl, $C_{1-6}$ linear alkyl, $C_{3-6}$ branched alkyl, $C_{3-6}$ cycloalkyl, $C_{1-6}$ haloalkyl, $C_{1-6}$ linear alkoxy, $C_{3-6}$ branched alkoxy, $C_{1-6}$ haloalkoxy, thiol, $C_{1-6}$ linear thioalkyl, $C_{3-6}$ branched thioalkyl, cyano, nitro, and $NR^4R^5$, or two adjacent $R^1$ groups are joined to form a 5- to 7-membered heterocyclic ring containing 1 to 3 heteroatoms, $R^2$ is selected from the group consisting of hydrogen, $C_{1-6}$ linear alkyl, $C_{3-7}$ branched alkyl, $C_{3-7}$ cycloalkyl and $COR^6$;

$R^3$ is a bridged bicycloalkyl moiety selected from the group of consisting of:

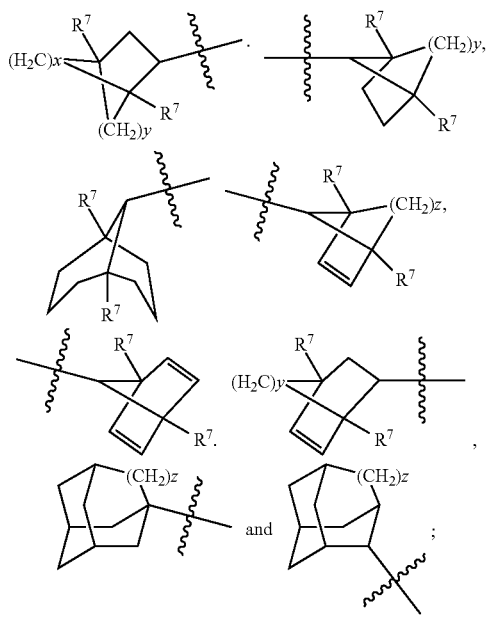

$R^4$ and $R^5$ are each independently selected from the group consisting of hydrogen, $C_{1-6}$ linear alkyl, and $C_{3-7}$ branched alkyl, or $R^4$ and $R^5$ are joined to form a 3- to 7-membered heterocycloalkyl ring;

$R^6$ is selected from the group consisting of hydrogen, $C_{1-6}$ linear alkyl, $C_{3-7}$ branched alkyl, $C_{1-6}$ linear alkoxy, $C_{3-7}$ branched alkoxy and $C_{3-7}$ cycloalkyl;

$R^7$ at each occurrence is independently selected from the group consisting of hydrogen or methyl;

x is 1, 2, or 3;

y is 1, 2, or 3; and z is 1, 2, or 3;

with the proviso that when the compound of Formula (I) is:

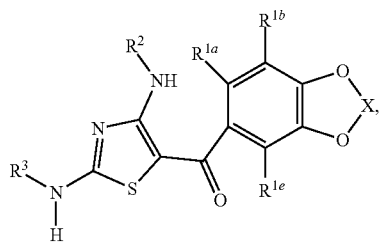

then X cannot be

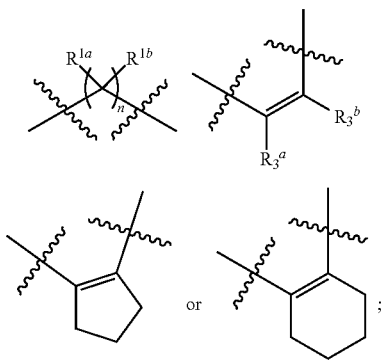

wherein:

$R^{1a}$ and $R^{1b}$ are at each occurrence independently selected from the group consisting of hydrogen, $C_{1-4}$ linear alkyl, and $C_{3-6}$ branched alkyl, or $R^{1a}$ and $R^{1b}$ are taken together with the atoms to which they are bound to form a three to six membered carbocyclic ring, or two $R^{1a}$ units on adjacent carbon atoms are taken together with the atoms to which they are bound to form a three to six membered carbocyclic ring;

$R^{3a}$ and $R^{3b}$ are each independently selected from the group consisting of hydrogen, $C_{1-4}$ linear alkyl, and $C_{3-6}$ branched alkyl.

In one embodiment, the compound of Formula (I) is a compound selected from the group consisting of:

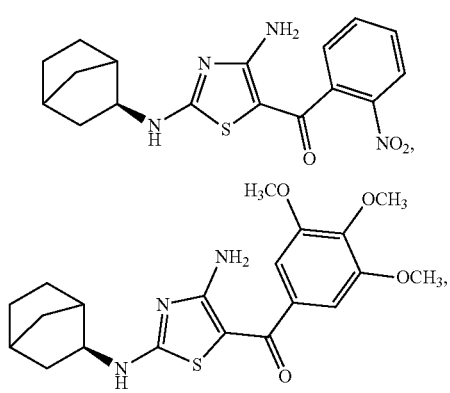

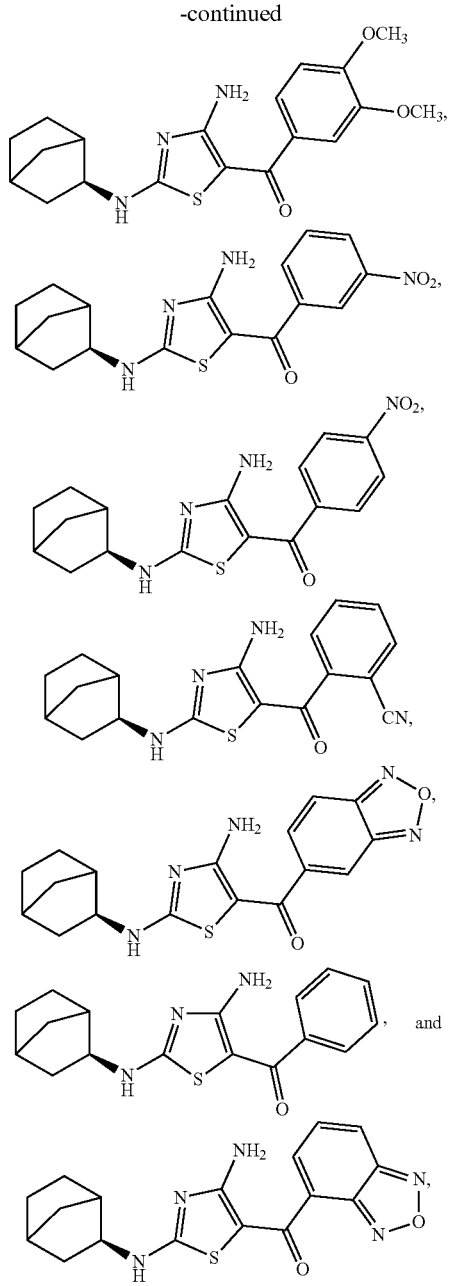

a salt or solvate thereof, and any combinations thereof.

The present invention also includes a composition comprising a compound of Formula (I). In one embodiment, the composition further comprises a pharmaceutically acceptable carrier. In another embodiment, the composition further comprises an additional therapeutic agent.

The present invention also includes a method of preventing or treating cancer in a subject in need thereof. In one embodiment, the method includes administering to the subject a therapeutically effective amount of a composition comprising at least one compound of Formula (I). In one embodiment, the cancer is selected from the group consisting of the cancer is selected from the group consisting of lung cancer, colon cancer, melanoma, breast cancer, ovarian cancer, prostate cancer, liver cancer, pancreatic cancer, a CNS tumor, neuroblastoma, leukemia, bone cancer, intestinal cancer, lymphoma, bladder cancer, sarcoma, bile duct cancer, stomach cancer, cervical cancer, testicular cancer, uterine cancer, gall bladder cancer, fallopian tube cancer, nasopharyngeal cancer, hypopharyngeal cancer, renal cancer, oral cavity cancer, head and neck cancer, thyroid cancer, parathyroid cancer, pituitary cancer, rectal cancer, retinoblastoma, Wilm's tumor, vaginal cancer, penile cancer, and combinations thereof. In another embodiment, the method further comprises administering to the subject at least one additional therapeutic agent. In another embodiment, the therapeutic agent is a chemotherapeutic agent. In another embodiment, the therapeutic agent is a Bcl-2 inhibitor selected from the group consisting of ABT-199, ABT-263, ABT-737, G3139 (genasense or oblimersen), GX15-070 (obatoclax mesylate), HA14-1, TW-37, sabutoclax, Gossypol (AT-101), antimycin A, apogossypol, and S44563. In another embodiment, the composition and the additional therapeutic agent are co-administered. In another embodiment, the composition and the additional therapeutic agent are co-formulated.

The present invention also includes a method of preventing or treating an inflammatory condition in a subject in need thereof. In one embodiment, the method includes administering to the subject a therapeutically effective amount of a composition comprising at least one compound of Formula (I).

The present invention also includes a method of preventing or treating cardiac dysfunction or cardiovascular disease in a subject in need thereof. In one embodiment, the method includes administering to the subject a therapeutically effective amount of a composition comprising at least one compound of Formula (I). In one embodiment, the cardiac dysfunction or cardiovascular disease is cardiac hypertrophy.

The present invention also includes a method of preventing or treating a viral infection in a subject in need thereof. In one embodiment, the method includes administering to the subject a therapeutically effective amount of a composition comprising at least one compound of Formula (I). In one embodiment, the viral infection is selected from the group consisting of human immunodeficiency virus (HIV) and herpes simplex virus (HSV).

The present invention also includes a method of treating or preventing a CDK9-mediated disorder in a subject in need thereof. In one embodiment, the method includes administering to the subject a therapeutically effective amount of a composition comprising at least one compound of Formula (I).

The present invention also includes a method of modulating the immune system in a subject in need thereof. In one embodiment, the method includes administering to the subject a therapeutically effective amount of a composition comprising at least one compound of Formula (I).

The present invention also includes a method of sensitizing cancer cells in a subject in need thereof. In one embodiment, the method includes administering to the subject a therapeutically effective amount of a composition comprising at least one compound of Formula (I). In one embodiment, the method further comprises administering to the subject a therapeutically effective amount of an immune-targeted drug. In one embodiment, wherein the immune-targeted drug is an inhibitor of PD-1 or PD-L1.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 4A-C, depicts structure and data on HH0, a representative aminothiazole compound. FIG. 4A depicts dose-dependent re-expression of GFP after 24 hr treatment of YB5 cells with HH0 (structure at the top). Depsipeptide (Depsi), an HDACi, was used as a positive control. Data are shown as mean±SD, n=3. Upper panels: representative pictures by fluorescent microscopy of YB5 cells treated with DMSO (left) and HH0 at 10 µM for 24 hours (right). *p<0.05, p<0.01, *p<0.001 (Student's t-test). FIG. 4C depicts FACS analysis of YB5 treated with DMSO (negative control), 5 µM TSA (positive control) and 10 µM HH0 for 24 hours. On the FACS scatter plot, the x-axis and the y-axis represent GFP and propidium iodide (PI) fluorescence, respectively.

FIG. 13 depicts the IC50s of three potent CDK inhibitors against different CDKs.

FIG. 14, comprising FIG. 14A depicts experimental data demonstrating the reactivation of GFP and endogenous hypermethylated genes upon dominant-negative CDK9 (dnCDK9) overexpression (72 hr). *p<0.05, p<0.01, *p<0.001 (Student's t-test). Data are shown as mean+SD, n=3. HH1 (25 µM, 24 hr) and DAC (100 nM, 72 hr) were used as positive controls. Western blot showed that dnCDK9 is overexpressed in the absence of tetracycline together with decreased phosphorylation of RNA Polymerase II at Ser2 (pSer2) and Ser5 (pSer5). FIG. 14B depicts experimental data demonstrating that two endogenously hypermethylated genes (PYGM and RRAD) were reactivated upon dominant negative CDK9 (dnCDK9) overexpression (72 hr) (n=3). Data are shown as mean±SD. HH1 (25 µM for 48 hr) and DAC (100 nM for 72 hr) were used as positive controls. ***p<0.001 (Student's t-test).

FIG. 17, comprising FIG. 17A depicts experimental data demonstrating that overexpression of CDK9 and Cyclin T1 (72 hr) abolished the effect of CDK9 inhibitors (24 hr) on the expression of GFP and hypermethylated genes. *p<0.05, p<0.01, *p<0.001 (Student's t-test). Data are shown as mean±SD, n=3. Depsipeptide was used as a negative control. Western blot showed the overexpression of CDK9 and Cyclin T1 after 72 hr viral transduction. Single transductions (CDK9 or Cyclin T1) were used as controls. FIG. 17B depicts experimental data demonstrating that CDK9 inhibition mediated GFP induction was abolished when overexpressing CDK9 and Cyclin T1. GFP florescence was detected by FACS (n=3). Data are shown as mean±SD. Depsipeptide was used as a negative control. ***p<0.001 (Student's t-test).

FIG. 19 depicts examples of reaction schemes for compounds of the invention.

FIG. 20, comprising FIGS. 20A and 20B, depicts experimental data demonstrating structure activity relationships of selective CDK9 inhibitor MC 180295. FIG. 20A depicts quantitative distribution of MC180295 inhibitory effect against a panel of 250 kinases at 1 µM in duplicate experiments. FIG. 20B depicts a kinase phylogenetic tree showing the distribution of inhibited kinases within the human kinome.

FIGS. 22A-B, depicts experimental data demonstrating various IC50 values and curves of MC180295. FIG. 22A depicts experimental data demonstrating IC50 values of MC180295 against 10 CDK/Cyclin kinases. FIG. 22B depicts the IC50 curve of MC180295 against CDK9. Staurosporine, a pan-CDK inhibitor, was used as a positive control

FIG. 35, comprising FIGS. 35A-B, depicts experimental data demonstrating the reactivation of silenced genes. FIG. 35A depicts lowly expressed genes (baseline RPKM<0.31) were significantly upregulated (FC>2, FDR<0.1) after four-day HH1 treatment at 10 μM. The yellow dotted lines represent two-fold change. The yellow solid line shows the mean value of fold changes at each time point. FIG. 35B depicts Gene Ontology analysis of upregulated genes after four-day HH1 treatment at 10 μM in (C).

FIG. 39 depicts Ingenuity Pathway Analysis of upstream regulators of genes that are activated or inhibited after four-day HH1 treatment at 10 μM based on genes in (FIG. 35A).

FIG. 41 depicts Ingenuity Pathway Analysis of upstream regulators of genes that are activated or inhibited after 8 hr HH1 treatment at 10 μM based on significantly upregulated genes (FC>2, FDR<0.1).

FIG. 43, comprising FIGS. 43A-B, depicts experimental data demonstrating co-immunoprecipitation (Co-IP) tests. FIG. 43A depicts experimental data demonstrating CDK9 interaction with SMARCA4. Protein lysates from YB5 cells were harvested in MPER lysis buffer. Immunoprecipitation was performed using antibody against CDK9, and the respective co-precipitation of SMARCA4 and CDK9 was assessed using Western blot analysis using a 4-15% gradient gel. FIG. 43B depicts experimental data demonstrating CDK9 interaction with SMARCA4. HEK293T cells were transiently transfected with either (Top) FLAG-SMARCA4, or (Bottom) GFP-CDK9. After 72 hours, protein lysate was extracted and IP was performed using antibodies against either FLAG, or SMARCA4 and the respective co-precipitation of CDK9 or GFP-CDK9 was assessed using Western blot analysis using a 4-15% gradient gel.

FIG. 46, comprising FIGS. 46A-B, depicts experimental data demonstrating the validation of CBX5 by time-course q-PCR and Western Blot. FIG. 46A depicts time-course qPCR showing CBX5 (which encodes HP1α) suppression after 10 μM HH1 treatment (n=6). Data are shown as mean+SD. *p<0.05, p<0.01, *p<0.001 (Student's t-test). FIG. 46B depicts a Western blot showing decreased expression of HP1α after 24 hr CDK9 inhibition (* marks a non-specific band). TATA box binding protein (TBP) was used as a nuclear loading control.

FIG. 47 depicts experimental data demonstrating GFP induction and CBX5 suppression after four-day treatment using different CDK9 inhibitors measured by qPCR (n=3). Data are shown as mean+SD. ***p<0.001 (Student's t-test).

FIGS. 48A-B, depicts experimental data demonstrating the inhibition of CBX5 upon overexpression of dnCDK9 in both YB5 and HCT116 cells. FIG.

48A depicts experimental data demonstrating GFP induction and CBX5 and MYC suppression upon dnCDK9 overexpression (72 hr) in YB5 (n=3). Data are shown as mean±SD.*p<0.05, p<0.01, *p<0.001 (Student's t-test). FIG. 48B depicts experimental data demonstrating GFP induction and CBX5 suppression upon dnCDK9 overexpression (72 hr) in HCT116-GFP (n=3). Data are shown as mean±SD. **p<0.01 (Student's t-test).

FIGS. 49A-B, depicts experimental data demonstrating the reactivation of GFP, as well as two hypermethylated silenced genes (SYNE1 and NPR3), upon CBX5 inhibition. FIG. 49A depicts knocking down of CBX5 using two siRNAs (siCBX5#1: ON-TARGETplus SMARTpool siCBX5. siCBX5#2: GGAUUGCCCUGAGCUAAUUUU (SEQ ID NO. 1) (Ambion)) reactivated GFP in YB5. Data are shown as mean±SD, n=4. p<0.01, *p<0.001 (Student's t-test). FIG. 49B depicts experimental data demonstrating knocking down of CBX5 using two siRNAs (siCBX5#1: ON-TARGETplus SMARTpool siCBX5. siCBX5#2: GGAUUGCCCUGAGCUAAUUUU (SEQ ID NO. 1) (Ambion)) reactivated SYNE1 and NPR3 (hypermethylated genes) in YB5. Data are shown as mean±SD, n=4. *p<0.05, **p<0.01 (Student's t-test).

FIG. 51, comprising FIGS. 51A-B, depicts experimental data demonstrating that HH1-upregulated genes are highly enriched for H3K9me2 at baseline and that the H3K9me2 mark is enriched at the CMV/GFP region. FIG. 51A depicts ChIP-seq for H3K9me2. Average read count per million mapped reads of genes unregulated by each condition in YB5 cells plotted around gene bodies. UNC0638, a G9a inhibitor was used as a positive control. FIG. 51B depicts experimental data demonstrating H3K9me2 occupancy at baseline CMV/GFP region checked by ChIP-qPCR. LINE-1, a repetitive repressive element was used as a positive control and ACTB was used as a negative control (n=4). Data are shown as mean+SD.

FIG. 52, comprising FIGS. 52A-C, depicts experimental data demonstrating proliferation of cancer cells after one-time HH1 or MC180295 exposure and cell cycle analysis after HH1 or MC180295 exposure. FIG. 52A depicts experimental data demonstrating the proliferation inhibition of normal epithelial cells (IMR90) and cancer cell lines treated with a single-dose of 5 µM HH1 or 0.1 µM MC180295 and counted four days after by trypan blue exclusion. Data are shown as mean±SD, n=3. *p<0.05, p<0.01, *p<0.001 (Student's t-test). FIG. 52B depicts cell cycle analysis after four-day drug treatment using different CDK9 inhibitors at multiple doses in YB5 (n=3). Data are shown as mean±SEM. FIG. 52C depicts experimental data demonstrating cell apoptosis measured by sub-G1 sub-population after four-day drug treatment in YB5 (n=3). Data are shown as mean±SEM.

FIG. 53, comprising FIGS. 53A-B, depicts experimental data demonstrating that single dose pre-exposure of HH1 and MC180295 for four days can blunt colony formation by 30-80% in YB5 and HCT116. FIG. 53A depicts soft agar assays of SW48 colon cancer cells following either HH1 or MC180295 four-day single-dose pre-treatment (n=3). Data are shown as mean+SD. p<0.01, *p<0.001 (Student's t-test). FIG. 53B depicts soft agar assays of HCT116 colon cancer cells following either HH1 or MC180295 four-day single-dose pre-treatment (n=3). Data are shown as mean+SD. *p<0.05, **p<0.01 (Student's t-test).

FIG. 54, comprising FIGS. 54A-B, depicts experimental data demonstrating a test on the differentiation marker CD11b using the HL60 cell line. FIG. 54A depicts HL60 cell differentiation measured by expression of CD11b antigen before and after HH1 and MC180295 four-day single-dose treatment (n=3). 1 µM ATRA and high concentrations of DMSO (1.25%) were used as positive controls. Data are shown as mean+SD. All drugs were in 0.5% final DMSO concentration. p<0.01, *p<0.001 (Student's t-test). FIG. 54B depicts histograms of HL60 cell differentiation measured as CD11b expression under different conditions. The x-axis represents FITC-CD11b fluorescence intensity.

FIG. 55, comprising FIGS. 55A-B, depicts experimental data demonstrating the effects of MC180295 treatment on tumors in mice. FIG. 55A depicts an image of NSG mice that were inoculated (i.p.) with $1 \times 10^5$ SW48-luc cells. One week later, at which time substantial tumor burden was evident by bioluminescence imaging, 5-20 mg/kg MC180295 or vehicle was administered (i.p) every other day. Images of mice before drug treatment (week 1) after one-week (week 2), two-week (week 3) or three-week (week 4) drug treatment are shown. Quantitative analysis of bioluminescence is shown on the right for each mouse. FIG. 55B depicts an image of NSG mice that were inoculated (i.p.) with $5 \times 10^5$ SW48-luc cells. Four days later, at which time substantial tumor burden was evident by bioluminescence imaging, 10 mg/kg MC180295 or vehicle was administered (i.p) daily. Images of mice after one-week (top) or two-week drug treatment (bottom). Each group contains three vehicle control mice (left three) and three drug-treated mice (right three). Quantitative analysis of bioluminescence is shown on the right. Data are shown as mean±SD. *p<0.05 (Student's t-test).

FIG. 56, comprising FIGS. 56A-B, depicts tests of the anti-tumor efficacy of SNS-032 in vivo. FIG. 56A depicts experimental data demonstrating the measurement of ascites fluid in the VEGF-DEF ID8 ovarian cancer mouse model is an indicator of tumor burden; large volumes of ascites indicate a high tumor burden and are correlated with decreased survival. In vivo treatment of this mouse model with CDK9 inhibitor SNS-032 every 3 days demonstrated a decrease in tumor burden at weeks 4 and 5 in a dose dependent manner. Addition of α-PD-1 led to a further decrease in tumor burden. Data are shown as mean+SEM. *p<0.05, p<0.01, *p<0.001 (Mann Whitney test). FIG. 56B depicts experimental data demonstrating survival of the mice in days, with median survival shown. Significance was calculated using a log-rank (Mantel-Cox) test. *p<0.05, p<0.01, *p<0.001. 10 mg/kg SNS-032 can significantly extend survival of the mice and sensitize with α-PD1.

FIGS. 58A-B, depicts experimental data demonstrating that HH1 or MC180295 treatment activated the expression of several ERVs. FIG. 58A depicts ERV activation after four-day one-dose CDK9 inhibitor treatment in YB5 cells (n=3). DAC was used as a positive control. Data are shown as mean±SD. *p<0.05, **p<0.01,

***p<0.001 (Student's t-test). FIG. 58B depicts experimental data demonstrating endogenous retroviruses (ERV) activation after four-day CDK9 inhibition in HCT116 cells (n=3). Data are shown as mean±SD. *p<0.05, **p<0.01 (Student's t-test).

FIGS. 60A-B, depicts experimental data demonstrating CIM (CDK9 Immune Signature) gene expression panels. FIG. 60A depicts CIM clusters TCGA melanoma patients into high and low immune signatures and CIM-high patients have a longer survival than CIM-low patients. FIG. 60B depicts CIM clusters TCGA colon cancer patients into high and low immune signatures. CIM-high patients tend to have a better survival than CIM-low patients.

FIGS. 62A-B, depicts experimental data demonstrating the effects of CDK9 inhibition on immune cells, T-cells, and dendritic cells. FIG. 62A depicts experimental data demonstrating that in vivo treatment of mice with SNS-032 resulted in increased populations of immune cells (CD45+) and T cells (CD3+) in the tumor microenvironment. *p<0.05, p<0.01, *p<0.001 (Mann Whitney test). Mononuclear cells isolated from ascites fluid were washed and stained for cell surface markers and analyzed via flow cytometry. FIG. 62B depicts experimental data demonstrating that in vivo treatment of mice with SNS-032 resulted in increased populations of activated dendritic cells (CD80/CD86+ and CD11c/MHCII+) in the tumor microenvironment, particularly with the addition of α-PD-1. Mean±SEM are shown. *p<0.05, **p<0.01 (Mann Whitney test). Mononuclear cells isolated from ascites fluid were washed and stained for cell surface markers and analyzed via flow cytometry.

FIG. 66 depicts experimental data demonstrating comparing the activity of MC180295, a compound of the invention, to other compounds.

FIG. 67 depicts experimental data demonstrating the effects of MC180295 treatment on tumors in mice in an SW48 model.

FIG. 71 depicts experimental data demonstrating in vitro ADME properties of compounds of the invention.

DETAILED DESCRIPTION OF THE INVENTION

Figure 1:
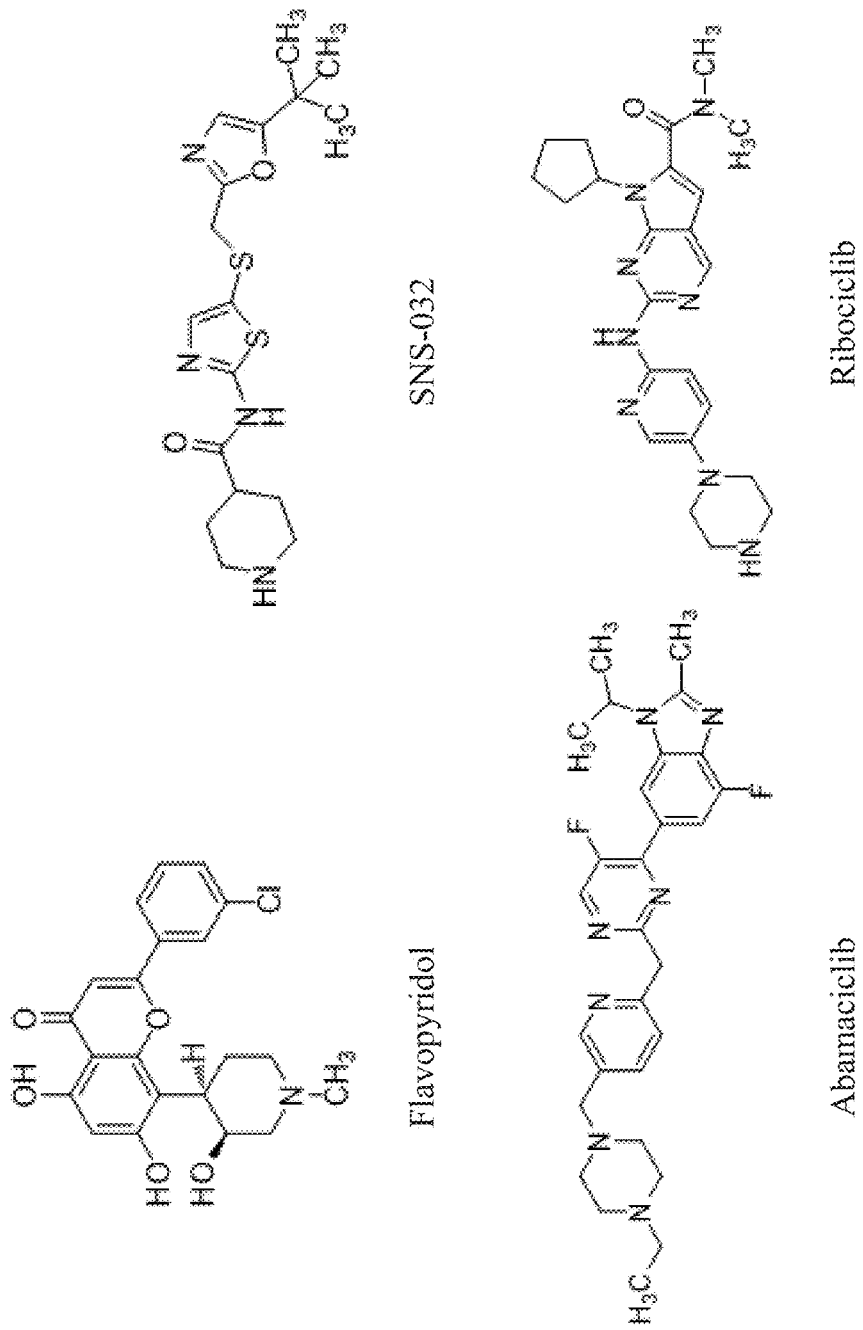
FIG. 1 depicts the structures of flavopyridol, SNS-032, abamaciclib, and ribociclib.

This invention includes the unexpected identification of novel aminothiazole compounds that are useful as epigenetic compounds for the treatment of cancer. As demonstrated herein, compounds of the invention were found to reactivate silenced gene expression in YB5 cells and other cancer cells, including MCF7 cells. The compounds were also found to inhibit Cyclin Dependent Kinases (CDKs), and therefore the CDK inhibitors of the invention can be useful as anti-cancer compounds. The compounds of the invention are expected to have desirable pharmocokinetic and pharmacodynamic properties, and appear to be more potent than other CDK inhibitors not developed by targeting silenced tumor-suppressor genes expression. Moreover, the combination of epigenetic modulation and CDK inhibition observed using the compounds of the invention suggests that these compounds are superior treatments for cancer compared to known compounds that act through only one of these mechanisms of action, such as flavopyridol, SNS-032, abamaciclib, and ribociclib (FIG. 1).

In one embodiment, the invention provides a novel class of compounds that reactivate silenced tumor-suppressor genes in-vitro and show selective cancer cell killing. These compounds are novel epigenetic drugs having anti-cancer activity.

The present invention also includes novel methods of treating or preventing cancer using the compounds of the invention. In one embodiment, the cancer includes but is not limited to lung cancer, colon cancer, melanoma, breast cancer, ovarian cancer, prostate cancer, liver cancer, pancreatic cancer, a CNS tumor, neuroblastoma, leukemia, bone cancer, intestinal cancer, lymphoma, bladder cancer, sarcoma, bile duct cancer, stomach cancer, cervical cancer, testicular cancer, uterine cancer, gall bladder cancer, fallopian tube cancer, nasopharyngeal cancer, hypopharyngeal cancer, renal cancer, oral cavity cancer, head and neck cancer, thyroid cancer, parathyroid cancer, pituitary cancer, rectal cancer, retinoblastoma, Wilm's tumor, vaginal cancer, penile cancer, and the likes. However, the invention should not be limited to only these cancers but the invention is applicable to any cancers.

The present invention includes a composition comprising at least one compound of the invention, wherein the composition optionally further comprises at least one additional therapeutic agent. In one embodiment, the additional therapeutic agent is a chemotherapeutic agent. In one embodiment, the therapeutic agent is a Bcl-2 inhibitor selected from the group consisting of ABT-199, ABT-263, ABT-737, G3139 (genasense or oblimersen), GX15-070 (obatoclax mesylate), HA14-1, TW-37, sabutoclax, Gossypol (AT-101), antimycin A, apogossypol, and S44563.

The present invention also includes novel methods of treating or preventing an inflammatory condition using the compounds of the invention.

The present invention also includes novel methods of treating or preventing cardiac dysfunction or cardiovascular disease using the compounds of the invention. In one embodiment, the cardiac dysfunction or cardiovascular disease is cardiac hypertrophy.

The present invention also includes novel methods of treating or preventing a viral infection using the compounds of the invention. In one embodiment, the viral infection is selected from the group consisting of human immunodeficiency virus (HIV), herpes simplex virus (HSV), Hepatitis A, Hepatitis B, Hepatitis C, Human Papilloma Virus, Epstein Barr Virus, Human Adenovirus, Cytomegalovirus, Poxvirus, Sindbis Virus, and Human Herpes Virus.

In one embodiment, the invention includes compounds and methods for treating a disease, disorder or condition associated with dysfunctional CDK activity or expression.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The term "cardiac dysfunction" refers to a pathological decline in cardiac performance. Cardiac dysfunction may be manifested through one or more parameters or indicies including changes to stroke volume, ejection fraction, end diastolic fraction, stroke work, arterial elastance (defined as the ratio of left ventricular (LV) end-systolic pressure and stroke volume), or an increase in heart weight to body weight ratio. Unless otherwise noted, cardiac dysfunctions encompass any cardiac disorders or aberrant conditions that are associated with or induced by the various cardiomyopathies, cardiomyocyte hypertrophy, cardiac fibrosis, or other cardiac injuries described herein. Specific examples of cardiac dysfunction include cardiac remodeling, cardiac hypertrophy, and heart failure. In one embodiment, the cardiac dysfunction is due to LV systolic dysfunction.

As used herein, the terms "congestive heart failure, (CHF)" "chronic heart failure," "acute heart failure," and "heart failure" are used interchangeably, and refer to any condition in which the heart is unable to pump blood at an adequate rate or to do so only in the presence of increased left ventricular filling pressures. When the heart is unable to adequately pump blood to the rest of the body at normal filling left ventricular pressures, blood can back up into the lungs, causing the lungs to become congested with fluid. Typical symptoms of heart failure include shortness of breath (dyspnea), fatigue, weakness, difficulty breathing when lying flat, and swelling of the legs, ankles or abdomen (edema). Causes of heart failure are related to various disorders including coronary artery disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction. Heart failure can occur in the presence of a normal (≥50%) or a reduced (<50%) left ventricular ejection fraction. There is increased recognition that these two conditions represent two different disease states, rather than a continuum (Borlaug B A, Redfield M M. Circulation. 2011 May 10; 123 (18):2006-13).

As used herein, the term "cardiovascular disease" or "CVD," generally refers to heart and blood vessel diseases, including atherosclerosis, coronary heart disease, cerebrovascular disease, and peripheral vascular disease. Cardiovascular disorders are acute manifestations of CVD and include myocardial infarction, stroke, angina pectoris, transient ischemic attacks, and congestive heart failure. Cardiovascular disease, including atherosclerosis, usually results from the build-up of cholesterol, inflammatory cells, extracellular matrix and plaque. As used herein, the term "coronary heart disease" or "CHD" refers to atherosclerosis in the arteries of the heart causing a heart attack or other clinical manifestation such as unstable angina.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a sign or symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of a sign, a symptom, or a cause of a disease or disorder, or any other desired alteration of a biological system. An appropriate therapeutic amount in any individual case may be determined by one of ordinary skill in the art using routine experimentation.

For the purposes of the present invention the terms "compound," "analog," and "composition of matter" stand equally well for the aminothiazole compounds described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such acids include hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, mesylic, aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —$NH_2$, amino, azido, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

   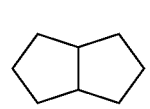

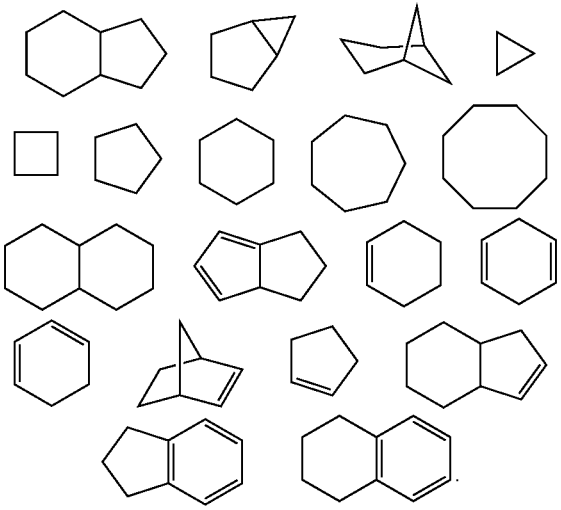

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

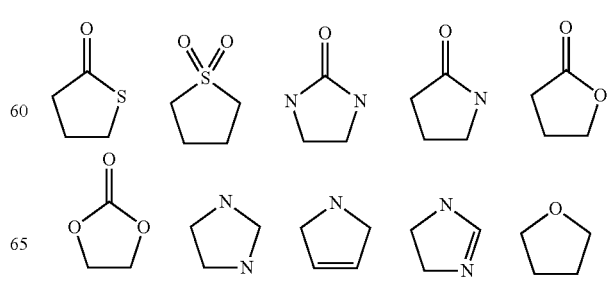

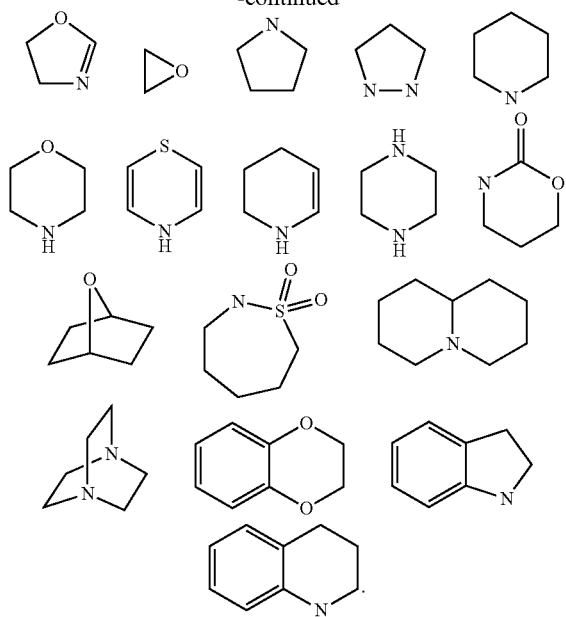

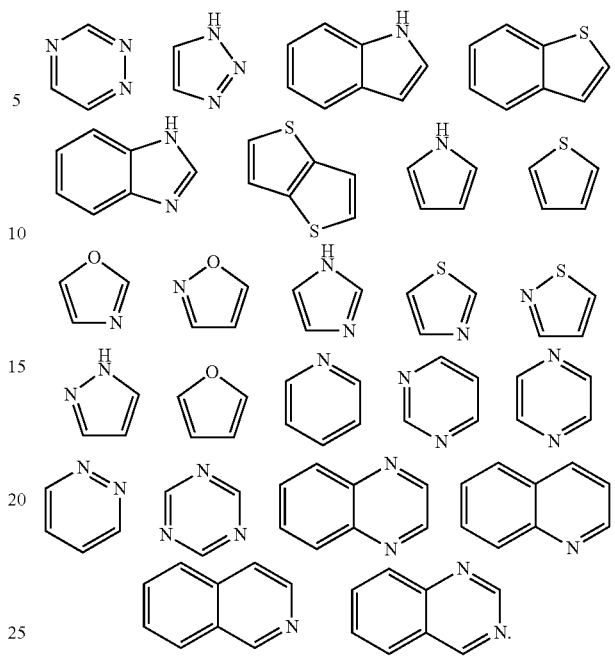

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —$CH_2CH_2$-pyridyl. The term "substituted heteroaryl-($C_1$-$C_3$)alkyl" means a heteroaryl-($C_1$-$C_3$)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, —ON(O)$_2$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds Useful within the Invention

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of Formula (I):

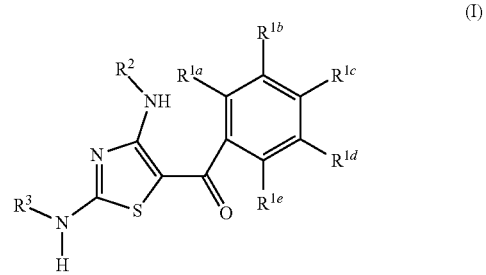

(I)

including enantiomers, diastereomers, hydrates, solvates, pharmaceutically acceptable salts, prodrugs and complexes thereof;

wherein in Formula (I):

$R^{1a}$, $R^{1b}$, $R^{1c}$, $R^{1d}$ and $R^{1e}$ are each independently selected from the group consisting of hydrogen, halogen, hydroxyl, C$_{1-6}$ linear alkyl, C$_{3-6}$ branched alkyl, C$_{3-6}$ cycloalkyl, C$_{1-6}$ haloalkyl, C$_{1-6}$ linear alkoxy, C$_{3-6}$ branched alkoxy, C$_{1-6}$ haloalkoxy, thiol, C$_{1-6}$ linear thioalkyl, C$_{3-6}$ branched thioalkyl, cyano, nitro, and NR$^4$R$^5$, or two adjacent R$^1$ groups are joined to form a 5- to 7-membered heterocyclic ring containing 1 to 3 heteroatoms, $R^2$ is selected from the group consisting of hydrogen, C$_{1-6}$ linear alkyl, C$_{3-7}$ branched alkyl, C$_{3-7}$ cycloalkyl and COR$^6$;

$R^3$ is a bridged bicycloalkyl moiety selected from the group of consisting of:

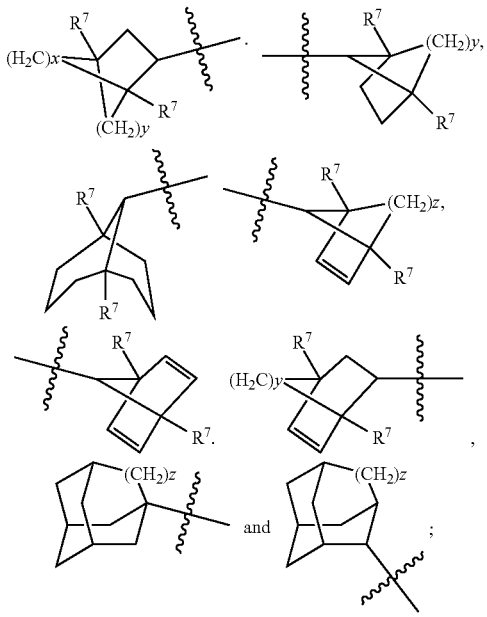

$R^4$ and $R^5$ are each independently selected from the group consisting of hydrogen, C$_{1-6}$ linear alkyl, and C$_{3-7}$ branched alkyl, or $R^4$ and $R^5$ are joined to form a 3- to 7-membered heterocycloalkyl ring;

$R^6$ is selected from the group consisting of hydrogen, C$_{1-6}$ linear alkyl, C$_{3-7}$ branched alkyl, C$_{1-6}$ linear alkoxy, C$_{3-7}$ branched alkoxy and C$_{3-7}$ cycloalkyl;

$R^7$ at each occurrence is independently selected from the group consisting of hydrogen or methyl;

x is 1, 2, or 3;
y is 1, 2, or 3; and
z is 1, 2, or 3;

with the proviso that when the compound of Formula (I) is:

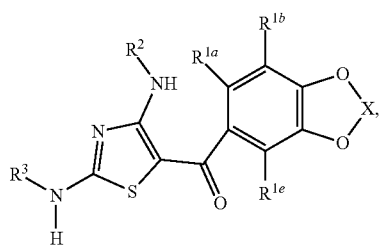

then X cannot be

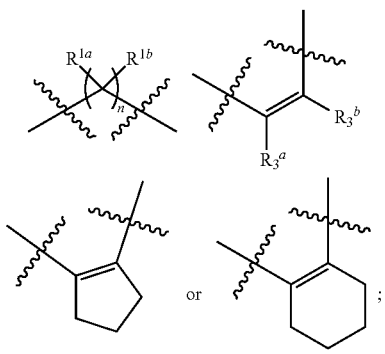

wherein:

$R^{1a}$ and $R^{1b}$ are at each occurrence independently selected from the group consisting of hydrogen, $C_{1-4}$ linear alkyl, and $C_{3-6}$ branched alkyl, or $R^{1a}$ and $R^{1b}$ are taken together with the atoms to which they are bound to form a three to six membered carbocyclic ring, or two $R^{1a}$ units on adjacent carbon atoms are taken together with the atoms to which they are bound to form a three to six membered carbocyclic ring;

$R^{3a}$ and $R^{3b}$ are each independently selected from the group consisting of hydrogen, $C_{1-4}$ linear alkyl, and $C_{3-6}$ branched alkyl.

In one embodiment, two adjacent $R^1$ groups are joined to form a 5- to 7-membered heterocyclic ring containing 1 to 3 heteroatoms. In another embodiment, the 1 to 3 heteroatoms are selected from the group consisting of N, O, and S.

In one embodiment, $R^{1a}$, $R^{1b}$, $R^{1c}$, $R^{1d}$ and $R^{1e}$ are each hydrogen.

In another embodiment, $R^{1b}$ is $C_{1-6}$ linear alkoxy.

In another embodiment, $R^{1c}$ is $C_{1-6}$ linear alkoxy.

In another embodiment, $R^{1c}$ is nitro.

In another embodiment, $R^{1d}$ is $C_{1-6}$ linear alkoxy.

In another embodiment, $R^{1d}$ is nitro.

In another embodiment, $R^{1e}$ is cyano.

In another embodiment, $R^{1e}$ is nitro.

In another embodiment, $R^{1c}$ and $R^{1d}$ are joined to form a 5- to 7-membered heterocyclic ring containing 1 to 3 heteroatoms In another embodiment, $R^{1d}$ and $R^{1e}$ are joined to form a 5- to 7-membered heterocyclic ring containing 1 to 3 heteroatoms In another embodiment, $R^2$ is hydrogen.

In another embodiment, $R^3$ is

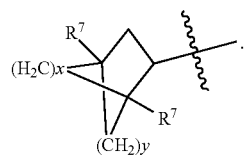

In another embodiment, y is 2.

In one embodiment, x is 1.

In one embodiment, the compound of Formula (I) is a compound selected from the group consisting of:

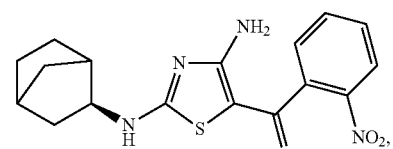

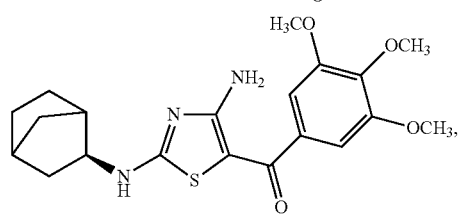

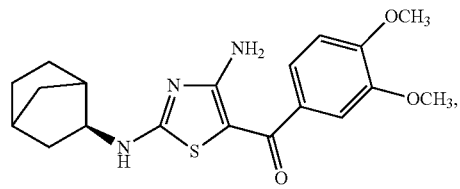

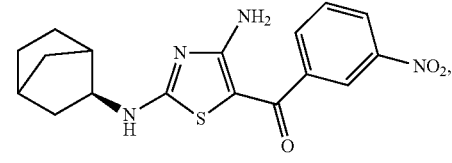

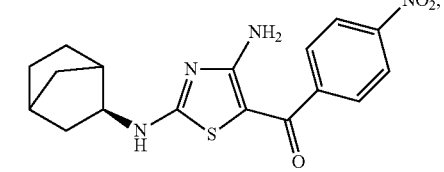

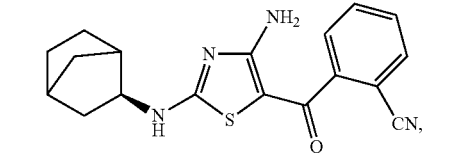

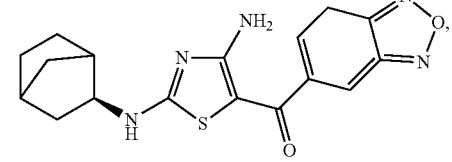

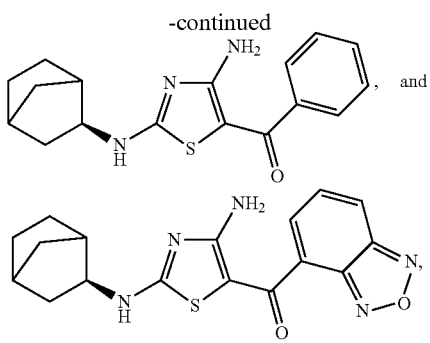

a salt or solvate thereof, and any combinations thereof.

Process

The present invention further relates to a process for preparing the compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art of organic chemistry. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions.

Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while coexisting amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

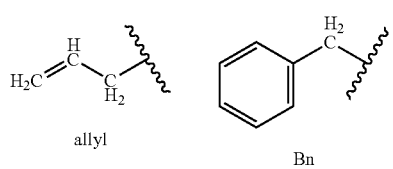

allyl

Bn

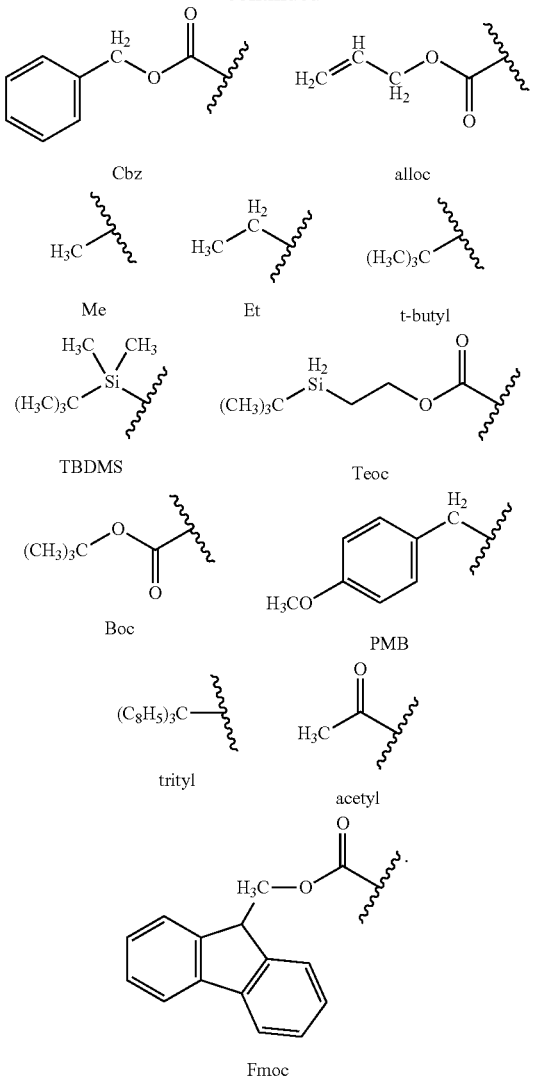

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

Exemplary General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of Formula (I) may be prepared according to the process outlined in Schemes 1-2.

Scheme 1

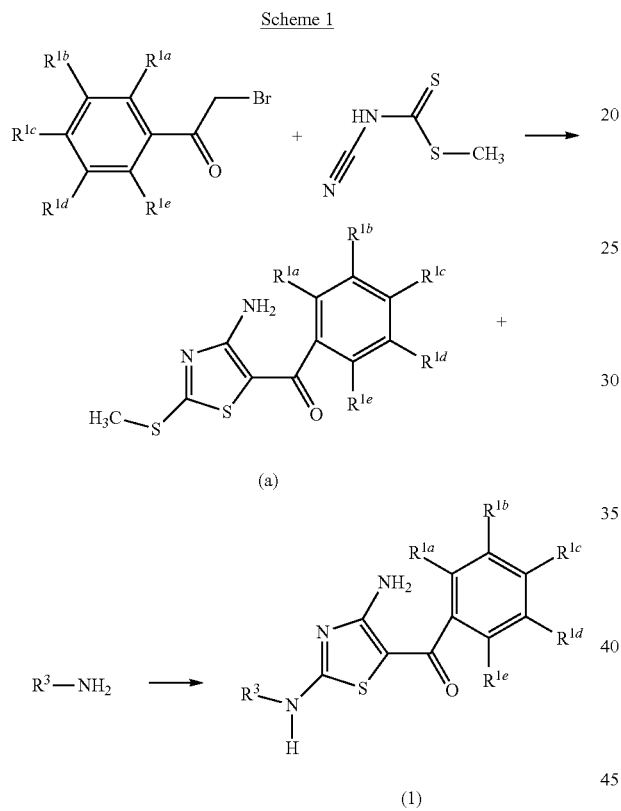

In a non-limiting example, Scheme 1 demonstrates a method of preparing the compounds of Formula (I) where $R^2$ is H. An appropriately substituted 2-bromoacetophenone is reacted with cyanimidodithiocarbonic acid S-methyl ester S-potassium salt in an appropriate solvent like dimethylformamide to give intermediate (a). Treatment of intermediate (a) with an appropriately substituted amine provides the final compounds of Formula (I).

Scheme 2

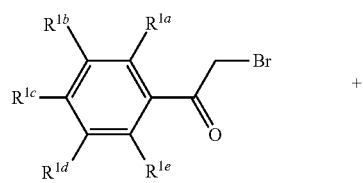

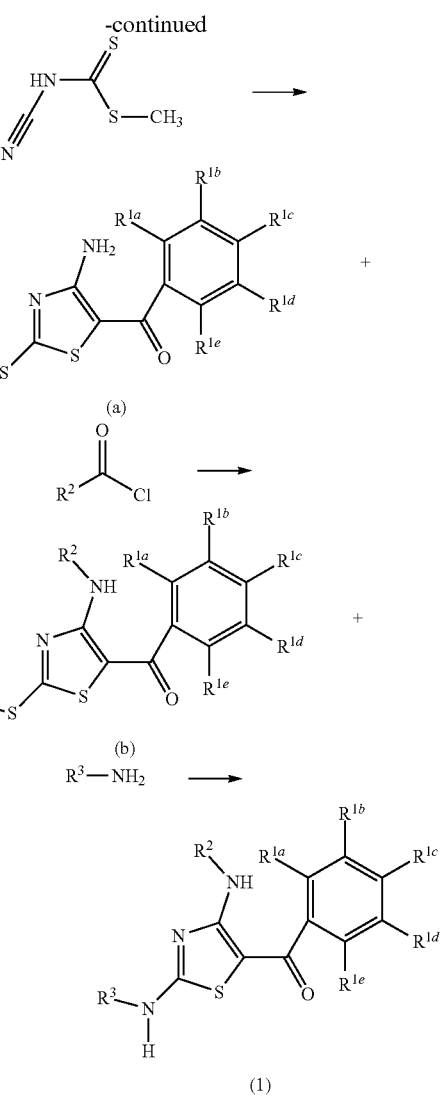

In a non-limiting example, Scheme 2 demonstrates a method of preparing the compounds of Formula (I) where $R^2$ is not H. Intermediate (a) is prepared as shown in Scheme 1 above. Treatment of intermediate (a) with an appropriate acid chloride gives intermediate (b), which is then treated with an appropriately substituted amine to give the final compounds of Formula (1).

Methods of the Invention

The invention includes a method of treating or preventing cancer in a subject in need thereof. The method comprises administering to the subject a therapeutically effective amount of a composition comprising a compound of the invention. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the compounds of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers that can be treated with the compositions of the invention include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Non-limiting examples of types of cancer that may be treated using compounds of the invention include Acute Lymphoblastic Leukemia (ALL), Acute Myeloid Leukemia (AML), Adrenocortical Carcinoma, Childhood Adrenocortical Carcinoma, AIDS-Related Cancers, Kaposi Sarcoma (Soft Tissue Sarcoma), AIDS-Related Lymphoma, Primary CNS Lymphoma, Anal Cancer, Appendix Cancer, Astrocytomas, Atypical Teratoid/Rhabdoid Tumor, Basal Cell Carcinoma, Bile Duct Cancer, Bladder Cancer, Childhood Bladder Cancer, Bone Cancer, Brain Tumors, Breast Cancer, Childhood Breast Cancer, Bronchial Tumors, Burkitt Lymphoma, Carcinoid Tumor, Childhood Carcinoid Tumors, Cardiac (Heart) Tumors, Embryonal Tumors, Germ Cell Tumor, Primary CNS Lymphoma, Cervical Cancer, Childhood Cervical Cancer, Childhood Cancers, Cholangiocarcinoma, Chordoma, Chronic Lymphocytic Leukemia (CLL), Chronic Myelogenous Leukemia (CML), Chronic Myeloproliferative Neoplasms, Colorectal Cancer, Childhood Colorectal Cancer, Craniopharyngioma, Cutaneous T-Cell Lymphoma, Ductal Carcinoma In Situ (DCIS), Embryonal Tumors, Endometrial Cancer, Endometrial Uterine Cancer, Ependymoma, Esophageal Cancer, Childhood Esophageal Cancer, Esthesioneuroblastoma, Ewing Sarcoma, Extracranial Germ Cell Tumor, Extragonadal Germ Cell Tumor, Eye Cancer, Childhood Intraocular Melanoma, Intraocular Melanoma, Retinoblastoma, Fallopian Tube Cancer, Fibrous Histiocytoma of Bone, Gallbladder Cancer, Gastric (Stomach) Cancer, Childhood Gastric (Stomach) Cancer, Gastrointestinal Carcinoid Tumor, Gastrointestinal Stromal Tumors (GIST) (Soft Tissue Sarcoma), Childhood Gastrointestinal Stromal Tumors, Germ Cell Tumors, Childhood Central Nervous System Germ Cell Tumors, Childhood Extracranial Germ Cell Tumors, Germ Cell Tumors, Ovarian, Germ Cell Tumors, Testicular Cancer, Gestational Trophoblastic Disease, Hairy Cell Leukemia, Head and Neck Cancer, Childhood Head and Neck Cancers, Heart Tumors, Hepatocellular (Liver) Cancer, Histiocytosis, Langerhans Cell, Hodgkin Lymphoma, Hypopharyngeal Cancer, Islet Cell Tumors, Pancreatic Neuroendocrine Tumors, Kaposi Sarcoma, Kidney (Renal Cell) Cancer, Langerhans Cell Histiocytosis, Laryngeal Cancer, Childhood Laryngeal Cancer and Papillomatosis, Leukemia, Lip and Oral Cavity Cancer (Head and Neck Cancer), Liver Cancer, Lung Cancer (Non-Small Cell and Small Cell), Childhood Lung Cancer, Lymphoma, Male Breast Cancer, Malignant Fibrous Histiocytoma of Bone and Osteosarcoma, Childhood Melanoma, Merkel Cell Carcinoma, Malignant Mesothelioma, Childhood Mesothelioma, Metastatic Cancer, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Chronic Myeloproliferative Neoplasms, Nasal Cavity and Paranasal Sinus Cancer, Nasopharyngeal Cancer, Childhood Nasopharyngeal Cancer, Neuroblastoma, Non-Hodgkin Lymphoma, Non-Small Cell Lung Cancer, Oral Cancer, Lip and Oral Cavity Cancer and Oropharyngeal Cancer, Childhood Oral Cavity Cancer, Osteosarcoma and Malignant Fibrous Histiocytoma of Bone, Ovarian Cancer, Childhood Ovarian Cancer, Pancreatic Cancer, Childhood Pancreatic Cancer, Pancreatic Neuroendocrine Tumors (Islet Cell Tumors), Papillomatosis, Paraganglioma, Childhood Paraganglioma, Paranasal Sinus and Nasal Cavity Cancer, Parathyroid Cancer, Penile Cancer, Pharyngeal Cancer, Pheochromocytoma, Childhood Pheochromocytoma, Tumor, Plasma Cell Neoplasm/Multiple Myeloma, Pleuropulmonary Blastoma, Primary Central Nervous System (CNS) Lymphoma, Primary Peritoneal Cancer, Prostate Cancer, Cancer, Recurrent Cancer, Renal Cell (Kidney) Cancer, Childhood Retinoblastoma, Rhabdomyosarcoma, Salivary Gland Cancer, Childhood Salivary Gland Tumors, Childhood Rhabdomyosarcoma, Childhood Vascular Tumors, Ewing Sarcoma, Kaposi Sarcoma (Soft Tissue Sarcoma), Osteosarcoma (Bone Cancer), Uterine Sarcoma, Sézary Syndrome, Skin Cancer, Childhood Skin Cancer, Small Cell Lung Cancer, Small Intestine Cancer, Soft Tissue Sarcoma, Squamous Cell Carcinoma of the Skin, Stomach (Gastric) Cancer, Stomach (Gastric) Cancer, Testicular Cancer, Childhood Testicular Cancer, Throat Cancer, Nasopharyngeal Cancer, Oropharyngeal Cancer, Hypopharyngeal Cancer, Thymoma and Thymic Carcinoma, Thyroid Cancer, Childhood Thyroid Tumors, Transitional Cell Cancer of the Renal Pelvis and Ureter, Carcinoma of Unknown Primary, Childhood Cancer of Unknown Primary, Urethral Cancer, Uterine Sarcoma, Vaginal Cancer, Childhood Vaginal Cancer, Vascular Tumors, Vulvar Cancer, Wilms Tumor and Other Childhood Kidney Tumors. In one embodiment, the compounds of the invention are useful for treating myeloid malignancies.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, that can be treated with the compositions of the invention, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases.

In one embodiment, the cancer is selected from the group consisting of lung cancer, colon cancer, melanoma, breast cancer, ovarian cancer, prostate cancer, liver cancer, pancreatic cancer, a CNS tumor, neuroblastoma, leukemia, bone cancer, intestinal cancer, lymphoma, bladder cancer, sarcoma, bile duct cancer, stomach cancer, cervical cancer, testicular cancer, uterine cancer, gall bladder cancer, fallopian tube cancer, nasopharyngeal cancer, hypopharyngeal cancer, renal cancer, oral cavity cancer, head and neck cancer, thyroid cancer, parathyroid cancer, pituitary cancer, rectal cancer, retinoblastoma, Wilm's tumor, vaginal cancer, penile cancer, and combinations thereof. In one embodiment, the method further comprises administering to the subject an additional therapeutic agent.

In another aspect, the invention includes a method of treating or preventing an inflammatory condition in a subject in need thereof. The method comprises administering to the subject a therapeutically effective amount of a composition comprising a compound of the invention. In one embodiment, the inflammatory condition is selected from the group consisting of arthritic disorders, psoriasis, allergies, opioid tolerance, Crohn's Disease, migraine headaches, periarteritis nodosa, thyroiditis, aplastic anemia, Hodgkin's disease, scleredoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, and myocardial ischemia. In one embodiment, the arthritic disorder is selected from the group consisting of rheumatoid arthritis, spondyloarthropathies, gouty arthritis, osteoarthritis, systemic lupus erythematosus and juvenile arthritis. In one embodiment, the method further comprises administering to the subject an additional therapeutic agent.

In another aspect, the invention includes a method of treating or preventing cardiac dysfunction or cardiovascular disease in a subject in need thereof. The method comprises administering to the subject a therapeutically effective amount of a composition comprising a compound of the invention. In one embodiment, the cardiac dysfunction or cardiovascular disease is cardiac hypertrophy. In another embodiment, the cardiac dysfunction or cardiovascular disease is an early cardiac or cardiovascular disease. In one embodiment the early cardiac or early cardiovascular disease is selected from the group consisting of left ventricular hypertrophy, coronary artery disease, essential hypertension, acute hypertensive emergency, cardiomyopathy, heart insufficiency, exercise intolerance, chronic heart failure, arrhythmia, cardiac dysrhythmia, syncopy, atteroschlerosis, mild chronic heart failure, angina pectoris, cardiac bypass reocclusion, intermittent claudication (atteroschlerosis oblitterens), diastolic dysfunction and systolic dysfunction.

In another aspect, the invention includes a method of treating or preventing a CDK9-mediated disorder or condition in a subject in need thereof. The method comprises administering to the subject a therapeutically effective amount of a composition comprising a compound of the invention. A "CDK9-mediated disorder or condition" is characterized by the participation of one or more CDK9 kinases in the inception, manifestation of one or more symptoms or disease markers, severity, or progression of a disorder or condition. An example of a CDK9-mediated disorder or condition is cancer, including cancers such as, not limited to, acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

In another aspect, the invention includes a method of modulating the immune system in a subject in need thereof. The method comprises administering to the subject a therapeutically effective amount of a composition comprising a compound of the invention. In one embodiment, the method includes stimulating the immune system in a subject in need thereof.

In another aspect, the invention includes a method of sensitizing cancer cells. In one embodiment, the method comprises administering to the subject a therapeutically effective amount of a composition comprising a compound of the invention. In one embodiment, the cells are sensitized to the activity of immune-targeted drugs. Non-limiting examples of immune-targeted drugs include inhibitors of PD-1 or PD-L1. In one embodiment, the method further comprises administering to the subject a therapeutically effective amount of an immune-targeted drug.

In another aspect, the method comprises administering to a subject a therapeutically effective amount of a composition comprising a compound of the invention in combination with one or more immune checkpoint inhibitors. "Checkpoint inhibitor" as used herein includes inhibitors or molecules that block immune checkpoints as commonly understood in the field of cancer immunotherapy. Commonly the checkpoint inhibitors are antibodies that block the immune checkpoint proteins. Immune checkpoint proteins include, but are not limited to, PD1, PDL1, PDL2, CTLA-4, LAG3, TIM3, B7-H3, BTLA, VISTA, CD40, CEACAM1, CD80, CD86, OX40, CD27, GITR, DNAM-1, TIGIT, TMIGD2 and DC-SIGN. Some examples of known checkpoint inhibitors include, but are not limited to, ipilimumab, pembrolizumab, nivolumab, pidilizumab, atezolizumab, avelumab, druvbalumab and others. In one embodiment, the composition as described above can comprise a compound of the present invention in combination with an antibody to a checkpoint protein.

The methods and compositions of the present invention may be used to treat advanced class 3B and class 4 heart failure, acute decompensated heart failure, cardio renal syndrome defined by biventricular failure, decreased glomerular filtration rate and systemic congestion, as well as acute coronary syndromes and microvascular angina. These compositions and methods have the possibility to reduce symptoms, reduce hospitalizations and increase the quality of life for patients with these conditions. In preferred embodiments the compositions are administered by continuous intravenous infusion which may be combined with standard therapies.

In another embodiment the patient suffers from a disease selected from the group consisting of myocardial infarct, acute coronary syndrome, unstable angina, non-Q-wave cardiac necrosis, Q-wave myocardial infarct and morbidity after stroke.

In another embodiment, the patient having the cardiovascular disease is a diabetic patient. In yet another embodiment, the patient having the cardiovascular disease is a non-diabetic patient.

The methods and compositions of the present invention may be used to provide acute cardioprotective effects, such as reducing the incidence of sudden death due to arrhythmias or contractile failure in a subject with an acute occlusion of a coronary artery (myocardial infarction); reducing damage occurring during reperfusion of the heart muscle after ischemia ('hypoxia-reperfusion injury' or 'ischemia-reperfusion injury'); reducing the amount of cardiac muscle that is damaged or reducing the severity of damage to the heart muscle caused by an acute coronary artery occlusion (often referred to as 'reducing infarct size') Chronic cardioprotective effects include, but are not limited to, reducing pathologic remodeling of the cardiac chambers, including chamber dilation, consequent to an acute coronary artery occlusion; reducing apoptosis in cardiac muscle consequent to an acute coronary artery occlusion; reducing the impairment of contractility of cardiac muscle consequent to an acute coronary occlusion; and reducing long-term mortality in subjects have suffered damage to the heart muscle caused by an acute coronary occlusion.

Acute and/or chronic cardioprotective effects can be desirable in subjects with chronic coronary artery disease (in which blood flow to the heart muscle is compromised without an acute coronary occlusion, also referred to as ischemic heart disease), myocarditis, idiopathic dilated cardiomyopathy, hypertrophic cardiomyopathy, restrictive cardiomyopathy, infiltrative cardiomyopathy, valvular heart disease, adult congenital heart disease, toxic cardiomyopathy (including but not limited to doxorubicin-induced cardiomyopathy), hypertensive cardiomyopathy, cardiomyopathy associated with endocrine disease, including diabetes, cardiomyopathy associated with connective tissue disease, cor pulmonale, pulmonary arterial hypertension, pulmonary embolism.

The methods and compositions of the present invention can also have an inotropic effect, increasing the strength of contraction in a failing heart. Acute and chronic inotropic effects may be desirable in acute coronary artery disease, chronic coronary artery disease (in which blood flow to the heart muscle is compromised without an acute coronary occlusion, also referred to as ischemic heart disease), myocarditis, idiopathic dilated cardiomyopathy, hypertrophic cardiomyopathy, restrictive cardiomyopathy, infiltrative cardiomyopathy, valvular heart disease, adult congenital heart disease, toxic cardiomyopathy (including but not limited to doxorubicin-induced cardiomyopathy), hypertensive cardiomyopathy, cardiomyopathy associated with endocrine disease, including diabetes, cardiomyopathy associated with connective tissue disease, cor pulmonale, pulmonary arterial hypertension, pulmonary embolism.

The methods and compositions of the present invention may also have an anti-arrhythmic effect. This effect can be acute or chronic, and can include effects that are attributable to prevention and/or reduction of injury to the heart muscle. Examples of anti-arrthymic effects include, but are not limited to, reducing the incidence and altering the rates of cardiac arrhythmias (including but not limited to atrial fibrillation, other supraventricular arrhythmias, ventricular tachycardia and ventricular fibrillation) following coronary occlusion.

The methods and compositions of the present invention may also have an anti-hypertrophic effect. Anti-hypertrophic effects can be desirable in subjects with acute coronary artery disease, chronic coronary artery disease (in which blood flow to the heart muscle is compromised without an acute coronary occlusion, also referred to as ischemic heart disease), myocarditis, idiopathic dilated cardiomyopathy, hypertrophic cardiomyopathy, restrictive cardiomyopathy, infiltrative cardiomyopathy, valvular heart disease, adult congenital heart disease, toxic cardiomyopathy (including but not limited to doxorubicin-induced cardiomyopathy), hypertensive cardiomyopathy, cardiomyopathy associated with endocrine disease, including diabetes, cardiomyopathy associated with connective tissue disease, cor pulmonale, pulmonary arterial hypertension, pulmonary embolism.

The methods and compositions of the present invention can also have lusitropic effects, improving the relaxation of the heart muscle during diastole. Lusitropic effects can be desirable in subjects with acute coronary artery disease, chronic coronary artery disease (in which blood flow to the heart muscle is compromised without an acute coronary occlusion, also referred to as ischemic heart disease), myocarditis, idiopathic dilated cardiomyopathy, hypertrophic cardiomyopathy, restrictive cardiomyopathy, infiltrative cardiomyopathy, valvular heart disease, adult congenital heart disease, toxic cardiomyopathy (including but not limited to doxorubicin-induced cardiomyopathy), hypertensive cardiomyopathy, cardiomyopathy associated with endocrine disease, including diabetes, cardiomyopathy associated with connective tissue disease, cor pulmonale, pulmonary arterial hypertension, pulmonary embolism.

The methods and compositions of the present invention can also have anti-arrhythmic effects of benefit in the treatment of disorders of the heart rhythm, examples of which include but are not limited to atrial fibrillation, ventricular tachycardia and ventricular fibrillation. These effects, which can include reductions in the incidence and rate of the arrhythmias, can be desirable in subjects with acute coronary artery disease, chronic coronary artery disease (in which blood flow to the heart muscle is compromised without an acute coronary occlusion, also referred to as ischemic heart disease), myocarditis, idiopathic dilated cardiomyopathy, hypertrophic cardiomyopathy, restrictive cardiomyopathy, infiltrative cardiomyopathy, valvular heart disease, adult congenital heart disease, toxic cardiomyopathy (including but not limited to doxorubicin-induced cardiomyopathy), hypertensive cardiomyopathy, cardiomyopathy associated with endocrine disease, including diabetes, cardiomyopathy associated with connective tissue disease, cor pulmonale, pulmonary arterial hypertension, pulmonary embolism.

The patient treated using the methods and compositions of the present invention can also be at an increased risk of developing heart disease. This can include (but is not limited to) individuals with hypertension (systemic or pulmonary), obesity, endocrine disease (including diabetes, thyroid disease, adrenal disease, dysregulation of homocysteine metabolism), iron storage disease, amyolidosis, renal disease, connective tissue disease, infectious diseases, thromboembolic disease, immune diseases, hematologic diseases.

Provided herein are methods of increasing or enhancing the chances of survival of a subject with heart disease, comprising administering to a subject in need thereof a compound of the invention, thereby increasing or enhancing the chances of survival of the subject treated by a certain period of time, for example, by at least 10 days, 1 month, 3 months, 6 months, 1 year, 1.5 years, 2 years, 3 years, 4 years, 5 years, 8 years, or 10 years. The increase in survival of a subject can be defined, for example, as the increase in survival of a preclinical animal model by a certain period of time, for example, by at least 10 days, 1 month, 3 months, 6 months, or 1 year, or at least 2 times, 3 times, 4 times, 5 times, 8 times, or 10 times, more than a control animal model (that has the same type of disease) without the treatment with the inventive method. Optionally, the increase in survival of a mammal can also be defined, for example, as the increase in survival of a subject with heart disease by a certain period of time, for example, by at least 10 days, 1 month, 3 months, 6 months, 1 year, 1.5 years, 2 years, 3 years, 4 years, 5 years, 8 years, or 10 years more than a subject with the same type of heart disease but without the treatment with the inventive method. The control subject may be on a placebo or treated with supportive standard care such as chemical therapy, biologics and/or radiation that do not include the inventive method as a part of the therapy.

In another aspect, the invention includes a method of treating or preventing a viral infection in a subject in need thereof. The method comprises administering to the subject a therapeutically effective amount of a composition comprising a compound of the invention. In one embodiment, the viral infection is a chronic viral infection. Non-limiting examples of viral infections include human immunodeficiency virus (HIV), herpes simplex virus (HSV), Hepatitis A, Hepatitis B, Hepatitis C, Human Papilloma Virus, Epstein Barr Virus, Human Adenovirus, Cytomegalovirus, Poxvirus, Sindbis Virus, and Human Herpes Virus. In one embodiment, the viral infection includes but is not limited human immunodeficiency virus (HIV), hepatitis B virus (HBV), hepatitis C virus (HCV), Epstein-Barr virus (EBV), cytomegalovirus (CMV), varicella zoster virus (VZV) and herpes simplex virus (HSV). In one embodiment, the HSV is HSV1. In one embodiment, the viral infection is selected from the group consisting of HIV and HSV. In one embodiment, the viral infection is caused by a DNA virus. Non-limiting examples of DNA viruses include herpesviridae such as Simplexvirus, Varicellovirus, Cytomegalovirus, Roseolovirus, Lymphocryptovirus, Rhadinovirus; Adenoviridae such as Mastadenovirus; Papillomaviridae such as Alphapapillomavirus, Betapapillomavirus, Gammapapilloma, Mupapillomavirus, and Nupapillomavirus; Polyomaviridae such as Polyomavirus; Poxviridae such as Molluscipoxvirus, Orthopoxvirus, and Parapoxvirus; Anelloviridae such as Alphatorquevirus, Betatorquevirus, Gammatorquevirus; Mycodnaviridae such as Gemycircular; Parvoviridae such as Erythrovirus, Dependovirus, and Bocavirus; and Hepadnaviridae such as Orthohepadnavirus. However, the invention should not be limited to only these types of viral infection. Rather, the invention is applicable to any type of viral infection. In one embodiment, the invention is applicable to viral infections associated with dysregulated CDK. In one embodiment, the method further comprises administering to the subject an additional therapeutic agent.

In another aspect, the invention includes a method of treating or preventing cartilage degradation and/or chondrocyte death in a subject in need thereof. The method comprises administering to the subject a therapeutically effective amount of a composition comprising a compound of the invention. In one embodiment, the subject has generally experienced or imminently will experience an injury to cartilage tissue. For example, the subject may have experienced an injury (e.g., a traumatic injury) that damages cartilage tissue. The subject may also undergo or have undergone surgery to repair damaged cartilage tissue and/or to receive an osteochondral explant.

In another aspect, the invention includes a method of regulating, modulating, or inhibiting protein kinase activity to a subject in need thereof. The method comprises administering to the subject a therapeutically effective amount of a composition comprising a compound of the invention. In one embodiment, the protein kinase is selected from the group consisting of CDK1, CDK2, CDK3, CDK4, CDK5, CDK6, CDK7, CDK8 and CDK9, or any combination thereof. In another embodiment, the protein kinase is selected from the group consisting of CDK1 CDK2 and CDK9, or any combination thereof. In one embodiment, the protein kinase is CDK9. In another embodiment, the protein kinase is in a cell culture. In yet another embodiment, the protein kinase is in a mammal.

In another aspect, the invention includes a method of treating a protein kinase associated disorder to a subject in need thereof. The method comprises administering to the subject a therapeutically effective amount of a composition comprising a compound of the invention. Non-limiting examples of protein-kinase associated disorders include proliferative diseases, such as viral infections, auto-immune diseases, fungal disease, cancer, psoriasis, vascular smooth cell proliferation associated with atherosclerosis, pulmonary fibrosis, arthritis glomerulonephritis, chronic inflammation, neurodegenerative disorders, such as Alzheimer's disease, and post-surgical stenosis and restenosis. Protein kinase-associated diseases also include diseases related to abnormal cell proliferation, including, but not limited to, cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia. Additional non-limiting examples of protein kinase-associated cancers include carcinomas, hematopoietic tumors of lymphoid lineage, hematopoietic tumors of myeloid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

Protein kinase-associated disorders include diseases associated with apoptosis, including, but not limited to, cancer, viral infections, autoimmune diseases and neurodegenerative disorders.

Non-limiting examples of protein-kinase associated disorders include viral infections in a patient in need thereof, wherein the viral infections include, but are not limited to, HIV, human papilloma virus, herpes virus, poxvirus, Epstein-Barr virus, Sindbis virus and adenovirus.

Non-limiting examples of protein-kinase associated disorders include tumor angiogenesis and metastasis. Non-limiting examples of protein-kinase associated disorders also include vascular smooth muscle proliferation associated with atherosclerosis, postsurgical vascular stenosis and restenosis, and endometriosis.

Further non-limiting examples of protein-kinase associated disorders include those associated with infectious agents, including yeast, fungi, protozoan parasites such as Plasmodium falciparum, and DNA and RNA viruses.

In one embodiment, administering the compound of the invention to the subject allows for administering a lower dose of the therapeutic agent compared to the dose of the therapeutic agent alone that is required to achieve similar results in treating or preventing cancer in the subject. For example, in one embodiment, the compound of the invention enhances the anti-cancer activity of the additional therapeutic compound, thereby allowing for a lower dose of the therapeutic compound to provide the same effect. In another embodiment, the compound of the invention enhances the anti-inflammatory activity of the additional therapeutic compound, thereby allowing for a lower dose of the therapeutic compound to provide the same effect.

In one embodiment, the compound of the invention and the therapeutic agent are co-administered to the subject. In another embodiment, the compound of the invention and the therapeutic agent are coformulated and co-administered to the subject.

In one embodiment, the subject is a mammal. In another embodiment, the mammal is a human.

Therapies

The invention provides compositions and methods for treating cancer. In one embodiment, the invention provides a new class of compounds that have anti-cancer properties by targeting CDKs and reactivating silenced gene expression.

In one embodiment, the compounds of the invention are CDK-9 inhibitors that inhibit virally induced transcription, such as HSV1 and HIV, and may be useful to treat viral infections.

In one embodiment, the compounds of the invention are CDK-9 inhibitors that block the derepression of CDK-9 associated with cardiac hypertrophy and may be useful to treat cardiac hypertrophy.

In one embodiment, the compounds of the invention are CDK-9 inhibitors that block CDK-9 phosphorylation and subsequent activation of inflammatory modulators NF-kB and STAT3, and may be useful for treating conditions associated with inflammation.

In one embodiment, the compounds of the invention are useful as epigenetic modulators that reactivate silenced gene expression in cancer cells and may be used to treat various forms of cancer.

In one embodiment, the compounds of the invention are CDK inhibitors. In one embodiment, the compounds of the invention inhibit CDK-9. In one embodiment, the compounds of the invention are CDK-9 inhibitors that inhibit transcription in cancer cells by preventing phosphorylation and subsequent activation of RNA polymerase II and may be used to treat various forms of cancer.

In one embodiment, the compounds of the invention can be used to reverse the resistance that some cancers develop to Blc-2 inhibitors.

In one embodiment, the compounds of the invention can be used in combination with other epigenetic drugs to synergistically induce gene induction.

In one embodiment, the compounds are useful in combination with one or more additional compounds. In certain embodiments, these additional compounds may comprise compounds of the present invention or therapeutic agents known to treat or reduce the symptoms or effects of cancer. Such compounds include, but are not limited to, chemotherapeutics and the like.

In non-limiting examples, the compounds of the invention may be used in combination with one or more therapeutic agents (or a salt, solvate or prodrug thereof).

The compounds of the invention can either be used alone or in combination with other anti-cancer drugs to treat cancer. One type of anti-cancer drug includes cytotoxic agents (i.e., drugs that kill cancer cells in different ways). These include the alkylating agents, antimetabolites, antitumor antibiotics, and plant drugs.

Another type of anti-cancer drug includes hormones and hormone antagonists. Some tumors require the presence of hormones to grow. Many of these drugs block the effects of hormones at its tissue receptors or prevent the manufacture of hormones by the body.

Another type of anti-cancer drug includes biological response modifiers. These drugs increase the body's immune system to detect and destroy the cancer.

Non-limiting examples of anti-cancer drugs include but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine, mechlorethamine oxide hydrochloride rethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, improsulfan, benzodepa, carboquone, triethylenemelamine, triethylenephosphoramide, triethylenethiophosphoramide, trimethylolomelamine, chlomaphazine, novembichin, phenesterine, trofosfamide, estermustine, chlorozotocin, gemzar, nimustine, ranimustine, dacarbazine, mannomustine, mitobronitol, aclacinomycins, actinomycin F(1), azaserine, bleomycin, carubicin, carzinophilin, chromomycin, daunorubicin, daunomycin, 6-diazo-5-oxo-1-norleucine, doxorubicin, olivomycin, plicamycin, porfiromycin, puromycin, tubercidin, zorubicin, denopterin, pteropterin, 6-mercaptopurine, ancitabine, 6-azauridine, carmofur, cytarabine, dideoxyuridine, enocitabine, pulmozyme, aceglatone, aldophosphamide glycoside, bestrabucil, defofamide, demecolcine, elfornithine, elliptinium acetate, etoglucid, flutamide, hydroxyurea, lentinan, phenamet, podophyllinic acid, 2-ethylhydrazide, razoxane, spirogermanium, tamoxifen, taxotere, tenuazonic acid, triaziquone, 2,2',2"-trichlorotriethylamine, urethan, vinblastine, vincristine, vindesine and related agents. 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cisporphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; nemoronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; taxel; taxel analogues; taxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride;

pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

In certain embodiments, the compounds of the invention may be administered to a subject in conjunction with (e.g. before, simultaneously, or following) any number of relevant treatment modalities including chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, torisel, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the compounds of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the compounds of the present invention are administered following B-cell ablative therapy such as agents that react with CD20, e.g., Rituxan. In one embodiment, the additional therapeutic agent is Decitabine. In another embodiment, the additional therapeutic agent is an antimitotic agent. Non-limiting examples of antimitotic agents include paclitaxel, docetaxel, vinblastine, vincristine, topoisomerase inhibitors such as irenotecan, doxorubicin, and emcitabine.

In one embodiment, the compounds of the invention may be administered to a subject in conjunction with a Blc-2 inhibitor. In one embodiment, this combination is used for the treatment of hematologic malignancies, such as non-Hodgkin's lymphoma (NHL) and acute myelogenous leukemia (AML). Non-limiting examples of Bcl-2 inhibitors include ABT-199, ABT-263, ABT-737, G3139 (genasense or oblimersen), GX15-070 (obatoclax mesylate), HA14-1, TW-37, sabutoclax, Gossypol (AT-101), antimycin A, apogossypol, and 544563. In one embodiment, the compounds of the invention are useful for treating myelodyplastic syndromes.

In some embodiments, the compounds of the invention may be administered to a subject in conjunction with (e.g. before, simultaneously, or following) an anti-inflammatory agent. Non-limiting examples of anti-inflammatory agents include nonsteroidal agents ("NSAIDS") such as salicylates (e.g., salsalate, mesalamine, diflunisal, choline magnesium trisalicylate), diclofenac, diflunisal, etodolac, fenoprofen, flurbiprofen, ibuprofen, indomethacin, mefenamic acid, nabumetone, naproxen, piroxicam, phenyl butazone, ketoprofen, S-ketoprofen, ketorolac tromethamine, sulindac, tolmetin). Other anti-inflammatory drugs include steroidal agents such as beclomethasone, betamethasone, cortisone, dexamethasone, fluocinolone, flunisolide, fluticasone proprionate, fluorinated-corticoids, triamcinolone-diacetate, hydorcortisone, prednisolone, methylprednisolone, and prednisone. Immunosuppressive agents (e.g., adenocorticosteroids, cyclosporin), antihistamines and decongestants (e.g. cetirizine, astemizole (histamine III-receptor antagonist), azatidine, brompheniramine, clemastine, chlorpheniramine, cromolyn, cyproheptadine, diphenylimidazole, diphenhydramine hydrochloride, hydroxyzine, glycyrrhetic acid, homochlorocyclizine hydrochloride, ketotifen, loratadine, naphazoline, phenindamine, pheniramine, promethazine, terfenadine, trimeprazine, tripelennamine, tranilast, and the decongestants phenylpropanolamine and pseudoephedrine.

In some embodiments, the compounds of the invention may be administered to a subject in conjunction with (e.g. before, simultaneously, or following) conventional therapeutics of cardiac dysfunction or cardiovascular disease such as diuretics, inotropes, coronary vasodilators and beta blockers or conventional therapeutics of circulatory diseases such as hypertension (e.g. angiotensin converting enzyme (ACE) inhibitors, angiotensin receptor blockers (ARBs) and/or calcium channel blockers), either simultaneously or at different times. Diuretics are generally used for relief of congestive symptoms and help the kidneys rid the body of excess fluid, thereby reducing blood volume and the heart's workload. Diuretics can include, but are not limited to loop diuretics (e.g. furosemide, bumetanide); thiazide diuretics (e.g. hydrochlorothiazide, chlorthalidone, chlorothiazide); potassium-sparing diuretics (e.g. amiloride); spironolactone and eplerenone. Inotropes, such as a cardiac glycoside, a beta-adrenergic agonist or a phosphodiesterase inhibitor, strengthen the heart's pumping action in patients with low cardiac output; inotropes can include but are not limited to digoxin, dobutamine, milrinone, istaroxime, omecamtiv mecarbil. Vasodilators, cause the peripheral arteries to dilate, making it easier for blood to flow; examples of vasodilators include, but are not limited, nitroglycerin, nitorprusside, and neseritide. Activation of neurohormonal systems that include the renin-andiotensin-aldosterone system (RAAS) and the sympathetic nervous system also contribute to the pathophysiology of heart failure. Drugs that inhibit activation of RAAS fall into three major categories: ACE inhibitors (including but not limited to ramipril, enalapril, and captopril), ARBs (including but not limited to valsartan, candesartan, irbesarten and losartan), and aldosterone receptor blockers (e.g., spironolactone and eplerenone.) Beta blockers counter the effects of activation of the sympathetic nervous system and slow the heart rate by blocking the effects of adrenalin; beta blockers include, but are not limited to carvedilol, metoprolol, bisoprolol, atenolol, propranolol, timolol and bucindolol.

In some embodiments, the compounds of the invention may be administered to a subject in conjunction with (e.g. before, simultaneously, or following) an anti-viral agent. Non-limiting examples of anti-viral agents include reverse transcriptase inhibitors (e.g., AZT, ddI, ddC, d4T, and 3TC) or protease inhibitors (e.g., NEVIROAPLNE, SAQULNAVIR, RITNOVIR, and INDINARVIR).

In another aspect, the compounds useful within the methods of the invention may be used in combination with one or more additional compounds useful for treating HIV infections. These additional compounds may comprise compounds that are commercially available or synthetically accessible to those skilled in the art. These additional compounds are known to treat, prevent, or reduce the symptoms of HIV infections.

In non-limiting examples, the compounds useful within the invention may be used in combination with one or more of the following anti-HIV drugs:

HIV Combination Drugs: efavirenz, emtricitabine or tenofovir disoproxil fumarate (Atripla®/BMS, Gilead); lamivudine or zidovudine (Combivir®/GSK); abacavir or lamivudine (Epzicom®/GSK); abacavir, lamivudine or zidovudine (Trizivir®/GSK); emtricitabine, tenofovir disoproxil fumarate (Truvada®/Gilead).

Entry and Fusion Inhibitors: maraviroc (Celsentri®, Selzentry®/Pfizer); pentafuside or enfuvirtide (Fuzeon®/Roche, Trimeris). Integrase Inhibitors: raltegravir or MK-0518 (Isentress®/Merck).

Non-Nucleoside Reverse Transcriptase Inhibitors: delavirdine mesylate or delavirdine (Rescriptor®/Pfizer); nevirapine (Viramune®/Boehringer Ingelheim); stocrin or efavirenz (Sustiva®/BMS); etravirine (Intelence®/Tibotec).

Nucleoside Reverse Transcriptase Inhibitors: lamivudine or 3TC (Epivir®/GSK); FTC, emtricitabina or coviracil (Emtriva®/Gilead); abacavir (Ziagen®/GSK); zidovudina, ZDV, azidothymidine or AZT (Retrovir®/GSK); ddI, dideoxyinosine or didanosine (Videx®/BMS); abacavir sulfate plus lamivudine (Epzicom®/GSK); stavudine, d4T, or estavudina (Zerit®/BMS); tenofovir, PMPA prodrug, or tenofovir disoproxil fumarate (Viread®/Gilead).

Protease Inhibitors: amprenavir (Agenerase®/GSK, Vertex); atazanavir (Reyataz®/BMS); tipranavir (Aptivus®/Boehringer Ingelheim); darunavir (Prezist®/Tibotec); fosamprenavir (Telzir®, Lexiva®/GSK, Vertex); indinavir sulfate (Crixivan®/Merck); saquinavir mesylate (Invirase®/Roche); lopinavir or ritonavir (Kaletra®/Abbott); nelfinavir mesylate (Viracept®/Pfizer); ritonavir (Norvir®/Abbott).

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In one embodiment, the therapeutic agent is a hypomethylating drug (HMA). In another embodiment, the therapeutic agent is an immune oncology (IO) product.

Administration/Dosage/Formulations

The regimen of administration may affect what constitutes an effective amount. The therapeutic formulations may be administered to the subject either before or after the onset of cancer. Further, several divided dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, (e.g., human), may be carried out using known procedures, at dosages and for periods of time effective to treat cancer in the patient. An effective amount of the therapeutic compound necessary to achieve a therapeutic effect may vary according to factors such as the state of the disease or disorder in the patient; the age, sex, and weight of the patient; and the ability of the therapeutic compound to treat a cancer in the patient. Dosage regimens may be adjusted to provide the optimum therapeutic response. For example, several divided doses may be administered daily. In another example, the dose may be proportionally reduced as indicated by the exigencies of the therapeutic situation. A non-limiting example of an effective dose range for a therapeutic compound of the invention is from about 1 mg/kg to about 5,000 mg/kg of body weight/per day. One of ordinary skill in the art would be able to assess the relevant factors and make the determination regarding the effective amount of the therapeutic compound without undue experimentation.

Actual dosage levels of the active ingredients in the pharmaceutical compositions of this invention may be varied to obtain an amount of the active ingredient that is effective to achieve the desired therapeutic response for a particular patient, composition, and mode of administration, without generating excessive side effects in the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical professional, e.g., physician or veterinarian, having ordinary skill in the art may readily determine and prescribe the effective amount of the pharmaceutical composition required. For example, the physician or veterinarian could start with a dosage of the compound of the invention in the pharmaceutical composition at a level that is lower than the level required to achieve the desired therapeutic effect, and then increase the dosage over time until the desired effect is achieved.

In particular embodiments, it is advantageous to formulate the compound in dosage unit form for ease of administration and uniformity of dosage. "Dosage unit form" as used herein refers to a physically discrete unit containing a predetermined quantity of therapeutic compound calculated to produce the desired therapeutic effect, in association with the required pharmaceutical vehicle. The dosage unit forms of the invention can be selected based upon (a) the unique characteristics of the therapeutic compound and the particular therapeutic effect to be achieved, and (b) the limitations inherent in the art of compounding/formulating such a therapeutic compound for the treatment of cancer in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), vegetable oils, and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is useful to include isotonic agents, for example, sugars, sodium chloride, or polyalcohols such as mannitol and sorbitol, in the composition. Prolonged absorption of the injectable compositions can be achieved by including in the composition an agent which delays absorption, for example, aluminum monostearate or gelatin. In one embodiment, the pharmaceutically acceptable carrier is DMSO, alone or in combination with other carriers.

The therapeutically effective amount or dose of a compound of the present invention depends on the age, sex and weight of the patient, the current medical condition of the patient and the severity of the cancer in the patient being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the compound of the invention for administration may be in the range of from about 1 µg to about 10,000 mg, from about 20 µg to about 9,500 mg, from about 40 µg to about 9,000 mg, from about 75 µg to about 8,500 mg, from about 150 µg to about 7,500 mg, from about 200 µg to about 7,000 mg, from about 3050 µg to about 6,000 mg, from about 500 µg to about 5,000 mg, from about 750 µg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second compound as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are administered to the patient from about one to about five times per day or more. In various embodiments, the compositions of the invention are administered to the patient, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the invention will vary from individual to individual depending on many factors including, but not limited to, age, the disease or disorder to be treated, the severity of the disease or disorder to be treated, gender, overall health, and other factors. Thus, the invention should not be construed to be limited to any particular dosing regime and the precise dosage and composition to be administered to any patient is determined by the medical professional taking all other factors about the patient into account.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, may be reduced to a level at which the improved disease is retained. In some embodiments, a patient may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the present invention is directed to a packaged pharmaceutical composition comprising a container holding a therapeutically effective amount of a compound of the invention, alone or in combination with a second pharmaceutical agent; and instructions for using the compound to treat or prevent cancer in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral administration, suitable forms include tablets, dragees, liquids, drops, suppositories, or capsules, caplets and gelcaps. The compositions formulated for oral use may be prepared according to any method known in the art and such compositions may contain one or more agents selected from the group consisting of inert, non-toxic pharmaceutically acceptable excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art recognize, or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Synthesis of Compounds

Synthesis of 4-amino-2-(exo-bicyclo[2.2.1]heptan-2-ylamino)thiazol-5-yl)(2-nitrophenyl)-methanone

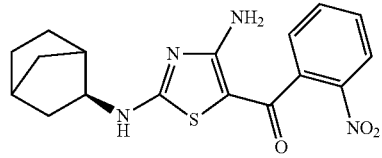 [SMILES: Nc1nc(N[C@H]2CC3CCC2C3)sc1C(=O)c1ccccc1[N+](=O)[O-]]

Step 1: Synthesis of (4-amino-2-(methylthio)thiazol-5-yl)(2-nitrophenyl)methanone

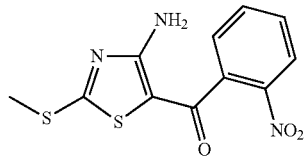 [SMILES: CSc1nc(N)c(C(=O)c2ccccc2[N+](=O)[O-])s1]

2-Bromo-2'-nitroacetophenone (1.005 mmol; 245 mg) and triethylamine (1.296 mmol; 180 μL) were added sequentially to a solution of cyanimidodithiocarbonic acid S-methyl ester S-potassium salt (0.902 mmol; 154 mg) in anhydrous dimethylformamide (4.0 mL). This mixture was stirred at 80° C. for 3 hours. It was cooled to room temperature and concentrated down. The residue was partitioned between ethyl acetate and water. The insoluble solids suspended between the organic and aqueous layers were filtered off and washed with ethyl acetate to afford the product as a yellow solid. $^1$H NMR (400 MHz, DMSO) δ 8.13 (dd, J=8.08 Hz, J=0.92 Hz, 1H), 7.97 (bs, 2H), 7.84 (td, J=7.48 Hz, J=1.08 Hz, 1H), 7.74 (td J=8.08 Hz, J=1.44 Hz, 1H), 7.68 (dd, J=7.48 Hz, J=1.36 Hz, 1H), 2.62 (s, 3H); MS(ESI): m/z 296.0 [(M+H)$^+$].

Step 2: Synthesis of 4-amino-2-(exo-bicyclo[2.2.1]heptan-2-ylamino)thiazol-5-yl)(2-nitrophenyl)methanone

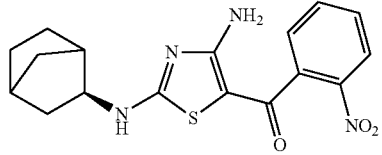 [SMILES: Nc1nc(N[C@H]2CC3CCC2C3)sc1C(=O)c1ccccc1[N+](=O)[O-]]

A solution of (4-amino-2-(methylthio)thiazol-5-yl)(2-nitrophenyl)methanone (0.1693 mmol; 50 mg) and exo-2-aminonorbornane (3.386 mmol; 401 μL) in ethanol (2 mL) was stirred at 100° C. in a glass pressure vessel overnight. The solution was cooled to room temperature and concentrated down. The crude product was purified by column chromatography on silica gel using a gradient solvent system of 0 to 100% of ethyl acetate in hexanes to afford the 4-amino-2-(exo-bicyclo[2.2.1]heptan-2-ylamino)thiazol-5-yl)(2-nitrophenyl)methanone as an orange glassy solid. $^1$H NMR (400 MHz, CDCl$_3$) δ 8.08 (d, J=7.84 Hz, 1H), 7.67 (t, J=7.52 Hz, 1H), 7.56 (t, J=7.68 Hz, 2H), 5.65 (bd, J=6.12 Hz, 1H), 3.17 (bs, 1H), 2.31 (bs, 2H), 1.82 (m, 1H), 1.49 (m, 3H), 1.32 (m, 1H), 1.25 (m, 1H), 1.11 (m, 2H); MS(ESI): m/z 359.0 [(M+H)$^+$].

Synthesis of (4-amino-2-((tetrahydro-2H-pyran-4-yl)amino)thiazol-5-yl)(2-nitrophenyl)methanone

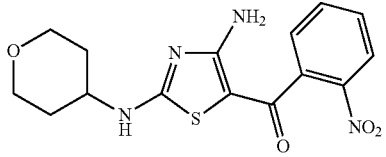 [SMILES: Nc1nc(NC2CCOCC2)sc1C(=O)c1ccccc1[N+](=O)[O-]]

Prepared using the same procedure as described for 4-amino-2-(exo-bicyclo[2.2.1]heptan-2-ylamino)thiazol-5-yl)(2-nitrophenyl)methanone substituting tetrahydro-2H-pyran-4-amine in place of exo-2-aminonorbornane to afford the titled compound as an orange solid. $^1$H NMR (400 MHz, CD$_3$OD) δ 8.10 (dd, J=8.20 Hz, J=0.96 Hz, 1H), 7.76 (td, J=7.52 Hz, J=1.16 Hz, 1H), 7.64 (td, J=7.52 Hz, J=1.44 Hz, 1H), 7.56 (dd, J=7.56 Hz, J=1.40 Hz, 1H), 3.93 (m, 2H), 3.47 (m, 2H), 3.32 (m, 1H), 1.97 (m, 2H), 1.55 (m, 2H); ESIMS: m/z 719.4 [(2M+Na)$^+$].

Synthesis of 2-(4-amino-2-(((2S)-bicyclo[2.2.1]heptan-2-yl)amino)thiazole-5-carbonyl)benzonitrile

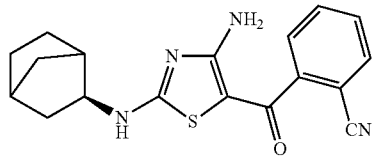 [SMILES: N#Cc1ccccc1C(=O)c1sc(N[C@H]2CC3CCC2C3)nc1N]

Step 1: Synthesis of 2-(2-bromoacetyl)benzonitrile

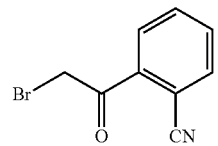 [SMILES: N#Cc1ccccc1C(=O)CBr]

Phenyltrimethyl ammonium tribromide (0.6889 mmol; 259 mg) was added to a solution of 2-acetylbenzenecarbonitrile (0.6889; 100 mg) in acetonitrile (2.5 ml). This solution was stirred for 3 hours at room temperature and then concentrated down. The residue was partitioned between ethyl acetate and water. The aqueous phase was removed. The organic phase was washed with brine, dried over anhydrous sodium sulfate and concentrated to afford the titled compound as a purple solid. This product was taken on to the next step without further purification.

Step 2: Synthesis of 2-(4-amino-2-(methylthio)thiazole-5-carbonyl)benzonitrile

2-(2-bromoacetyl)benzonitrile (0.6248 mmol; 140 mg) and triethylamine (0.8058 mmol; 113 μl) were added sequentially to a solution of cyanimidodithiocarbonic acid S-methyl ester S-potassium salt (0.5608 mmol; 196 mg) in anhydrous dimethylformamide (3.0 ml). This mixture was stirred at 80° C. for 3 hours. It was cooled to room temperature and concentrated down. The residue was partitioned between ethyl acetate and water. The aqueous layer was drained off. The organic layer was washed with brine, dried over anhydrous sodium sulfate and concentrated. The crude product was purified by flash column chromatography on silica gel using a gradient solvent system of 0 to 50% ethyl acetate in hexanes to afford the titled compound as an orange-yellow solid. $^1$H NMR (400 MHz, CDCl$_3$) δ 7.79 (d, J=7.64 Hz, 1H), 7.67 (m, 2H), 7.56 (td, J=7.52 Hz, J=1.48 Hz, 1H), 2.65 (s, 3H); ESIMS: m/z 275.7 [(M+H)$^+$].

Step 3: Synthesis of 2-(4-amino-2-(((2S)-bicyclo[2.2.1]heptan-2-yl)amino)thiazole-5-carbonyl)benzonitrile

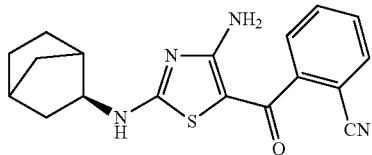 [SMILES: N#Cc1ccccc1C(=O)c1sc(N[C@H]2CC3CCC2C3)nc1N]

Prepared using the same procedure as described for step 2 of the synthesis of 4-amino-2-(exo-bicyclo[2.2.1]heptan-2-ylamino)thiazol-5-yl)(2-nitrophenyl)methanone to afford the titled compound as a yellow solid. $^1$H NMR (400 MHz, CDCl$_3$) δ 7.76 (d, J=8.00 Hz, 1H), 7.64 (m, 2H), 7.51 (td, J=7.56 Hz, J=1.52 Hz, 1H), 3.22 (bs, 1H), 2.34 (bs, 2H), 1.86 (m, 1H), 1.46-1.61 (m, 2H), 1.24-1.42 (m, 3H), 1.08-1.21 (m, 2H); ESIMS: m/z 338.7 [(M+H)$^+$].

Synthesis of (4-amino-2-(((2S)-bicyclo[2.2.1]heptan-2-yl)amino)thiazol-5-yl)(benzo[c][1,2,5]oxadiazol-4-yl)methanone

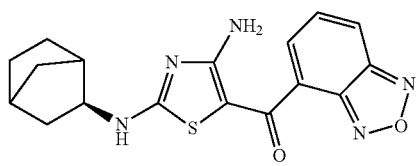 [SMILES: Nc1nc(N[C@H]2CC3CCC2C3)sc1C(=O)c1cccc2nonc12]

Step 1: Synthesis of 1,3-dibromo-2-nitrosobenzene

3-Chloroperoxybenzoic acid (77%, 11.97 mmol, 2.68 g) was added to a solution of 2,6-dibromoaniline (3.39 mmol; 1.00 g) in chloroform (24 ml). The resulting thick light green suspension was stirred at room temperature overnight. The reaction mixture was diluted with chloroform, washed with saturated aqueous sodium thiosulfate solution (2×), saturated aqueous sodium bicarbonate solution (3×) and brine, dried over anhydrous sodium sulfate and concentrated to afford the titled compound as a light tan solid. This product was taken on to the next step without further purification. $^1$H NMR (400 MHz, CDCl$_3$) δ 7.74 (d, J=7.96 Hz, 1H), 7.67 (dd, J=33.6 Hz, J=8.12 Hz, 1H), 7.25 (m, 1H).

Step 2: Synthesis of 4-bromobenzo[c][1,2,5]oxadiazole

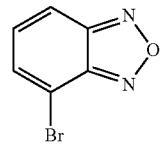

Sodium azide (4.05 mmol; 263 mg) was added to a solution of 1,3-dibromo-2-nitrosobenzene (3.68 mmol; 976 mg) in anhydrous dimethylsulfoxide (30 ml). This solution was stirred at room temperature for 2 hours and then heated at 120 degrees centigrade for 10 minutes. It was cooled to room temperature and poured over ice. The resulting precipitate was filtered off, washed with water, dissolved into methylene chloride, dried over anhydrous sodium sulfate and concentrated to afford the titled compound as an orange-tan solid. This product was taken on to the next step without further purification. $^1$H NMR (400 MHz, CDCl$_3$) δ 7.82 (d, J=9.00 Hz, 1H), 7.64 (d, J=6.96 Hz, 1H), 7.30 (m, 1H).

Step 3: Synthesis of 1-(benzo[c][1,2,5]oxadiazol-4-yl)ethan-1-one

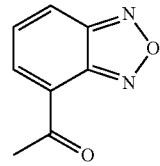

A solution of 4-bromobenzo[c][1,2,5]oxadiazole (0.5025 mmol; 100 mg) in anhydrous toluene (2 ml) was degassed and blanketed under nitrogen gas. 1-Ethoxy vinyl tributyltin (0.5528 mmol; 187 ul) and bis(triphenylphosphine) palladium (II) dichloride (0.0553 mmol; 39 mg) were added sequentially. The reaction mixture was stirred at 90° C. overnight. The resulting dark mixture was filtered through a plug of celite to yield an orange filtrate. 6N aqueous hydrogen chloride (2 ml) was added and the resulting biphasic mixture was vigorously stirred at room temperature for one hour. This mixture was concentrated down to dryness and the resulting residue was partitioned between dichloromethane and saturated aqueous sodium bicarbonate. The organic layer was removed, dried over anhydrous sodium sulfate and concentrated. The crude product was purified by flash chromatography on silica gel using a gradient solvent system of 0 to 40% ethyl acetate in hexanes to afford the titled compound as a pale yellow solid. $^1$H NMR (400 MHz, CDCl$_3$) δ 8.12 (m, 2H), 7.57 (m, 1H), 2.94 (s, 3H).

Step 4: Synthesis of 1-(benzo[c][1,2,5]oxadiazol-4-yl)-2-bromoethan-1-one

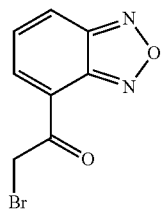 [SMILES: O=C(CBr)c1cccc2nonc12]

1-(benzo[c][1,2,5]oxadiazol-4-yl)ethan-1-one (1.332 mmol; 216 mg), ammonium acetate (0.133 mmol; 10.3 mg) and N-bromosuccinimide (1.665 mmol; 296 mg) were combined in anhydrous diethyl ether (6 ml) and stirred at room temperature for one hour. Carbon tetrachloride (6 ml) was added, the reaction solution was heated to 80° C. and half of the diethyl ether was allowed to evaporate off. The remaining solvent mixture was refluxed at 80 degrees centigrade. Extra N-bromosuccinimide was added portionwise at reflux until the reaction went to completion. The solution was cooled to room temperature and the precipitate was filtered off. The resulting clear filtrate was concentrated down. The residue was dissolved into dichloromethane, washed with water, dried over anhydrous sodium sulfate and concentrated. The crude product was purified by flash chromatography on silica gel using a gradient solvent system of 0 to 30% ethyl acetate in hexanes to afford the titled compound as an orange-yellow solid. $^1$H NMR (400 MHz, CDCl$_3$) δ 8.28 (dd, J=6.80 Hz, J=0.76 Hz, 1H), 8.16 (dd, J=9.00 Hz, J=0.76 Hz, 1H), 7.62 (m, 1H), 4.90 (s, 2H).

Step 5: Synthesis of (4-amino-2-(methylthio)thiazol-5-yl)(benzo[c][1,2,5]oxadiazol-4-yl)methanone

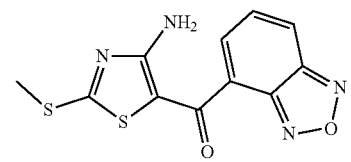 [SMILES: CSc1nc(N)c(C(=O)c2cccc3nonc23)s1]

Prepared using the same procedure as described for step 1 of the synthesis of 4-amino-2-(exo-bicyclo[2.2.1]heptan-2-ylamino)thiazol-5-yl)(2-nitrophenyl)-methanone to afford the titled compound as a black solid. $^1$H NMR (400 MHz, CD$_3$OD) δ 8.24 (bs, 2H), 8.22 (dd, J=9.12 Hz, J=0.64 Hz, 1H), 7.90 (dd, J=6.60 Hz, J=0.64 Hz, 1H), 7.71 (m, 1H), 2.65 (s, 3H); ESIMS: m/z 293.0 [(M+H)$^+$].

Step 3: Synthesis of (4-amino-2-(((2S)-bicyclo[2.2.1]heptan-2-yl)amino)thiazol-5-yl)(benzo[c][1,2,5]oxadiazol-4-yl)methanone

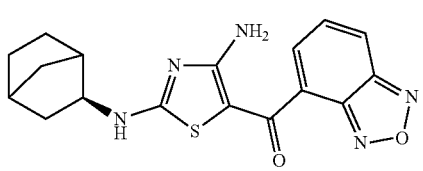 [SMILES: Nc1nc(N[C@H]2CC3CCC2C3)sc1C(=O)c1cccc2nonc12]

Prepared using the same procedure as described for step 2 of the synthesis of 4-amino-2-(exo-bicyclo[2.2.1]heptan-2-ylamino)thiazol-5-yl)(2-nitrophenyl)methanone to afford the titled compound as a reddish-brown solid. $^1$H NMR (400 MHz, CD$_3$OD) δ 7.99 (dd, J=90.4 Hz, J=0.48 Hz, 1H), 7.72 (d, J=6.52 Hz, 1H), 7.59 (m, 1H), 3.30 (bs, 1H), 2.31 (bs, 2H), 1.79 (m, 1H), 1.36-1.59 (m, 3H), 1.12-1.30 (m, 4H); ESIMS: m/z 356.1 [(M+H)$^+$].

Synthesis of (4-amino-2-(((2S)-bicyclo[2.2.1]heptan-2-yl)amino)thiazol-5-yl)(3,4,5-trimethoxyphenyl)methanone

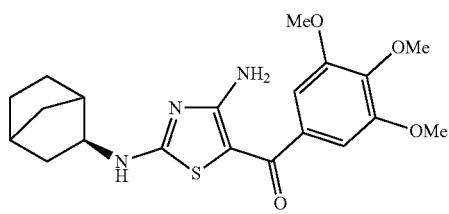 [SMILES: COc1cc(C(=O)c2sc(N[C@H]3CC4CCC3C4)nc2N)cc(OC)c1OC]

Step 1: Synthesis of 2-bromo-1-(3,4,5-trimethoxyphenyl)ethan-1-one

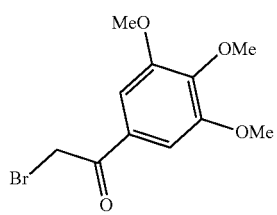 [SMILES: COc1cc(C(=O)CBr)cc(OC)c1OC]

Bromine (4.7567 mmol, 240 µl) was added dropwise to a solution of 3',4',5'-trimethoxyacetophenone (4.7567 mmol, 1.00 g) in diethyl ether (30 ml). This solution was stirred at room temperature for 3.5 hours, washed with saturated aqueous sodium bicarbonate solution, dried over anhydrous sodium sulfate and concentrated. The residual orange oil was dissolved into boiling ethanol (15 ml), allowed to cool to room temperature and then cooled in an ice bath. The resulting precipitate was filtered off and washed with cold ethanol to afford the titled compound as a white crystalline solid. $^1$H NMR (400 MHz, CDCl$_3$) δ 7.25 (s, 2H), 4.41 (s, 2H), 3.94 (s, 3H), 3.93 (s, 6H).

Step 2: Synthesis of (4-amino-2-(methylthio)thiazol-5-yl)(3,4,5-trimethoxyphenyl)methanone

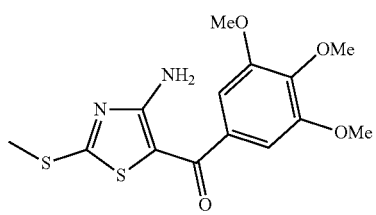 [SMILES: COc1cc(C(=O)c2sc(SC)nc2N)cc(OC)c1OC]

A solution of 2-bromo-1-(3,4,5-trimethoxyphenyl)ethan-1-one (2.2378 mmol; 647 mg) in dimethylformamide (5 ml) was added dropwise to a second solution of cyanimidodithiocarbonic acid S-methyl ester S-potassium salt (2.2378 mmol; 381 mg) in anhydrous dimethylformamide (5.0 ml) at 50° C. This mixture was stirred at 50° C. for 2 hours. Potassium carbonate (2.2378 mmol, 309 mg) was added and stirring at 50° C. was continued for one hour. It was cooled to room temperature and concentrated down. The residue was partitioned between ethyl acetate and water. The aqueous layer was removed and extracted with ethyl acetate twice. The combined ethyl acetate solutions were washed with water and brine, dried over anhydrous sodium sulfate and concentrated. The crude product was purified by flash chromatography on silica gel using a gradient solvent system of 0 to 100% ethyl acetate in hexanes to afford the titled compound as an orange-yellow solid. $^1$H NMR (400 MHz, CDCl$_3$) δ 7.03 (s, 2H), 3.913 (s, 3H), 3.907 (s, 6H), 2.67 (s, 3H); ESIMS: m/z 703.1 [(2M+Na)$^+$].

Step 3: Synthesis of 1(4-amino-2-(((2S)-bicyclo[2.2.1]heptan-2-yl)amino)thiazol-5-yl)(3,4,5-trimethoxyphenyl)methanone

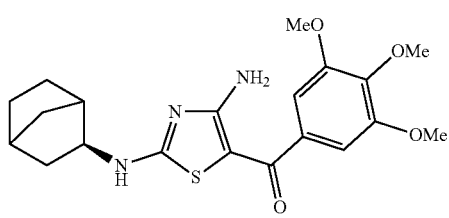 [SMILES: COc1cc(C(=O)c2sc(N[C@H]3CC4CCC3C4)nc2N)cc(OC)c1OC]

Prepared using the same procedure as described for step 2 of the synthesis of 4-amino-2-(exo-bicyclo[2.2.1]heptan-2-ylamino)thiazol-5-yl)(2-nitrophenyl)methanone to afford the titled compound as an orange-yellow solid. $^1$H NMR (400 MHz, CDCl$_3$) δ 7.02 (s, 2H), 5.57 (bd, J=6.32 Hz, 1H), 3.91 (s, 6H), 3.89 (s, 3H), 3.30 (m, 1H), 2.35 (m, 2H), 1.89 (m, 1H), 1.46-1.62 (m, 2H), 1.38 (m, 2H), 1.11-1.34 (m, 4H); ESIMS: m/z 404.2 [(M+H)$^+$].

Synthesis of (4-amino-2-(exo-bicyclo[2.2.1]heptan-2-ylamino)thiazol-5-yl)(phenyl)methanone

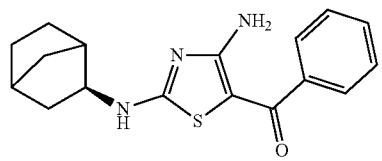 [SMILES: Nc1nc(N[C@H]2CC3CCC2C3)sc1C(=O)c1ccccc1]

Step 1: Synthesis of (4-amino-2-(methylthio)thiazol-5-yl)(phenyl)methanone

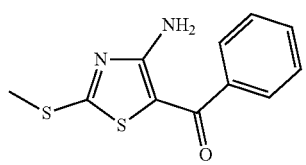 [SMILES: CSc1nc(N)c(C(=O)c2ccccc2)s1]

2-Bromoacetophenone (1.005 mmol; 200 mg) and triethylamine (1.296 mmol; 180 ul) were added sequentially to a solution of cyanimidodithiocarbonic acid S-methyl ester S-potassium salt (0.902 mmol; 154 mg) in anhydrous dimethylformamide (4.0 ml). This mixture was stirred at 80° C. for 3 hours. It was cooled to room temperature and concentrated down. The residue was partitioned between ethyl acetate and water. The aqueous layer was drained off. The organic layer was separated, washed with brine, dried over anhydrous sodium sulfate and concentrated. The crude product was purified by flash column chromatography on silica gel using a gradient solvent system of 0 to 50% of ethyl acetate in hexanes to afford the titled compound as an orange-yellow solid. $^1$H NMR (400 MHz, CDCl$_3$) δ 7.76 (m, 2H), 7.48 (m, 3H), 6.90 (bs 2H), 2.66 (s, 3H); ESIMS: m/z 251.0 [(M+H)$^+$].

Step 2: Synthesis of (4-amino-2-(exo-bicyclo[2.2.1]heptan-2-yl)amino)thiazol-5-yl)(phenyl)methanone

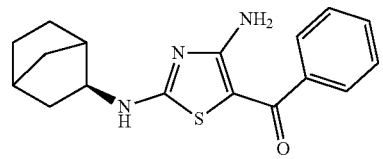 [SMILES: Nc1nc(N[C@H]2CC3CCC2C3)sc1C(=O)c1ccccc1]

A solution of (4-amino-2-(methylthio)thiazol-5-yl)(phenyl)methanone (0.1838 mmol; 46 mg) and exo-2-aminonorbornane (3.676 mmol; 436 ul) in ethanol (1.5 ml) was stirred at 100° C. in a glass pressure vessel overnight. This solution was cooled to room temperature and concentrated down. The crude product was purified by flash column chromatography on silica gel using a gradient solvent system of 0 to 100% of ethyl acetate in hexanes to afford (4-amino-2-(exo-bicyclo[2.2.1]heptan-2-yl)amino)thiazol-5-yl)(phenyl)methanone as a foamy yellow solid. $^1$H NMR (400 MHz, CDCl$_3$) δ 7.74 (m, 2H), 7.45 (m, 3H), 6.11 (bs, 1H), 3.26 (bs, 1H), 2.35 (m, 2H), 1.88 (m, 1H), 1.54 (m, 2H), 1.40 (m, 1H), 1.33 (m, 1H), 1.27 (m, 1H), 1.17 (m, 2H); ESIMS: m/z 314.1 [(M+H)$^+$].

Figure 2:
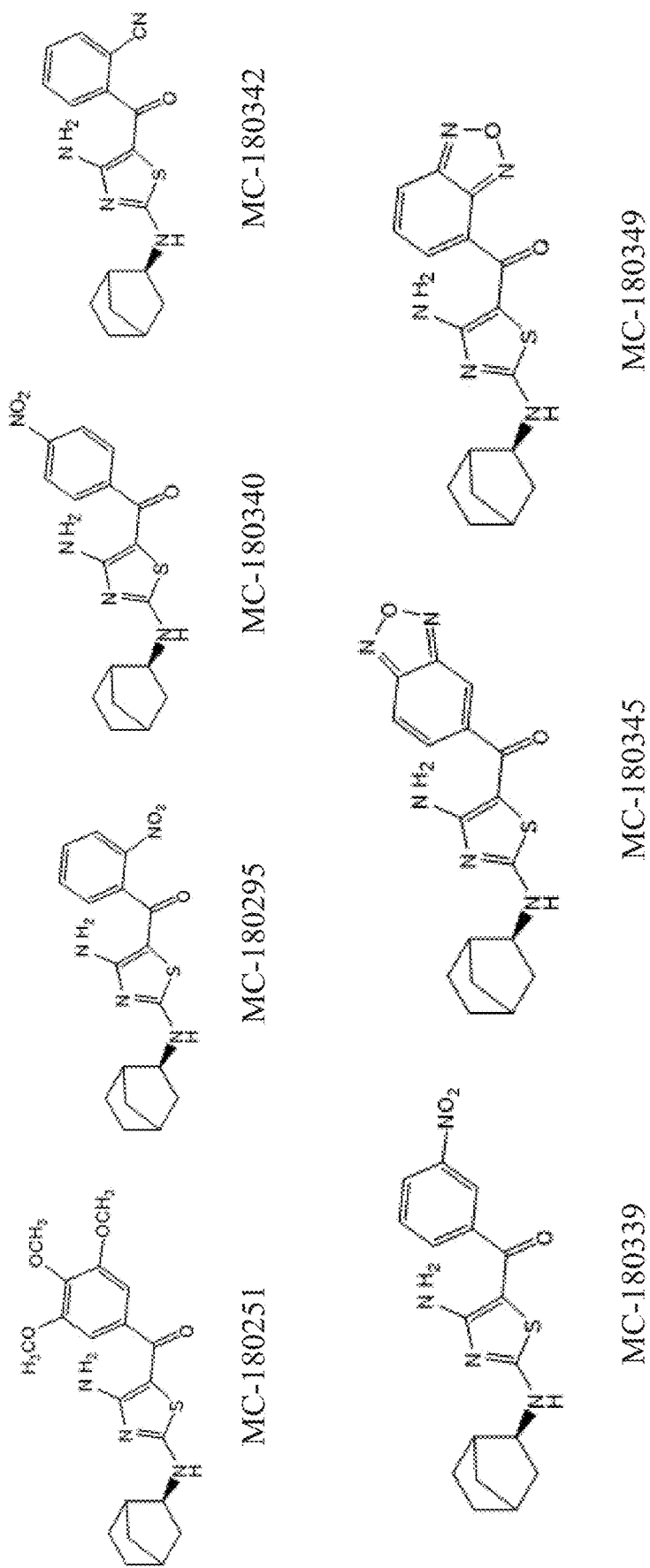
FIG. 2 depicts the structures of exemplary compounds of the invention.

Non-limiting examples of compounds of the invention are shown in FIG. 2.

Example 2: Methods of Testing

To screen the compounds of the invention for epigenetic anti-cancer activity the YB5 cell-based system, which is derived from the human colon cancer cell line SW48, was used (Si et al., 2010, Cancer Res. 70:6968-6977; Raynal et al., 2012, Cancer Res. 72:1170-1181). YB5 cells contain a single insertion of cytomegalovirus (CMV) promoter driving green fluorescent protein (GFP) gene. GFP expression is silenced in >99.9% of YB5 cells by epigenetic mechanisms. In YB5 cells, the inserted GFP gene behaves similarly to endogenous tumor suppressor genes (TSGs) silenced by epigenetic mechanisms, and it can be reactivated by epigenetic anti-cancer agents such as DNA methylation inhibitors and/or HDAC inhibitors such as depsipeptide (Si et al., 2010, Cancer Res. 70:6968-6977; Raynal et al., 2012, Cancer Research, 72:1170-1181; Wu et al., 2008, Mol. Cell Biol, 28:3219-3235). Thus, reactivation of GFP expression and the resulting fluorescence is a measure of epigenetic anti-cancer activity.

The following procedure may be used to identify compounds of useful in the invention. YB5 cells cultured in L-15 medium supplemented with 10% fetal bovine serum and 1% P/S are treated for 24 hours with varying concentrations (50 nM, 100 nM, 500 nM, 1 µM, 5 µM, 10 µM, 25 µM, and 50 µM) of test compounds. After treatment, cells are trypsinized and re-suspended in cell culture media with propidium iodide (PI) to stain dead cells. Reactivation of GFP is measured using flow cytometry to identify the GFP positive population. The relative activities are expressed as the percent of the response compared to treatment with 20 nM HDACi depsipeptide for 24 hours. YB5 cells are grown in 1% $CO_2$ atmosphere at 37° C.

Example 3: Targeting CDK9 Reactivates Epigenetically Silenced Genes in Cancer

The materials and methods employed in these experiments are now described.

Materials and Methods

Cell Culture

YB5 cell line was derived from SW48 colon cancer cell line in the lab (Si, et al., 2010, Cancer Res 70:6968-6977). SW48/YB5 cells were maintained in L-15 supplemented with 10% FBS and 1% penicillin/streptomycin at 1% $CO_2$ in 37° C. MCF7-GFP cell line was derived from MCF7 breast cancer cell line in the lab. HCT116-GFP colon cancer cell line (Cui, et al. (2014). A recombinant reporter system for monitoring reactivation of an endogenously DNA hypermethylated gene. Cancer Res 74, 3834-3843) was also utilized. DU145 and LnCaP prostate cancer cell lines, IMR90 normal fibroblasts, and leukemia cell lines KG-1 and HL-60 were obtained from ATCC. MCF7/MCF7-GFP, HCT116/HCT116-GFP, IMR90, DU145 and LnCaP cells were cultured in DMEM, McCoy's 5A, MEM, MEM and RPMI-1640, respectively, with 10% FBS and 1% penicillin/streptomycin at 37° C. in 5% $CO_2$. KG-1 and HL-60 were cultured in IMDM supplemented with 20% FBS at 37° C. in 5% $CO_2$. Mouse ovarian cancer ID8 cells were grown in RPMI 1640, 10% FBS and gentamicin sulfate (5 mg/mL) at 5% $CO_2$ in 37° C.

NDL-3040 Library Screening and Drug Treatments

Figure 3:
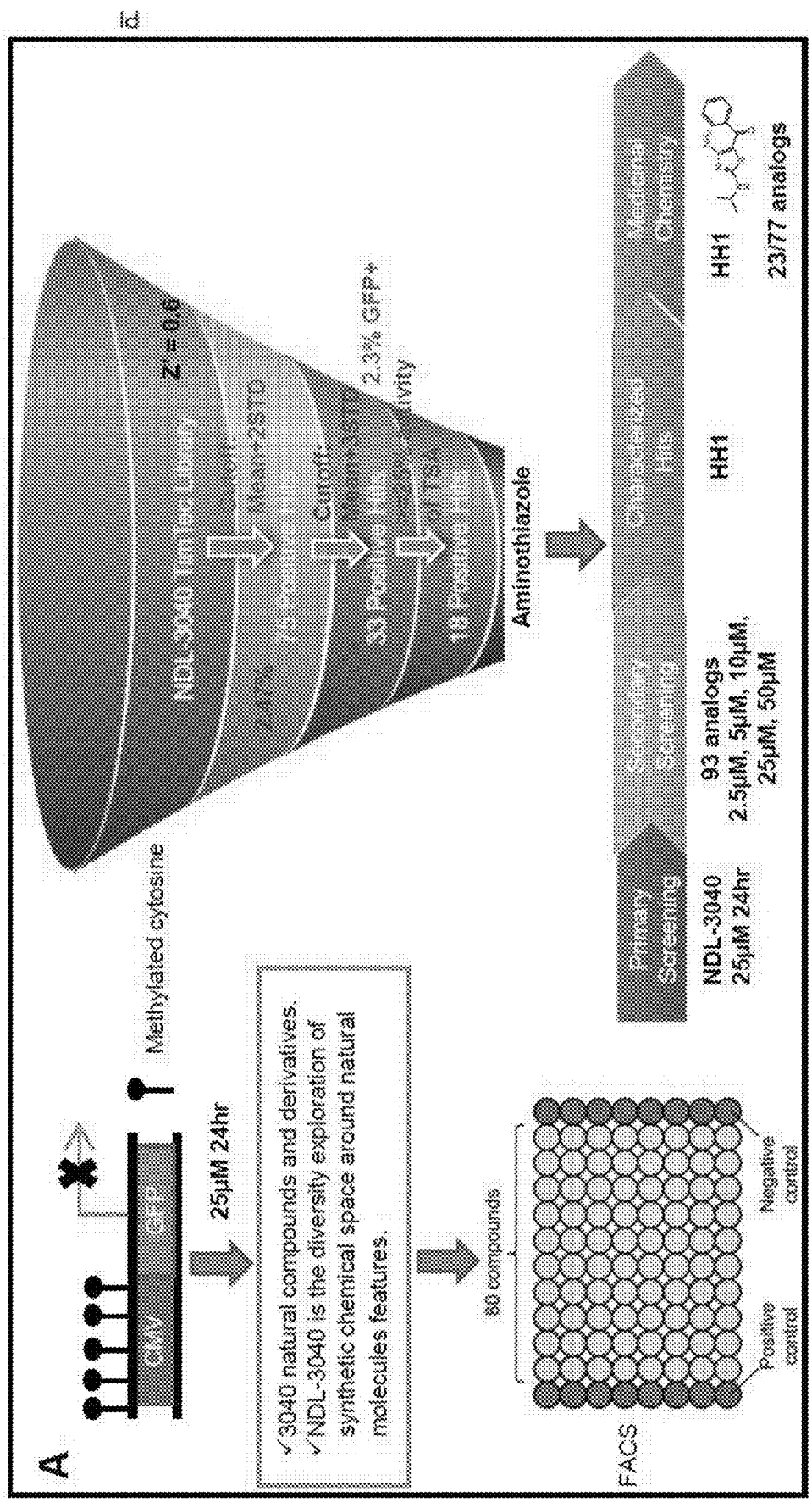
FIG. 3 depicts drug screening workflow using YB5 as a phenotypic based screening system. Drug development funnel shows the criteria for the selection of top hits.

NDL-3040 compound library consists of 3040 chemically diverse compounds that are semi-natural, derived from natural compounds, or synthetic compounds that are natural-compound-like. The small molecules were arrayed in 96-well plates as 10 mM stocks in 100% DMSO and were purchased from TimTec Inc. An aminothiazole analog library (93 small molecules) was also purchased from the same vendor and was in a 96-well plate format as 10 mM stocks in 100% DMSO. The 3040 compounds were screened at 25 µM for 24 hr. All plates were kept at −80° C. before use. YB5 cells growing in log phase (70-80% confluency) in 96-well plates were used. Each experimental 96-well plate contained 80 different compounds. A negative control (DMSO) and a positive control (5 µM TSA) were placed at the edges as shown in FIG. 3. Compounds were dispensed using an INTEGRA VIAFLO96 96-well pipette. After a 24 hr drug treatment, cells were trypsinized for 10 mins and re-suspended in L-15 medium containing propidium iodide (PI) to stain for dead cells. A total of 10000 cells per well were analyzed using Millipore Guava flow cytometer (EMD, Millipore). GFP positive percentage was calculated by excluding all the PI positive cells. After finishing the screening, the average Z-factor $$\left(Z\text{-factor} = 1 - \frac{3(\sigma_p + \sigma_n)}{|\mu_p - \mu_n|}\right)$$

was calculated to test the robustness of the assay (the means (µ) and standard deviations (σ) of both the positive control (TSA) and negative controls (DMSO) ($\mu_p$, $\sigma_p$ and $\mu_n$,$\sigma_n$)). For a single-dose, four-day treatment schedule, different drugs were added 24 hours after cell seeding, drug-free medium was replenished three days later, and downstream experiments were performed on the following day. For daily treatment schedules, drug-free media were changed every day before supplementing new drugs. All drugs were originally in 100% DMSO stocks. The final concentration of DMSO in drug-treated cultures was 5%. Eighteen compounds identified as positive hits by the screening were purchased in powder form from TimTec Inc for validation. Several multi-CDK inhibitors (alsterpaullone (Sigma-Aldrich, A4847), GW8510 (Sigma-Aldrich, G7791), roscovitine (Millipore Sigma, 557360), RGB286147 (Millipore Sigma, 219491), dinaciclib (Selleckchem, S2768), SNS-032 (Selleckchem, S1145), iCDK9 (Chemscene, LLC) and flavopiridol (Santa Cruz, sc-202157)) were also purchased and used in this project. Other chemicals used include PFI-3 (Selleckchem, S7315), CHIR99021 (Cayman, 252917-06-9), trichostatin A (TSA) (Sigma-Aldrich, T8552), SAHA (Sigma-aldrich, SML0061), depsipeptide (Sigma-Aldrich, SML1175), valproic acid (Sigma-Aldrich, 1708707), decitabine (DAC, Sigma-Aldrich, A3656) and tretinoin (ATRA, Selleckchem, S1653). All the compounds above were dissolved in 100% DMSO at 10 mM stock concentration except for ATRA (dissolved in ethanol) and DAC (dissolved in water).

DNA Extraction and DNA Methylation Analysis

DNA extraction, bisulfite conversion, and pyrosequencing was carried out using previously described methods (Si, J., Boumber, Y. A., Shu, J., Qin, T., Ahmed, S., He, R., Jelinek, J., and Issa, J. P. (2010). Cancer Res 70, 6968-6977).

siRNA Knockdown

ON-TARGETplus Non-targeting siRNA (siN) (D-001810-10), SMARTpool siSMARCA4 (L-010431-00-0005), CBX5 (L-004296-00-0005) and CDK9 (L-003243-00-0010) were ordered from GE Dharmacon and diluted in water. A previously validated siCBX5 oligo (GGAUUGCC-CUGAGCUAAUUUU (SEQ ID NO. 1) (Ambion)) was also used for transfection. Transfection was performed using Lipofectamine® RNAiMAX Reagent (ThermoFisher Scientific) according to the manufacturer's instructions at a 20 nM final working concentration.

Plasmids Transfection and Viral Transduction

Cells were transfected with Cdc2-DN-HA, CDK2-DN-HA, Rc-dnCDK9, pCMV5 BRG1-Flag, GFP-CDK9 and pcDNA-HA-HP1α plasmids for 72 hr to overexpress dnCDK1, dnCDK2, dnCK9, BRG1, CDK9 and HP1α using Lipofectamine 3000 (ThermoFisher Scientific) according to the manufacturer's instructions. YB5 and HCT116-GFP cells were infected with Ad-T-dnCDK9 plus Adeno-X™ Tet-Off™ adenoviruses (dnCDK9) in the presence or absence of doxycycline (tet) as previously described (Garriga, J., Xie, H., Obradovic, Z., and Grafia, X. (2010). J Cell Physiol 222, 200-208) for 72 hr before processing for analysis. Wild type Ad-CyclinT1 and Ad-CDK9 were also transduced for 72 hr to overexpress CyclinT1 and CDK9 (Garriga, J., Bhattacharya, S., Calbó, J., Marshall, R. M., Truongcao, M., Haines, D. S., and Grafia, X. (2003). Mol Cell Biol 23, 5165-5173). Cdc2-DN-HA (#1889), CDK2-

DN-HA (#1885), pCMV5 BRGI-Flag (#19143) and pcDNA-HA-HP1α (#24078) plasmids were purchased from Addgene. GFP-CDK9 plasmid was a generous gift from Bassel E. Sawaya, Temple University.

Biochemistry Assays

HDAC inhibitory activity assays were performed using FLUOR DE LYS® HDAC fluorometric activity assay kit from Enzo following the manufacturer's instructions. Glo-Max®-Multi Detection System (Promega) was used to read the fluorescence signals. Histone methyltransferase and demethylase enzymatic assays were performed by BPS Bioscience at 10 µM in duplicates. Kinase enzymatic assays were performed by Nanosyn using microfluidic technology. 250 kinome screening was done in duplicates using MC180295 at 1 µM. IC50 curves against 10 CDKs were created for MC180295. The human kinome tree was annotated using the online Kinome Render software (Chartier, M., Chénard, T., Barker, J., and Najmanovich, R. (2013). PeerJ 1, e126). Isotope kinase assay was performed using previously described methods (Garriga, J., Peng, J., Parreño, M., Price, D. H., Henderson, E. E., and Graña, X. (1998). Oncogene 17, 3093-3102) using recombinant active full-length CDK9/CyclinT1 (Millipore, 14-685) and SMARCA4 (Abcam, ab82237) in the presence or absence of CDK9 inhibitors.

Flow Cytometry

For drug screening and dose response validations, GFP positive cells were detected by Millipore Guava flow cytometer (EMD, Millipore). Cell cycle analysis was performed using BD FACSCalibur™ by propidium iodide staining four days after drug treatment. Sub-G1 population percentage was also included to measure apoptotic cell proportion. Data were analyzed using FlowJo software version 10.2. For the cell differentiation analysis, cells were washed and stained with propidium iodide (PI), CD11 b (BD Biosciences, #562793) and the isotype control IgG (BD Biosciences, #555748). Flow cytometry analysis was performed on a Millipore Guava flow cytometer (EMD, Millipore). For the ID8 in vivo experiments, ascites was drained from 5-10 mice per group and incubated in ACK buffer (Thermo Fisher) to lyse red blood cells for 10 minutes, then washed. Ascites from each mouse was individually lysed and prepared for flow cytometry. Mononuclear cells collected were cultured for 4 hours in RPMI with 5% Fetal Bovine Serum and in the presence of Cell Stimulation Cocktail (plus protein transport inhibitors; eBioscience). Cells were then washed and stained for cell surface markers including Live/Dead (eBioscience #65-0865-18), CD45 (BD Biosciences, #563891), CD3 (BD Biosciences, #560527), MHC II (Biolegend #107619, Isotype Control #400627), CD80 (BD Biosciences, #553769), CD86 (BD Biosciences, #558703) and CD11c (BD Biosciences, #564079). Flow cytometry acquisition was performed on an LSRII cytometer (BD Biosciences) and data were analyzed using FlowJo software version 10.2.

Co-Immmunoprecipitation

For endogenous Co-IP experiments, YB5 cells were used. For over-expression studies, HEK293T cells were transiently transfected with either empty vector or GFP-CDK9 or FLAG-SMARCA4. Cells were washed with ice-cold PBS and lysed in M-PER lysis buffer (Pierce, catalogue #78501) containing Protease inhibitor cocktail (Sigma, catalogue #11836170001). Protein was quantified by standard BCA protocol (Thermo Scientific). Cell extracts were incubated with antibody against CDK9 or GFP or FLAG-M2 tag. Separate lysate tube was prepared from samples for incubation with species—matched normal mouse IgG. Samples were incubated overnight with gentle rotation at 4° C. Protein G Dynabeads (Life Technologies) were incubated with the antigen-antibody complex for 2.5 hours the following day. Beads were washed four times with lysis buffer with gentle agitation for 5 minutes per wash. 2× Laemmli sample buffer (Bio-Rad) was used for elution of complex from beads followed by Western blotting along with the whole cell extract.

Immunoprecipitation

YB5 cells were harvested after 15 minutes to 4 hours of treatment using M-PER lysis buffer containing Protease inhibitor cocktail (Sigma, catalogue #11836170001) and phosphatase inhibitor cocktail (Sigma, catalogue #4906845001). The total protein concentration was measured in all samples by standard BCA protocol (Thermo Scientific) to ensure that equal amounts of protein were added to each sample. IP was performed overnight at 4° C. using normal mouse IgG (control) or SMARCA4 (BRG1) antibody (Santa Cruz G7). The following day immunecomplexes were incubated for 2.5 hours at 4° C. with Protein G Dynabeads (Invitrogen). Immunoprecipitates were washed with gentle agitation to remove non-specific binding to the beads. Samples were eluted in 2× Laemmli buffer, denatured by boiling, and subjected to sodium dodecyl sulphate polyacrylamide-gel electrophoresis (SDS-PAGE) using Bio-Rad mini system (Bio-Rad). The blots were then processed as mentioned above.

qPCR

Total RNA was extracted using TRIzol reagent (Invitrogen) following the manufacturer's protocol and RNA concentrations were measured using Nanodrop. cDNAs were synthesized using High Capacity cDNA Reverse Transcription Kit (ThermoFisher) and qPCR was performed using either ready-made TaqMan® assays or SYBR-green using custom-designed primers. All the data were analyzed using Applied Biosystems software (StepOne™ Software V2.3). For all experiments, relative expression levels of the target genes were determined by calculating the $2^{-\Delta\Delta Ct}$ values. All experiments were performed at least in triplicates. Either GAPDH or 18S rRNA was used as an internal normalization control for protein coding genes. RPLPO was used as an internal normalization control for ERVs. All SYBR-green primers were described previously and are listed in Table 1 along with TaqMan® probes used.

| SYBR green primers for quantitative PCR | Sequence |
|---|---|
| ERVMER34-1 F | GAATTCAGTGCCACTAAGCAGAC (SEQ ID NO. 5) |
| ERVMER34-1 R | TCGGTATATCCAAGACATGATCC (SEQ ID NO. 6) |
| ERV-Fb1 F | ATATCCCTCACCACGATCCTAATA (SEQ ID NO. 7) |
| ERV-Fb1 R | CCCTCTGTAGTGCAAAGACTGATA (SEQ ID NO. 8) |
| ERV9-1 F | TCTTGGAGTCCTCACTCAAACTC (SEQ ID NO. 9) |
| ERV9-1 R | ACTGCTGCAACTACCCTTAAACA (SEQ ID NO. 10) |
| ERV-F F | CAGGAAACTAACTTTCAGCCAGA (SEQ ID NO. 11) |
| ERV-F R | TAAAGAGGGCATGGAGTAATTGA (SEQ ID NO. 12) |

| | |
|---|---|
| MLTA10 F | TCTCACAATCCTGGAGGCTG (SEQ ID NO. 13) |
| MLTA10 R | GACCAAGAAGCAAGCCCTCA (SEQ ID NO. 14) |
| RPLPO F | CAGACAGACACTGGCAACA (SEQ ID NO. 15) |
| RPLPO R | ACATCTCCCCCTTCTCCTT (SEQ ID NO. 16) |
| Taqman probes for quantitative PCR | Catalog Number/Sequence |
| GFP | Previously published (Si et al., 2010) |
| MGMT | Hs01037698_m1 |
| RARB | Hs00977140_m1 |
| SYNE1 | Hs00323942_m1 |
| NPR3 | Hs01099013_m1 |
| PYGM | Hs00989942_m1 |
| RRAD | Hs00188163_m1 |
| MYC | Hs00153408_m1 |
| CBX5 | Hs01127577_m1 |
| FAT4 | Mm01291141_m1 |
| CHD5 | Mm01258676_m1 |
| RECK | Mm01299530_m1 |
| GAPDH | Mm99999915_g1 |

RNA-seq

RNA from experiments in biological triplicates was isolated using RNeasy Mini Plus Kit (QIAGEN) following the manufacturer's instructions. Strand-specific RNA libraries were generated from 1 µg of RNA using TruSeq stranded total RNA with Ribo-Zero Gold (Illumina). Sequencing was performed using single end reads (50 bp, average 50 million reads per sample) on the HiSeq2500 platform (Illumina) at Fox Chase Cancer Center Genomic Facility. Sequenced reads were aligned to the hg19 genome assembly using TopHat2 (Kim, D., Pertea, G., Trapnell, C., Pimentel, H., Kelley, R., and Salzberg, S. L. (2013). Genome Biol 14, R36). The expression level and fold change of each treatment group was evaluated using EdgeR (Robinson, M. D., McCarthy, D. J., and Smyth, G. K. (2010), Bioinformatics 26, 139-140). Genes that had 0 reads across all samples were excluded. In order to get rid of batch effects, samples were normalized using RUVr method from the RUVseq package (Risso, D., Ngai, J., Speed, T. P., and Dudoit, S. (2014). Normalization of RNA-seq data using factor analysis of control genes or samples. Nat Biotechnol 32, 896-902). RNA data were deposited in the GEO database with the accession number GSE104837.

RRBS

Triplicate samples of YB5 cells treated with 10 µM HH1 and DMSO controls were analyzed for DNA methylation changes by reduced representation bisulfite sequencing (RRBS) (Gu, H., Smith, Z. D., Bock, C., Boyle, P., Gnirke, A., and Meissner, A. (2011). Nat Protoc 6, 468-481). The NEB protocol was followed for methylated adaptors. Briefly, 1 microgram of genomic DNA was spiked 100 picograms of lambda phage DNA as the unmethylated standard and digested with MspI. Ends of restriction fragments were filled in, 3'-dA tailed and methylated adaptors (NEB E7535) were ligated to the ends of restriction fragments. Bisulfite treatment using the Epitect kit (Qiagen) followed. Bisulfite-converted libraries were amplified using EpiMark Taq DNA polymerase (NEB) and primers with barcode indices. The libraries were pooled and sequenced at Fox Chase Cancer Center Genomics Facility on Illumina HiSeq2500 instrument using single end reads of 50 bases. Bismark v0.18.1 (Krueger, F., and Andrews, S. R. (2011), Bioinformatics 27, 1571-1572) was used to align the sequences to hg19 human genome assembly. Differential methylation was analyzed using methylKit v1.3.3 (Akalin, A., Kormaksson, M., Li, S., Garrett-Bakelman, F. E., Figueroa, M. E., Melnick, A., and Mason, C. E. (2012), Genome Biol 13, R87). RRBS data were deposited in the GEO database with the accession number GSE104998.

Digital Restriction Enzyme Analysis of Methylation (DREAM)

DREAM is a method for DNA methylation analysis at tens of thousands of CpG sites across the genome (Jelinek, J., Liang, S., Lu, Y., He, R., Ramagli, L. S., Shpall, E. J., Estecio, M. R., and Issa, J. P. (2012), Epigenetics 7, 1368-1378). Sequential digests of genomic DNA with restriction endonucleases SmaI and XmaI creates specific signatures at unmethylated and methylated CpG sites. The signatures are resolved by high throughput sequencing. Briefly, two samples of 2 µg of genomic DNA from ID8 ovarian cancer cell line were digested with 20 units of SmaI (8 h at 25° C., NEB) and 20 units of XmaI (~16 h at 37° C., NEB), resulting in distinct DNA methylation signatures at CCCGGG (SEQ ID NO. 2) sites. 3' ends of the DNA fragments were repaired using Klenow fragment (3'→5' exo-) DNA polymerase and dCTP, dGTP, and dATP nucleotides. Illumina sequencing adapters were ligated to the DNA fragments and the libraries were sequenced by paired-end 40 nt sequencing on Illumina HiSeq2500. The sequencing reads were mapped to the mm9 genome and methylation values were calculated as the ratio of the number of the reads with the methylated XmaI signature over the total number of tags mapped to a given SmaI/XmaI site. The coverage threshold was set to greater than 10 reads per sample. DNA methylation data are deposited in the GEO database with the accession number GSE104997.

Anti-Proliferation Assay

Cells were seeded in 96-well plates at 40% confluency in triplicates. Fresh medium was changed the next day and drugs were added directly. After mixing thoroughly, plates were cultured in a 37° C. incubator for two more days. Drug-free fresh medium was changed the fourth day. The cells were collected on day 5 by trypsin, suspended in medium, mixed with trypan blue (1:1 ratio), and counted using LUNA II automated cell counter. Each sample was counted at least three times and the average numbers were used for the analysis. Each treatment condition was performed at least in triplicates.

Soft Agar Colony Formation Assay

Cells for colony-formation assays were pretreated with different concentrations of HH1 and MC180295 and drugs were kept in the medium for two more days and drug-free medium was changed the day before seeding (four days total). 1000 cells were then seeded in 35 mm×10 mm tissue culture dishes and cultured in a 37° C. incubator for two weeks before staining using 0.005% crystal violet (dissolved in autoclaved water with 10% EtOH). Difco™ Agar Noble (BD Biosciences, 214200) was used to make soft agar. 2× medium supplemented with 20% FBS and 2% penicillin/streptomycin was used to culture colonies. Bottom layer was made of 0.6% agarose and top layer was made of 0.3% agarose. Feeder layer with 0.3% agarose was added every week. All visible colonies were counted manually.

Histone Extraction

Histones were extracted and prepared from isolated nuclei as described previously (Sidoli, S., Bhanu, N. V., Karch, K. R., Wang, X., and Garcia, B. A. (2016). Complete Workflow for Analysis of Histone Post-translational Modifications Using Bottom-up Mass Spectrometry: From Histone Extraction to Data Analysis. J Vis Exp.). Briefly, nuclei were incubated with 0.2 M $H_2SO_4$ for 2 hours and precipitated with 33% trichloroacetic acid (TCA) overnight to extract histones from the chromatin. Purified histones were dissolved in 30 µL of 50 mM $NH_4HCO_3$, pH 8.0, and a mixture of propionic anhydride with acetonitrile (ratio of 1:3 (v/v)) was added to the histone sample in the ratio of 1:4 (v/v) for 20 minutes at room temperature. This reaction was performed twice. Histones were then digested with trypsin (enzyme:sample ratio 1:20, 6 hours, room temperature) in 50 mM $NH_4HCO_3$. After digestion, derivatization was repeated to propionylate peptide N-termini. Samples were desalted prior LC-MS analysis using C18 Stage-tips.

Mass Spectrometry Analysis

Samples were then separated using a 75 µm ID×17 cm Reprosil-Pur C18-AQ (3 µm; Dr. Maisch GmbH, Germany) nano-column mounted on an EASY-nLC nanoHPLC (Thermo Scientific, San Jose, Ca, USA). The HPLC gradient was as follows: 2% to 28% solvent B (A=0.1% formic acid; B=95% MeCN, 0.1% formic acid) over 45 minutes, from 28% to 80% solvent B in 5 minutes, 80% B for 10 minutes at a flow-rate of 300 nL/min. nLC was coupled online to an LTQ-Orbitrap Elite mass spectrometer (Thermo Scientific) and data were acquired using targeted scans and data-dependent acquisition (DDA). MS acquisition was divided into three segments, each beginning with a full MS scan: (i) MS/MS of the top seven most abundant ions (14 min), (ii) targeted CID fragmentation of common isobaric species (H3 peptide aa 9-17 with 1 acetyl, H3 peptide aa 18-26 with 1 acetyl and histone H4 peptide aa 4-17 with 1/2/3 acetyl groups) followed by CID fragmentation of the top five most abundant ions (27 min), (iii) CID fragmentation of the top ten most abundant ions (19 min). MS/MS was acquired using collision induced dissociation (CID) with normalized collision energy of 35 and collected in centroid mode. Data were searched using EpiProfile (Yuan, Z. F., Lin, S., Molden, R. C., Cao, X. J., Bhanu, N. V., Wang, X., Sidoli, S., Liu, S., and Garcia, B. A. (2015), Mol Cell Proteomics 14, 1696-1707). The peptide relative ratio was calculated using the total area under the extracted ion chromatograms of all peptides with the same amino acid sequence (including all of its modified forms) as 100%. For isobaric peptides, the relative ratio of two isobaric forms was estimated by averaging the ratio for each fragment ion with different mass between the two species. The mass spectrometry proteomics data have been deposited to the ProteomeXchange Consortium via the PRIDE (Vizcaino, J. A., Csordas, A., del-Toro, N., Dianes, J. A., Griss, J., Lavidas, I., Mayer, G., Perez-Riverol, Y., Reisinger, F., Tement, T., et al. (2016), Nucleic Acids Res 44, D447-456) (partner repository with the dataset identifier PXD007925 and 10.6019/PXD007925.

Phosphorproteomics

YB5 cells were treated with or without 500 nM MC180295 for 4 hours. Nuclear fraction was enriched using a hypotonic lysis buffer as previously described (Boden, G., Homko, C., Barrero, C. A., Stein, T. P., Chen, X., Cheung, P., Fecchio, C., Koller, S., and Merali, S. (2015), Sci Transl Med 7, 304-307). Proteins from the nuclear fraction were extracted with M-PER Mammalian Protein Extraction Reagent (Thermo Scientific, #78501) in the presence of protease and phosphatase inhibitors (Halt™ Protease Inhibitor Cocktail, #87785 and Halt™ Phosphatase Inhibitor Single-Use Cocktail, #78428). Phosphoproteins were enriched from 500 µg of nuclear extracted proteins, using a phosphoprotein purification kit (QIAGEN, #37101). Both samples were processed using in-StageTip method for digestion and peptide purification before performing LC-MS/MS proteomics analysis. The mass spectrometry proteomics data have been deposited to the ProteomeXchange Consortium via the PRIDE (Vizcaino, J. A., Csordas, A., del-Toro, N., Dianes, J. A., Griss, J., Lavidas, I., Mayer, G., Perez-Riverol, Y., Reisinger, F., Tement, T., et al. (2016). 2016 update of the PRIDE database and its related tools. Nucleic Acids Res 44, D447-456) partner repository with the dataset identifier PXD008040.

The label-free proteomics analysis was performed using the nanoelectrospray ionization (ESI) tandem MS with a LTQ Orbitrap Elite mass spectrometer (Thermo Scientific). The complete system was fully controlled by Xcalibur software (Version 3.0.63). Mass spectra processing was performed using Proteome Discoverer 2.2.0.388. The generated de-isotoped peak list was submitted to an in-house Mascot Server 2.2.07 for searching against the Homo sapiens SwissProt database (TaxID=9606, released 2017-05-10. 42,153 sequences). Mascot search parameters were set as follows: species, Homo sapiens; enzyme: trypsin; maximal two missed cleavage; dynamic modifications: phospho (S, T) and phospho (Y); mass tolerance: 20 ppm for precursor peptide ions and 0.4 dalton tolerance for MS/MS fragment ions. Phosphopeptides matches were filtered using an ion score cutoff of 30.

ChIP-qPCR

Chromatin immunoprecipitation (ChIP) was performed as described previously Raynal, N. J., Si, J., Taby, R. F., Gharibyan, V., Ahmed, S., Jelinek, J., Estecio, M. R., and Issa, J. P. (2012), Cancer Res 72, 1170-1181) (using antibodies for rabbit anti-IgG (Abcam, ab46540) and anti-histone H3K9 dimethylation (Abcam, ab1220). Signal was quantified by qPCR and was normalized as described previously (Raynal, N. J., Si, J., Taby, R. F., Gharibyan, V., Ahmed, S., Jelinek, J., Estecio, M. R., and Issa, J. P. (2012), Cancer Res 72, 1170-1181).

NSG Mice Treated with MC180295

SW48-luc cell line was generated by transfecting ffluc2ires-h2b-egfp into SW48 cells. GFP positive cells were sorted out one week after transfection and expanded for the in vivo experiments. NSG mice were then inoculated (i.p.) with 1×10$^5$ SW48-luc cells. One week later, at which time substantial tumor burden was evident by bioluminescence imaging, 5-20 mg/kg MC180295 or drug solvent was administered (i.p) every other day. 200 uL of diluted Pierce™ D-Luciferin, Monosodium Salt (Fisher, 88292) (working concentration: 15 mg/mL) was administered (i.p) into each mouse and was imaged using IVIS imaging system 5 minutes after the administration. Three vehicle treated mice and five drug treated mice were used in this study. MC180295 was dissolved in NMP, Captisol (20% w/v), PEG-400 and normal saline (PBS) in a ratio of 1:4:4:11. NMP first, followed by Captisol and PEG-400. PBS was added last.

Mouse Experiments with In Vivo Treatment of SNS-032

$2.5 \times 10^5$ ID8-VEGF-Defensin cells were injected i.p. into 7-8-week-old female C57BL/6NHsd (C57Bl/6) mice. Three days after injection, 1 mg/kg SNS-032, 10 mg/kg SNS-032, or 5% DMSO in PBS (vehicle control) was administered i.p. every 3 days for the duration of the experiment. α-PD-1 (200 ug/mouse) or IgG control were given on days 17, 20, 24, and 27 after injection. α-PD-1 (1 mg/mL in saline) was utilized. Mouse IgG isotype control was purchased from Leinco Technologies and diluted in PBS.

Comparative Modeling of MC180295 in Complex with CDK9

The SMILES string NC1=C(C(C2=C([N+]([O—])=O)C=CC=C2)=O)SC(N[C@H]3CC4CCC3C4)=N1 (corresponding to compound MC180295) was used to generate 100 low-energy conformers using the program OMEGA (Hawkins, P. C., and Nicholls, A. (2012), J Chem Inf Model 52, 2919-2936; Hawkins, P. C., Skillman, A. G., Warren, G. L., Ellingson, B. A., and Stahl, M. T. (2010), J Chem Inf Model 50, 572-584)), via the command line: omega2-in input_file.smi-out output_file.sdf.gz-prefix ligand_name-warts-maxconfs 100 At the time of our study, the Protein Data Bank (PDB) contained 389 structures of CDK kinases in complex with ligands bound at the ATP site. The protein component from each structure was aligned to a single reference structure: for this we selected the crystal structure of human CDK9/cyclinT1 in complex with ATP (PDB ID: 3BLQ) (Baumli, S., Lolli, G., Lowe, E. D., Troiani, S., Rusconi, L., Bullock, A. N., Debreczeni, J. E., Knapp, S., and Johnson, L. N. (2008), EMBO J 27, 1907-1918). The transformation applied to the protein was also applied to the ligand from each complex, yielding starting models of CDK9 in complex with a diverse variety of template ligand poses.

Each of the 100 low-energy conformers of MC180295 was sequentially aligned to each of the 389 ligand templates (i.e. a total of 38,900 overlays) using the ROCS software (Hawkins, P. C., Skillman, A. G., and Nicholls, A. (2007), J Med Chem 50, 74-82), via the command line: rocs-dbase 180295_conformers.sdf.gz-query/extracted_ligand_library.pdb-prefix structure name-cutoff-1.0-oformat sdf-scdbase true-maxhits 100-maxconfs 100-outputquery false-qconflabel title By concatenating the protein structure from human CDK9 bound to ATP with the MC180295 pose from aligning to these 389 ligand templates, this approach provided a set of complete, but unrefined, comparative modeling templates. A full-atom gradient-based energy minimization for each complex was carried out using the Rosetta macromolecular modeling suite (Leaver-Fay, et al. (2011), Methods Enzymol 487, 545-574)), then the resulting models were sorted on the basis of protein-ligand interaction energy. Four of the top-scoring ten models adopted a nearly identical pose, whereas the other six had a broad variety of other poses. Although not wishing to be bound by any particular theory, based on consistency with the available structure-activity data, this dominant cluster was confirmed as the most likely pose.

The results are now described.

In order to discover new epigenetic drugs that can be rapidly tested in the clinic, various drug libraries have been screened and positive hits have been optimized (Raynal, N. J., et al., (2017), Mol Cancer Ther 16, 397-407; Raynal, N. J., et al. (2016), Cancer Res 76, 1494-1505). As a platform for epigenetic drug screening, the well-characterized YB5 cell-based system which is derived from the human colon cancer cell line, SW48 (Raynal, et al., (2012), Cancer Res 72, 1170-1181; Si, et al., (2010), Cancer Res 70, 6968-6977), was used. YB5 cells contain a single insertion of the cytomegalovirus (CMV) promoter driving green fluorescent protein (GFP) gene. GFP expression is silenced in >99.9% of YB5 cells by epigenetic mechanisms including DNA hypermethylation leading to closed chromatin with histone deacetylation and histone methylation marks (Si, et al., (2010), Cancer Res 70, 6968-6977), and expression can be reactivated by treatment with DNA methylation inhibitors and/or HDAC inhibitors (Raynal, et al., (2012), Cancer Res 72, 1170-1181; Si, et al., (2010), Cancer Res 70, 6968-6977). Since the goal of epigenetic therapy is to reactivate silenced TSGs, the YB5 system was used as a live-cell assay for epigenetic drug screening. NDL-3040, a natural compound and derivative library consisting of 3040 compounds expanding diverse chemical structures, was screened. A novel drug class was identified that shares an aminothiazole core structure, and has epigenetic effects that are equivalent to DNA methyltransferase inhibitor (DNMTi) by targeting CDK9 without affecting DNA methylation status. Although not wishing to be bound by any particular theory, this result may be explained by showing that CDK9 is—paradoxically—also required for maintaining gene silencing in cancer cells. Based on this screen and on gene expression-based chemical optimization, MC180295 was developed to be a selective CDK9 inhibitor that may be useful for epigenetic therapy and for immunotherapy.

Identification of CDK9 as a Novel Epigenetic Target.

Figure 4:
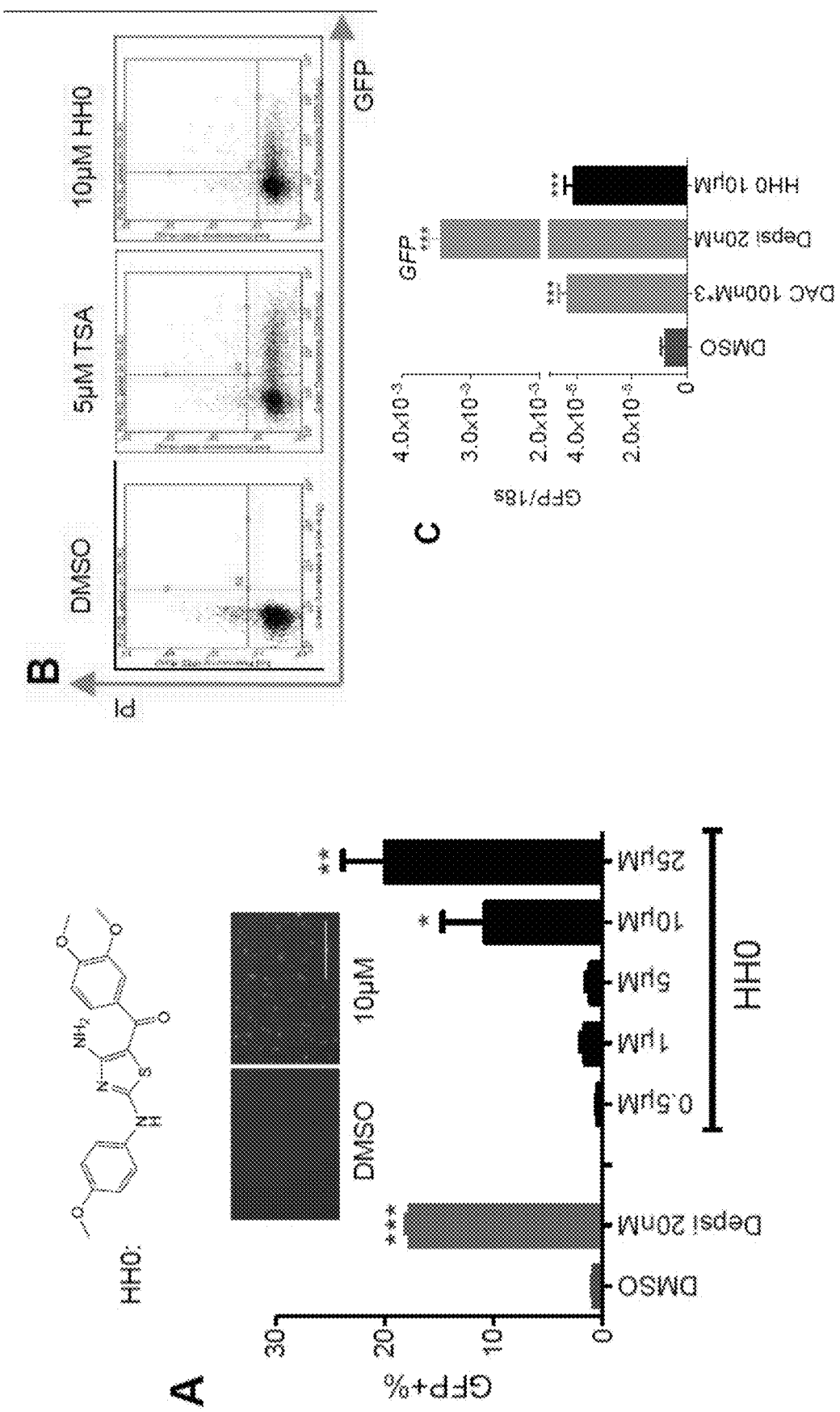
FIG. 4, comprising

Phenotypic screens provide an unbiased approach for identifying novel targets and drugs. Alive cell assay was used for epigenetic silencing (colon cancer cells, SW48/YB5 containing methylated and silenced GFP) and the NDL-3040 library was screened for potential natural compounds with epigenetic activity (FIG. 3). This assay had a robust z-factor of 0.6, indicating adequacy for high-throughput screening. At a stringent criterion of [(mean of all compounds)+3 standard deviations] for GFP induction, 33 compounds were positive (positive rate=1.1%). A further selection of hits with >25% relative activity compared to the positive control (TSA), yielded 18 compounds, 15 of which were validated by 24 hr dose curves, fluorescence microscopy, and qPCR. Five of these validated hits had similar structures including an aminothiazole core, and we focused on these for further analysis (FIG. 3). Structure and data on HH0, a representative aminothiazole compound are shown in FIGS. 4A-4C.

Figure 5:
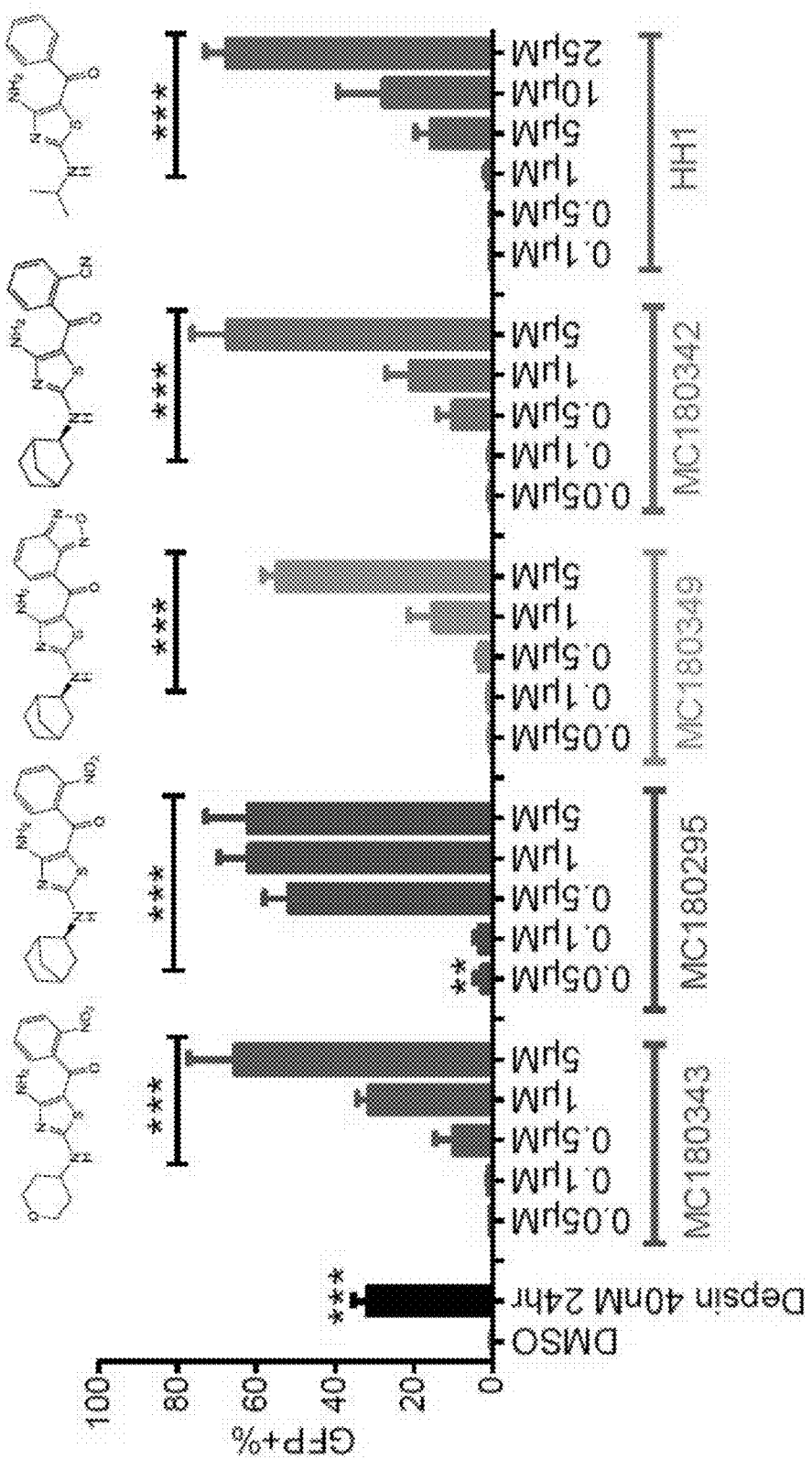
FIG. 5 depicts experimental data demonstrating GFP re-expression dose-response after four-day single-dose treatment of YB5 cells with aminothiazole analogs. Corresponding structures are shown on top. Data are shown as mean±SD, n=3. p<0.01, *p<0.001 (Student's t-test).
Figure 6:
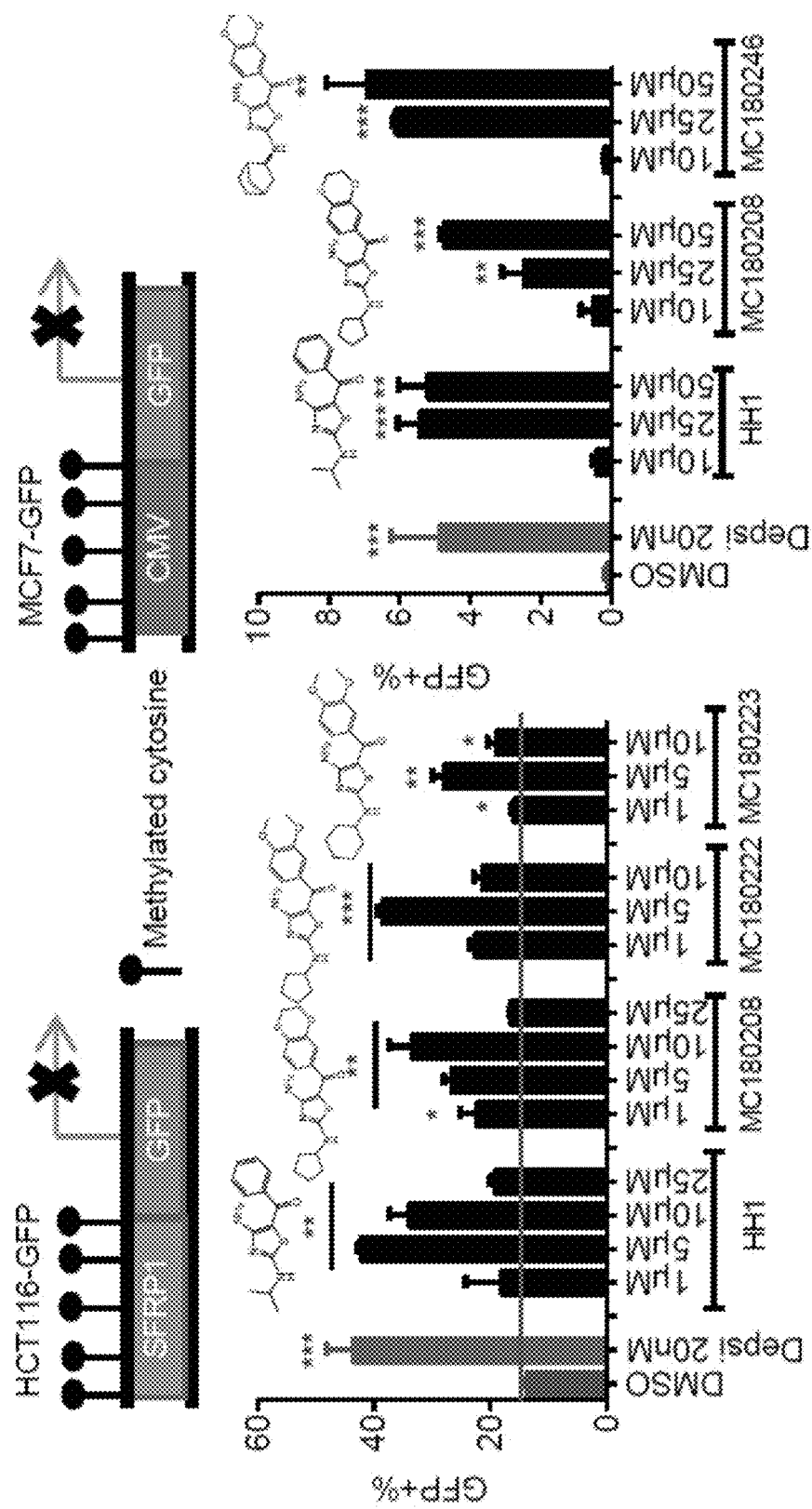
FIG. 6 depicts experimental data demonstrating GFP re-expression using different doses of HH1 and analogs in HCT116 (24 hr) and MCF7 cells (one-dose, four-day) (n=3). Data are shown as mean±SD. *p<0.05, p<0.01, *p<0.001 (Student's t-test).

Next, a second library consisting of 93 aminothiazole analogs at multiple doses (ranging from 2.5 μM to 50 μM) was screened and HH1 was identified as the most potent in this series (FIG. 3). HH1 was active at 5 μM in YB5 cells (FIG. 5) and was also successfully validated in HCT116-GFP, a colon cancer cell line where GFP was inserted downstream of the endogenous hypermethylated promoter SFRP1 (Cui, Y., et al., (2014), Cancer Res 74, 3834-3843), as well as in MCF7-GFP, a breast cancer line derived by introducing GFP under the control of a methylated CMV promoter (FIG. 6). Thus, HH1 (and other aminothiazole analogs) can reactivate silenced GFP in three distinct live cell assays.

Figure 7:
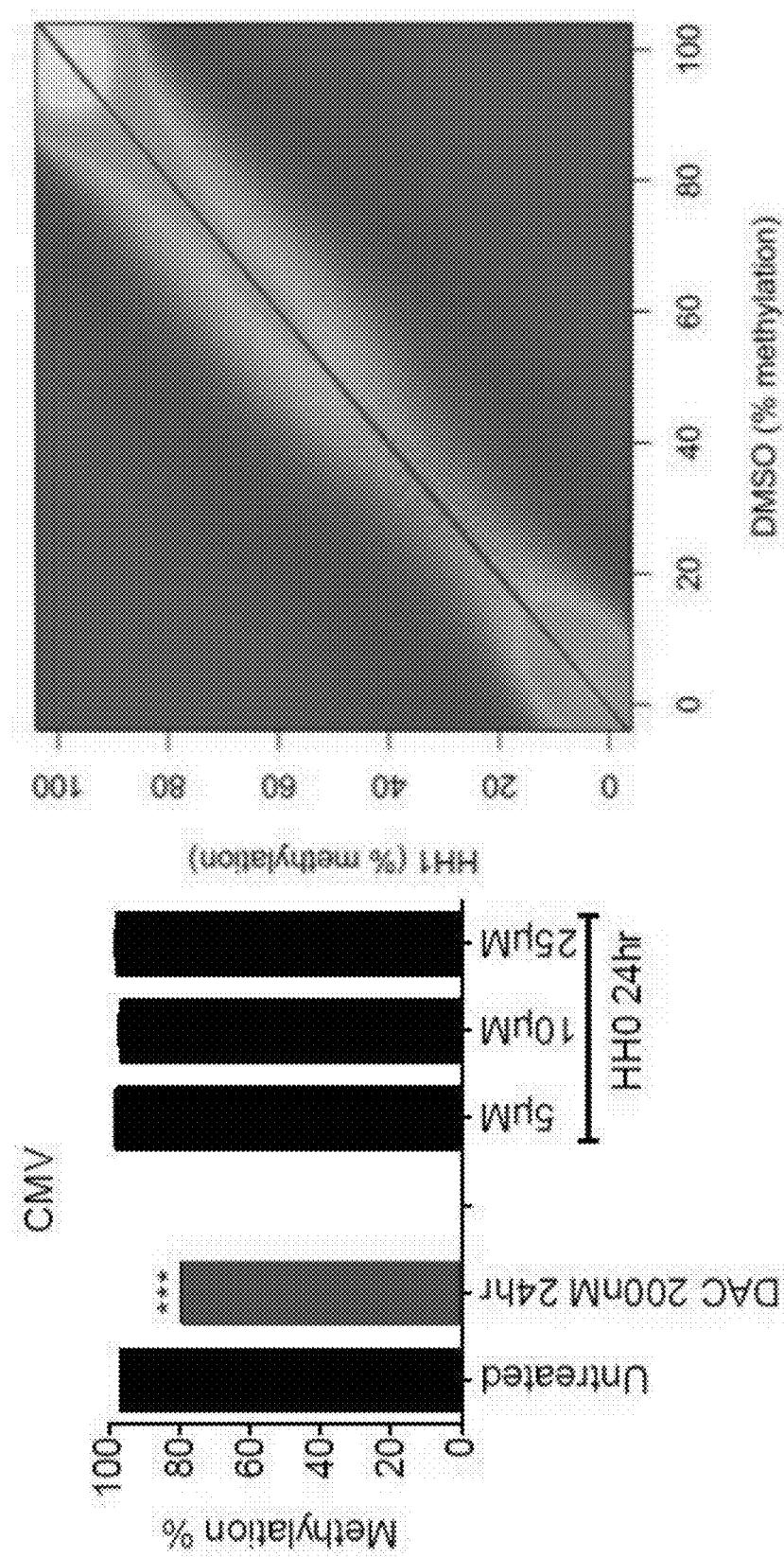
FIG. 7 depicts experimental data demonstrating (Left) DNA methylation analysis of CMV promoter after drug treatment (24 hr) analyzed by bisulfite pyrosequencing. DAC (24 hr) was used as a positive control (n=3). Data are shown as mean±SD, ***p<0.001 (Student's t-test). (Right) HH1 one-dose, four-day treatment did not change DNA methylation compared to DMSO control, as measured by RRBS (Reduced representation bisulfite sequencing) at 218879 CpG sites with the minimum coverage of 1 reads. Red line shows linear regression. R^2=0.98, p<2.2e-16.
Figure 8:
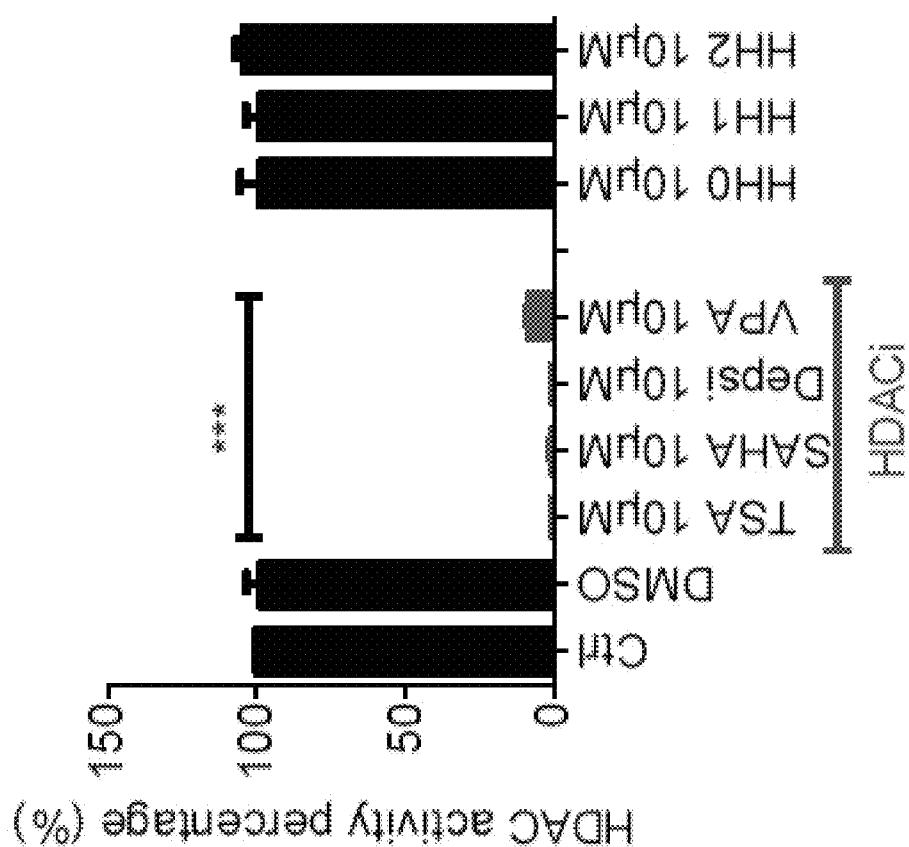
FIG. 8 depicts experimental data demonstrating HDAC inhibitory activity assays that were analyzed in vitro at 10 µM in triplicates. Three aminothiazole compounds (HH0, HH1 and HH2) have no HDAC inhibitory activity. Four known HDAC is (TSA, SAHA, Depsipeptide (Depsi) and Valproic acid (VPA)) were used as positive controls. Data are shown as mean±SD. ***p<0.001 (Student's t-test).
Figure 9:
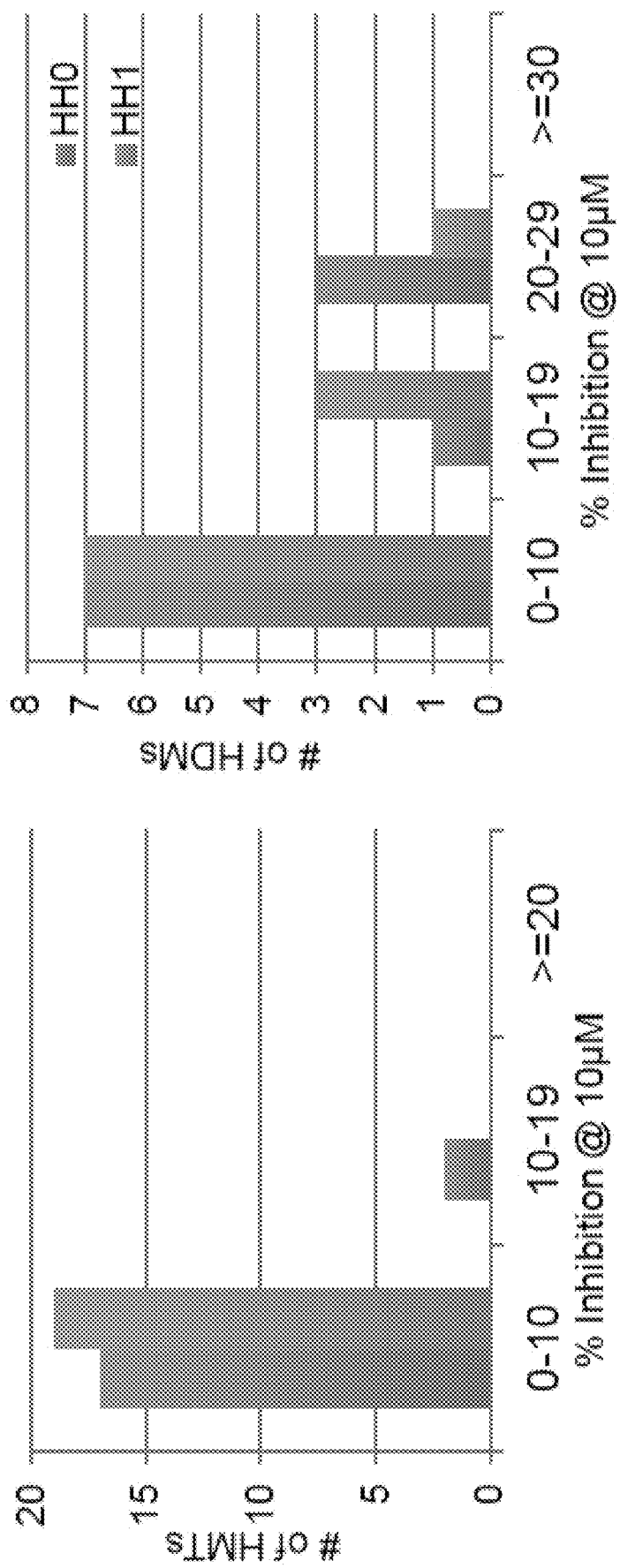
FIG. 9 depicts experimental data demonstrating histone methyltransferase and demethylase inhibitory activities performed using either HH0 or HH1 at 10 µM. No significant enzymatic inhibition was found for either HH0 or HH1.
Figure 10:
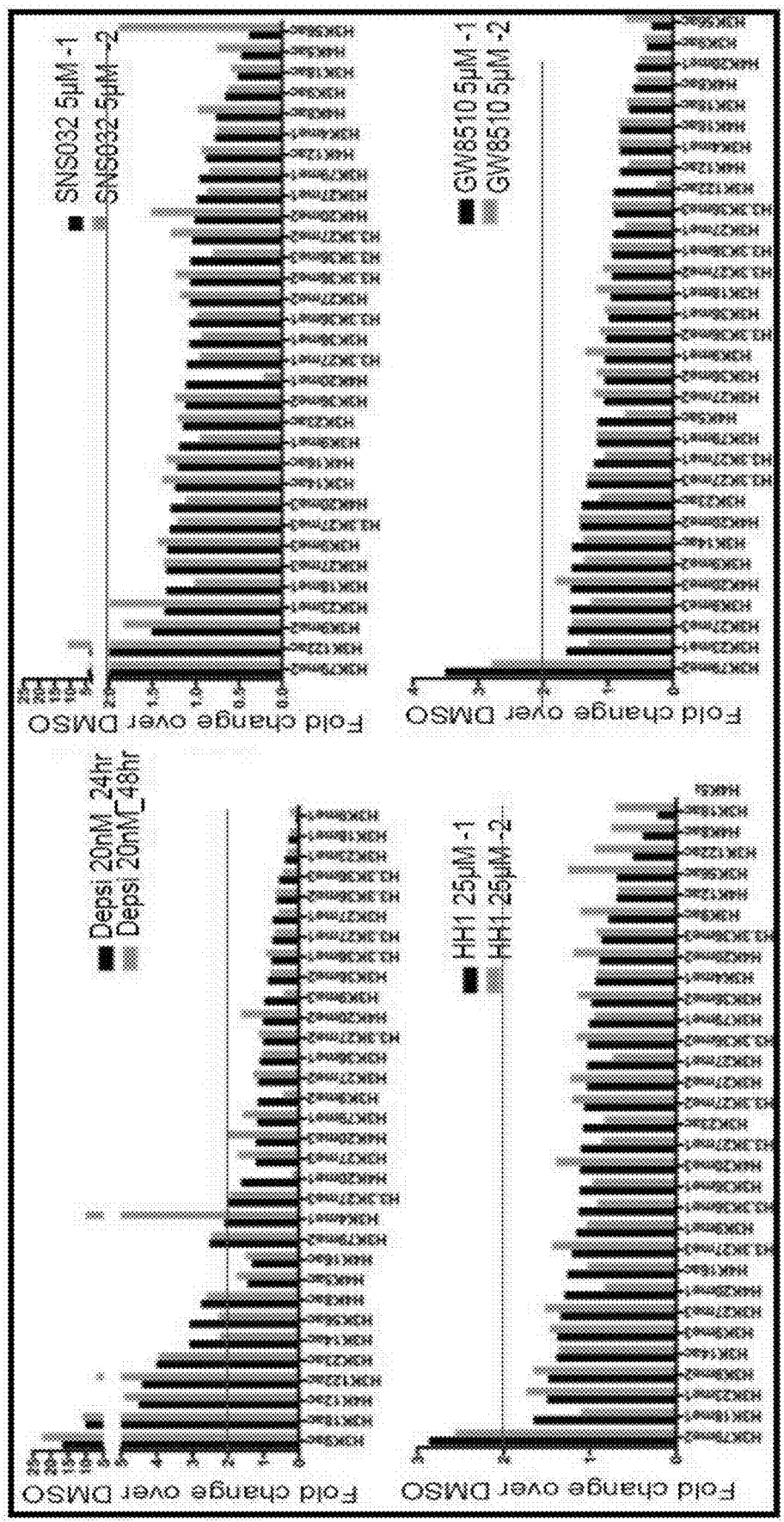
FIG. 10 depicts experimental data demonstrating that global histone acetylation and methylation analysis after 48 hr treatment with different CDK9 inhibitors showed a modest H3K79me2 increase. Depsipeptide was used as a positive control. SNS-032 and GW8510 are two known CDK inhibitors. Fold change was calculated over the DMSO baseline (average value of duplicates).

Chemically, HH1 does not resemble any known epigenetic drug. To determine its relevant target(s), a bisulfite pyrosequencing was performed before and after treatment and found no DNA demethylation at either CMV, LINE1 or globally (by Reduced representation bisulfite sequencing (RRBS)), indicating that these compounds are not DNMT inhibitors (FIG. 7). To explore the potential histone deacetylase inhibitory activity associated with the compounds, an enzymatic-based biochemistry assay was used, a panel of HDACs (class I, IIb and IV) was analyzed, and no activity was found (FIG. 8). HH1 effects on a panel of 30 histone methylases and demethylases was screened and no significant inhibition of enzymatic activity was found (FIG. 9). Global histone acetylation and methylation after 48 hr treatment with HH1 was also measured and no significant changes were found, except for a modest increase in H3K79 methylation, a mark of transcriptional elongation (FIG. 10). Thus, the aminothiazole compounds had no substantial activity against the main known epigenetic targets.

Figure 11:
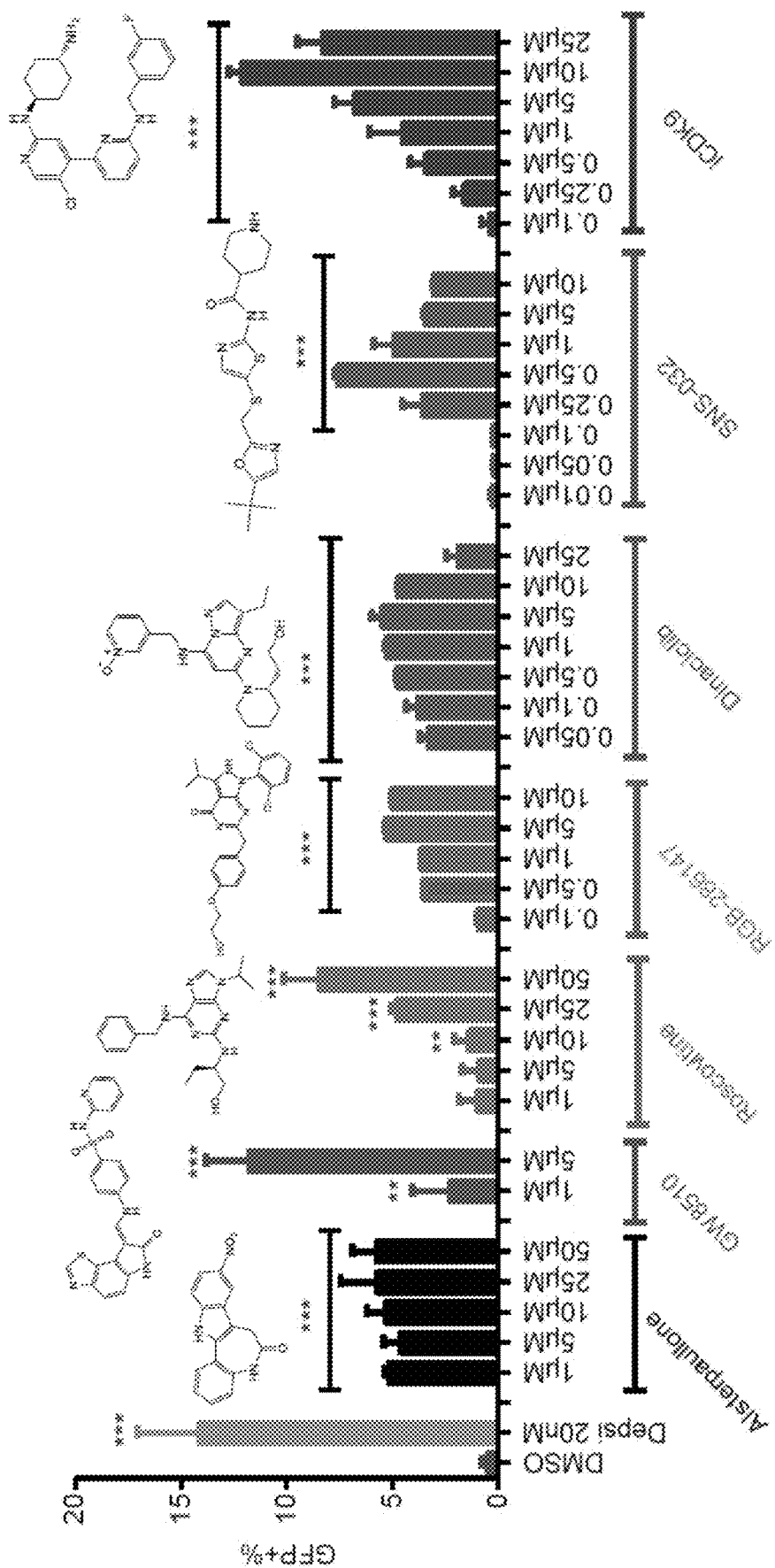
FIG. 11 depicts GFP re-expression dose-responses after 24 hr treatment with different CDK inhibitors. Corresponding structures are shown on top of each bar group. Data are shown as mean±SD, n=3. p<0.01, *p<0.001 (Student's t-test).
Figure 12:
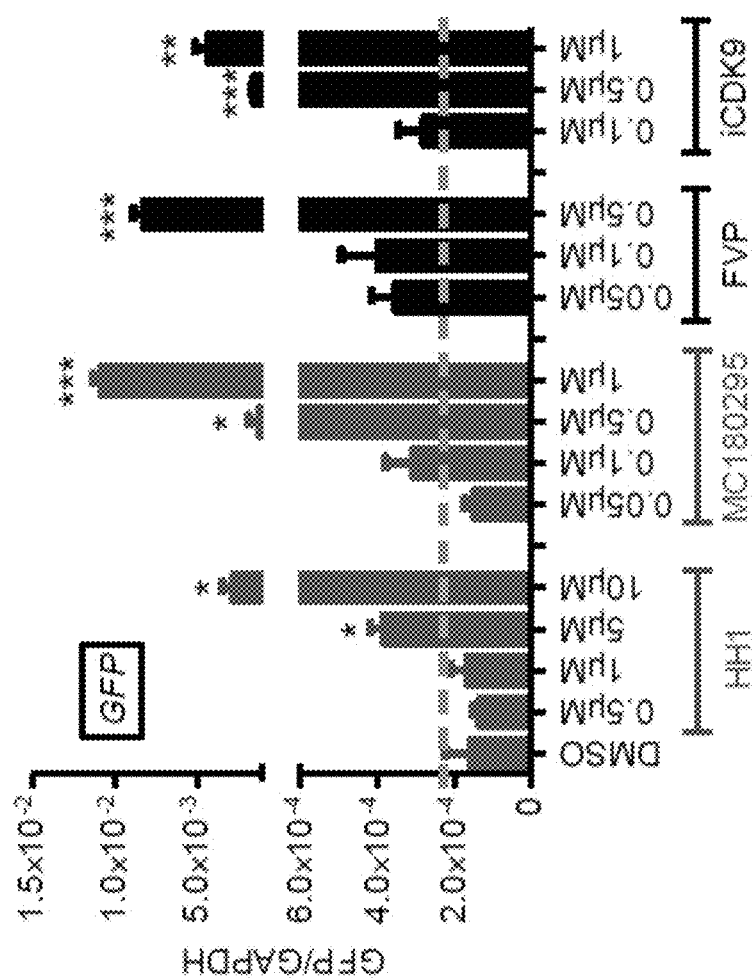
FIG. 12 depicts reactivation of GFP and endogenous hypermethylated genes (SYNE1 and MGMT) after treatment with CDK9 inhibitors for 24 hr detected by qPCR. Data are shown as mean±SD, n=3. *p<0.05, p<0.01, *p<0.001 (Student's t-test).

Furthermore, the potential mechanism of action of these drugs was studied using connectivity mapping (Lamb, et al. (2006), Science 313, 1929-1935), which identifies drugs with similar transcriptional profiles. Using RNA-seq data after HH1 treatment for 24 hr, the closest drugs to HH1 were inhibitors of cyclin-dependent kinases (CDKs). To validate these unexpected targets, 7 different CDK inhibitors were tested and all were found to induce GFP in YB5 with a range of 5-15% after 24 hr treatment (FIG. 11). The fact that these drugs with very diverse chemical structures (FIG. 11) are all active suggests that CDKs are indeed the relevant drug targets. The expression of SYNE1 and MGMT, two known tumor suppressor genes hypermethylated in YB5, was also tested and it was found that HH1 together with two known CDK inhibitors (Flavopiridol and iCDK9 (Lu, et al. (2015), Elife 4, e06535), all led to gene reactivation after 24 hr treatment (FIG. 12).

Figure 14A:
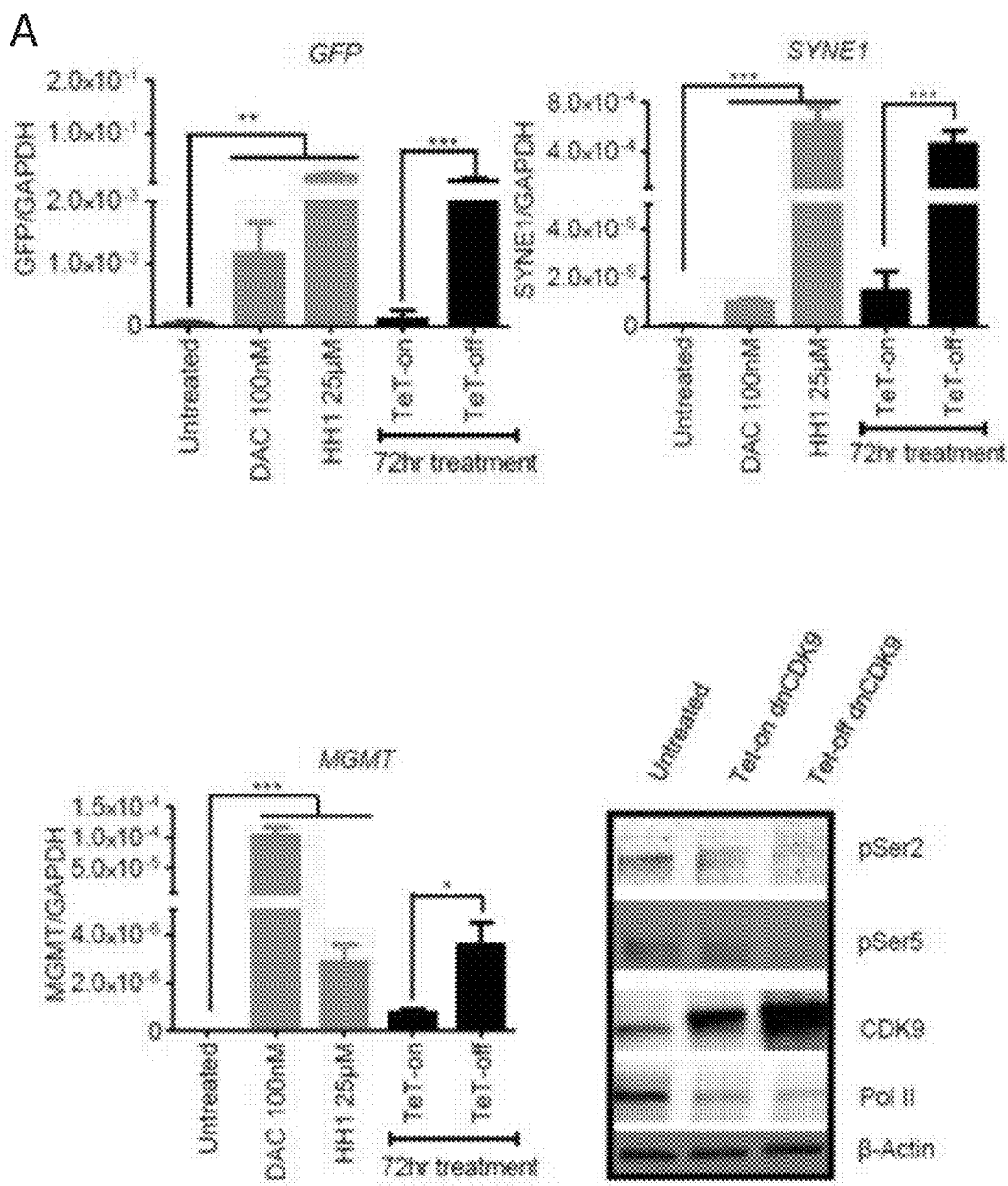
FIG. 14A-14B, depicts experimental data demonstrating the reactivation of GFP and endogenous hypermethylated genes upon dominant-negative CDK9 (dnCDK9) overexpression.
Figure 14B:
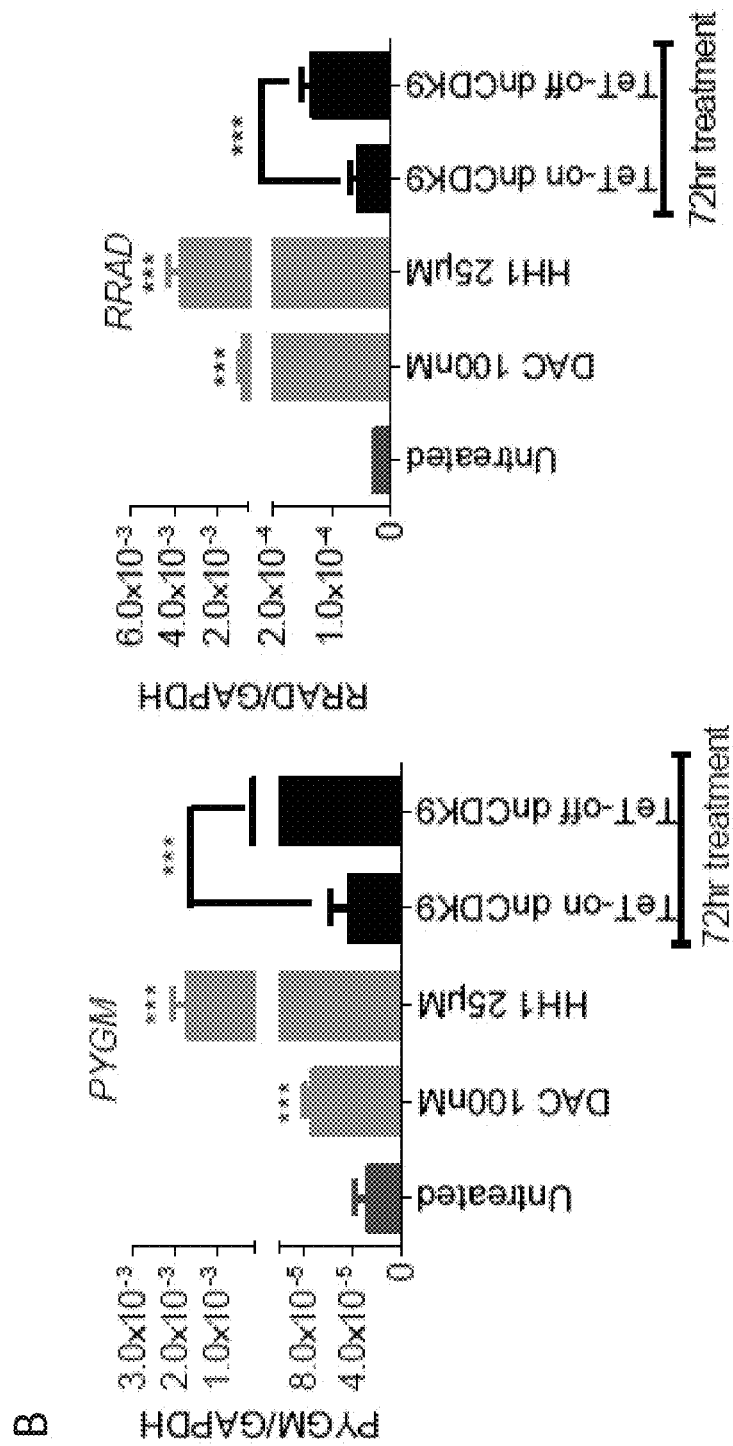
Figure 15:
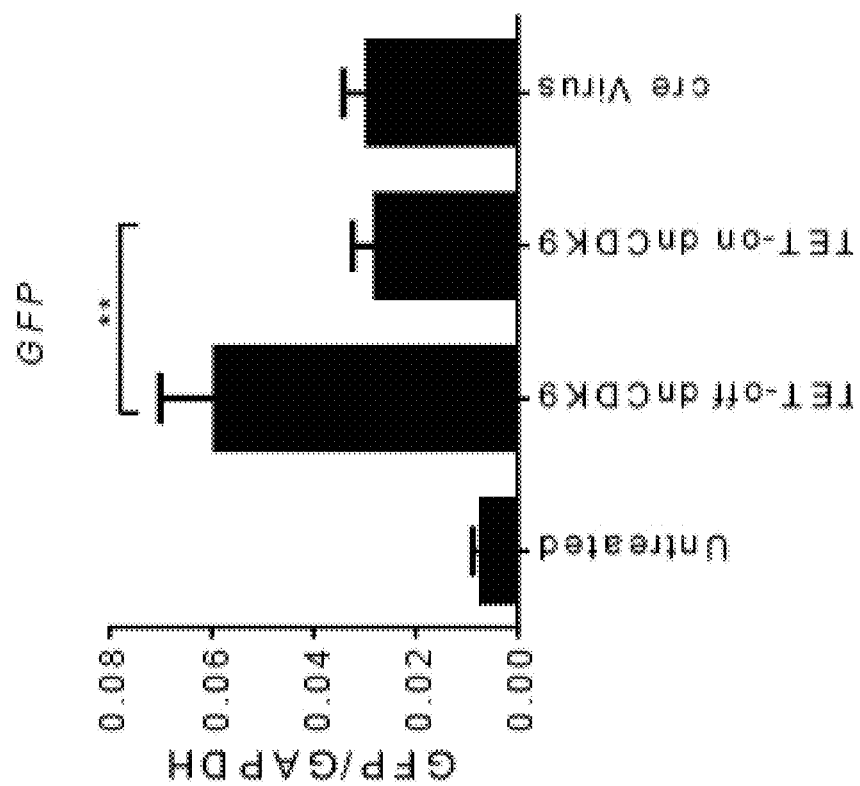
FIG. 15 depicts experimental data demonstrating GFP reactivation upon dominant negative CDK9 (dnCDK9) overexpression (72 hr) in HCT116-GFP cells (n=3). Cre Virus was used as a negative control. Data are shown as mean±SD. **p<0.01 (Student's t-test).
Figure 16:
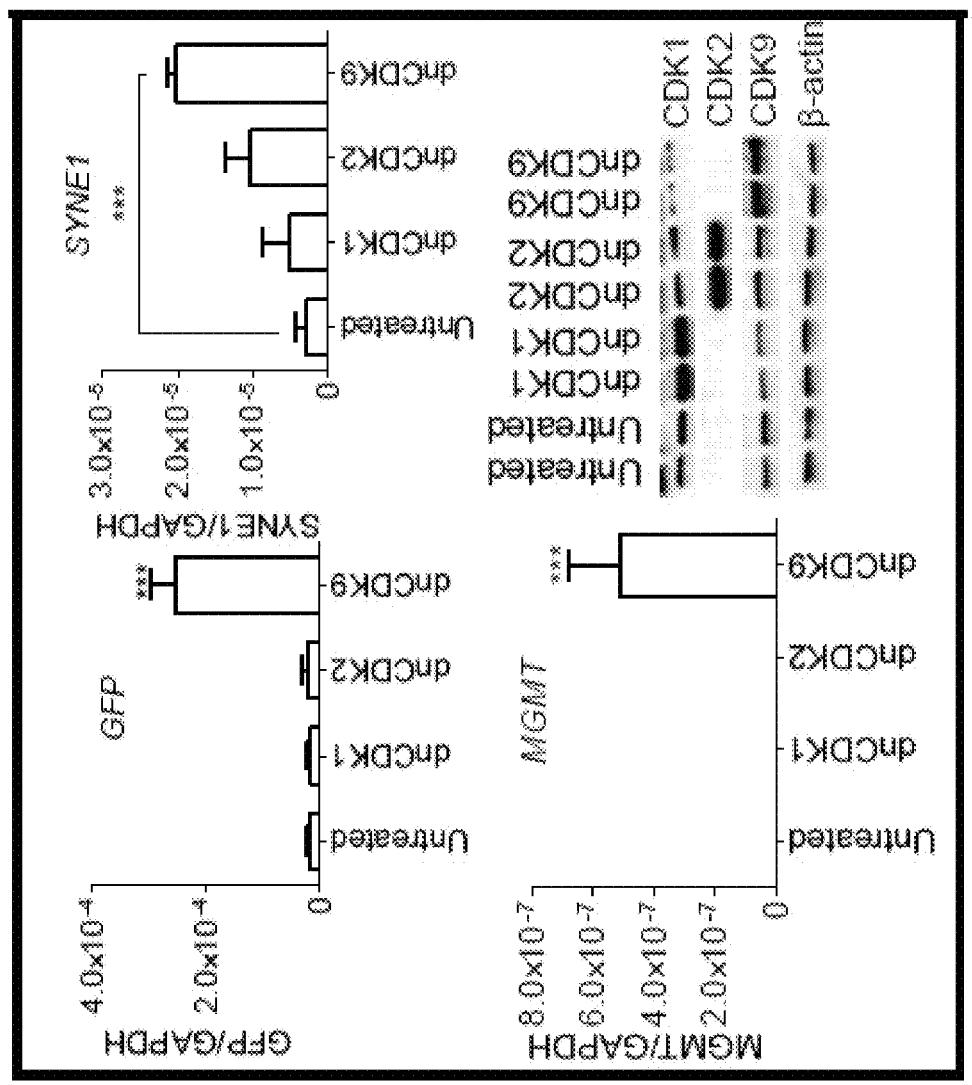
FIG. 16 depicts experimental data demonstrating that GFP and two endogenously hypermethylated genes (MGMT and SYNE1) were reactivated upon CMV-dnCDK9 construct overexpression (72 hr) (n=3). CMV-dnCDK1 and CMV-dnCDK2 constructs (72 hr) did not trigger gene reactivation in YB5. Western blot showed the overexpression of dnCDK1, dnCDK2 and dnCDK9 after transfection. Data are shown as mean±SD. ***p<0.001 (Student's t-test).
Figure 17A:
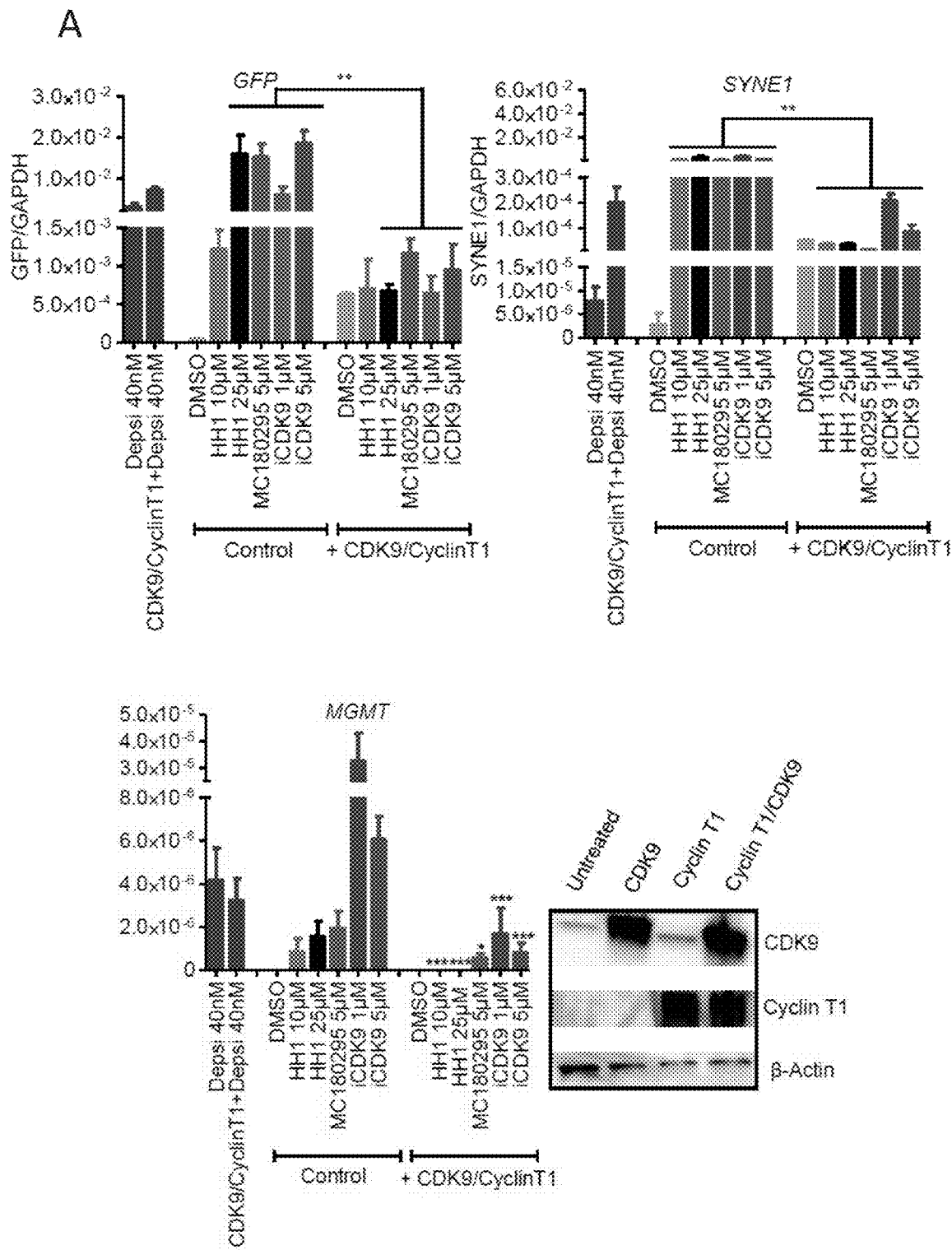
FIGS. 17A and 17B, depicts experimental data demonstrating that activation of GFP and of endogenously silenced gene expression by HH1 and other CDK inhibitors was prevented by overexpression of CDK9 and Cyclin T1.
Figure 17B:
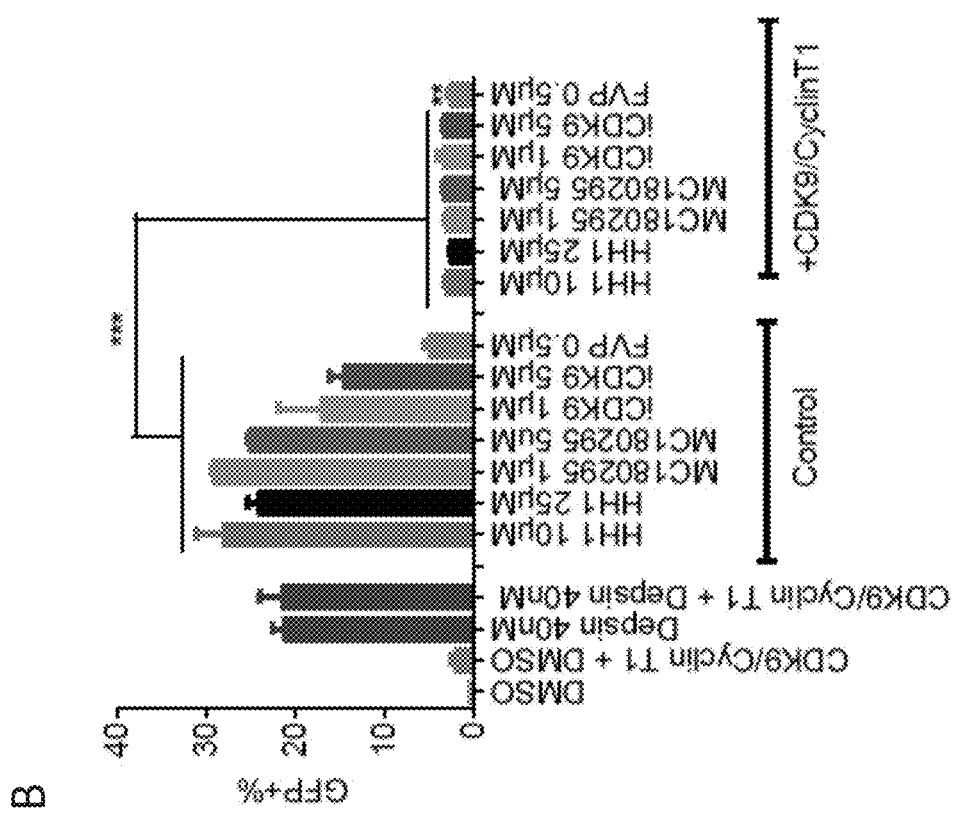

CDKs are divided into cell cycle regulators (e.g. CDK1, 2, 4, 6, 7) and transcriptional regulators (e.g. CDK7, 9). The tested CDK inhibitors target multiple CDKs spanning both classes. By examining their IC50s against individual CDKs, it was found that the drugs most effective at gene reactivation had very low IC50s against CDK9 (FIG. 13). Although not wishing to be bound by any particular theory, these results suggest that CDK9 might be the potential target. CDK9 is known to enhance transcriptional elongation but has not previously been linked to epigenetic silencing. An inducible CDK9 dominant negative (dnCDK9) adenoviral vector was used to see if CDK9 inhibition can phenocopy HH1 effects. Indeed, a striking re-expression of GFP and of endogenously silenced genes upon induction of dnCDK9 was found (FIG. 14). This effect could also be seen in HCT116-GFP cells (FIG. 15). By contrast, dnCDK1 or dnCDK2 showed no effects (FIG. 16). Moreover, activation of GFP and of endogenously silenced gene expression by HH1 and other CDK inhibitors (FIG. 17) was prevented by overexpression of CDK9 and Cyclin T1. Although not wishing to be bound by any particular theory, collectively, these data strongly suggest that CDK9 is the target of the newly identified aminothiazole compounds and is therefore required to maintain transcriptional repression at epigenetically silenced loci.

Development of Novel CDK9 Inhibitors Using a Gene Expression-Based Structure Activity Relationship (SAR) Approach.

Figure 18:
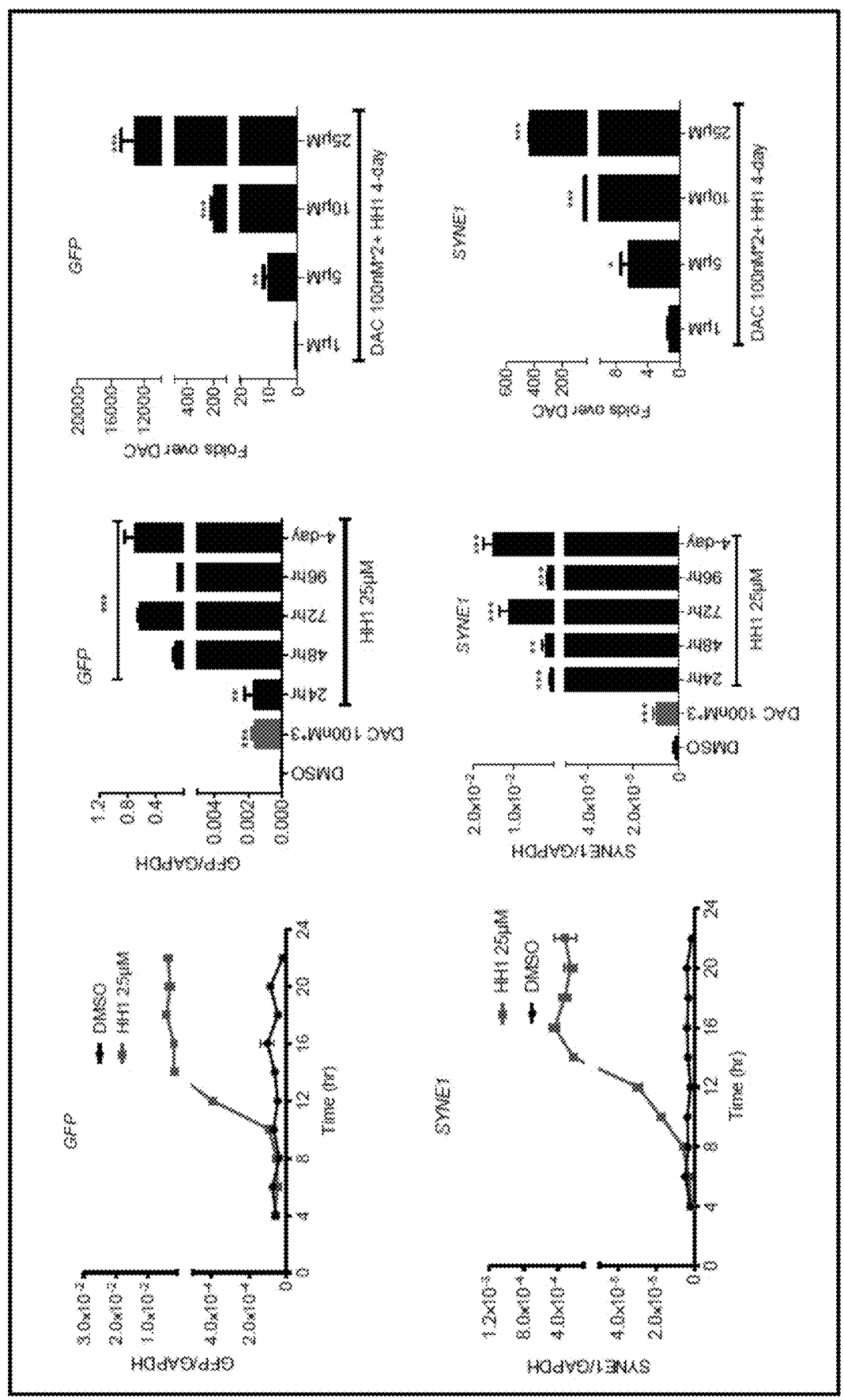
FIG. 18 depicts experimental data demonstrating time course GFP and SYNE1 expression after HH1 treatment (25 µM) for up to 22 hr (left), 24 hr, 48 hr, 72 hr, 96 hr daily treatment, and four-day (one dose) treatment (middle) and in combination with DAC (right). Data are shown as mean±SD. *p<0.05, p<0.01, *p<0.001 (Student's t-test).
Figure 21:
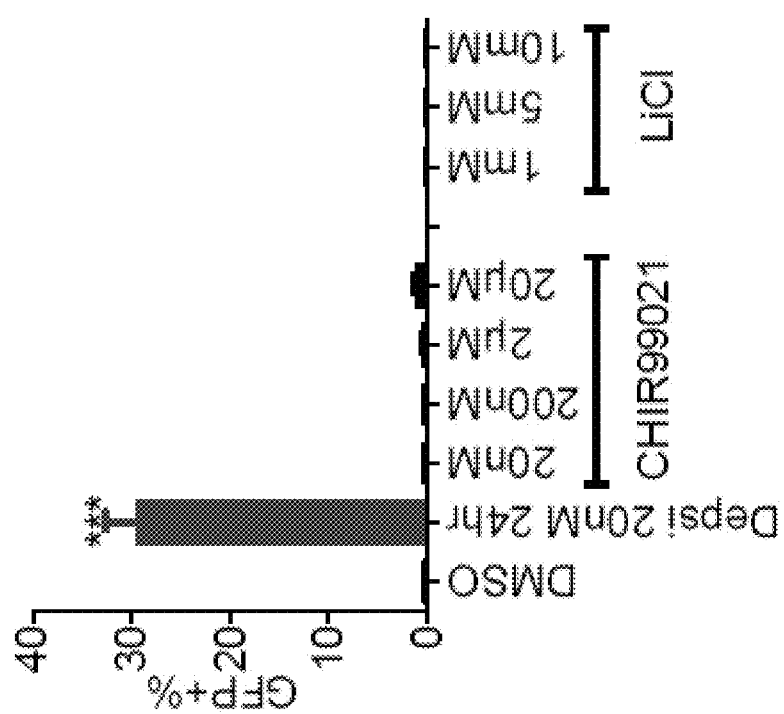
FIG. 21 depicts experimental data demonstrating of two GSK-3 inhibitors (CHIR99021 and LiCl) tested at multiple doses after four-day drug treatment in YB5 with no GFP reactivation (n=3). Data are shown as mean±SD. Depsipeptide was used as a positive control. ***p<0.001 (Student's t-test).
Figure 22:
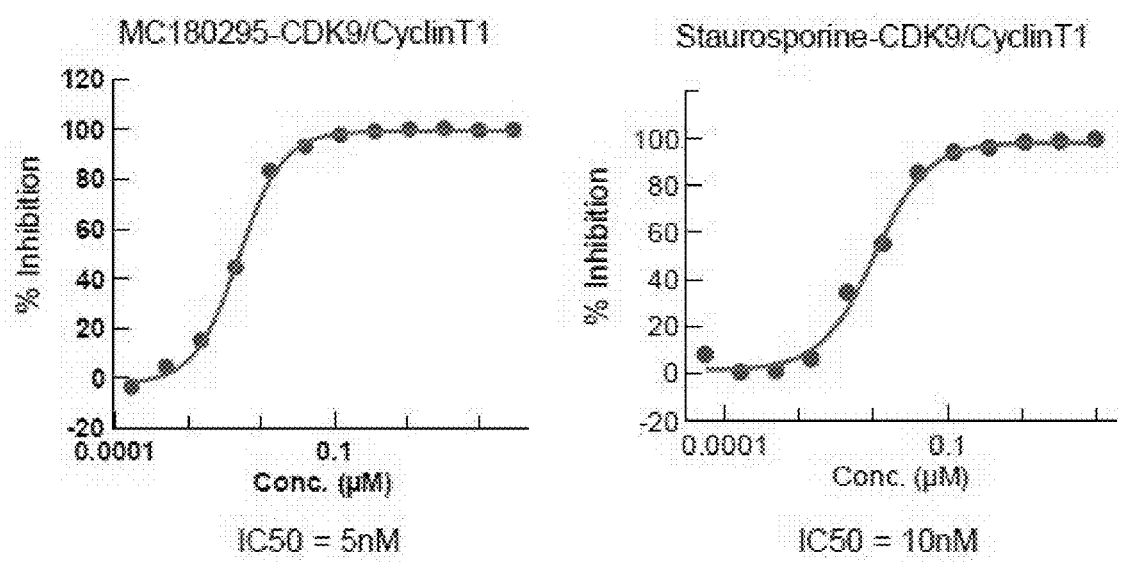
FIG. 22, comprising
Figure 23:
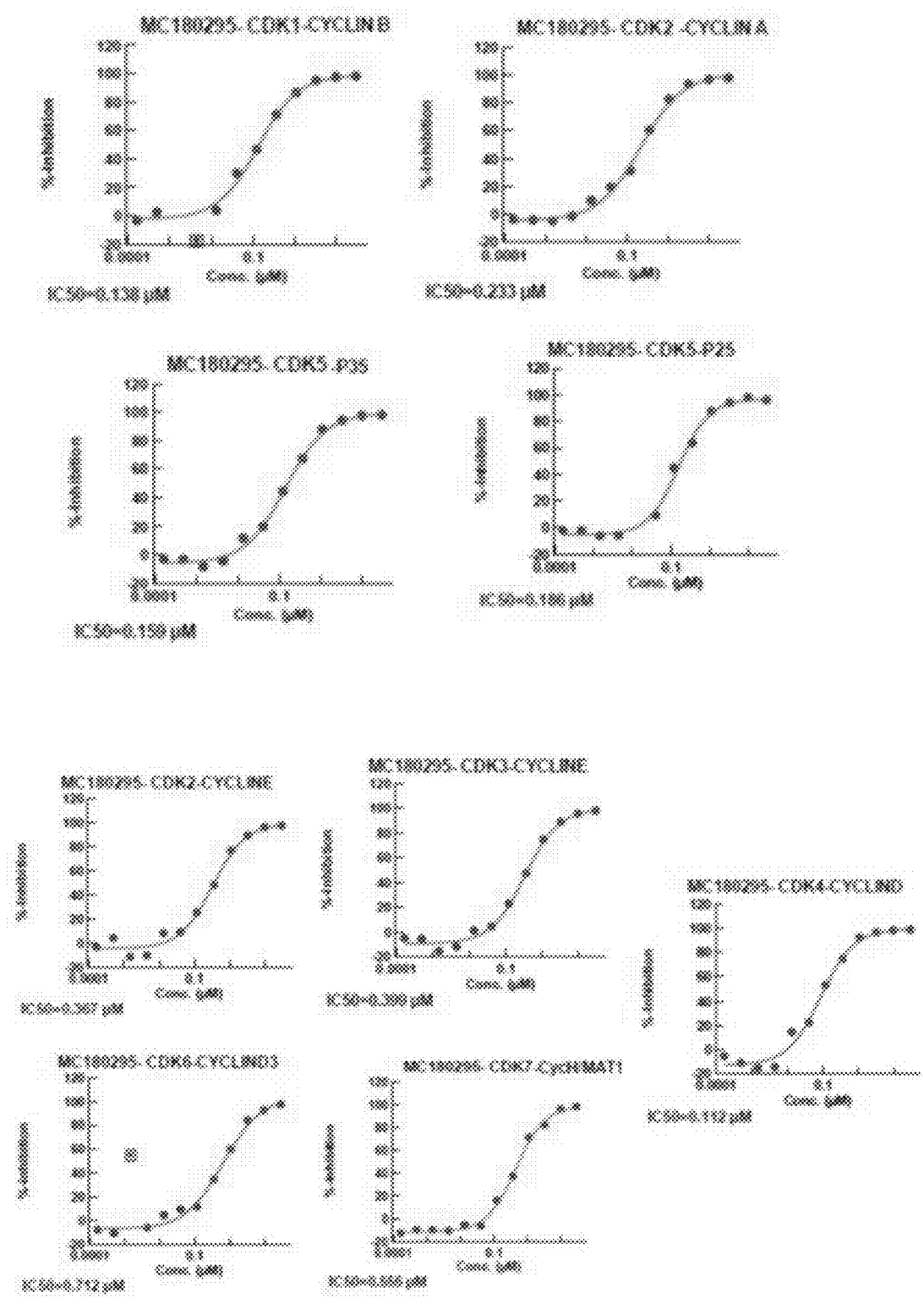
FIG. 23 depicts experimental data demonstrating IC50 curves of MC180295 against different CDKs.

Next, newly-synthesized HH1 analogs for gene expression-based SAR discovery were tested. To explore the optimal time point for drug testing, a time course qPCR was performed and it was found that a one-time 4-day treatment with 25 µM HH1 induced the highest levels of GFP and endogenously hypermethylated genes in YB5 (FIG. 18). Seventy-seven aminothiazole analogs were synthesized and tested using this approach and MC180295 was identified as the most potent lead compound (active at 50 nM and leading to ~60% GFP+ cells at 500 nM) (FIG. 5), together with three other analogs with similar activities (FIGS. 5 and 19). The selectivity of MC180295 was then tested against a panel of 250 kinases at 1 µM and was found to be highly selective against CDKs within the human kinome, though glycogen synthase kinase 3 (GSK-3a and GSK-3β) was also inhibited at this concentration (FIGS. 20A-20B). However, two specific GSK-3 inhibitors (CHR99021 and LiCl) showed no GFP reactivation activity in YB5. Although not wishing to be bound by any particular theory, these results suggest that GSK-3 is not the key epigenetic target of MC180295 (FIG. 21). A dose-response curve for MC180295 was then generated against 10 different CDKs. The drug was most active against CDK9 (IC50=5 nM) and was at least 22-fold more selective for CDK9 over other CDKs (FIGS. 22A-22B and FIG. 23). Thus, optimization of HH1 based on gene expression alone yielded a highly specific CDK9 inhibitor, providing additional unbiased evidence that CDK9 is the most relevant epigenetic target for GFP and endogenous gene reactivation.

To better understand MC180295 specificity, a model of the CDK9-MC180295 complex was needed. From its planar aminothiazole core with alternating hydrogen bond donors and acceptors, it was hypothesized that MC180295 would be an ATP-competitive inhibitor with a pattern of interactions matching other kinase inhibitors (Roskoski, R. (2016), Pharmacol Res 103, 26-48; Wang, et al. (2015), Cell 163, 174-186). Based on this, it was decided that the structure of MC180295 bound to CDK9 should be modeled by analogy to other ligands in complex with CDKs.

First, a set of all 389 structures of CDKs with bound ligands available in the Protein Data Bank (PDB) was compiled. As described elsewhere herein, low-energy conformations of MC180295 were structurally aligned to each of these ligands, and then the kinase structure was replaced with that of CDK9. This provided a set of 389 crude models of MC180295 in complex with CDK9, with poses that used MC180295 to mimic the interactions used by a different CDK ligands. These models were refined and it was found that a single dominant cluster emerged among the top-scoring complexes (i.e. an identical binding mode in 14 of the top 30 models). Although not wishing to be bound by any particular theory, this was taken as the predicted pose for the MC180295-CDK9 complex and this model was examined in further detail.

Figure 24:
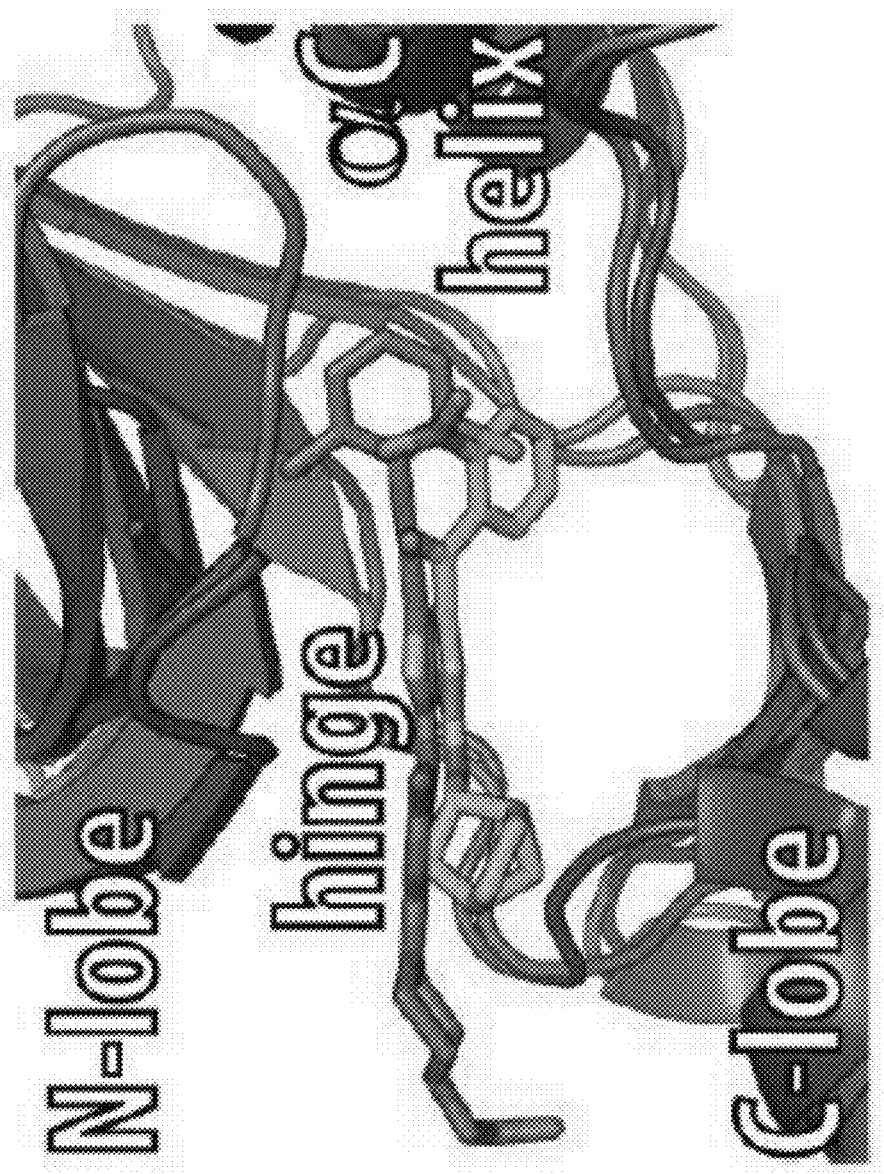
FIG. 24 depicts a model (green), the aminothiazole core of MC180295 engaged the CDK9 hinge region with interactions that mimic that of dasatinib (shown here bound to cSrc, PDB ID 3G5D, pink) and many other canonical kinase inhibitors.
Figure 25:
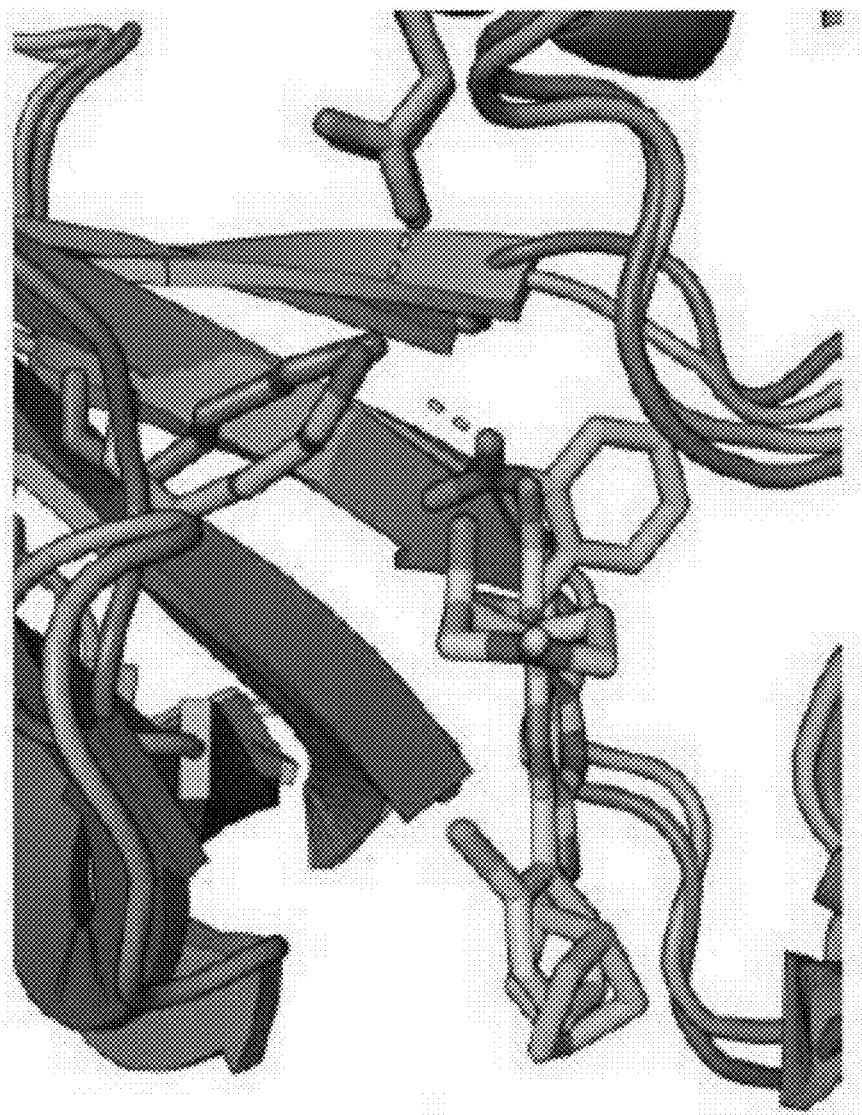
FIG. 25 depicts experimental data demonstrating that inventive compound MC180295 engaged the conserved Lys48-Glu66 hydrogen bond (green); the multi-CDK inhibitor flavopiridol also made a similar interaction (PDB ID 3BLR, pink). The interactions of this nitro group fully explain the observed SAR on this side of MC180295, but cannot explain the compound's selectivity for CDK9.

In this model, the aminothiazole core makes canonical hydrogen bonding interactions to the CDK9 hinge region. Dasatinib is a broad-spectrum inhibitor that is also built on an aminothiazole core (FIG. 24). Like dasatinib, MC180295 is modeled in a "DFG-in" conformation (making it a Type I inhibitor), and its binding mode strongly resembles that of the CDK4/6 inhibitor palbociclib (Lu, H., and Schulze-Gahmen, U. (2006), J Med Chem 49, 3826-3831). Whereas palbociclib hydrogen bonds directly to the backbone of the DFG motif, however, MC180295 uses a nitro group to engage the Lys-Glu salt bridge that is invariant in essentially all kinases; a similar interaction to this has also been observed in the structure of CDK9 bound to the multi-CDK inhibitor Flavopiridol (Alvocidib) (Baumli, S., et al., (2008), EMBO J 27, 1907-1918) (FIG. 25). The model also supports the observed structure-activity relationship for all our analogs at this position, on the basis of which substituents preserve hydrogen bonding to this lysine. However, although not wishing to be bound by any particular theory, the strong similarity in this part of the binding site among CDKs, coupled with the similarity of these interactions to those of other multi-CDK inhibitors, suggests that the basis for CDK9-selectivity did not derive from this part of the compound.

Figure 26:
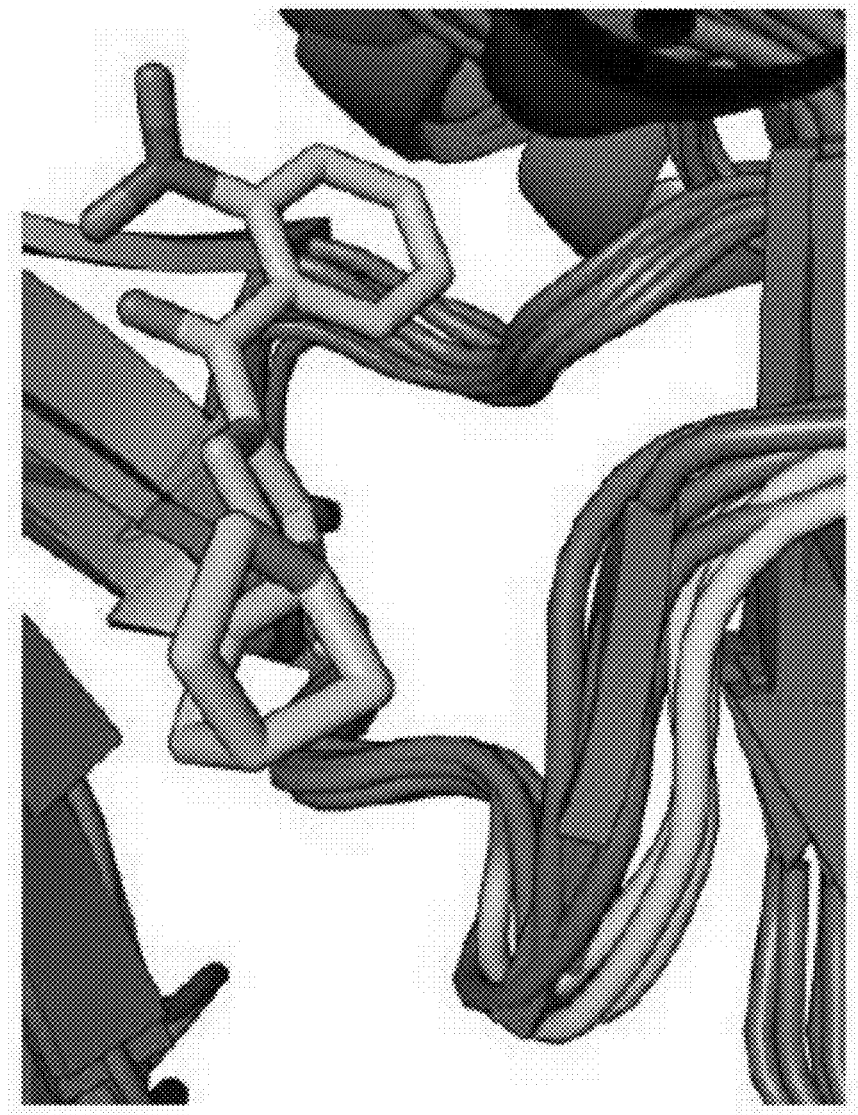
FIG. 26 depicts experimental data demonstrating that the adamantyl group from MC180295 requires that the C-terminus of the hinge region adopts a slightly lower conformation; this conformation is shared amongst the many crystal structures of CDK9 (yellow: structures of CDK9 bound to ATP and to another Type I inhibitor (PDB IDs 3BLQ and 4BCJ), and the model of MC180295), but this loop conformation is rarely observed in structures of other CDK kinases (blue: representative structures of CDK1/2/5/6/7, each bound to ATP or a Type I inhibitor (PDB IDs 5LQF/1HCK/1UNH/2EUF/1UA2)).

On the opposite site of the MC180295 model, an adamantyl group fits on top of the C-terminus of the hinge region and occupies a shallow hydrophobic cleft. This region of the binding site is also occupied by many other inhibitors of CDKs; however, each of these uses individual (flat) ring structures instead of the bulkier adamantane. Careful comparison amongst all CDK crystal structures available in the PDB revealed a subtle difference: the C-terminal part of the CDK9 hinge region can adopt a slightly lower conformation that distinguishes it from the other CDKs where this loop has a higher conformation that sterically prevents the adamantyl group from being accommodated (FIG. 26). This model supports not only the observed SAR for analogs of MC180295, but also this compound's preference for CDK9 over other CDKs.

CDK9 Inhibition Leads to Reactivation of Epigenetically Silenced Genes Genome-Wide.

Figure 27:
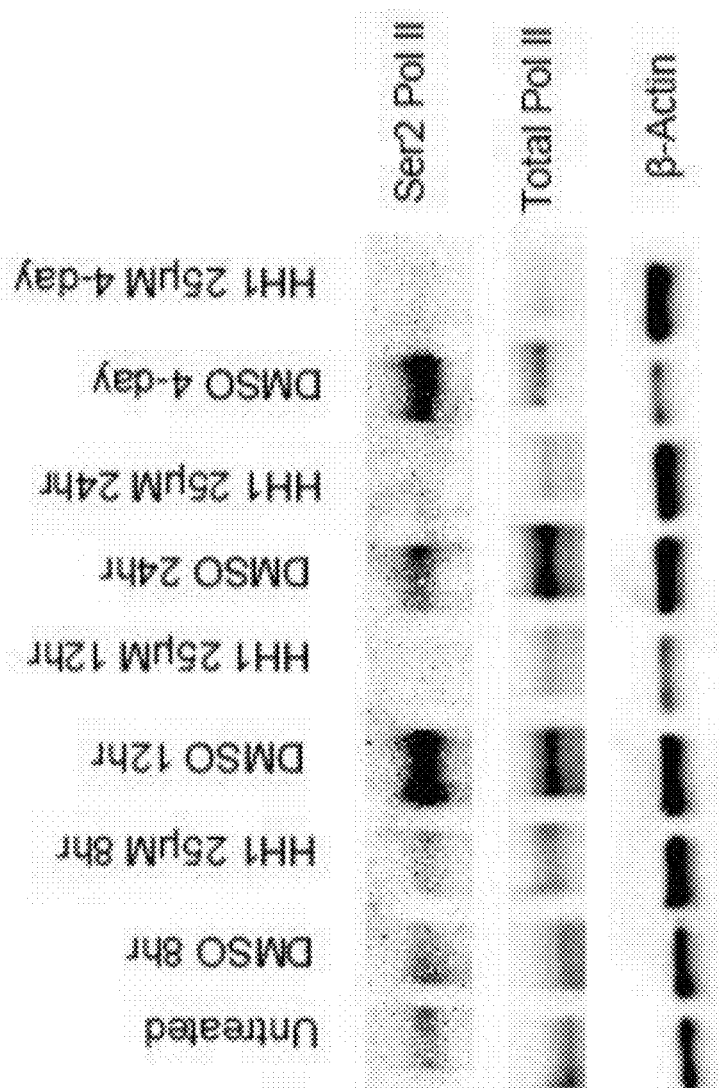
FIG. 27 depicts experimental data demonstrating that phosphorylation levels of Ser2 (pSer2) on the heptad repeats the CTD of RNAPII decreased upon 25 µM HH1 treatment at different time points.
Figure 28:
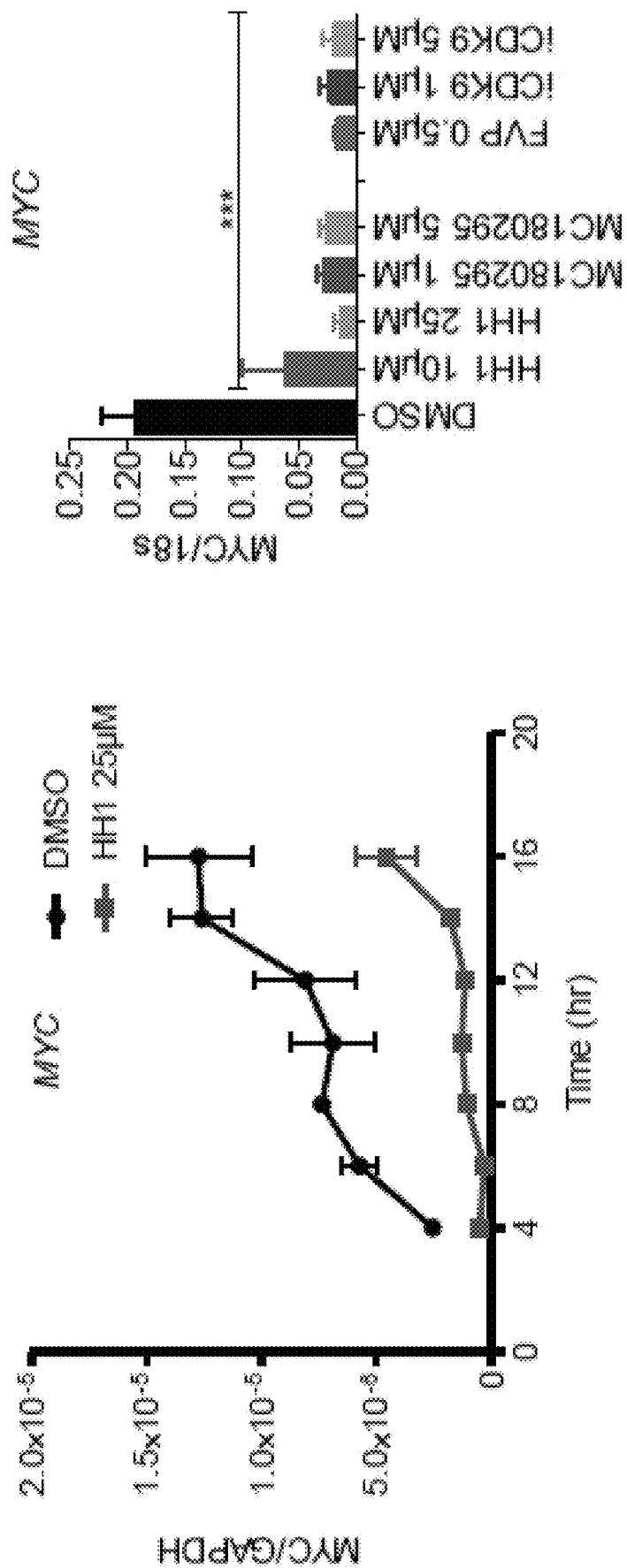
FIG. 28 depicts experimental data demonstrating time course MYC suppression after 25 µM HH1 treatment for up to 16 hr (left). MYC was sustainably suppressed after four-day one dose treatment by multiple CDK9 inhibitors (right) (n=3). Data are shown as mean±SD. ***p<0.001 (Student's t-test).

To further characterize profiles of CDK9 target genes dynamically, assays were optimized by performing a qPCR time course on GFP and SYNE1. It was found that they could both be induced as early as 8 hr and their expression levels peaked four days after first exposure (FIG. 18). To confirm that the gene induction profile is associated with on-target CDK9 inhibition, the phosphorylation levels of Ser2 (pSer2) on the heptad repeats the CTD of RNAPII were measured, which is phosphorylated by pTEFb at these time points, and it was found that Ser2 was consistently dephosphorylated as expected (FIG. 27). The expression of MYC, a known pTEFb target, was also measured and it was found to be suppressed at all these time points (FIG. 28).

Figure 29:
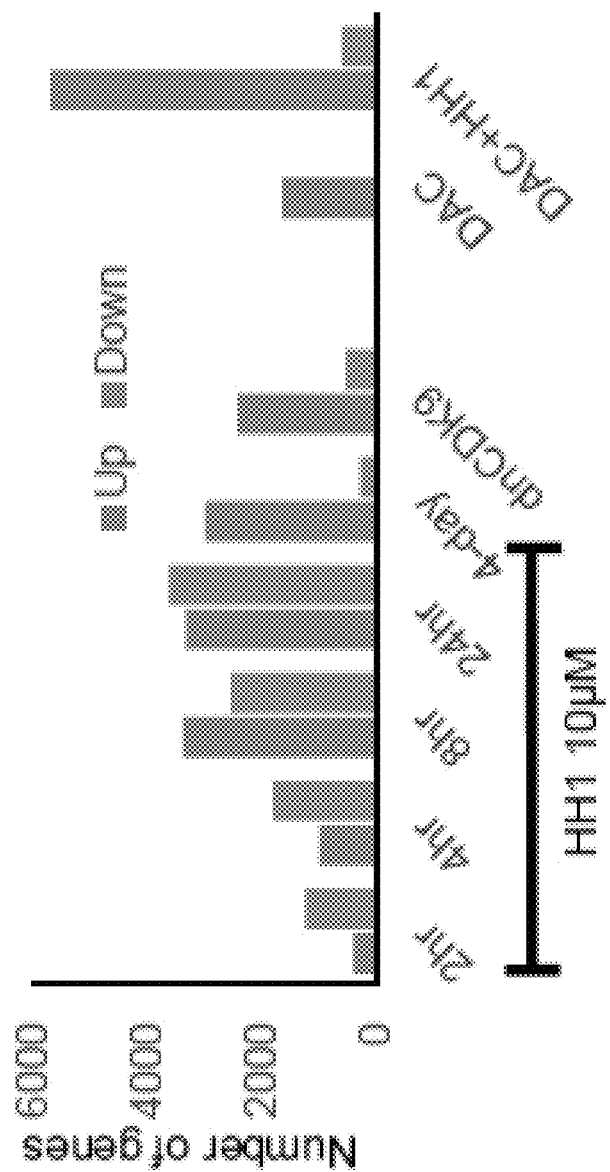
FIG. 29 depicts experimental data demonstrating numbers of upregulated and downregulated genes by 10 µM HH1 at each time point, DAC (100 nM for 48 hr) and combinatorial treatment (DAC 100 nM 48 hr followed by HH1 four-day at 10 µM) in YB5 cells. dnCDK9 overexpression was also included (n=3). (FC>2 OR<0.5, FDR<0.1)
Figure 30:
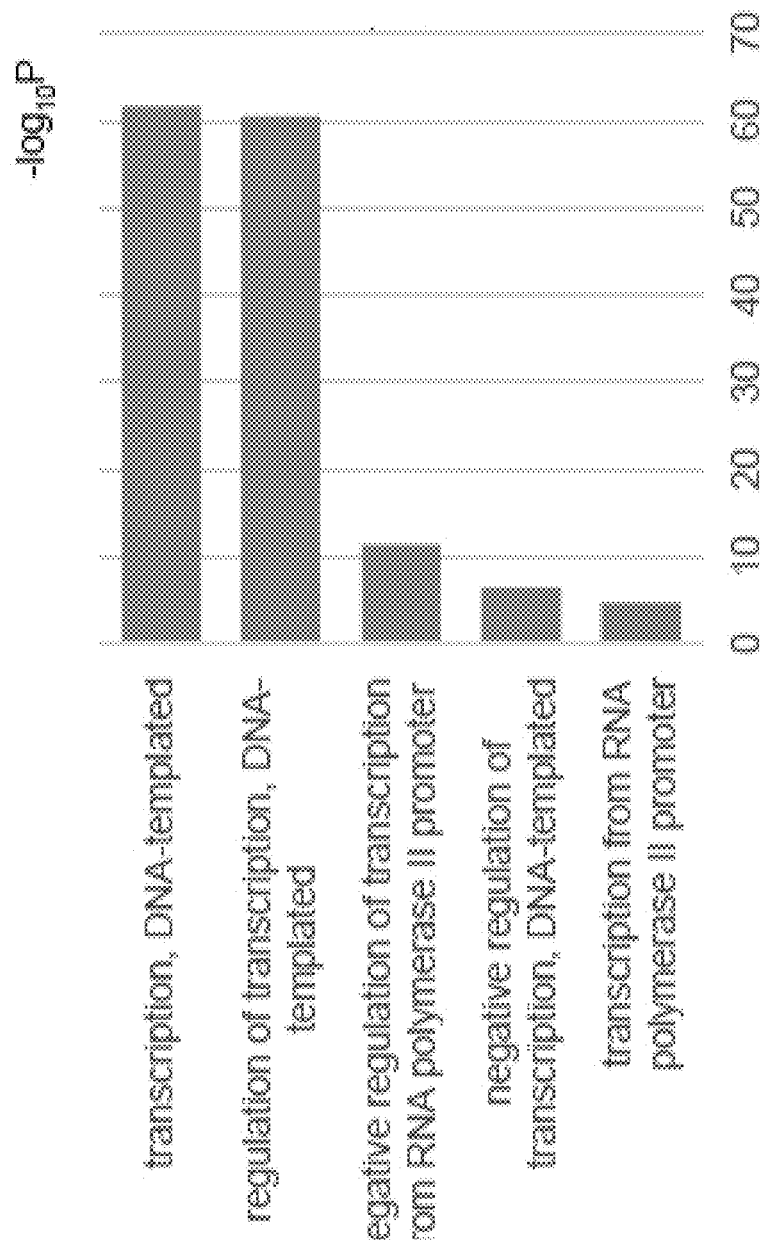
FIG. 30 depicts gene ontology analysis of genes that are significantly downregulated (FC<0.5, FDR<0.1) after two-hour HH1 treatment at 10 μM.
Figure 31:
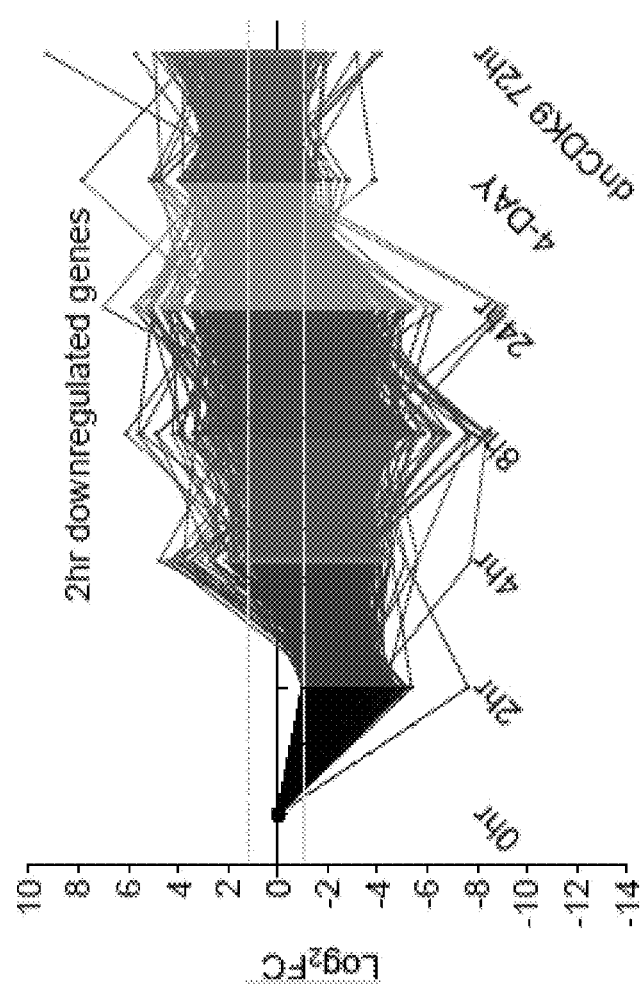
FIG. 31 depicts experimental data demonstrating the dynamics of genes that are significantly downregulated (FC<0.5, FDR<0.1) after 2 hr HH1 treatment at 10 μM.
Figure 32:
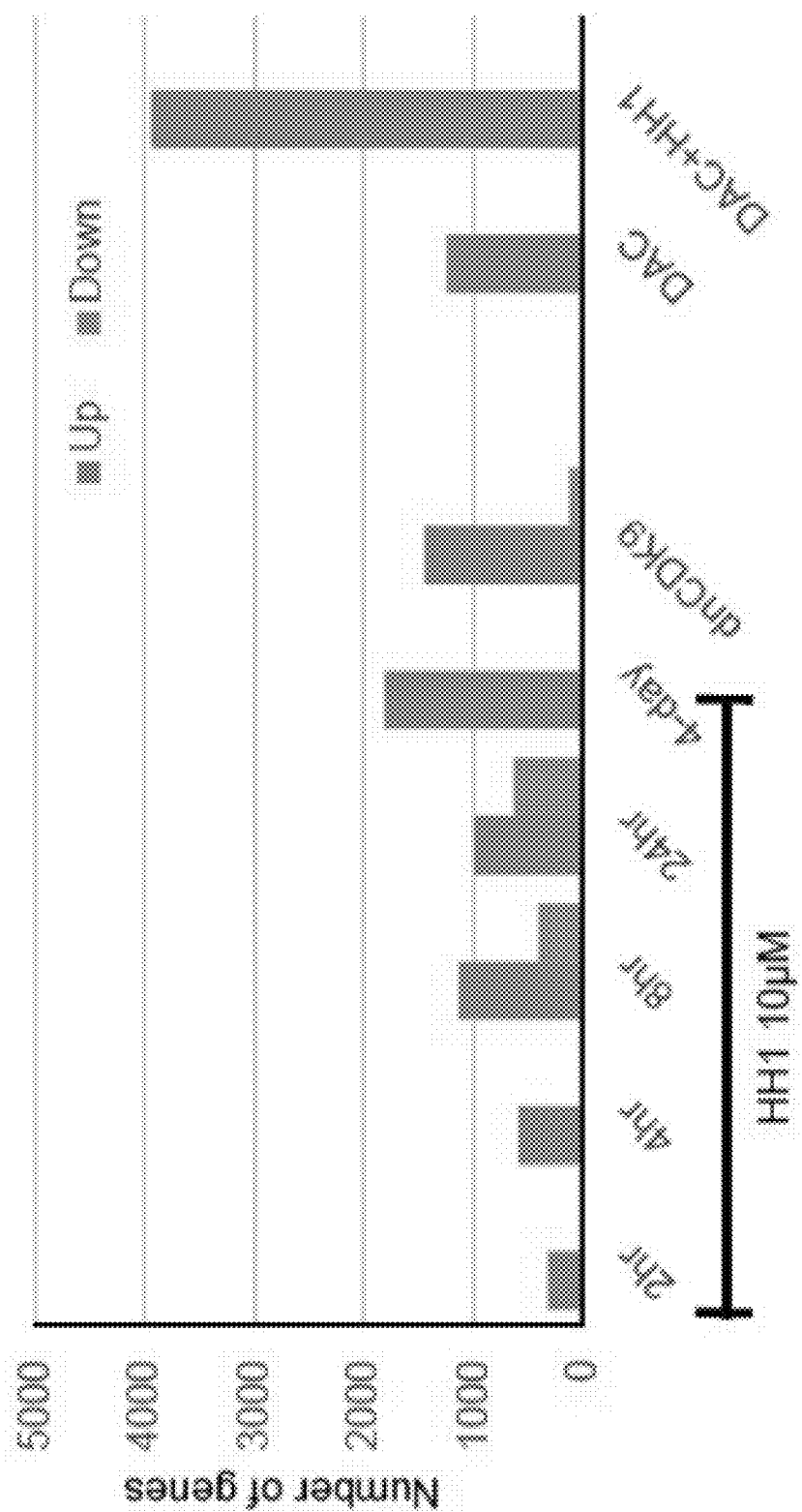
FIG. 32 depicts experimental data demonstrating the number of genes upregulated and downregulated by 10 μM HH1 treatment at each time point. dnCDK9 (72 hr), DAC (48 hr, 100 nM) and combinatorial treatment (DAC at 100 nM for 48 hr followed by HH1 four-day at 10 μM) were also included (n=3). (FC>2 OR<0.5, FDR<0.1)
Figure 33:
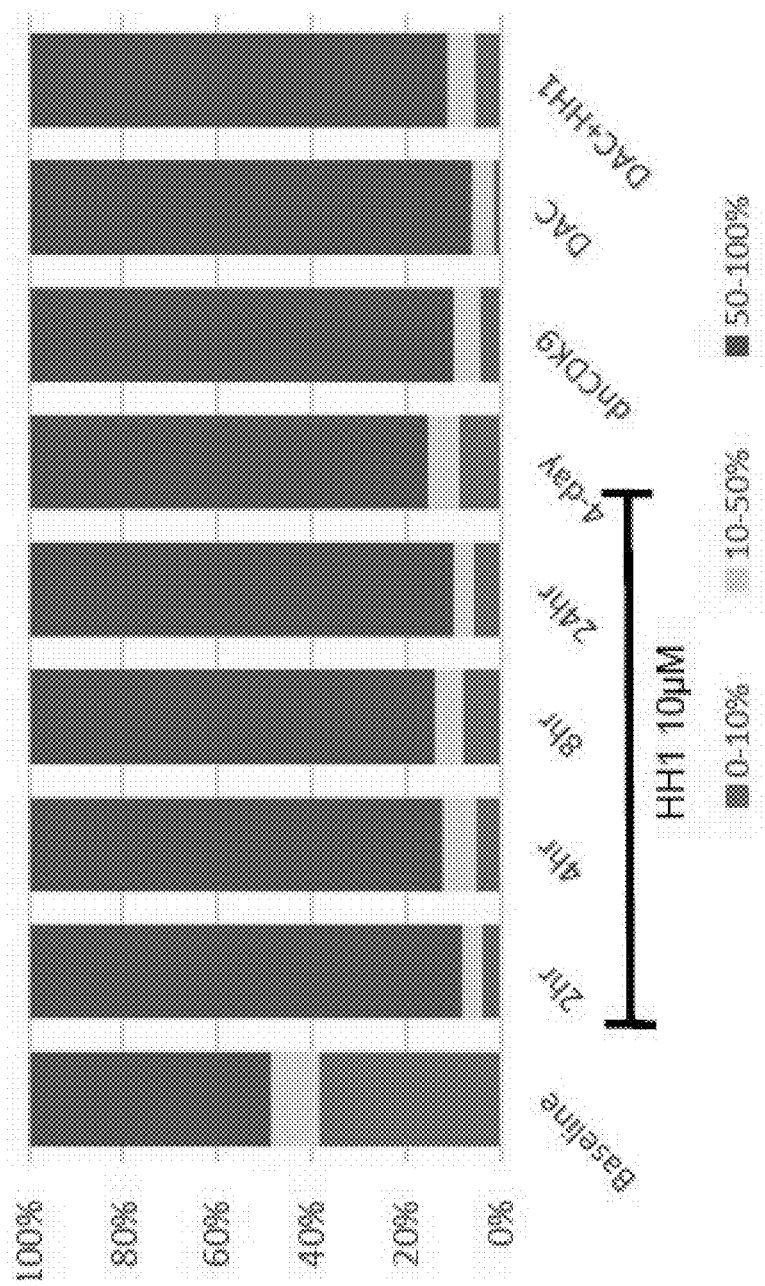
FIG. 33 depicts experimental data demonstrating the percentage of genes upregulated by HH1, dnCDK9, DAC and combinatorial treatment that have low (0%-10%), moderate (10%-50%), or high (50%-100%) promoter DNA methylation.
Figure 34:
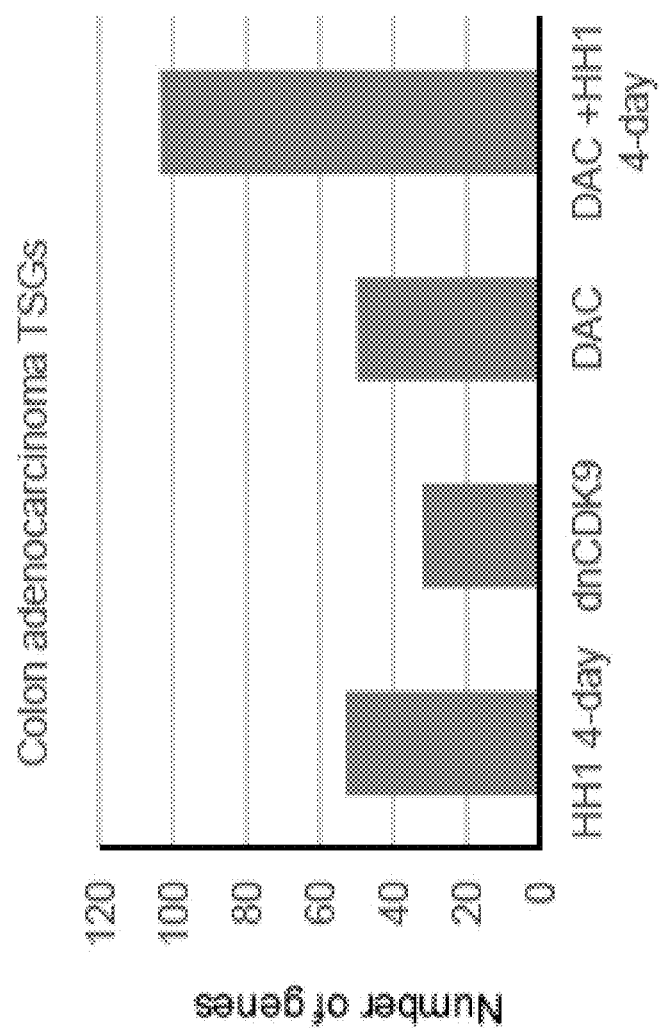
FIG. 34 depicts experimental data demonstrating the numbers of colon cancer tumor suppressor genes (TSGs) that were activated under different conditions.

Next, a time-course RNA-seq was performed using HH1 at 10 µM (FIG. 29). Short term CDK9 inhibition (2 hr, 4 hr) led mainly to gene downregulation (e.g. 1242 genes down vs. 404 genes up at 2 hr). Gene Ontology analysis showed that genes downregulated after 2 hr were enriched for negative regulation of transcription (FIG. 30). These genes started to recover by 4 hr and showed delayed upregulation as previously shown for pTEFb targets (Garriga, J., and Grafia, X. (2014), BMC Res Notes 7, 301; Keskin, H., et al., (2012). Cell Div 7, 11; Lu, et al., (2015). Elife 4, e06535) (FIG. 31). In contrast to this early response, when RNA-seq data was examined 4 days after first drug exposure, massive gene upregulation (2981 up vs. 278 down) was observed. Even after excluding the pTEFb targets identified earlier (downregulated at 2 hr/4 hr), upregulation of 2597 genes was still observed. This large effect (12.3% of the transcriptome) was consistent with the GFP data and indicated an unexpected effect of CDK9 on epigenetic silencing. Silenced genes are characterized by very low level of expression and repressive epigenetic marks. To better characterize the effects of HH1 on silencing, the genes that showed very low expression at baseline (RPKM<0.31) were focused on and were induced by HH1 (FIG. 32). 1801 genes fit this profile, confirming a strong effect of HH1 on silenced genes. Based on RRBS analysis, many of these upregulated genes are highly hypermethylated in the promoter regions (FIG. 33). Indeed, 53 of these were TSGs based on the TSGene database (Zhao, et al., (2016), Nucleic Acids Res 44, D1023-1031) (FIG. 34). The 1801 genes peaked at four-day generally showed progressive induction starting to be detectable at 4 to 8 hours after treatment (FIG. 35A). Gene Ontology analysis showed that they are enriched for cell adhesion, a signature that was also observed for upregulated genes after treatment with the DNMT inhibitor decitabine (DAC) (FIG. 35B).

Figure 36:
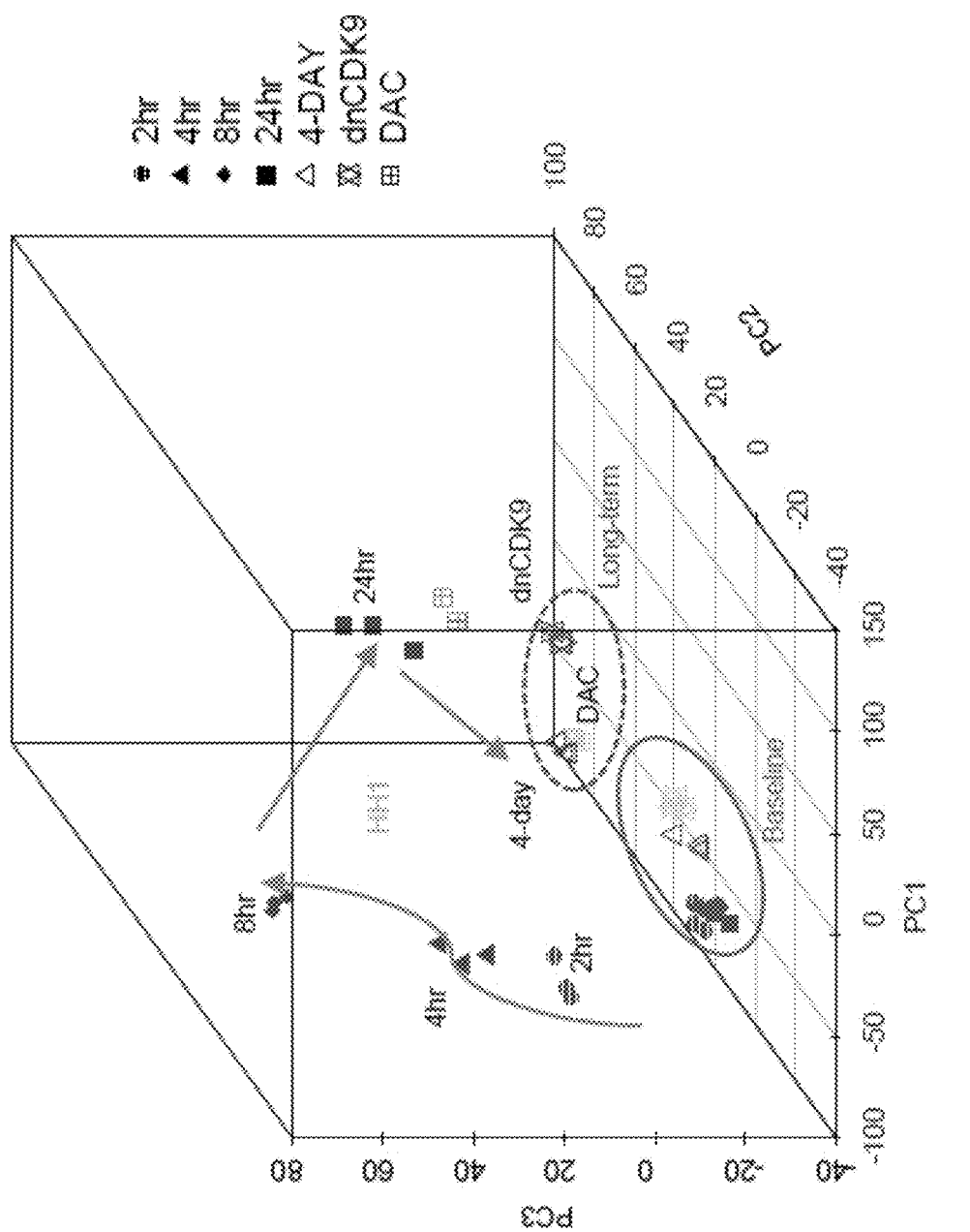
FIG. 36 depicts 3D principal component analysis on normalized counts values of the entire transcriptome of time-course RNA-seq upon either DMSO (in red) or HH1 10 μM treatment (in blue) (n=3). dnCDK9 (72 hr treatment) (in yellow (dnCDK9-off) and purple (dnCDK9-on)), 48 hr DAC treatment at 100 nM (in pink) and sequential combinatorial treatment (DAC 100 nM 48 hr followed by HH1 four-day at 10 μM (in green)) (n=3). All DMSO conditions and dnCDK9-off clustered together and are circled in green (baseline). DAC, dnCDK9-on and 4-day HH1 also clustered together and are circled in red (long-term). Different time points are shown in different shapes and labeled in the legend.
Figure 37:
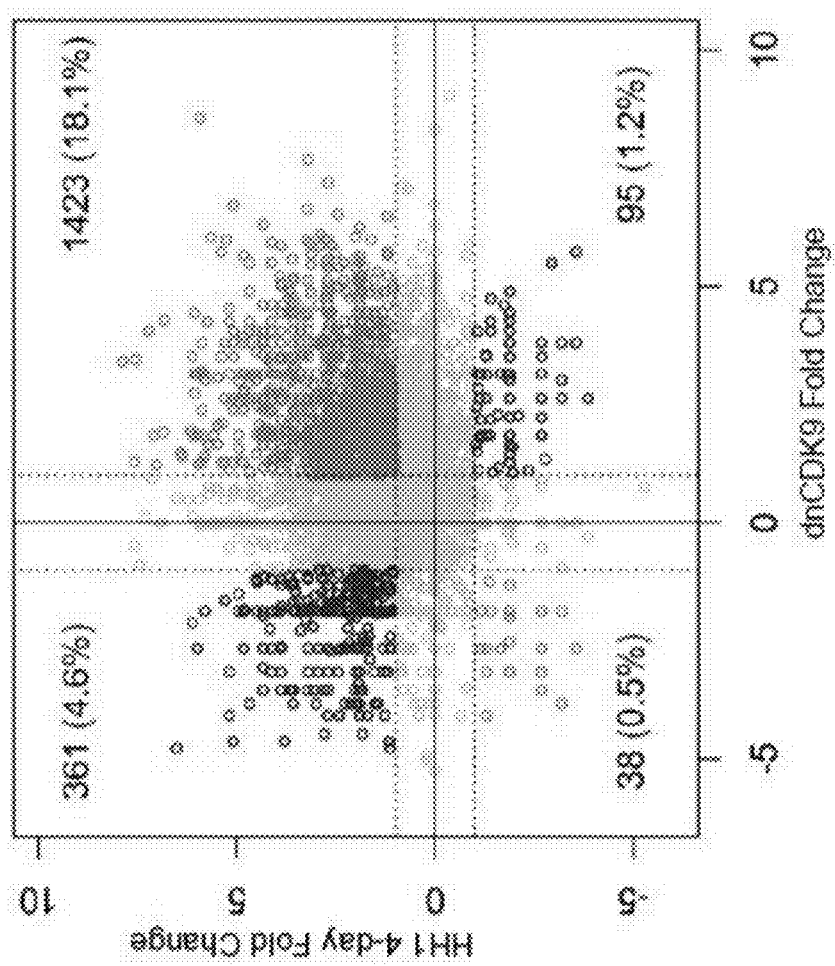
FIG. 37 depicts experimental data demonstrating gene expression changes after HH1 treatment recapitulate the effect of dominant negative CDK9. The scatter plot shows log 2 fold gene expression changes caused by dominant negative CDK9 (x-axis) and by a 4-day treatment of YB5 cells with 10 μM of the HH1 compound (y-axis). Concordant changes are in orange, discordant changes in blue, changes smaller than two-fold are in grey. The numbers in each quadrant show the number of genes with greater than 2-fold expression changes and the percentage of total genes analyzed by RNA-seq.
Figure 38:
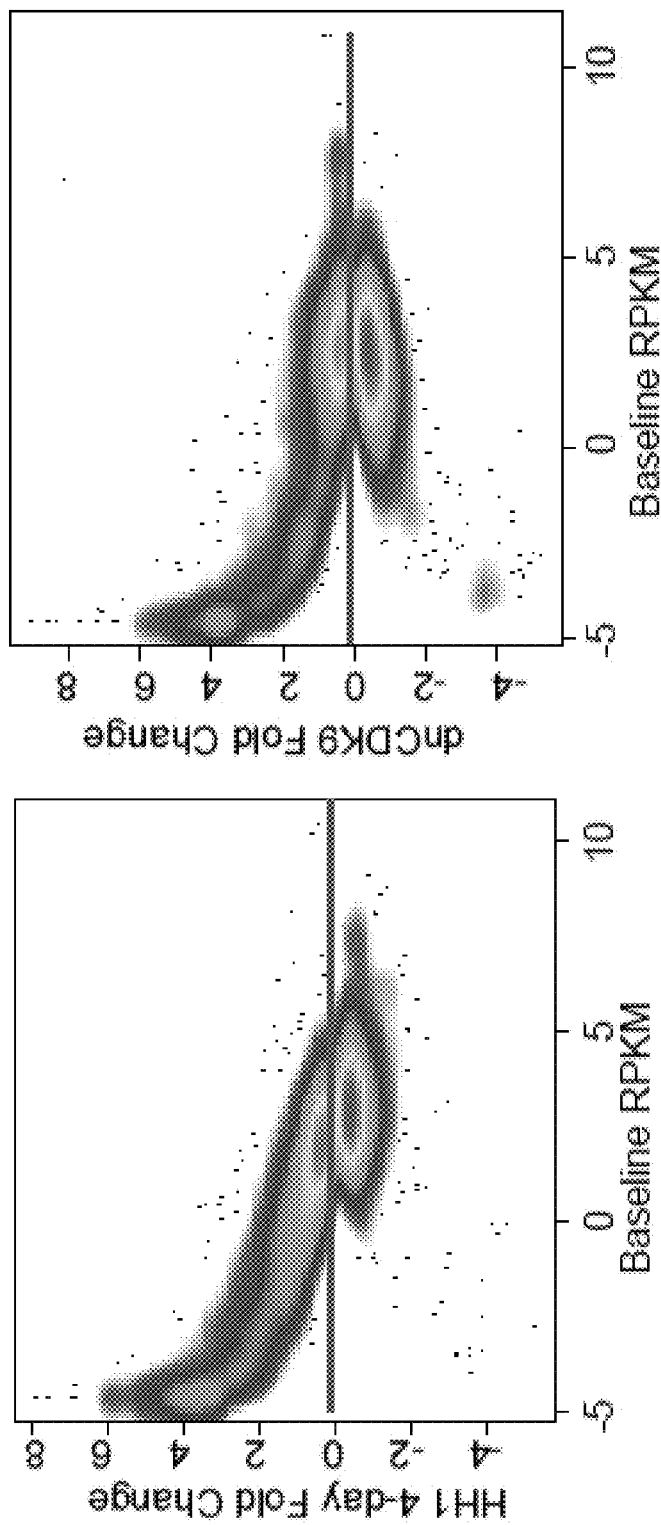
FIG. 38 depicts density plots showing the distributions of differentially expressed genes after four-day HH1 treatment at 10 μM or dnCDK9 overexpression (72 hr). The red lines represent no change.

The data shown above indicate that HH1 has a bimodal effect (one gene subset downregulated early and another upregulated late). To verify that this is due to CDK9 inhibition, RNA-seq after dnCDK9 was examined and it was found to be highly similar to HH1. Principal component analysis of the entire transcriptome showed that all the baseline conditions (cells treated with DMSO at different time points and TET-on dnCDK9) clustered together and there was time-dependent progressive gene induction after HH1 treatment (FIG. 36). Strikingly, dnCDK9 overexpression clustered closest to four-day HH1 treatment and there was a strong correlation between HH1 and dnCDK9 effects by RNA-seq (FIG. 37). Genes upregulated after either HH1 four-day treatment or dnCDK9 overexpression had very low baseline expression, consistent with the hypothesis that CDK9 is essential to maintain epigenetic silencing (FIG. 38). Thus, CDK9 inhibition has biphasic effects: early downregulation due to pTEFb inhibition and late epigenetic activation by an unknown mechanism.

Figure 40:
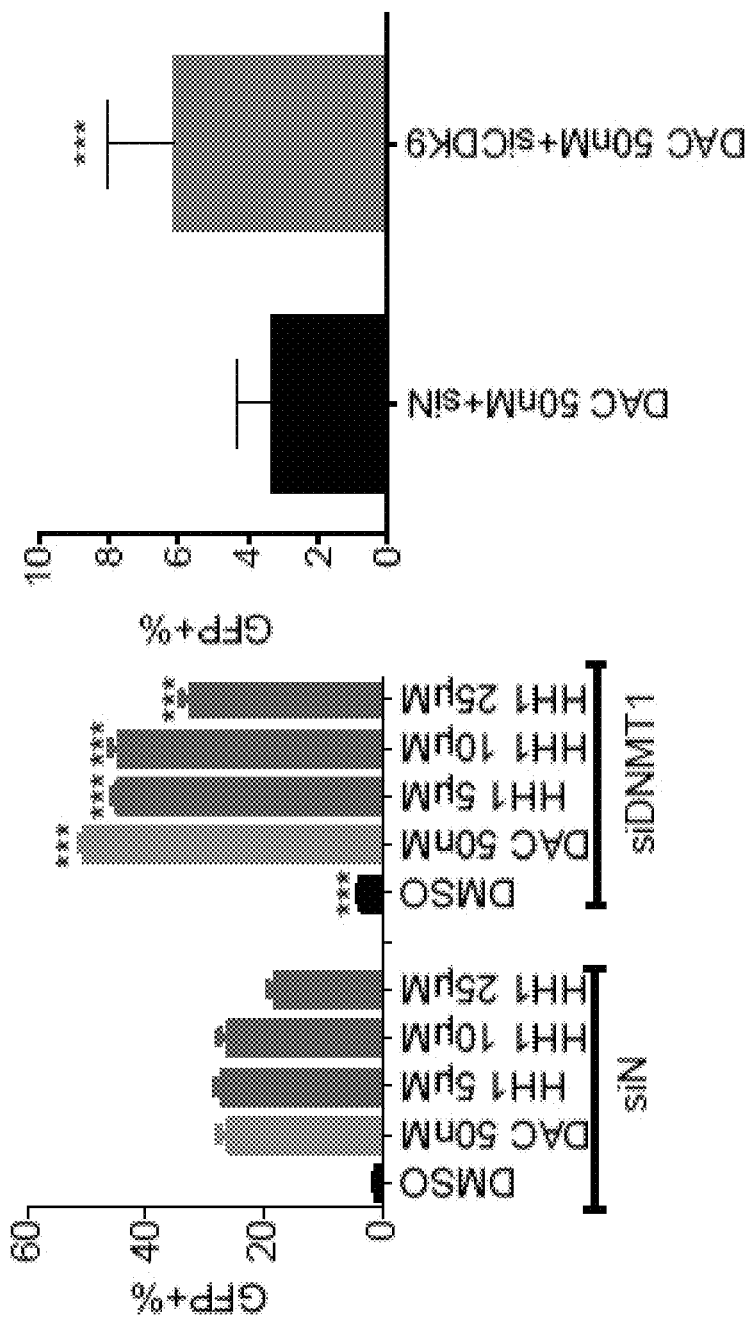
FIG. 40 depicts experimental data demonstrating the synergistic effect of HH1 with siDNMT1 (left) (either Non-targeting siRNA (siN) or siDNMT1 was transfected on day 0 and drugs were added on day 3. Drug-free media were changed on day 6 and FACS analysis was performed on day 7) and DAC with siCDK9 (right) (either Non-targeting siRNA (siN) or siCDK9 was transfected on day 0. 50 nM DAC was added on day 1 and FACS analysis was performed on day 4) in terms of GFP induction measured by FACS (n=3). Data are shown as mean±SD. ***p<0.001 (Student's t-test).

The initial screening assay was based on DNA methylation regulation of GFP. Indeed, a high degree of similarity between the late effect of HH1 and those induced by the DNMTi, DAC was found. The transcriptional profiles of DAC clustered close to 4-day Mil (FIG. 36) and 4-day HH1 inhibition behaved similarly to DAC treatment (FIG. 39). Because HH1 did not actually induce demethylation, it was decided to test for synergy between HH1 and DAC. The two drugs were highly synergistic for GFP and SYNE1 reactivation (FIG. 18). The synergistic effects were validated using either siDNMT1 or siCDK9 (FIG. 40). Next, RNA-seq using DAC in combination with HH1 was performed. After excluding the early response genes (downregulated at 2 hr/4 hr), it was found that, compared to DAC alone (1238 up vs. 7 down) or HH1 alone (1801 up vs. 13 down), low expressed genes (RPKM<0.31) were significantly upregulated by the combination (3940 up vs. 3 down) (FIG. 32). Thus, long-term CDK9 inhibition shows similar transcriptional profiles to DNMT inhibition and shows synergy with DNMT inhibition.

SMARCA4 and HP1 are Epigenetic Targets of CDK9.

CDK9 is the catalytic subunit of a positive transcriptional elongation factor. However, the data described herein also show that CDK9 appears to also serve as an epigenetic repressor. In a search for the mechanism of CDK9 mediated gene repression, Ingenuity Pathway Analysis (IPA) was used in RNA-seq data on genes upregulated by HH1. SMARCA4 and CBX5 were found to be the top regulators that can be activated and inhibited, respectively (FIG. 39 and FIG. 41).

Figure 42:
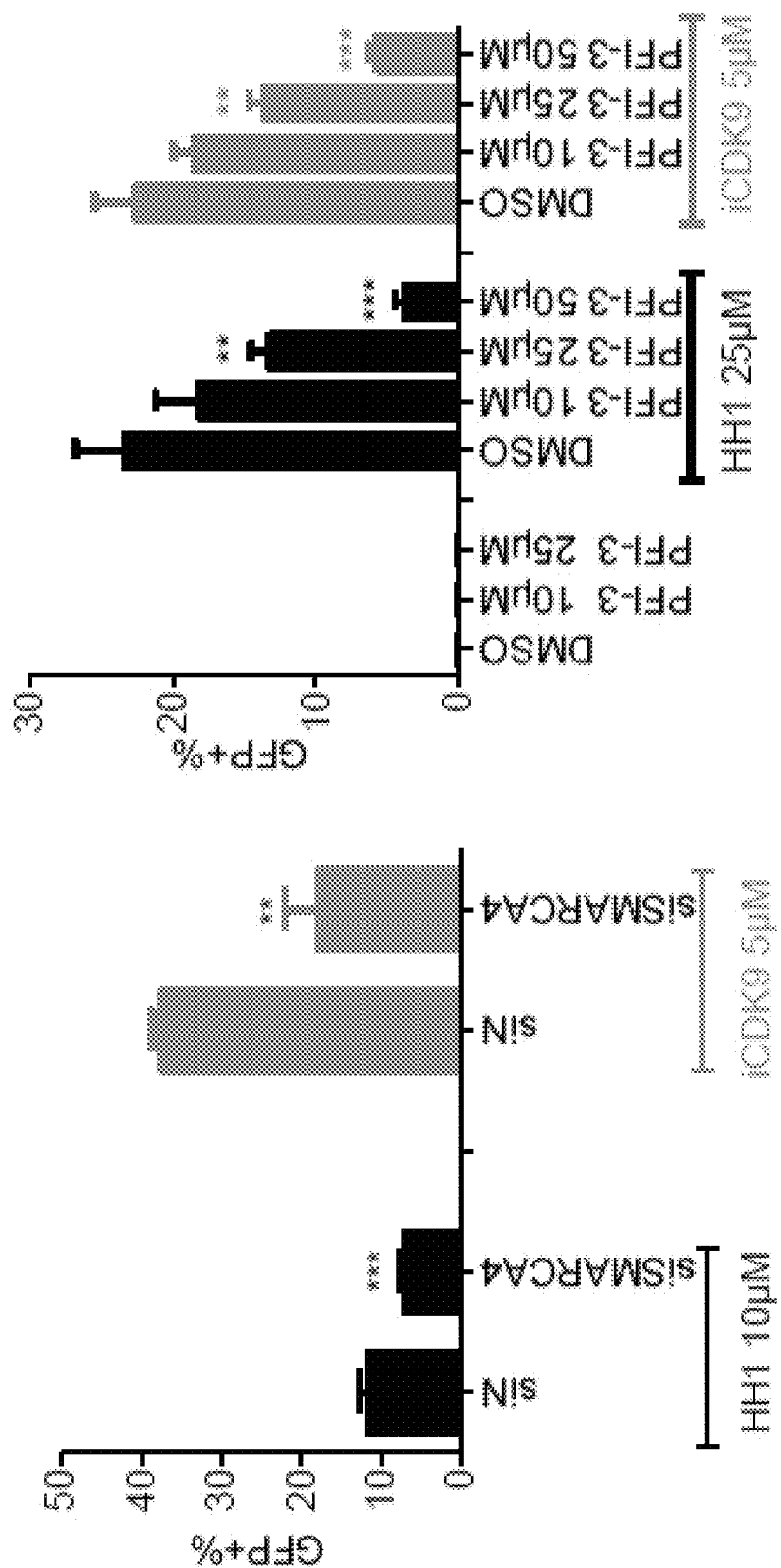
FIG. 42 depicts experimental data demonstrating the disruption of SMARCA4 activity by siSMARCA4 or by the PFI-3 inhibitor. To achieve a higher knock-down efficiency, transfection was done every other day for a total of three times. Drugs were added to the medium 48 hrs after the third transfection (left). PFI-3 was used to block SMARCA4 enzymatic activity (72 hr daily pre-treatment followed by 24 hr co-treatment) (right). Inhibition of SMARCA4 diminished the effect of CDK9 inhibitors on GFP induction in YB5. Data are shown as mean±SD, n=3. *p<0.05, p<0.01, *p<0.001 (Student's t-test).
Figure 44:
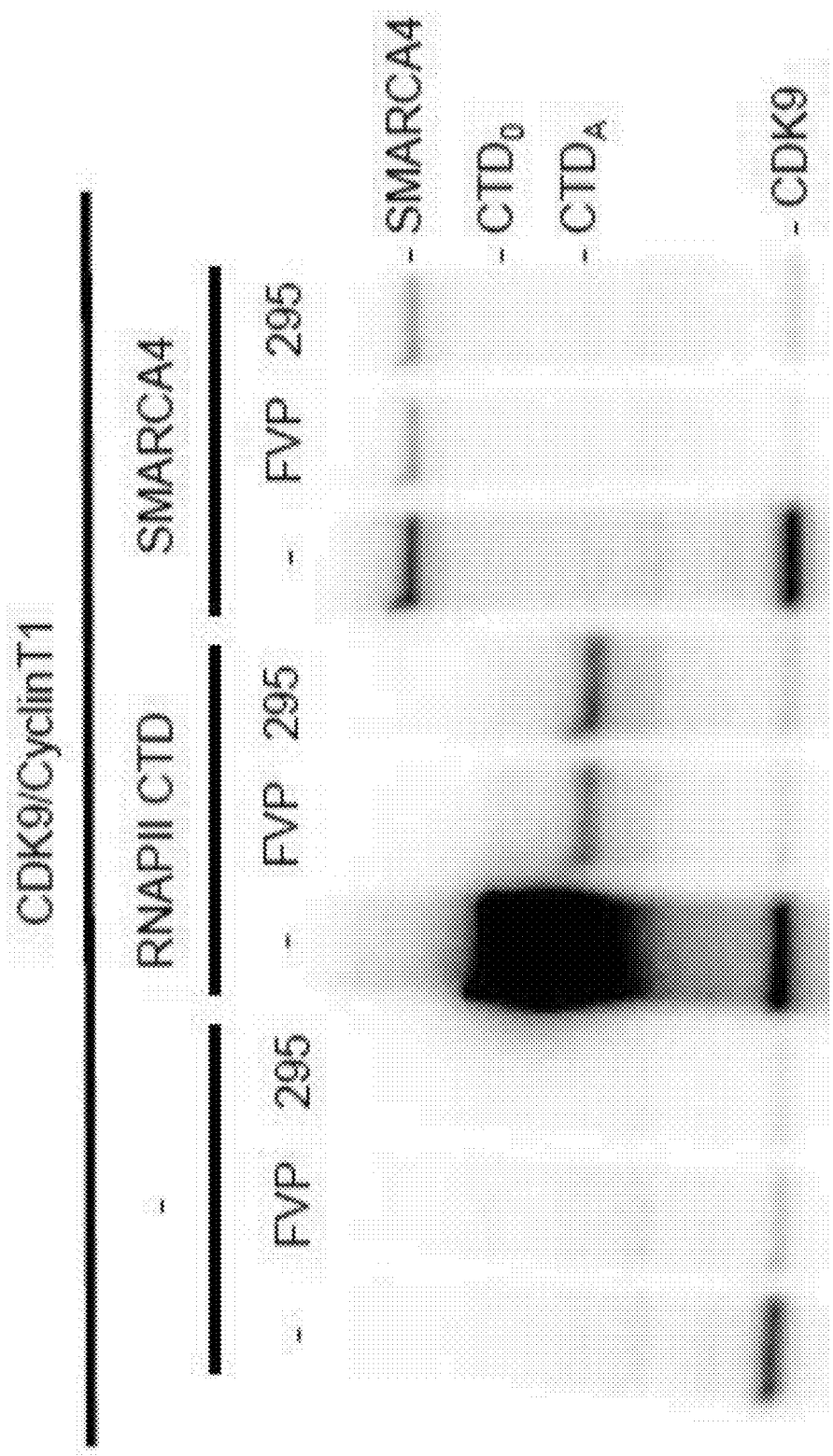
FIG. 44 depicts experimental data demonstrating anisotope kinase activity assay using recombinant active full-length CDK9 and SMARCA4 with or without CDK9 inhibitors (Flavopiridol (FVP) and MC180295 (295)) in the presence of $^{32}\gamma$-ATP. The C-terminal domain of RNA Polymerase II (CTD) was used as a positive control in this experiment. SMARCA4 was dephosphorylated after CDK9 inhibition.
Figure 45:
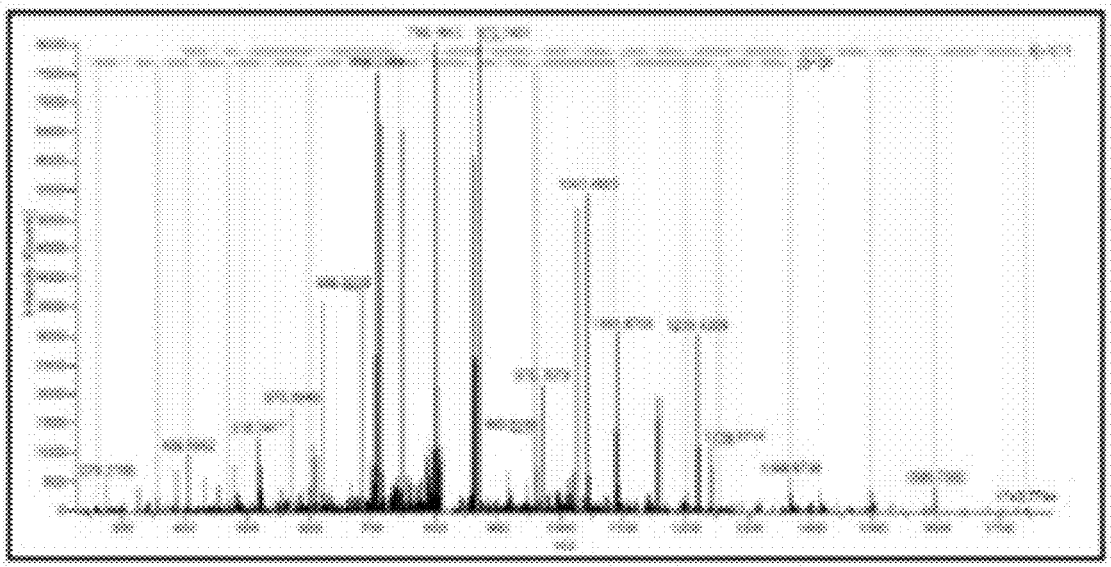
FIG. 45 depicts experimental data demonstrating phosphorylated peptides in control (DMSO) but absence with drug treatment (500 nM MC180295 for 4 hr). The phosphorylated sites are highlighted in red. Peptide consensus view of the amino acids that were dephosphorylated are also shown below.

SWI/SNF is an ATP-dependent nucleosome remodeling complex that allows the compaction and decompaction of DNA in the nucleus (Kadoch, C., and Crabtree, G. R. (2015), Sci Adv 1, e1500447). Whole-exome sequencing revealed that over 20% of human cancers harbor mutations in the genes encoding mammalian SWI/SNF subunits (Kadoch, C., et al., (2013), Nat Genet 45, 592-601). Most of the mutations are loss-of-function, indicating that these subunits may be bone fide tumor suppressors (St Pierre, R., and Kadoch, C. (2017), Curr Opin Genet Dev 42, 56-67). The most widely studied protein, SMARCA4, also known as BRG1, is an ATP-dependent helicase that is part of the SWI/SNF family and can use ATP hydrolysis to relax chromatin structure (Wilson, B. G., and Roberts, C. W. (2011), Nat Rev Cancer 11, 481-492). To test if SMARCA4 mediates HH1 induced gene reactivation, SMARCA4 was knocked down using siRNA followed by HH1 treatment and it was found that GFP induction was reduced significantly. iCDK9, another CDK9 inhibitor, showed similar results. To further confirm this, a SMARCA4 inhibitor, PFI-3 (Vangamudi, B., et al. (2015), Cancer Res 75, 3865-3878), was used, and it was found that PFI-3 inhibited GFP activation by either HH1 or iCDK9 in a dose-dependent manner (FIG. 42). Together these results support the finding that activation of transcription following CDK9 inhibition requires SMARCA4. Thus, it was hypothesized that CDK9 regulates SMARCA4 by direct phosphorylation. Indeed, public proteomic data showed possible binding of CDK9 to SMARCA4 (Rouillard, A. D., et al., (2016). Database (Oxford) 2016). Co-immunoprecipitation (Co-IP) was used to confirm this. IP using a CDK9 antibody successfully pulled down SMARCA4 (FIG. 43A). This was also true for exogenously expressed CDK9 and SMARCA4 IPs by GFP and FLAG antibodies (FIG. 43B). Next, an in vitro kinase assay was performed using purified CDK9 and SMARCA4 proteins and showed that CDK9 directly phosphorylates SMARCA4 in vitro (FIG. 44). Finally, to identify potential phosphorylation sites in SMARCA4 regulated upon CDK9 inhibition, LC-MS/MS was performed after 4 hr MC180295 treatment and several serine/threonine residues were found to be dephosphorylated (FIG. 45). Thus, SMARCA4 was found to be a direct phosphorylation target of CDK9 and may be useful for mediating gene activation upon CDK9 inhibition.

Figure 48:
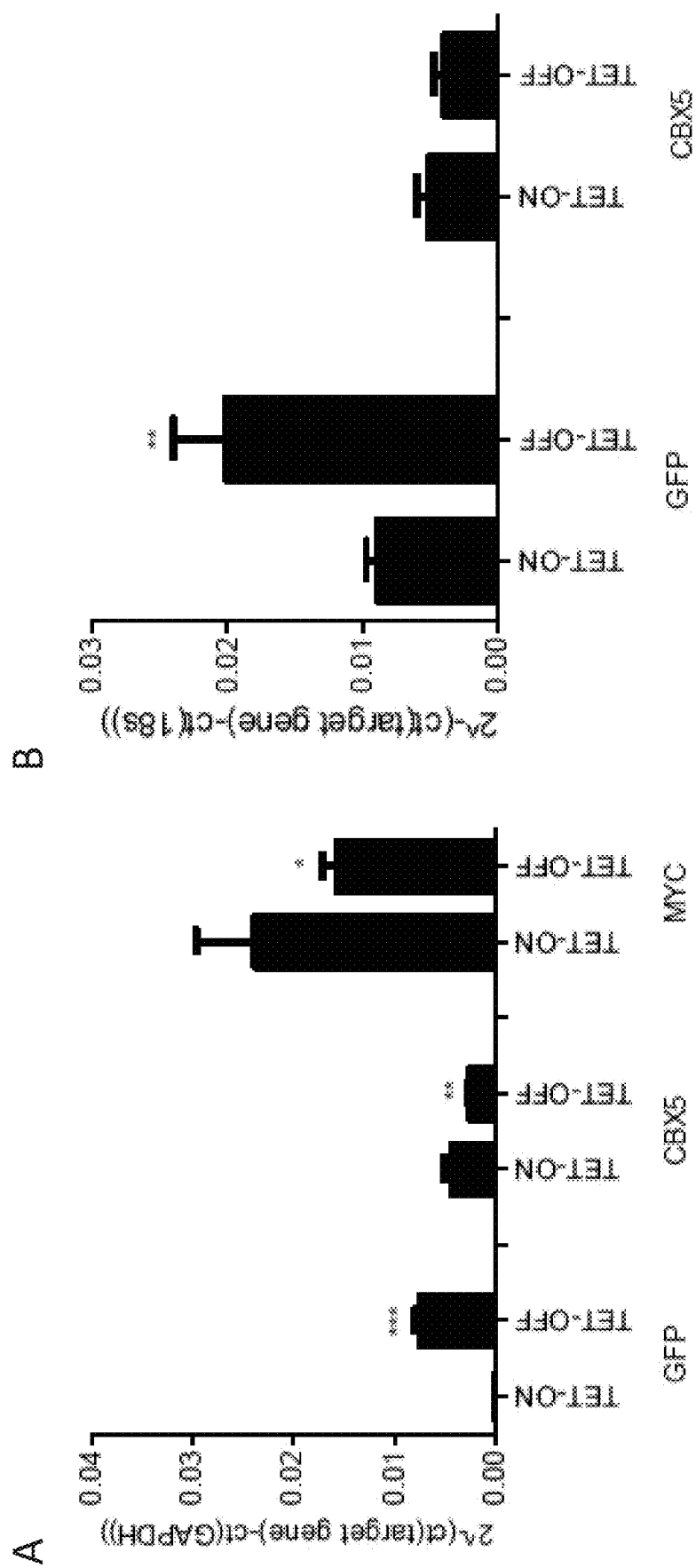
FIG. 48, comprising
Figure 49:
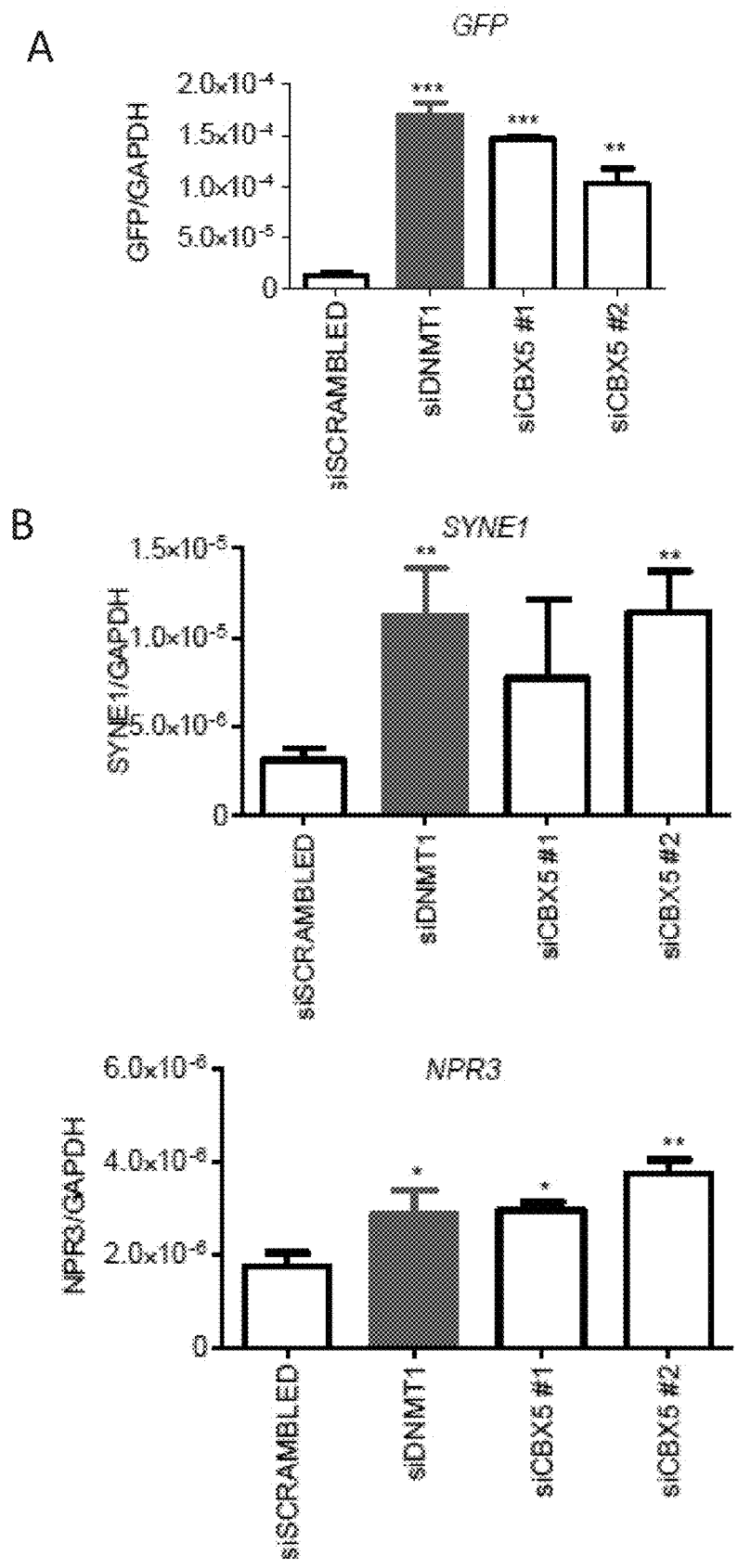
FIG. 49, comprising
Figure 50:
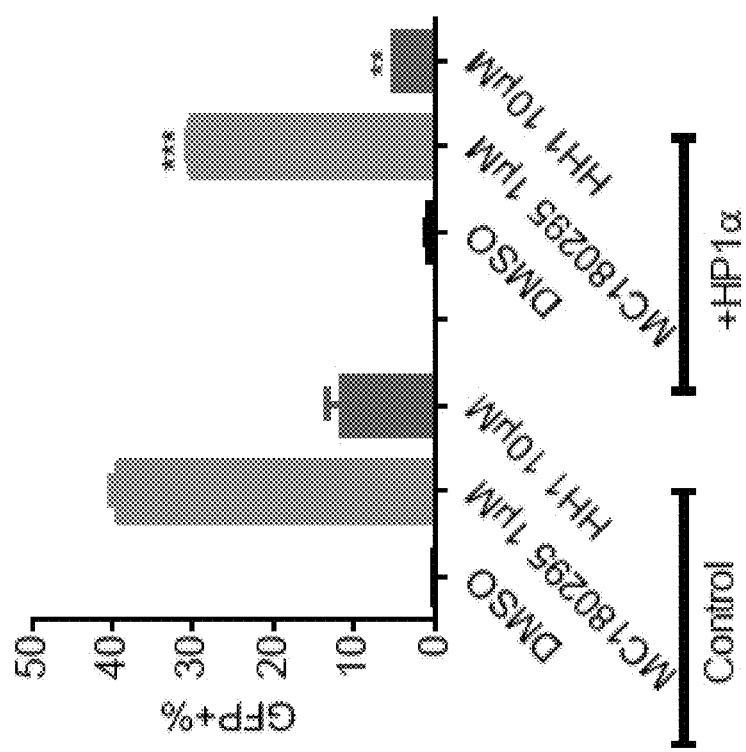
FIG. 50 depicts experimental data demonstrating that GFP expression was reduced significantly when overexpressing HP1α measured by FACS. A CMV-HP1α was overexpressed for 72 hr followed by CDK9 inhibitor treatment for an extra four days. Data are shown as mean±SD, n=3. p<0.01, *p<0.001 (Student's t-test).

CBX5, also known as HP1α, a known epigenetic mediator of gene silencing was next examined. The RNA-seq data for HH1 was examined and it was found that CBX5 was downregulated directly upon CDK9 inhibition. This downregulation was validated by time-course q-PCR and Western Blot (FIGS. 46A-46B). It was further found that the downregulation of CBX5 (by multiple CDK9 inhibitors) was most significant four days after one-time drug exposure, and that CBX5 expression negatively correlated with GFP induction in a dose-dependent manner (FIG. 47). Consistent with this, CBX5 was inhibited upon overexpression of dnCDK9 in both YB5 and HCT116 cells (FIGS. 48A-48B). CBX5 was then knocked down using two individual siRNAs and it was found that GFP, as well as two hypermethylated silenced genes (SYNE1 and NPR3), were reactivated upon CBX5 inhibition (FIGS. 49A-49B). Moreover, it was found that reactivation of GFP by HH1 and MC180295 was reduced significantly by overexpression of HP1α (FIG. 50). HP1α, encoded by CBX5, can recognize and bind to H3K9me2, a repressive mark for heterochromatin gene silencing. Consistent with this, it was found that the HH1-upregulated genes are highly enriched for H3K9me2 at baseline (FIG. 51A) and that the H3K9me2 mark is enriched at the CMV/GFP region (FIG. 51B). Thus, CDK9 inhibition rapidly suppresses CBX5, possibly through pTEFb effects, and this contributes to epigenetic reactivation upon drug treatment.

CDK9 Inhibition has Anti-Tumoral Effects In Vitro and In Vivo.

Figure 57:
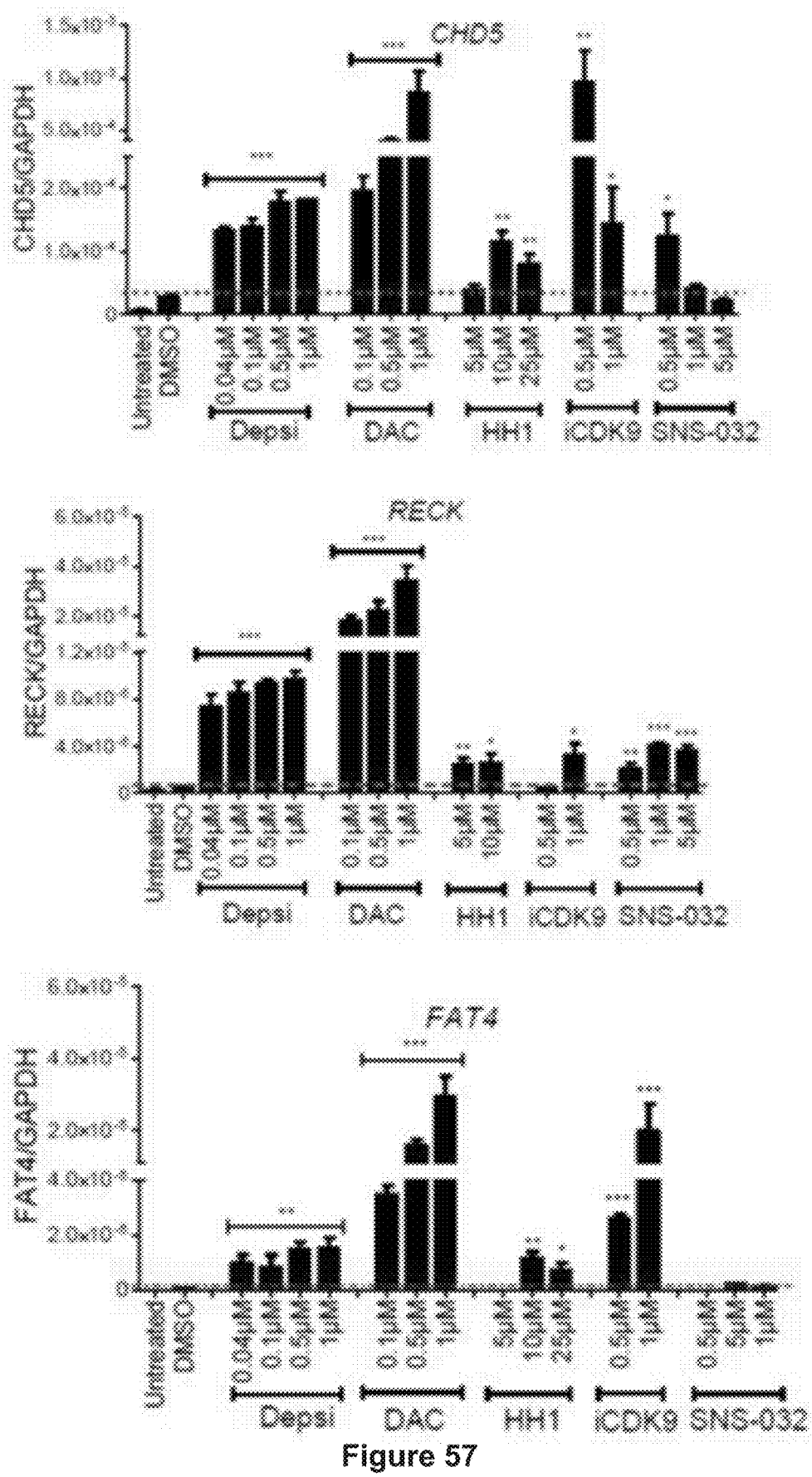
FIG. 57 depicts experimental data demonstrating the reactivation of three tumor suppressor genes hypermethylated in ovarian cancer (selected by merging promoter hypermethylated genes identified by DREAM assay) with known ovarian cancer tumor suppressor genes (by TSGene database)) after 24 hr treatment with CDK9 inhibitors in mouse ID8 ovarian cancer cells (n=3). Data are shown as mean±SD. *p<0.05, p<0.01, *p<0.001 (Student's t-test).

Although the literature discusses anti-tumoral effects of CDK9 inhibition, usually attributed to MCL-1 and/or MYC suppression, all these studies were based on drugs that inhibit multiple CDKs. For example, the "prototypical" CDK9 inhibitor flavopiridol also inhibits CDK1, 2 and 8 (IC50 20 nM for CDK9, 20 nM for CDK8, 30 nM for CDK1 etc.) (Asghar, et al, (2015), Nat Rev Drug Discov 14, 130-146). Therefore, whether specific CDK9 inhibitors also have anti-tumoral effects was tested. First, proliferation four days after one-time HH1 or MC180295 exposure was tested in multiple cell lines. Compared to normal lung epithelial cells (IMR90), both HH1 and MC180295 were more effective in reducing proliferation of cancer cells than normal control cells (FIG. 52A). Cell cycle analysis showed no cell cycle arrest after HH1 or MC180295 (FIG. 52B), but an increase in the sub-G1 subpopulation (FIG. 52C). Next, colony formation in soft agar was tested and it was found that a single dose pre-exposure of HH1 and MC180295 for four days can blunt colony formation by 30-80% in YB5 and HCT116 (FIGS. 53A-53B). Effects on the differentiation marker CD11b were also tested using the HL60 cell line and significant induction was found (FIGS. 54A-54B), which is consistent with the tretinoin signature found by IPA upstream regulator analysis for HH1 (FIG. 39 and FIG. 41). Lastly, in vivo effects of MC180295 and the structurally related CDK9 inhibitor, SNS-032, were tested. Luciferase labeled SW48 colon cancer cells were injected into NSG mice followed by 10 mg/kg MC180295 treatment. It was found that the tumors shrank significantly (by ~50%) after one-week drug exposure and the tumor burden was also lower after three weeks drug treatment, as measured by luciferase activity (FIG. 55A). A similar effect was observed by daily MC180295 treatment at 10 mg/kg in the same mouse model (FIG. 55B). Additionally, an ovarian cancer mouse cell line, ID8, was transplanted into syngeneic immunocompetent mice and the anti-tumor efficacy of SNS-032 in vivo was tested. It was found that 10 mg/kg SNS-032 can reduce tumor burden (FIG. 56A) and extend the survival of the mice significantly (FIG. 56B). Several ovarian cancer-specific hypermethylated TSGs were reactivated in ID8 cells after CDK9 inhibition (FIG. 57).

CDK9 Inhibition Activates Endogenous Retroviruses and an Interferon Response.

Figure 58:
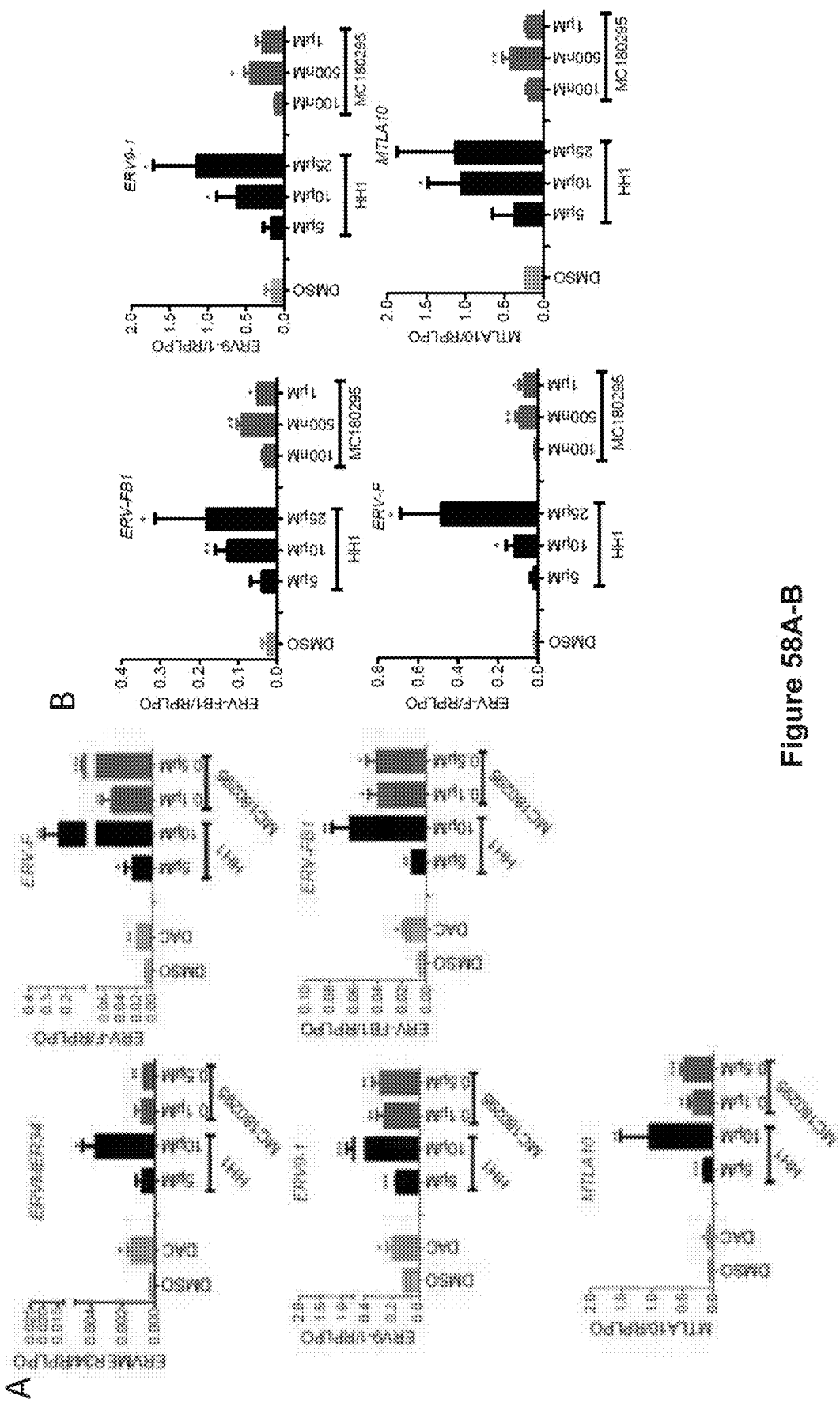
FIG. 58, comprising
Figure 59:
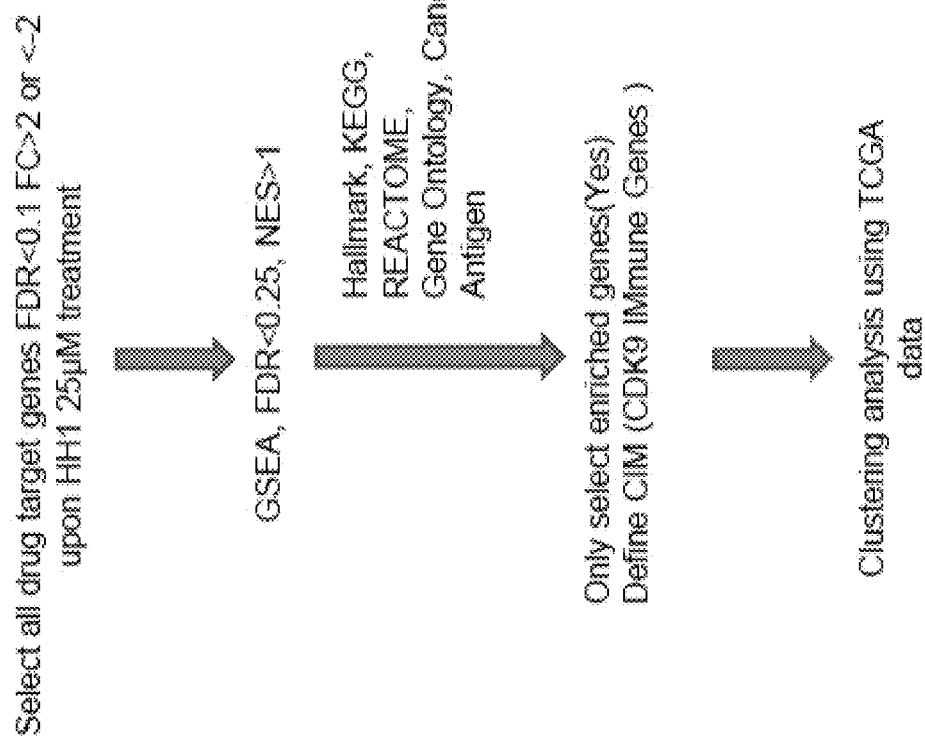
FIG. 59 depicts experimental data demonstrating the generation of CDK9 Immune Signature (CIM) gene panel. RNA-seq data was analyzed by GSEA and 328 immune related genes were identified and upregulated after HH1 four-day treatment.
Figure 60:
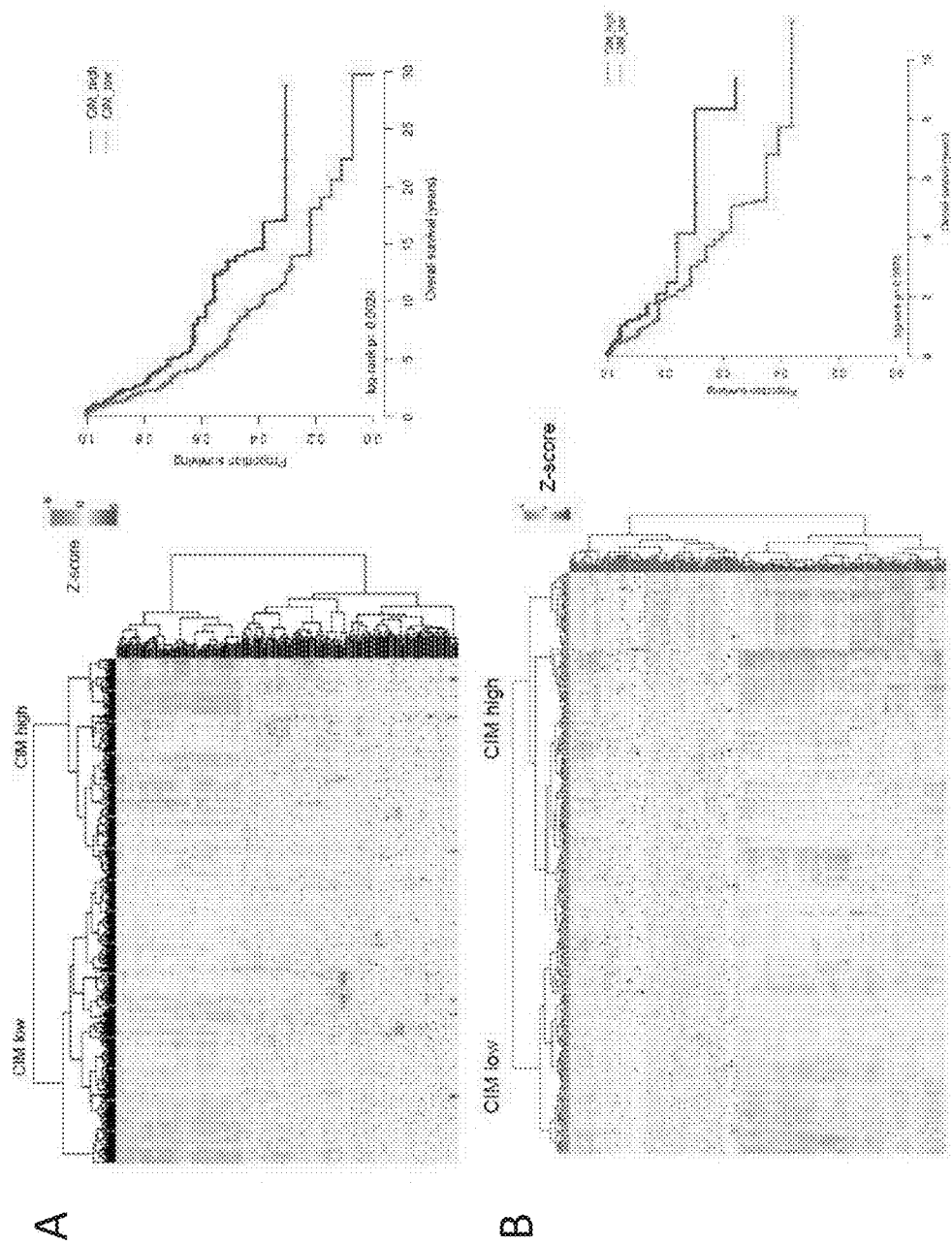
FIG. 60, comprising
Figure 61:
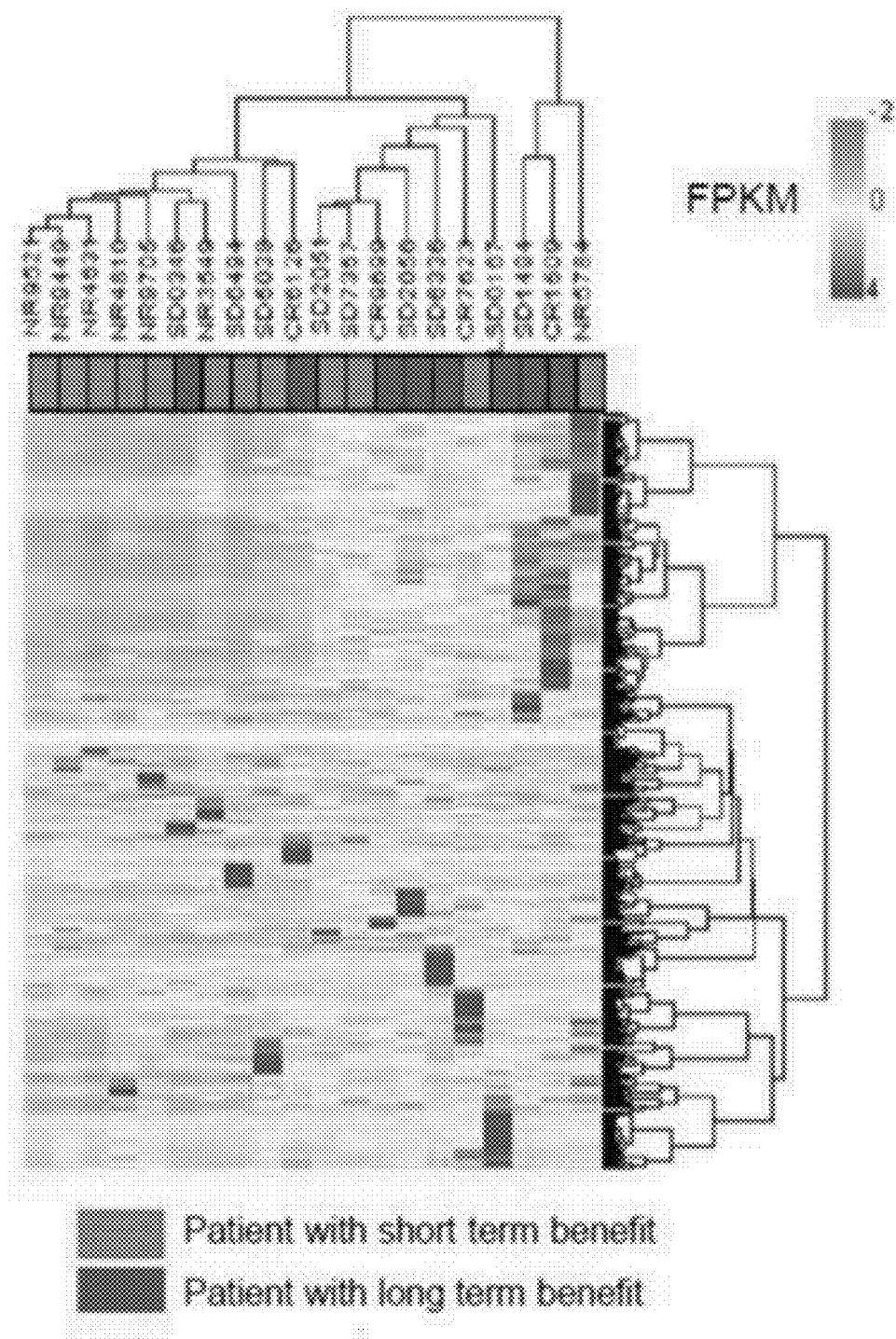
FIG. 61 depicts experimental data demonstrating anti-CTLA4 treated melanoma patients with long-term benefit tend to have higher expression levels of CIM signature related genes.
Figure 62:
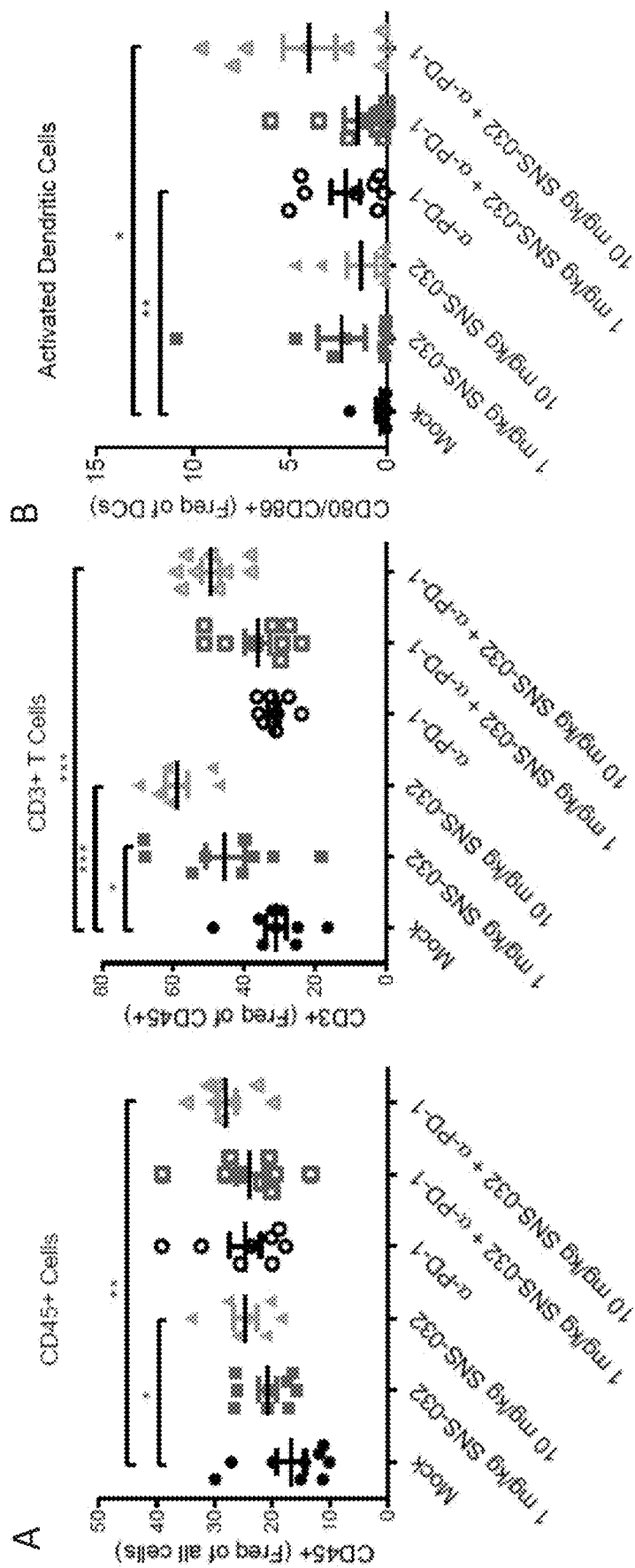
FIG. 62, comprising

Epigenetic drugs such as 5-azacytidine (a DNMTi) can trigger the IFNγ pathway within tumor cells, in part by activation of Endogenous Retroviruses (ERVs), leading to epigenetic immunosensitization (Chiappinelli, et al. (2015), Cell 162, 974-986; Roulois, et al. (2015), Cell 162, 961-973)). Although not wishing to be bound by any particular theory, the immune responses and ERVs may play an important role in the activity of 5-azacitidine in myeloid malignancies. (Licht, J. D. (2015), Cell 162, 938-939). RNA-seq after HH1 exposure identified DNMTi and IFNγ signatures (FIG. 39 and FIG. 41). Although not wishing to be bound by any particular theory, this result suggests that CDK9 can also influence intracellular immune pathways. To test for this directly, q-PCR for ERV expression was performed in SW48 and HCT116 cells. Four-day HH1 or MC180295 treatment activated the expression of several ERVs (FIGS. 58A-58B). Next, as previously shown for DNMTi (Li, et al. (2014), Oncotarget 5, 587-598)), 326 immune-related genes that can be activated by HH1 were identified (FIG. 59). This CDK9 immune signature (CIM) was queried in the TCGA database (Network, C. G. A. (2015), Cell 161, 1681-1696; Pal, S., and Tyler, J. K. (2016), Sci Adv 2, e1600584) and identified a subset of melanoma patients carrying high expression of CIM and significantly better outcomes (FIG. 60A). A similar pattern was also found in colon cancer (Network, C. G. A. (2012), Nature 487, 330-337) (FIG. 60B). The RNA-seq data from 19 melanoma patients treated with anti-CTLA4 was then queried (Snyder, et al. (2014), N Engl J Med 371, 2189-2199) and again it was found that the subset of cases with long-term benefit tended to have a higher expression level of CIM signature genes (FIG. 61). These data supported the hypothesis that CDK9 inhibition could sensitize to immune checkpoint inhibitors. This was directly tested in the ID8 immunocompetent mouse model and it was found that CDK9 inhibition could sensitize with anti-PD1 in vivo (FIGS. 56A-56B). In this same model, CDK9 inhibition increased the numbers of CD45+ immune cells and the percentages of CD3+ T cells and activated dendritic cells in the tumor environment, while combining CDK9 inhibition with checkpoint blockage further boosted the immune responses in vivo (FIGS. 62A-62B). In addition to having single-agent activity, these results suggest that CDK9 inhibition may be a promising strategy for epigenetic immunosensitization.

Here, a novel epigenetic silencing target—CDK9—and a new inhibitor, MC180295, that shows nanomolar potency and has 20-fold increased selectivity for CDK9 compared to other CDKs are described. Reactivation of silenced genes requires cell division to help reset chromatin (Taylor, S. M., and Jones, P. A. (1979), Cell 17, 771-779). Although not wishing to be bound by any particular theory, this may explain why the compound discovered shows high selectivity for CDK9 compared to cell cycle regulating CDKs (e.g. CDK1, CDK2), suggesting the selectivity for CDK9 and against pan-CDK inhibitors. Although not wishing to be bound by any particular theory, the model of the CDK9-MC180295 complex suggests that this inhibitor achieves selectivity through the adamantyl group, not by making direct interactions to sidechains that are unique to CDK9, but by taking advantage of a subtle structural variation in the active site. The selectivity of other selective Type I inhibitors has also been investigated (Müller, S., et al. (2015), Nat Chem Biol 11, 818-821; Wang, Q., et al., (2014), Methods Enzymol 548, 23-67). Analysis of a separate chemical series ascribes the inhibitors' selectivity to CDK9's malleability rather than to the uniqueness of this particular conformation (Hole, A. J., et al., (2013), J Med Chem 56, 660-670). This appears to be the first example of kinase inhibitors as potential drugs that reverse epigenetic silencing. This may be useful to develop strategies for clinical development, optimization and overcoming resistance; in contrast, other protein classes involved in epigenetic regulation may be much more difficult to target with drug-like compounds.

Figure 63:
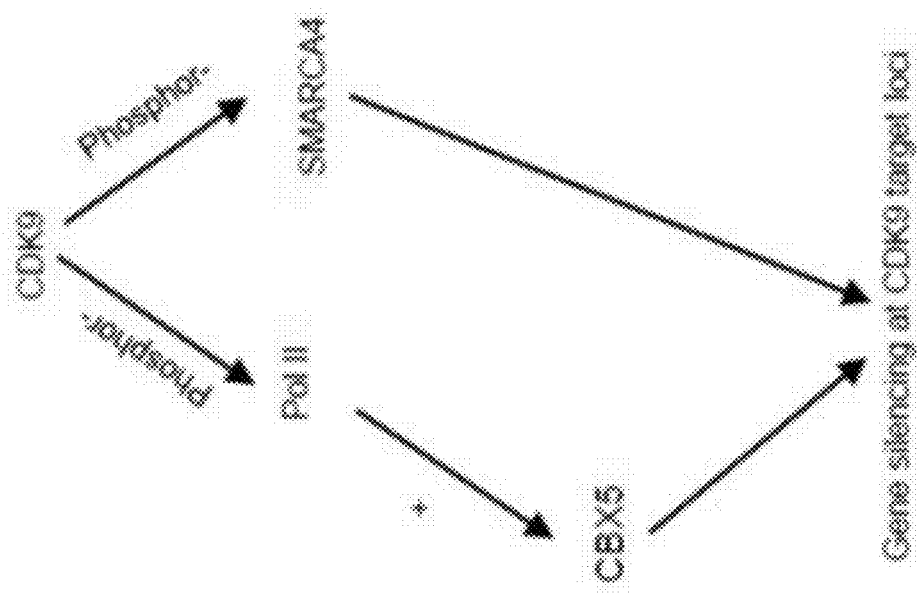
FIG. 63 depicts an example of a working model of CDK9 mediated gene suppression. CDK9 mediates gene silencing by indirectly suppressing CBX5 expression and directly phosphorylating SMARCA4.
Figure 64:
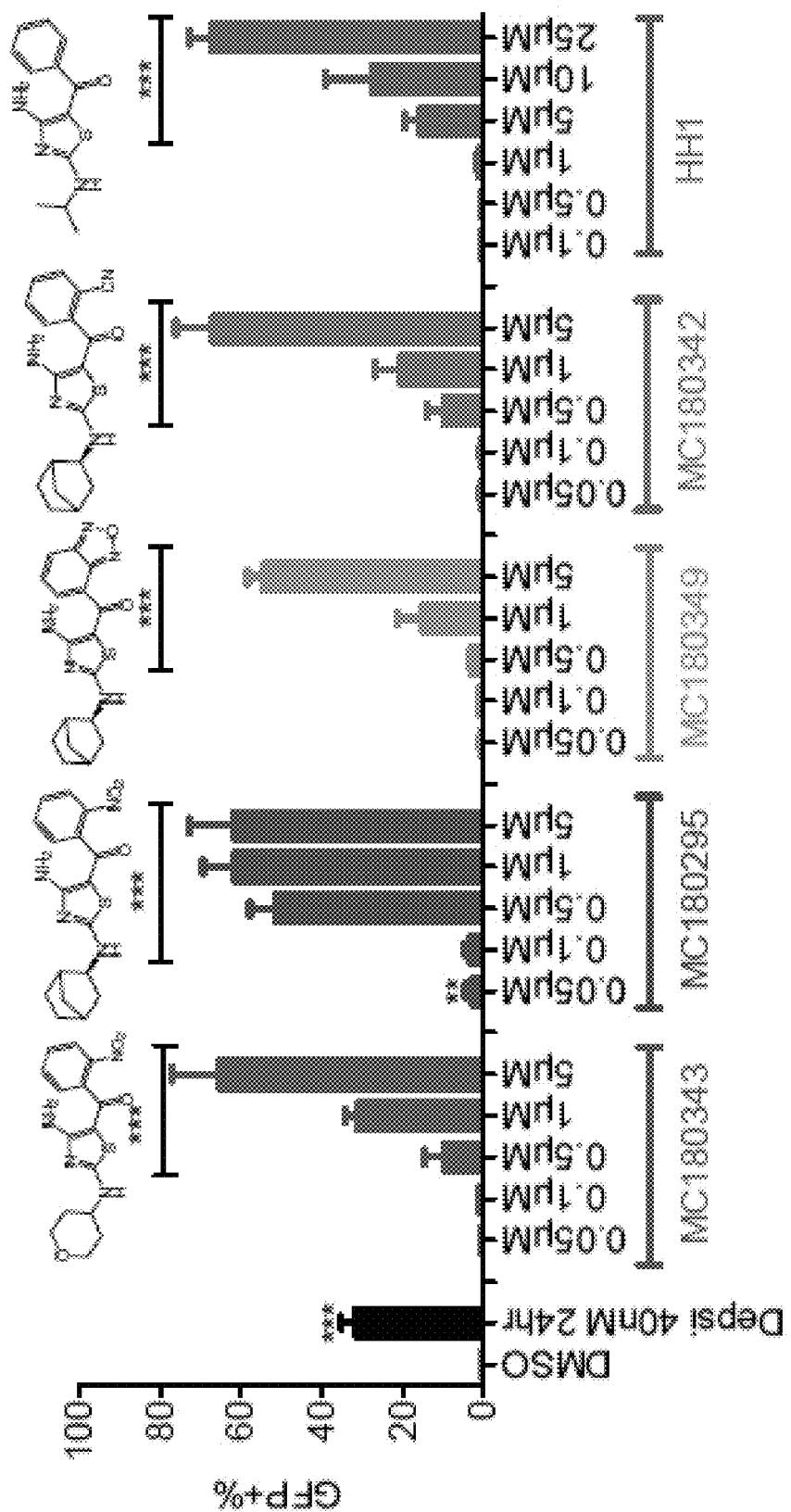
FIG. 64 depicts experimental data demonstrating GFP re-expression dose-responses after 24 hr treatment with different CDK inhibitors. Corresponding structures are shown on top of each bar group.
Figure 65:
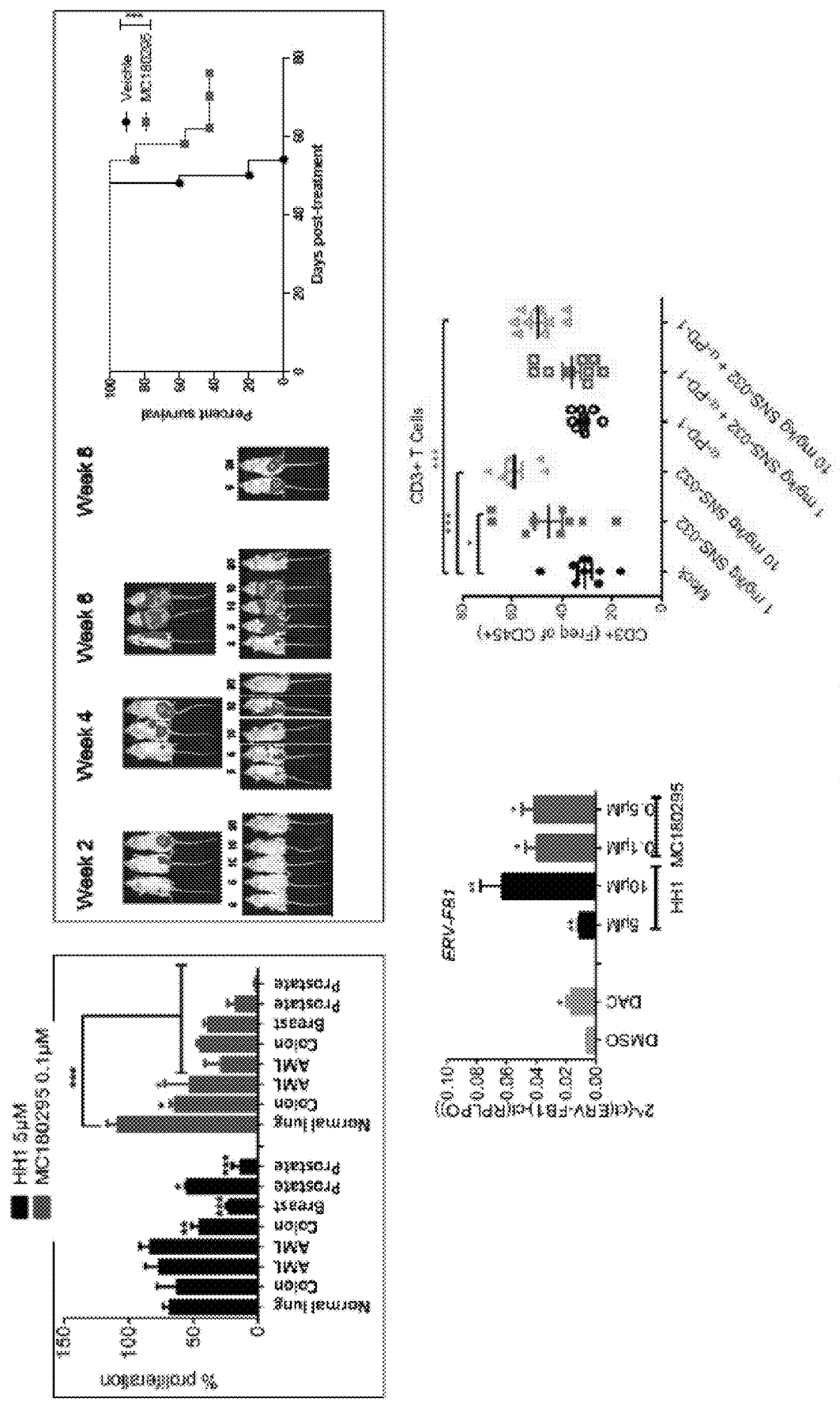
FIG. 65 depicts data demonstrating in-vitro and in-vivo efficacy of compounds of the invention.
Figure 68:
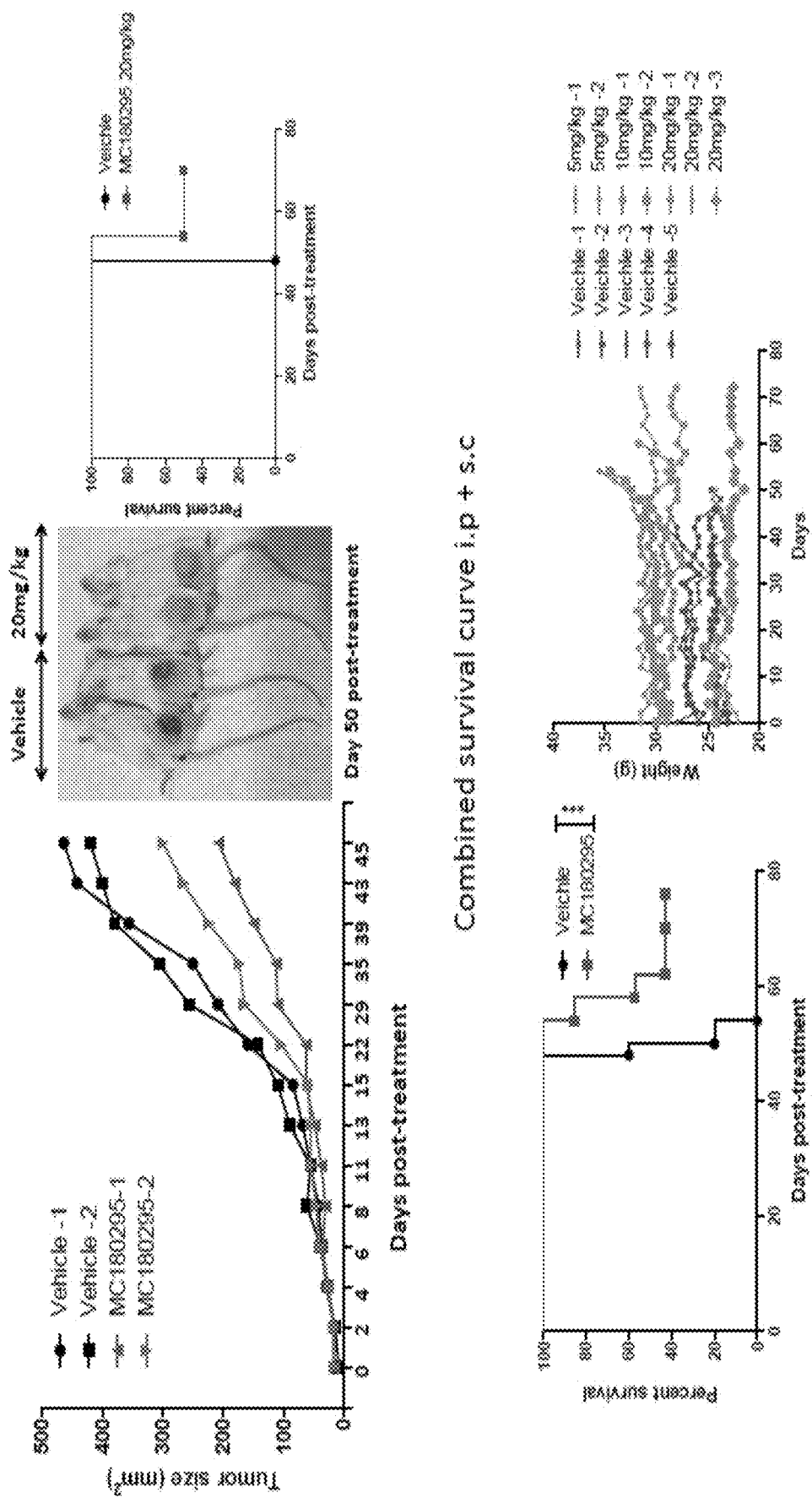
FIG. 68 depicts experimental data demonstrating the effects of MC180295 treatment on tumors in mice in an SW48 model.
Figure 69:
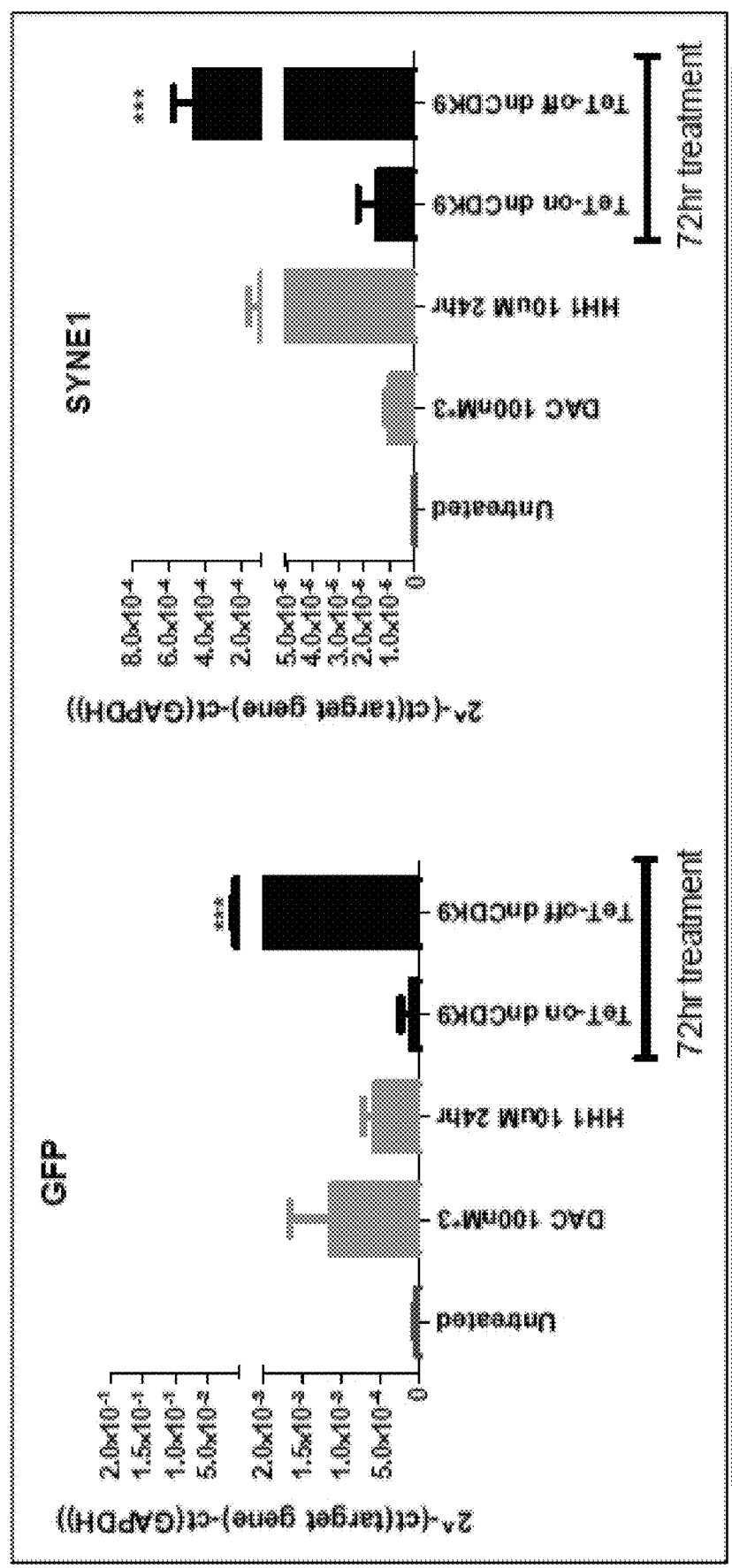
FIG. 69 depicts experimental data demonstrating that genetic inhibition of CDK9 (dominant negative) phenocopies drug treatment.
Figure 70:
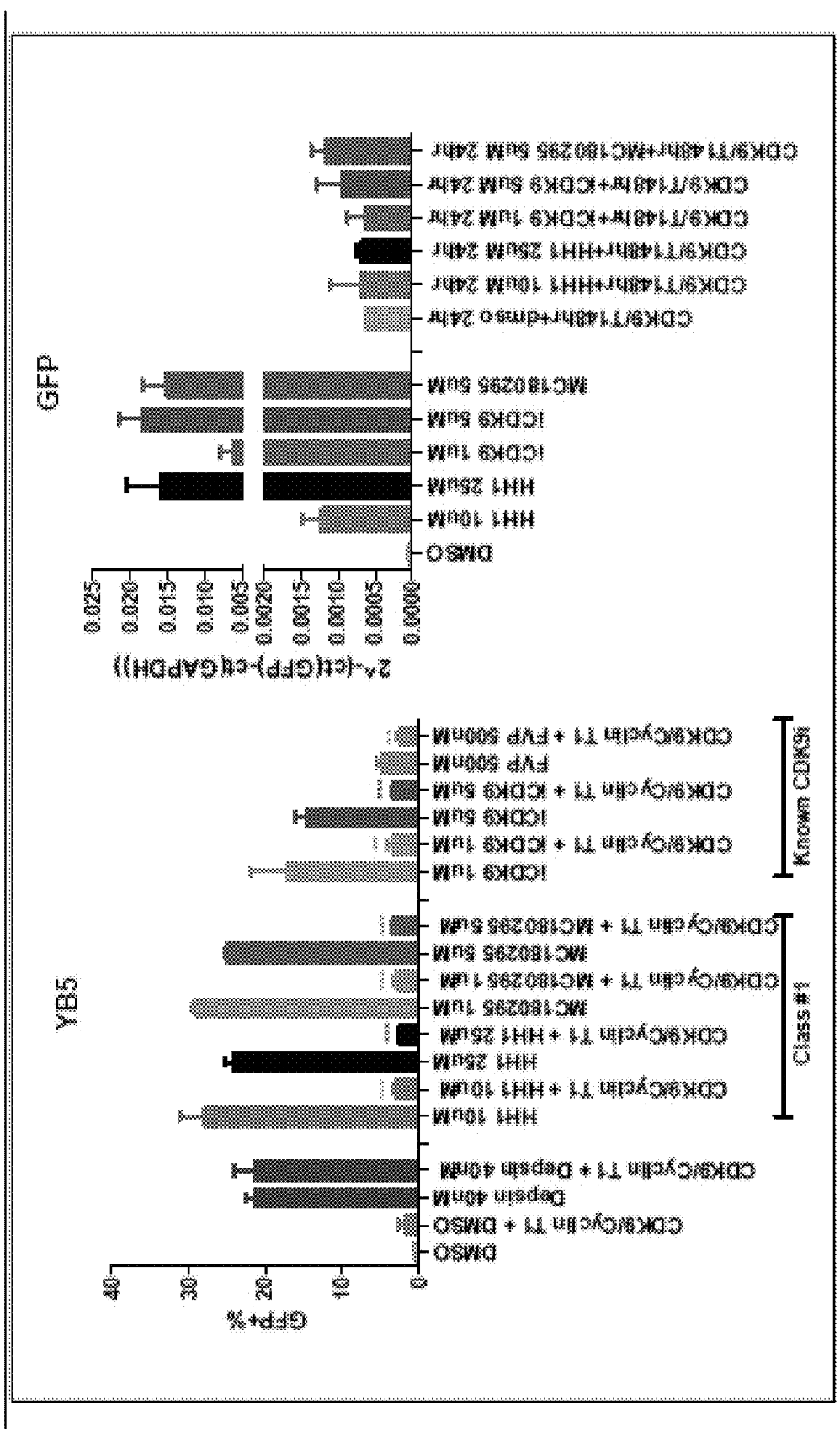
FIG. 70 depicts experimental data demonstrating that overexpression of CDK9/Cyclin T1 rescues the phenotype (prevents gene activation).
Figure 72:
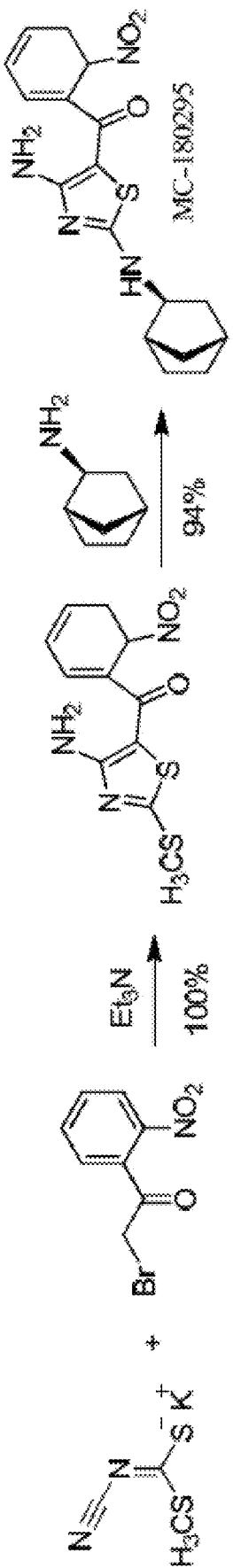
FIG. 72 depicts an example of a two-step synthesis of MC180295 with 95% overall yield (10-1,000 mg scale) with no chromatography.
Figure 73:
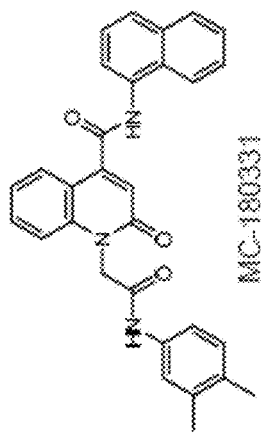
FIG. 73 depicts experimental data demonstrating in vitro ADME properties of MC180331.
Figure 74:
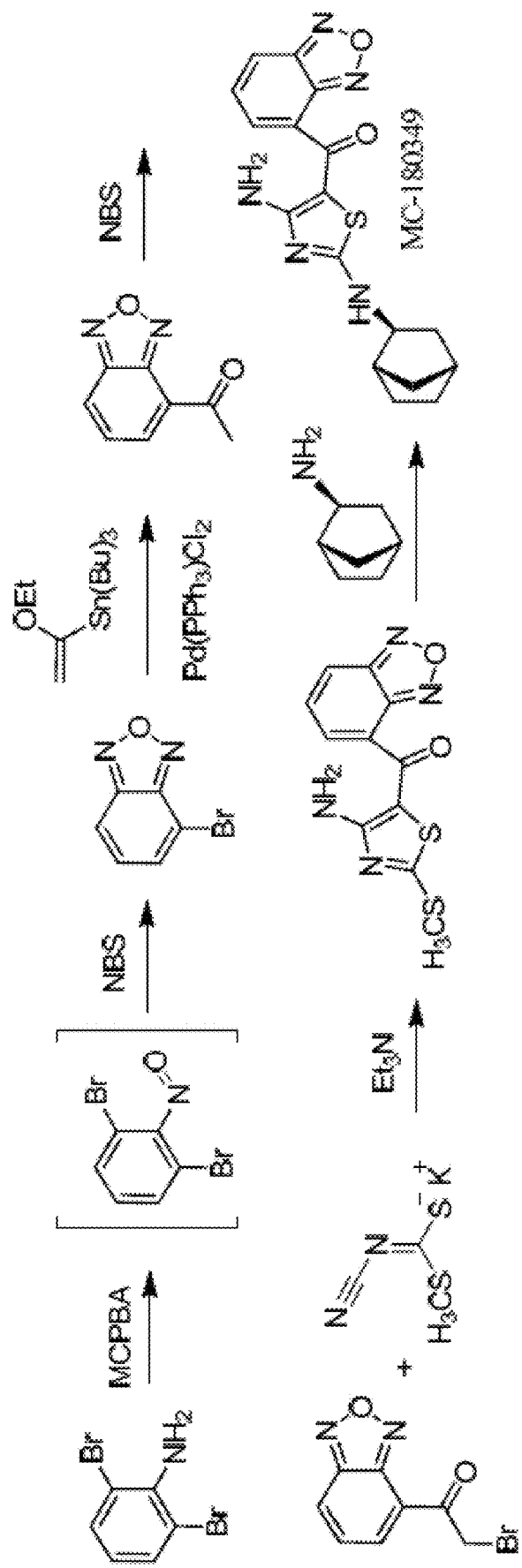
FIG. 74 depicts an example of a synthesis of MC180349.

This is the first time that CDK9 is linked to maintaining gene silencing at epigenetically repressed loci in mammals (including DNA methylated genes). The new data presented herein show that long-term CDK9 inhibition can preferentially reactivate epigenetically silenced genes with minimal downregulation effects, opposing to the canonical role of CDK9-mediated transcriptional elongation. This gene induction pattern is broadly similar to what is seen with DNMTi, and the synergy with DNMTi suggests potential pathways for clinical development. Mechanistically, it was found that CDK9 mediated regulation of both HP1α and SMARCA4 are potentially involved in this process. HP1α is known to recognize and bind to H3K9me2 targeted regions thus mediating heterochromatin gene silencing. It was shown that, consistent with previous data in the same model (Qin, T., et al. (2015), Clin Epigenetics 7, 97), loss of HP1α can lead to gene desilencing at H3K9me2 marked heterochromatin loci, including the CMV promoter region. The global gain of H3K79me2 seen after CDK9 inhibition might indicate a switch from a repressed H3K9me2 to an active H3K79me2 mark at these loci. The separate observation that SMARCA4 can be directly phosphorylated by CDK9 points to another mechanism by which CDK9 mediates gene silencing. CDK9 mediated phosphorylation of SWI/SNF complex components, including SMARCA4, has previously been reported in HIV-1 infected T-cells and phosphorylation of the SWI/SNF component Baf53 can lead to its release from DNA (Van Duyne, et al. (2011), J Mol Biol 411, 581-596). Thus, it is hypothesized that CDK9 mediated phosphorylation of SMARCA4 can also lead to its release from gene target loci, thus preventing those regions from being transcribed. In addition, HP1 itself has been shown to prevent SMARCA4 from binding to chromatin (Lavigne, et al., (2009), PLoS Genet 5, e1000769), suggesting multiple layers of regulation to ensure continued silencing at heterochromatin. Thus, it is speculated that upon CDK9 inhibition, HP1α is displaced from chromatin and dephosphorylated SMARCA4 can be recruited to the region, leading to gene induction (FIG. 63). It is interesting to consider why CDK9 evolved to simultaneously function to maintain high-level gene expression (at super-enhancer driven loci) and also gene silencing (at heterochromatin loci). Although not wishing to be bound by any particular theory, it is possible that rapidly cycling cells have the potential for transcription "errors" due to the need to wind and unwind chromatin for DNA replication, and it is likely that proteins such as CDK9 evolved to serve a rheostat function to ensure continued high and low-level expression at newly replicated loci.

CDK targeting has been an active area of research in oncology. CDK1/2 inhibitors have been tested as anti-cancer drugs but have generally not been very effective (Ghia, P., et al., (2017), Blood 129, 1876-1878), perhaps because their main effect is cytostatic through cycle arrest. CDK4/6 inhibitors were developed to treat Cyclin D-dependent cancers and were recently approved by the FDA for treating ER-positive and HER2-negative breast cancer (Sherr, C. J., Beach, D., and Shapiro, G. I. (2016). Targeting CDK4 and CDK6: From Discovery to Therapy. Cancer Discov 6, 353-367). These drugs, however, have minimal activity as single agents. A recent report on immune effects of CD4/6 inhibition (Goel, et al. (2017), Nature 548, 471-475) may explain their activity as combination therapeutics, and it is broadly similar to what was observed here with CDK9 inhibition. CDK7/9 targeting has previously been proposed as a strategy to suppress the expression of super-enhancer driven oncogenes (e.g. MYC) (Wang, Y., et al. (2015), Cell 163, 174-186). CDK9 inhibitors that are also multi-CDK inhibitors have previously been shown to have clinical activity in hematologic malignancies, but also with significant toxicity. Given the pleiotropic effects of CDKs, it is likely that broad inhibitors would indeed be toxic, and it is anticipated that more specific inhibitors (such as MC180295) would preserve anti-cancer activity with fewer side-effects.

Finally, consistent with the concept of immunosensitization triggered by epigenetic drugs, ERV activation upon CDK9 inhibition was identified and a CDK9 immune signature was defined that can potentially be used as a biomarker to predict patients' responses. A recent study on epigenetic drug (DNMTi and HDACi) mediated activation of cryptic transcription start sites in long terminal repeats extends the concept of immunosensitization to a genome wide scale and indicates that CDK9 inhibition might also trigger cryptic transcription start sites activation (Brocks, et al. (2017), Nat Genet 49, 1052-1060). Although not wishing to be bound by any particular theory, this may explain the mechanism of ERV activation upon CDK9 inhibition. The synergistic effects seen when combining CDK9 inhibition with anti-PD1 inhibition in vivo may be useful for new treatment options for cancer patients who are resistant to immunotherapy alone.

In summary, CDK9, which is overexpressed in many cancers (based on cBioPortal and The Human Protein Atlas analysis) (Cerami, E., et al. (2012), Cancer Discov 2, 401-404; Gao, J., et al. (2013), Sci Signal 6, pl1; Uhlen, et al. (2017), Science 357), has multiple properties that make it an excellent target for drug development in cancer. CDK9 inhibition simultaneously represses oncogenes (e.g. MYC), activates many tumor-suppressor genes, and induces a cellular immune response that sensitizes to immunotherapy. CDK9 specific inhibitors such as MC180295 may be useful in clinical trials as single agents, and in combination with other epigenetic drugs or with immunotherapy.

Example 4: Data Demonstrating Activity of Compounds of the Present Invention

Table 2 includes experimental data for the amount of activity of compounds of the present invention relative to the standard agent desipeptide at its optimal concentration. A value of "1" indicates that the compound displays the same level of activity as desipeptide at the concentration indicated. A value of "38" indicates that the analog was 38 times more effective than desipeptide.

TABLE 2

| STRUCTURE | MC # | MW | ST071842 analogs | relative activity to Depsipeptide @ 500 nM % | relative activity to Depsipeptide @ 1 μM % | relative activity to Depsipeptide @ 5 μM % | relative activity to Depsipeptide @ 10 μM % | relative activity to Depsipeptide @ 25 μM % | relative activity to Depsipeptide @ 50 μM % |
|---|---|---|---|---|---|---|---|---|---|
| 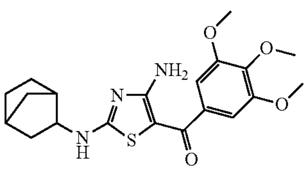 [SMILES: COc1cc(C(=O)c2sc(NC3CC4CCC3C4)nc2N)cc(OC)c1OC] | 180251 | 403.5 | MC180251 | | 0.00 | 0.00 | 0.00 | 0.00 | 0.00 |
| 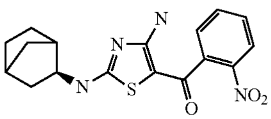 [SMILES: Nc1nc(N[C@H]2CC3CCC2C3)sc1C(=O)c1ccccc1[N+](=O)[O-]] | 180295 | 358.41 | MC180295 | 14.10 | 28.81 | 65.42 | 72.81 | 73.30 | 23.32 |
| 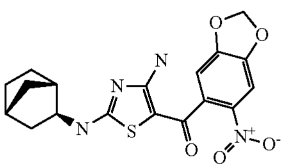 [SMILES: Nc1nc(N[C@H]2C[C@@H]3CC[C@H]2C3)sc1C(=O)c1cc2c(cc1[N+](=O)[O-])OCO2] | 180300 | 402.42 | MC180300 | 0.68 | 3.87 | 35.65 | 51.64 | 46.89 | |
| 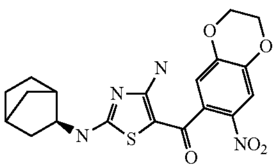 [SMILES: Nc1nc(N[C@H]2CC3CCC2C3)sc1C(=O)c1cc2c(cc1[N+](=O)[O-])OCCO2] | 180312 | 416.45 | MC180312 | | 9.73 | 35.64 | 42.34 | 9.00 | 6.38 |
| 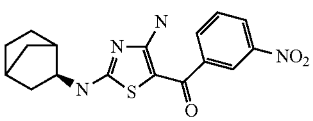 [SMILES: Nc1nc(N[C@H]2CC3CCC2C3)sc1C(=O)c1cccc([N+](=O)[O-])c1] | 180339 | 358.41 | MC180339 | 3.29 | 3.05 | 16.94 | 29.25 | 8.71 | |
| 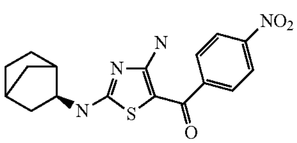 [SMILES: Nc1nc(N[C@H]2CC3CCC2C3)sc1C(=O)c1ccc([N+](=O)[O-])cc1] | 180340 | 358.41 | MC180340 | 3.54 | 2.83 | 12.99 | 11.61 | 3.41 | |
| 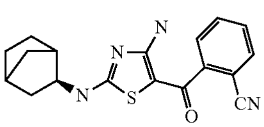 [SMILES: N#Cc1ccccc1C(=O)c1sc(N[C@H]2CC3CCC2C3)nc1N] | 180342 | 338.43 | MC180342 | 10.42 | 22.71 | 107.00 | 118 20 | 78.85 | |
| 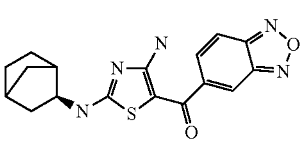 [SMILES: Nc1nc(N[C@H]2CC3CCC2C3)sc1C(=O)c1ccc2nonc2c1] | 180345 | 355.41 | MC180345 | 1.87 | 3.58 | 3.61 | 3.99 | 12.63 | |
| 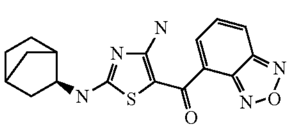 [SMILES: Nc1nc(N[C@H]2CC3CCC2C3)sc1C(=O)c1cccc2nonc12] | 180349 | 355.41 | MC180349 | 10.98 | 27.48 | 91.17 | 74.47 | 36.65 | |

TABLE 2-continued

| STRUCTURE | MC # | MW | ST071842 analogs | relative activity to Depsi-peptide @ 500 nM % | relative activity to Depsi-peptide @ 1 μM % | relative activity to Depsi-peptide @ 5 μM % | relative activity to Depsi-peptide @ 10 μM % | relative activity to Depsi-peptide @ 25 μM % | relative activity to Depsi-peptide @ 50 μM % |
|---|---|---|---|---|---|---|---|---|---|
| 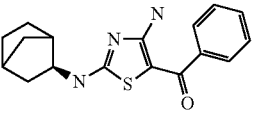 [SMILES: Nc1nc(N[C@H]2CC3CCC2C3)sc1C(=O)c1ccccc1] | 180373 | 310.39 | MC180373 | | | | | | |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of Formula (I):

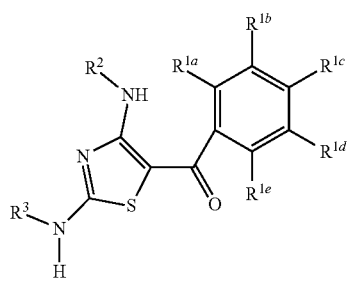

including enantiomers, diastereomers, hydrates, solvates, pharmaceutically acceptable salts, prodrugs and complexes thereof;
wherein in Formula (I):
$R^{1a}$, $R^{1b}$, $R^{1c}$, $R^{1d}$ and $R^{1e}$ are each independently selected from the group consisting of hydrogen, halogen, hydroxyl, $C_{1-6}$ linear alkyl, $C_{3-6}$ branched alkyl, $C_{3-6}$ cycloalkyl, $C_{1-6}$ haloalkyl, $C_{1-6}$ linear alkoxy, $C_{3-6}$ branched alkoxy, $C_{1-6}$ haloalkoxy, thiol, $C_{1-6}$ linear thioalkyl, $C_{3-6}$ branched thioalkyl, cyano, nitro, and $NR^4R^5$, or two adjacent $R^1$ groups are joined to form a 5- to 7-membered heterocyclic ring containing 1 to 3 heteroatoms,
$R^2$ is selected from the group consisting of hydrogen, $C_{1-6}$ linear alkyl, $C_{3-7}$ branched alkyl, $C_{3-7}$ cycloalkyl and $COR^6$;
$R^3$ is a bridged bicycloalkyl moiety selected from the group of consisting of:

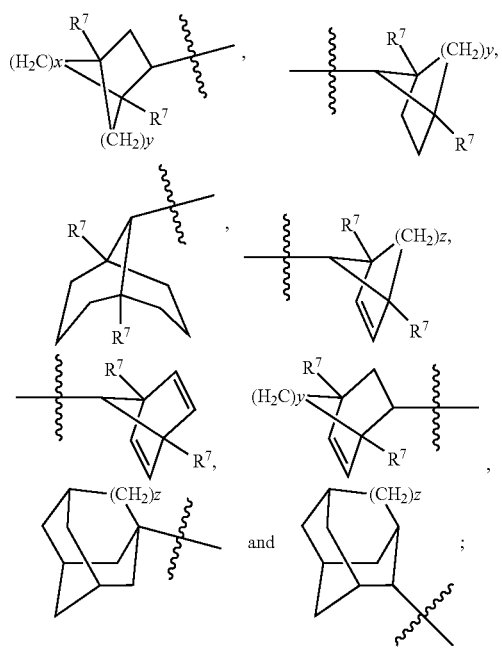

$R^4$ and $R^5$ are each independently selected from the group consisting of hydrogen, $C_{1-6}$ linear alkyl, and $C_{3-7}$ branched alkyl, or $R^4$ and $R^5$ are joined to form a 3- to 7-membered heterocycloalkyl ring;

$R^6$ is selected from the group consisting of hydrogen, $C_{1-6}$ linear alkyl, $C_{3-7}$ branched alkyl, $C_{1-6}$ linear alkoxy, $C_{3-7}$ branched alkoxy and $C_{3-7}$ cycloalkyl;
$R^7$ at each occurrence is independently selected from the group consisting of hydrogen or methyl;
x is 1, 2, or 3;
y is 1, 2, or 3; and
z is 1, 2, or 3;
with the proviso that when the compound of Formula (I) is:

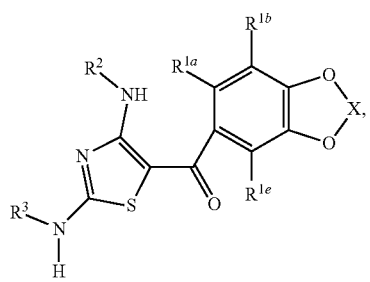

then X cannot

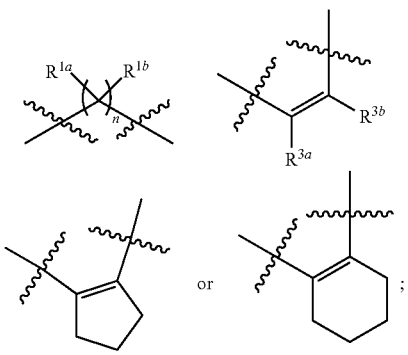

wherein:
$R^{1a}$ and $R^{1b}$ are at each occurrence independently selected from the group consisting of hydrogen, $C_{1-4}$ linear alkyl, and $C_{3-6}$ branched alkyl, or $R^{1a}$ and $R^{1b}$ are taken together with the atoms to which they are bound to form a three to six membered carbocyclic ring, or two $R^{1a}$ units on adjacent carbon atoms are taken together with the atoms to which they are bound to form a three to six membered carbocyclic ring;
$R^{3a}$ and $R^{3b}$ are each independently selected from the group consisting of hydrogen, $C_{1-4}$ linear alkyl, and $C_{3-6}$ branched alkyl.

2. The compound of claim 1, wherein the compound is selected from the group consisting of:

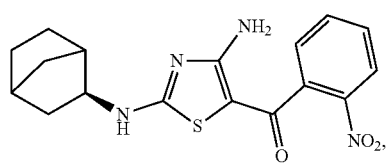

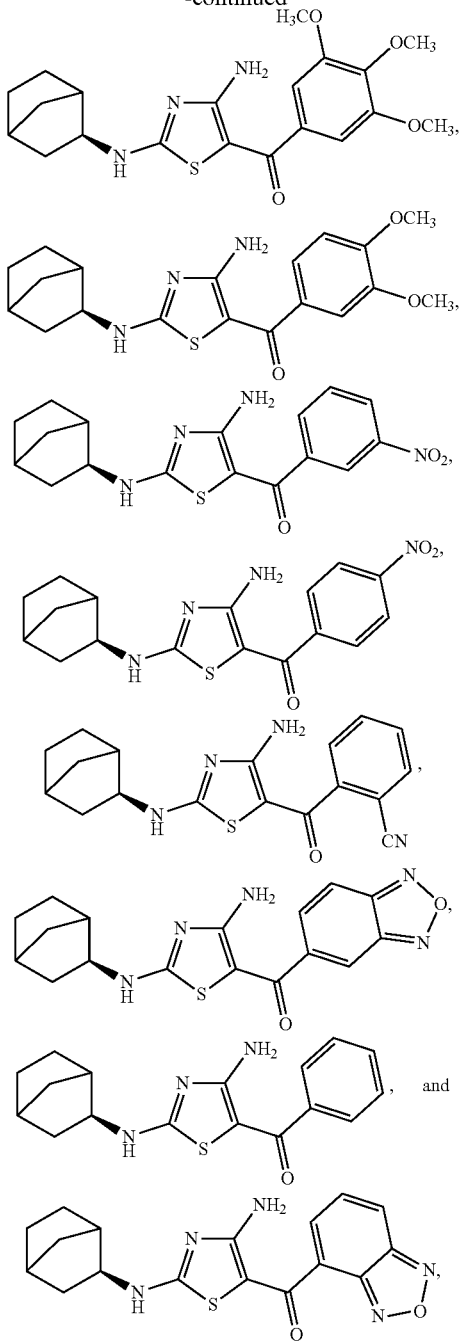

a salt or solvate thereof, and any combinations thereof.

3. A composition comprising a compound of claim 1.

4. The composition of claim 3, wherein the composition further comprises a pharmaceutically acceptable carrier.

5. The composition of claim 4, wherein the composition further comprises an additional therapeutic agent.

6. A method of treating a disease or disorder selected from the group consisting of cancer, an inflammatory condition, cardiac dysfunction, cardiovascular disease, a viral infection, and a CDK9-mediated disorder in a subject in need thereof, the method comprising administering to the subject a therapeutically effective amount of a composition comprising at least one compound of Formula (I):

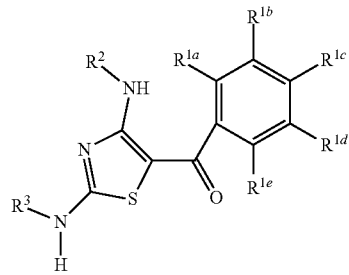

(I)

including enantiomers, diastereomers, hydrates, solvates, pharmaceutically acceptable salts, prodrugs and complexes thereof;

wherein in Formula (I):

$R^{1a}$, $R^{1b}$, $R^{1c}$, $R^{1d}$ and $R^{1e}$ are each independently selected from the group consisting of hydrogen, halogen, hydroxyl, $C_{1-6}$ linear alkyl, $C_{3-6}$ branched alkyl, $C_{3-6}$ cycloalkyl, $C_{1-6}$ haloalkyl, $C_{1-6}$ linear alkoxy, $C_{3-6}$ branched alkoxy, $C_{1-6}$ haloalkoxy, thiol, $C_{1-6}$ linear thioalkyl, $C_{3-6}$ branched thioalkyl, cyano, nitro, and $NR^4R^5$, or two adjacent $R^1$ groups are joined to form a 5- to 7-membered heterocyclic ring containing 1 to 3 heteroatoms, $R^2$ is selected from the group consisting of hydrogen, $C_{1-6}$ linear alkyl, $C_{3-7}$ branched alkyl, $C_{3-7}$ cycloalkyl and $COR^6$;

$R^3$ is a bridged bicycloalkyl moiety selected from the group of consisting of:

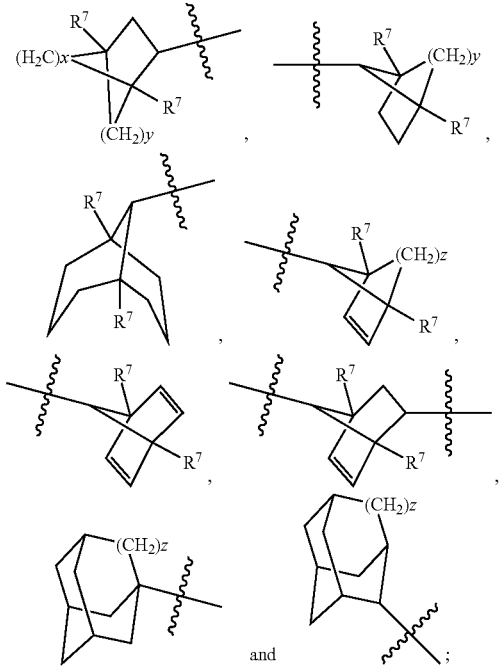

$R^4$ and $R^5$ are each independently selected from the group consisting of hydrogen, $C_{1-6}$ linear alkyl, and $C_{3-7}$ branched alkyl, or $R^4$ and $R^5$ are joined to form a 3- to 7-membered heterocycloalkyl ring;

$R^6$ is selected from the group consisting of hydrogen, $C_{1-6}$ linear alkyl, $C_{3-7}$ branched alkyl, $C_{1-6}$ linear alkoxy, $C_{3-7}$ branched alkoxy and $C_{3-7}$ cycloalkyl;

R$^7$ at each occurrence is independently selected from the group consisting of hydrogen or methyl;
x is 1, 2, or 3;
y is 1, 2, or 3; and
z is 1, 2, or 3;
with the proviso that when the compound of Formula (I) is:

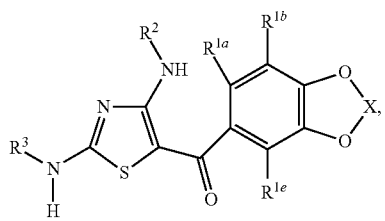

then X cannot be

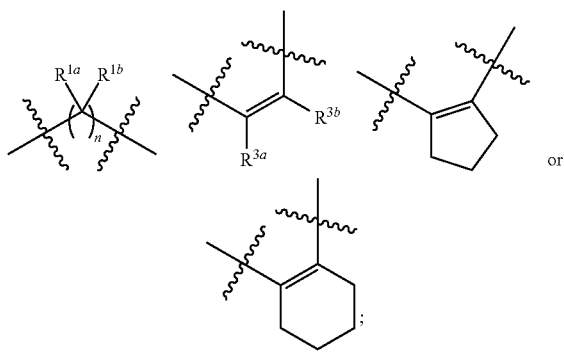

wherein:
R$^{1a}$ and R$^{1b}$ are at each occurrence independently selected from the group consisting of hydrogen, C$_{1-4}$ linear alkyl, and C$_{3-6}$ branched alkyl, or R$^{1a}$ and R$^{1b}$ are taken together with the atoms to which they are bound to form a three to six membered carbocyclic ring, or two R$^{1a}$ units on adjacent carbon atoms are taken together with the atoms to which they are bound to form a three to six membered carbocyclic ring;
R$^{3a}$ and R$^{3b}$ are each independently selected from the group consisting of hydrogen, C$_{1-4}$ linear alkyl, and C$_{3-6}$ branched alkyl.

7. The method of claim 6, wherein the compound of Formula (I) is selected from the group consisting of:

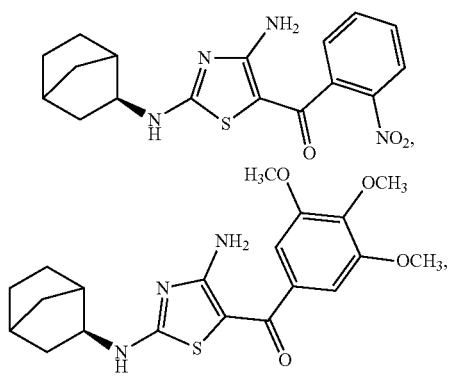

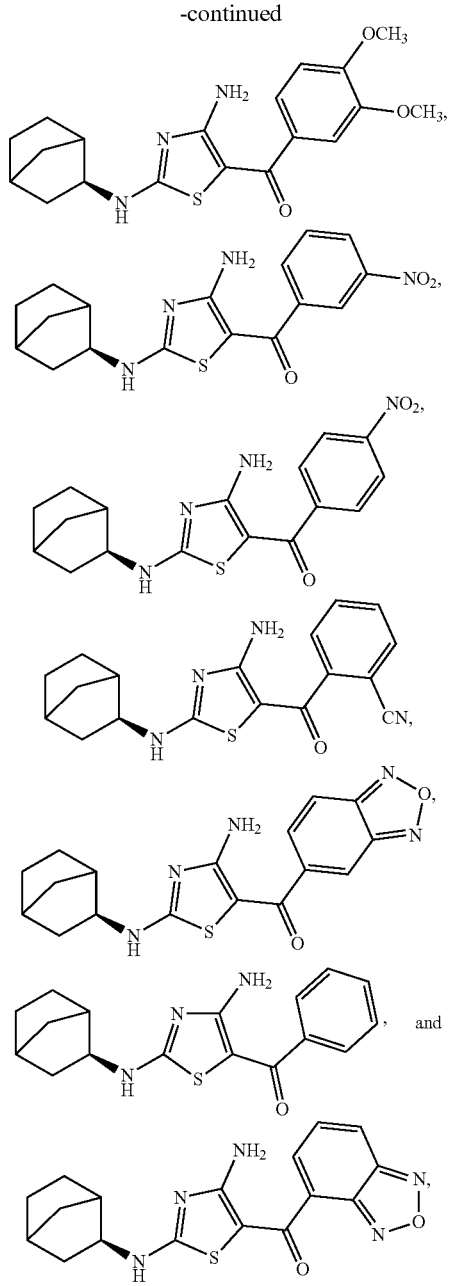

a salt or solvate thereof, and any combinations thereof.

8. The method of claim 6, wherein the cancer is selected from the group consisting of the cancer is selected from the group consisting of lung cancer, colon cancer, melanoma, breast cancer, ovarian cancer, prostate cancer, liver cancer, pancreatic cancer, a CNS tumor, neuroblastoma, leukemia, bone cancer, intestinal cancer, lymphoma, bladder cancer, sarcoma, bile duct cancer, stomach cancer, cervical cancer, testicular cancer, uterine cancer, gall bladder cancer, fallopian tube cancer, nasopharyngeal cancer, hypopharyngeal cancer, renal cancer, oral cavity cancer, head and neck cancer, thyroid cancer, parathyroid cancer, pituitary cancer, rectal cancer, retinoblastoma, Wilm's tumor, vaginal cancer, penile cancer, and combinations thereof.

9. The method of claim 6, wherein the method further comprises administering to the subject at least one additional therapeutic agent.

10. The method of claim 9, wherein the therapeutic agent is a chemotherapeutic agent.

11. The method of claim 9, wherein the therapeutic agent is a Bcl-2 inhibitor selected from the group consisting of ABT-199, ABT-263, ABT-737, G3139 (genasense or oblimersen), GX15-070 (obatoclax mesylate), HA14-1, TW-37, sabutoclax, Gossypol (AT-101), antimycin A, apogossypol, and S44563.

12. The method of claim 9, wherein the composition and the additional therapeutic agent are co-administered.

13. The method of claim 12, wherein the composition and the additional therapeutic agent are co-formulated.

14. The method of claim 6, wherein the cardiac dysfunction or cardiovascular disease is cardiac hypertrophy.

15. The method of claim 6, wherein the viral infection is selected from the group consisting of human immunodeficiency virus (HIV), herpes simplex virus (HSV), Hepatitis A, Hepatitis B, Hepatitis C, Human Papilloma Virus, Epstein Barr Virus, Human Adenovirus, Cytomegalovirus, Poxvirus, Sindbis Virus, and Human Herpes Virus.

16. A method of sensitizing cancer cells in a subject in need thereof, the method comprising administering to the subject a therapeutically effective amount of a composition comprising at least one compound of Formula (I):

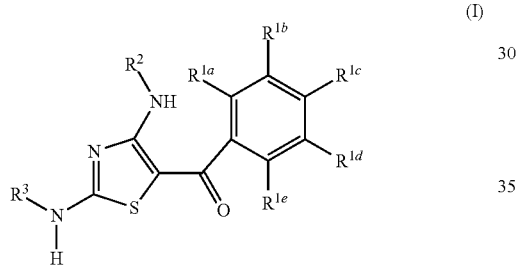

including enantiomers, diastereomers, hydrates, solvates, pharmaceutically acceptable salts, prodrugs and complexes thereof;

wherein in Formula (I):

$R^{1a}$, $R^{1b}$, $R^{1c}$, $R^{1d}$ and $R^{1e}$ are each independently selected from the group consisting of hydrogen, halogen, hydroxyl, $C_{1-6}$ linear alkyl, $C_{3-6}$ branched alkyl, $C_{3-6}$ cycloalkyl, $C_{1-6}$ haloalkyl, $C_{1-6}$ linear alkoxy, $C_{3-6}$ branched alkoxy, $C_{1-6}$ haloalkoxy, thiol, $C_{1-6}$ linear thioalkyl, $C_{3-6}$ branched thioalkyl, cyano, nitro, and $NR^4R^5$, or two adjacent $R^1$ groups are joined to form a 5- to 7-membered heterocyclic ring containing 1 to 3 heteroatoms, $R^2$ is selected from the group consisting of hydrogen, $C_{1-6}$ linear alkyl, $C_{3-7}$ branched alkyl, $C_{3-7}$ cycloalkyl and $COR^6$;

$R^3$ is a bridged bicycloalkyl moiety selected from the group of consisting of:

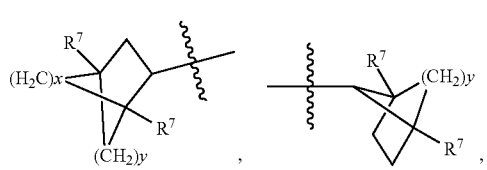

-continued

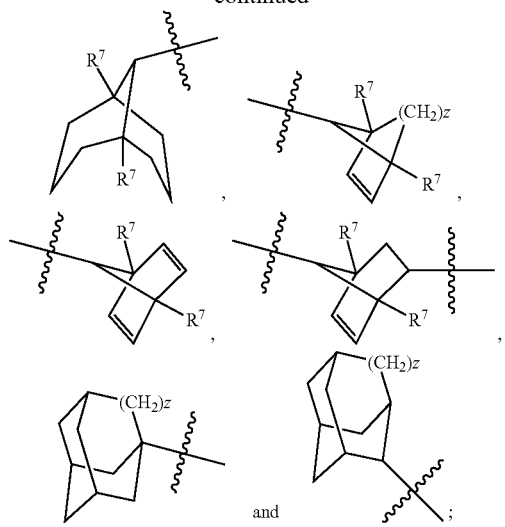

$R^4$ and $R^5$ are each independently selected from the group consisting of hydrogen, $C_{1-6}$ linear alkyl, and $C_{3-7}$ branched alkyl, or $R^4$ and $R^5$ are joined to form a 3- to 7-membered heterocycloalkyl ring;

$R^6$ is selected from the group consisting of hydrogen, $C_{1-6}$ linear alkyl, $C_{3-7}$ branched alkyl, $C_{1-6}$ linear alkoxy, $C_{3-7}$ branched alkoxy and $C_{3-7}$ cycloalkyl;

$R^7$ at each occurrence is independently selected from the group consisting of hydrogen or methyl;

x is 1, 2, or 3;

y is 1, 2, or 3; and z is 1, 2, or 3;

with the proviso that when the compound of Formula (I) is:

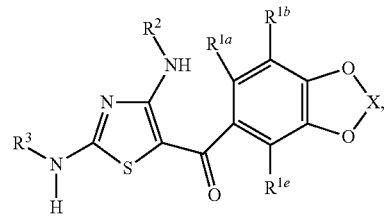

then X cannot be

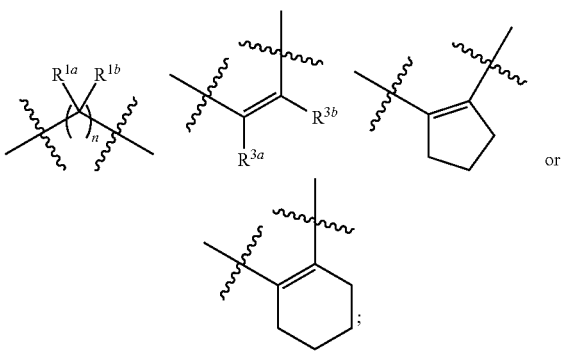

wherein:

$R^{1a}$ and $R^{1b}$ are at each occurrence independently selected from the group consisting of hydrogen, $C_{1-4}$ linear alkyl, and C$_{3-6}$ branched alkyl, or R$^{1a}$ and R$^{1b}$ are taken together with the atoms to which they are bound to form a three to six membered carbocyclic ring, or two R$^{1a}$ units on adjacent carbon atoms are taken together with the atoms to which they are bound to form a three to six membered carbocyclic ring;

R$^{3a}$ and R$^{3b}$ are each independently selected from the group consisting of hydrogen, C$_{1-4}$ linear alkyl, and C$_{3-6}$ branched alkyl.

17. The method of claim 16, wherein the compound of Formula (I) is selected from the group consisting of:

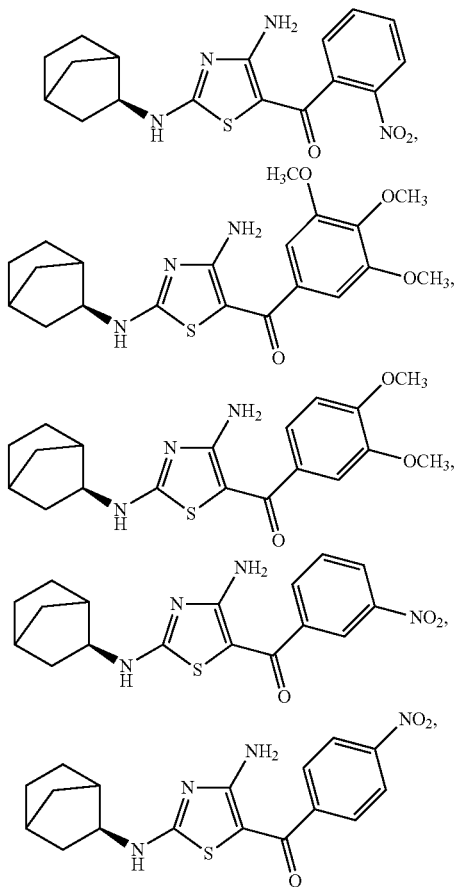

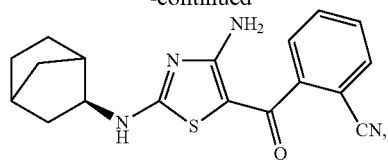

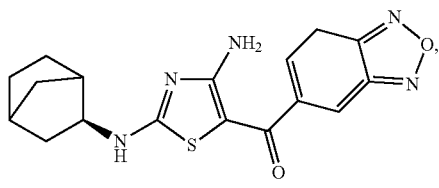

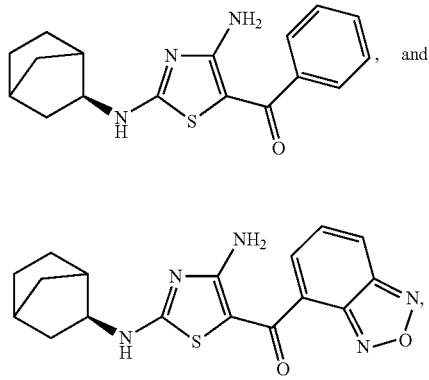

a salt or solvate thereof, and any combinations thereof.

18. The method of claim 16, wherein the method further comprises administering to the subject a therapeutically effective amount of an immune-targeted drug.

19. The method of claim 18, wherein the immune-targeted drug is an inhibitor of PD-1 or PD-L1.

20. The method of claim 16, wherein the method further comprises administering to the subject an immune checkpoint inhibitor selected from the group consisting of ipilimumab, pembrolizumab, nivolumab, pidilizumab, atezolizumab, avelumab, and druvbalumab.

* * * * *

UNITED STATES PATENT AND TRADEMARK OFFICE
CERTIFICATE OF CORRECTION

| | | |
|---|---|---|
| PATENT NO. | : 10,941,126 B2 | Page 1 of 1 |
| APPLICATION NO. | : 16/479317 | |
| DATED | : March 9, 2021 | |
| INVENTOR(S) | : Wayne E. Childers et al. | |

It is certified that error appears in the above-identified patent and that said Letters Patent is hereby corrected as shown below:

On the Title Page

Item (72) Inventors:
"Wayne C. Childers, New Hope, PA (US); Magid A. Abou-Gharbia, Exton, PA (US); George C. Morton, Collegeville, PA (US); Jean-Pierre J. Issa, Philadelphia, PA (US); Hanghang Zhang, Philadelphia, PA (US)"
Should read:
"Wayne E. Childers, New Hope, PA (US); Magid A. Abou-Gharbia, Exton, PA (US); George C. Morton, Collegeville, PA (US); Jean-Pierre J. Issa, Philadelphia, PA (US); Hanghang Zhang, Philadelphia, PA (US)".

Signed and Sealed this
Twenty-seventh Day of July, 2021

Drew Hirshfeld
*Performing the Functions and Duties of the
Under Secretary of Commerce for Intellectual Property and
Director of the United States Patent and Trademark Office*